US012472201B2

(12) United States Patent
Becker et al.

(10) Patent No.: US 12,472,201 B2
(45) Date of Patent: Nov. 18, 2025

(54) COMPLEXING AGENT SALT FORMULATIONS OF PHARMACEUTICAL COMPOUNDS

(71) Applicant: Bexson Biomedical, Inc., Santa Barbara, CA (US)

(72) Inventors: Jeffrey Becker, Santa Barbara, CA (US); Gregg Peterson, Santa Barbara, CA (US); Jason Wallach, Philadelphia, PA (US)

(73) Assignee: Bexson Biomedical, Inc., Santa Barbara, CA (US)

(*) Notice: Subject to any disclaimer, the term of this patent is extended or adjusted under 35 U.S.C. 154(b) by 0 days.

(21) Appl. No.: 17/981,348

(22) Filed: Nov. 4, 2022

(65) Prior Publication Data

US 2023/0124101 A1 Apr. 20, 2023

Related U.S. Application Data

(63) Continuation of application No. 17/546,880, filed on Dec. 9, 2021, now Pat. No. 11,534,454, which is a continuation of application No. PCT/US2021/059760, filed on Nov. 17, 2021.

(60) Provisional application No. 63/115,445, filed on Nov. 18, 2020, provisional application No. 63/115,458, filed on Nov. 18, 2020, provisional application No. 63/115,451, filed on Nov. 18, 2020, provisional application No. 63/115,453, filed on Nov. 18, 2020.

(51) Int. Cl.
*A61K 31/724* (2006.01)
*A61K 45/06* (2006.01)

(52) U.S. Cl.
CPC ............ *A61K 31/724* (2013.01); *A61K 45/06* (2013.01)

(58) Field of Classification Search
CPC ....... A61K 31/724; A61K 47/40; A61K 45/06
USPC ........................................................... 514/58
See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,212,162 | A | 5/1993 | Missel et al. |
| 5,352,683 | A | 10/1994 | Mayer et al. |
| 5,403,841 | A | 4/1995 | Lang et al. |
| 6,133,248 | A | 10/2000 | Stella |
| 6,153,746 | A | 11/2000 | Shah et al. |
| 6,605,635 | B1 | 8/2003 | Bai et al. |
| 6,831,172 | B1 | 12/2004 | Barbucci et al. |
| 7,034,013 | B2 | 4/2006 | Thompson et al. |
| 10,973,780 | B2 | 4/2021 | Becker et al. |
| 11,534,454 | B2 | 12/2022 | Becker et al. |
| 2003/0055023 | A1 | 3/2003 | Rajewski et al. |
| 2003/0216353 | A1 | 11/2003 | Mosher et al. |
| 2004/0186075 | A1 | 9/2004 | Loftsson et al. |
| 2005/0153999 | A1 | 7/2005 | Hu |
| 2007/0083186 | A1 | 4/2007 | Carter et al. |
| 2007/0149479 | A1 | 6/2007 | Fischer et al. |
| 2009/0028824 | A1 | 1/2009 | Chiang et al. |
| 2010/0172917 | A1 | 7/2010 | Ter Meulen et al. |
| 2012/0201874 | A1 | 8/2012 | Li et al. |
| 2012/0295893 | A1 | 11/2012 | Peled et al. |
| 2013/0296437 | A1 | 11/2013 | Young et al. |
| 2013/0296547 | A1 | 11/2013 | Yamasaki et al. |
| 2013/0345202 | A1 | 12/2013 | Amselem |
| 2014/0046061 | A1 | 2/2014 | Matos |
| 2014/0046064 | A1 | 2/2014 | Boaretto et al. |
| 2015/0150979 | A1 | 6/2015 | Yates et al. |
| 2015/0259110 | A1 | 9/2015 | Blackburn |
| 2015/0328335 | A1* | 11/2015 | Nerurkar .............. A61K 31/496 514/58 |
| 2016/0354558 | A1 | 12/2016 | Seguin et al. |
| 2017/0042878 | A1 | 2/2017 | Fava et al. |
| 2017/0043084 | A1 | 2/2017 | Estes |
| 2017/0049780 | A1 | 2/2017 | Wainer et al. |
| 2017/0150716 | A1 | 6/2017 | Chang et al. |
| 2017/0181966 | A1 | 6/2017 | Charney et al. |
| 2018/0060527 | A1 | 3/2018 | Kalyanpur et al. |
| 2019/0350881 | A1 | 11/2019 | Surakitbanharn |
| 2020/0360308 | A1 | 11/2020 | Becker et al. |
| 2020/0384188 | A1 | 12/2020 | Becker et al. |
| 2021/0186896 | A1 | 6/2021 | Becker et al. |
| 2022/0016025 | A1 | 1/2022 | Dendukuri |
| 2022/0152088 | A1 | 5/2022 | Becker et al. |
| 2023/0405018 | A1 | 12/2023 | Becker et al. |

FOREIGN PATENT DOCUMENTS

| | | | |
|---|---|---|---|
| CN | 1939298 | A | 4/2007 |
| CN | 111330019 | A | 6/2020 |
| DE | 102016014603 | A1 | 1/2018 |
| EP | 0657176 | A2 | 6/1995 |
| EP | 3498266 | A1 | 6/2019 |

(Continued)

OTHER PUBLICATIONS

Kim et al. Inclusion Complexation of Ziprasidone Mesylate with β-Cyclodextrin Sulfobutyl Ether. Journal of Pharmaceutical Sciences, vol. 87, No. 12, p. 1560-1567, 1998. (Year: 1998).*
2020 Guidance on Captisol ("How to Solubilize a Drug with Captisol") (2020).
Abilify Package Insert. Bristol-Myers Squibb Company. Otsuka America Pharmaceutical, Inc. 1- 53 (2006).
Al-Muhammed et al. In-vivo studies on dexamethasone sodium phosphate liposomes. J Microencapsul. 13(3):293-306 (1996).
Berge et al.: Pharmaceutical salts. Journal of Pharmaceutical Sciences 66:1-19 (1977).

(Continued)

*Primary Examiner* — Yih-Horng Shiao
(74) *Attorney, Agent, or Firm* — Wilson Sonsini Goodrich & Rosati

(57) ABSTRACT

Provided herein are pharmaceutical formulations and pharmaceutical compound salts which utilize complexing agents as counterions. Such formulations and salts are useful for treating a variety of disease and disorders.

23 Claims, 55 Drawing Sheets

(56) References Cited

FOREIGN PATENT DOCUMENTS

| | | | | |
|---|---|---|---|---|
| WO | WO-9500144 | A1 | 1/1995 | |
| WO | WO-0165657 | A1 | 9/2001 | |
| WO | WO-2005020929 | A2 * | 3/2005 | ........... A61K 31/496 |
| WO | WO-2014121235 | A2 | 8/2014 | |
| WO | WO-2017120639 | A1 | 7/2017 | |
| WO | WO-2017180589 | A1 | 10/2017 | |
| WO | WO-2019023770 | A1 | 2/2019 | |
| WO | WO-2020232274 | A1 | 11/2020 | |
| WO | WO-2022109050 | A1 | 5/2022 | |
| WO | WO-2022109052 | A1 | 5/2022 | |
| WO | WO-2023225113 | A1 | 11/2023 | |
| WO | WO-2025111482 | A1 | 5/2025 | |

OTHER PUBLICATIONS

Brewster et al.: Cyclodextrins as pharmaceutical solubilizers. Adv. Drug Deliv. Rev. 59:645-666 (2007).
Bundgaard. Design of Prodrugs: Bioreversible Derivatives for Various Functional Groups and Chemical Entities. Elsevier (pp. 1-92) (1985).
Chadeayne et al.: Norpsilocin: freebase and fumarate salt. Acta Cryst. E76:589-593 (2020).
Chiang et al. An Fc domain protein-small molecule conjugate as an enhanced immunomodulator. J. Am. Chem. Soc. 136(9):3370-73 (2014).
Chonn et al. Recent advances in liposomal drug-delivery systems. Curr Opin Biotechnol. 6(6):698-708 (1995).
Cyclodextrins used as excipients. Eur Med Agency Comm Hum Med Prod. Oct. 2017:16.
Dollo et al.: Complexation between local anesthetics and Beta-Cyclodextrin derivatives: Relationship between stability constants and in vitro membrane permeability of bupivacaine and lidocaine from their complexes. S.T.P. Pharma Practiques. pp. 1-21 (1998).
Donnelly: Stability of Diluted Ketamine Packaged in Glass Vials. CJHP. 66(3) 2013.
Eide et al.: Continuous subcutaneous administration of the N-methyl-D-aspartic acid (NMDA) receptor antagonist ketamine in the treatment of post-herpetic neuralgia. Pain. 61(2):221-228 (1995).
European Patent Application No. 18879075.2 European Search Report dated Aug. 4, 2021.
EYLES: Oral Delivery and Fate of Poly (lactic acid) Microsphere-encapsulated Interferon in Rats J. Pharm. Pharmacol. 49:669-674 (1997).
Gao et al.: Controlled release of a contraceptive steroid from biodegradable and injectable gel formulations: in vitro evaluation. Pharm Res. 12(6):857-863 (1995).
Gilotra et al.: Efficacy of intravenous furosemide versus a novel, pH-neutral furosemide formulation administered subcutaneously in outpatients with worsening heart failure. JACC: Heart Failure, 6(1), pp. 65-70 (2017).
Graven-Nielsen et al.: Quantification of local and referred muscle pain in humans after sequential in injections of hypertonic saline. Pain, 69(1-2), pp. 111-117 (1997).
Heinemann et al.: U-100, pH-Neutral formulation of VIAject®: faster onset of action than insulin lispro in patients with type 1 diabetes. Diabetes, Obesity and Metabolism, 14(3), pp. 222-227 (2012).
Hong et al.: Effect of cyclodextrin derivation and amorphous state of complex on accelerated degradation of ziprasidone. J. Pharm. Sci. 100(7):2703-2716 (2011).
Jahed et al.: NMR ($^1$H, ROESY) spectroscopic and molecular modelling investigations of supramolecular complex of β-cyclodextrin and curcumin. Food Chem. 165:241-246 (2014).
Javid et al.: Evaluation of a Low Dose Ketamine in Post Tonsillectomy Pain Relief: A randomized trial comparing intravenous and subcutaneous ketamine in pediatrics. Anesth Pain. 2(2):85-89 (2012).
Ketalar Insert 2018: website https://www.nps.org.au/medicine-finder/ketalar-solution-for- injection (2018).
Li et al. Current drug research on PEGylation with small molecular agents. Progress in Polymer Science 38:421-44 (2013).
Macintosh et al.: In Vitro and In Vivo Evaluation of a Sulfobutyl Ether β-Cyclodextrin Enabled Etomidate Formulation. Journal of Pharmaceutical Sciences. 93(10):2585-2594 (2004).
Mathaes et al.: Subcutaneous injection volume of biopharmaceuticals—pushing the boundaries. Journal of pharmaceutical sciences, 105(8), pp. 2255-2259 (2016).
Matthew et al.: Ketamine for Treatment-Resistant Unipolar Depression. CNS Drugs. 26(3):189-204 (2012).
Mauri et al.: Clinical pharmacokinetics of atypical antipsychotics: An Update Clin Pharmacokinet. 57:1493-1528 (2018).
Mion et al.: Ketamine Pharmacology: An Update (Pharmacodynamics and Molecular Aspects, Recent Findings). CNS Neuroscience & Therapeutics. 19:370-380 (2013).
Okimoto et al.: The interaction of charged and uncharged drugs with neutral (HP-Beta-CD) and Anionically Charged (SBE7-Beta-CD) Beta-Cyclodextrins. Pharm. Res. 13(2):256-264 (1996).
OSHIMA. Continuous subcutaneous injection of ketamine for cancer pain. Can. J. Anaesth. 37(3):385-92 (1990).
Ostro et al.: Use of liposomes as injectable-drug delivery systems; Am J. Hosp. Pharm. 46(8):1576-1587 (1989).
Pastor et al.: NMR spectroscopy in coordination supramolecular chemistry: A unique and powerful methodology. Coordination Chemistry Reviews. 252(21-22):2314-2345 (2008).
PCT/US2018/061121 International Preliminary Report on Patentability dated May 19, 2020.
PCT/US2018/061121 International Search Report and Written Opinion dated Jan. 28, 2019.
PCT/US2020/032941 International Preliminary Report on Patentability dated Nov. 16, 2021.
PCT/US2020/032941 International Search Report and Written Opinion dated Sep. 4, 2020.
PCT/US2020/032941 Invitation to Pay Additional Fees dated Jul. 7, 2020.
PCT/US2021/059760 International Search Report and Written Opinion dated Mar. 21, 2022.
PCT/US2021/059760 Invitation to Pay Additional Fees dated Jan. 13, 2022.
Peltoniemi et al.: A Review of Clinical Pharmacokinetics and Pharmacodynamics in Anesthesia and Pain Therapy. Clin Pharmacokinet. 55(9):1059-1077 (2016).
Pickar. Dosage Calculations. p. 1-8 (1999).
Puskás et al.: Sulfobutylether-cyclodextrins: structure, degree of substitution and functional performance. In Cyclodextrins: Synthesis, Chemical Applications and Role in Drug Delivery (pp. 293-320). Nova Science Publishers, Hauppauge, NY (2015).
Rao. Recent developments of collagen-based materials for medical applications and drug delivery systems. J Biomater Sci Polym Ed. 7(7):623-45 (1995).
Remington: The science and practice of pharmacy. 20th Edition. Gennaro, Eds. Lippincott Williams & Wilkins, 2003.
Rolan et al.: The absolute bioavailability of racemic ketamine from a novel sublingual formulation. Br J Clin Pharmacol. 77(6):1011-1016 (2013).
Schmuck et al.: A molecular flytrap for the selective binding of citrate and other tricarboxylates in water. J.Am. Chem. Soc. 127:3373-3379 (2005).
Stella et al.: Cyclodextrins. Toxicologic Pathology. 36:30-42 (2008).
U.S. Appl. No. 16/763,933 Final Office Action dated Feb. 3, 2023.
U.S. Appl. No. 16/763,933 Office Action dated Aug. 19, 2022.
U.S. Appl. No. 16/763,933 Restriction Requirement dated May 11, 2022.
U.S. Appl. No. 16/874,485 Notice of Allowance dated Dec. 30, 2020.
U.S. Appl. No. 16/874,485 Office Action dated Aug. 7, 2020.
U.S. Appl. No. 17/187,641 Office Action dated Mar. 29, 2023.
U.S. Appl. No. 17/546,880 Office Action dated Feb. 24, 2022.
Wang, W.: Tolerability of hypertonic injectables. International journal of pharmaceutics, 490(1-2), pp. 308-315 (2015).
Webster et al.: Safety and Efficacy of Prolonged Outpatient Ketamine Infusions for Neuropathic Pain: Am J Ther. 13(4):300-305 (2006).

(56) References Cited

OTHER PUBLICATIONS

Abdallah et al., Modulation of the antidepressant effects of ketamine by the mTORC1 inhibitor rapamycin. Neuropsychopharmacology. 45(6):990-997 (2020).
Al-Muhammed, J. et al. In-vivo Studies on Dexamethasone Sodium Phosphate Liposomes. Journal of Microencapsulation 13(3):293-305 (1996).
Andrade, Chittaranjan, Ketamine for Depression, 1: Clinical Summary of Issues Related to Efficacy, Adverse Effects, and Mechanism of Action. Journal of Clinical Psychiatry, vol. 78, No. 7, 852-857 (2017).
Chemical Abstracts Service. CAS Registry No. 78755-81-4. Flumazenil. STN Entry Date Mar. 25, 2005.
EP21895527.6 Supplementary European Search Report dated Sep. 9, 2024.
EP21895529.2 European Search Report dated Nov. 18, 2024.
Eyles, J E. et al. Oral Delivery and Fate of Poly(Lactic Acid) Microsphere-encapsulated Interferon in Rats. The Journal of pharmacy and pharmacology 49(7):669-674 (1997).
Japanese Patent Application No. 2021-568611 Office Action dated Apr. 22, 2024.
Javid, Mihan J., et al., Dissociative Conscious Sedation, an Alternative to General Anesthesia for Laparoscopic Peritoneal Dialysis Catheter Implantation: a Randomized Trial Comparing Intravenous and Subcutaneous Ketamine. International Society for Peritoneal Dialysis, vol. 31, 308-314 (2011).
Ostro, Mark J, and Pieter R Cullis. Use of Liposomes as Injectable-drug Delivery Systems. American Journal of Hospital Pharmacy 46(8):1576-1587 (1989).
PCT/US2021/059763 International Search Report and Written Opinion dated Mar. 2, 2022.
PCT/US2021/059763 Invitation to Pay Additional Fees dated Jan. 13, 2022.
PCT/US2023/022578 International Search Report and Written Opinion dated Aug. 31, 2023.
Rao, K Panduranga. Recent Developments of Collagen-based Materials for Medical Applications and Drug Delivery Systems. Journal of Biomaterials Science. Polymer Edition 7(7):623-645 (1995).
Russo et al., A novel compound analgesic cream (ketamine, pentoxifylline, clonidine, DMSO) for complex regional pain syndrome patients. Pain Pract. 16(1):E14-20 (2016).
Stella et al.: Sulfobutylether-Beta-cyclodextrin. International Journal of Pharmaceutics. 583:119396 p. 1-7 (2020).
U.S. Appl. No. 16/763,933 Office Action dated Sep. 15, 2023.
U.S. Appl. No. 17/187,641 Final Office Action dated Nov. 15, 2023.
Andersin, R. Solubility and acid-base behaviour of midazolam in media of different pH, studied by ultraviolet spectrophotometry with multicomponent software. Journal of pharmaceutical and biomedical analysis 9(6):451-455 (1991).
Bhalani, Dixit V. et al. Bioavailability Enhancement Techniques for Poorly Aqueous Soluble Drugs and Therapeutics. Biomedicines 10(9):2055, 1-33 (2022).
Chemical Abstracts Service. CAS Registry: 220620-09-7. Tigecycline: pp. 1-3. Retrieved Dec. 9, 2024. Retrieved from :https://www.tokue.com/content/product-documents/Product%20Data%20Sheet%20-%20T022.pdf#:% E2%80%94:text=Tigecycline%20is%20soluble%20in%20water,%3E3%20mg%2 FmL.
Committee for Medicinal Products for Human Use. Assessment Report Veklury International Non-Proprietary Name: Remdesivir; European Medicines Agency: The Netherlands, 2020; vol. Procedure No. EMEA/H/C/005622/0000.
Guthrie, J. Peter. Hydrolysis of esters of oxy acids: p K a values for strong acids; Bronsted relationship for attack of water at methyl; free energies of hydrolysis of esters of oxy acids; and a linear relationship between free energy of hydrolysis and p K a holding over a range of 20 p K units. Canadian Journal of Chemistry 56(17):2342-2354 (1978).
Hussein, Ahmad Q. et al. Alpha-Bromierung von 2-Adamantylisothiocyanat und Folgereaktionen. Chemische Berichte 112(4):1102-1109 (1979).
Krishnaiah, Yellela S.R. Pharmaceutical technologies for enhancing oral bioavailability of poorly soluble drugs. J Bioequiv Availab 2(2):28-36 (2010).
Loftsson, Thorsteinn, and Marcus E Brewster. Cyclodextrins as functional excipients: methods to enhance complexation efficiency. Journal of pharmaceutical sciences 101(9):3019-3032 (2012).
Loudon, Marc G. et al. Conversion of aliphatic amides into amines with [I,I-bis(trifluoroacetoxy)iodo]benzene. 1. Scope of the reaction. The Journal of Organic Chemistry 49(22):4272-4276 (1984).
Muller, Christa E. Prodrug approaches for enhancing the bioavailability of drugs with low solubility. Chemistry and Biodiversity 6(11):2071-2083 (2009).
Munegumi, Toratane. Where is the border line between strong acids and weak acids?. World J Chem Educ 1(1):12-16 (013).
PCT/US2023/022578 International Preliminary Report on Patentability dated Nov. 7, 2024.
PCT/US2024/056922 Invitation to Pay Additional Fees dated Jan. 8, 2025.
PCT/US2024/056926 International Search Report and Written Opinion dated Feb. 28, 2025.
PCT/US2024/056926 Invitation to Pay Additional Fees dated Jan. 8, 2025.
Poulson et al., Cyclodextrins: Structural, Chemical, and Physical Properties, and Applications, Polysaccharides, 3:1-31 (2022) Retrieved Mar. 26, 2025. Retrieved from https://www.mdpi.com/2673-4176/3/1/1.
Sapana et al., Preparation and Characterisation of β-Cyclodextrin Nebivolol Inclusion Complex, International Journal of Pharmaceutical Sciences and Research, 6(5):2205-2213 (2015) Retrieved Mar. 26, 2025. Retrieved from https://ijpsr.com/bft-article/preparation-and-characterisation-of-%ce%b2-cyclodextrin-nebivolol-inclusion-complex/.
Schonberger, B.P. et al. The Acid Hydrolysis of Cyclodextrins and Linear Oligosaccharies: A Comparative Study. Proceedings of the Fourth International Symposium on Cyclodextrins:61-63 (1988).
Szejtli, J. Interaction of Hydrochloric Acid with Cyclodextrin. Starch-Starke 29(12):410-413 (1977).
Thomas, Elizabeth, and Joseph Rubino. Solubility, melting point and salting-out relationships in a group of secondary amine hydrochloride salts. International journal of pharmaceutics 130(2):179-185 (1996).
Tutunji, Maha F. et al. An in vitro investigation on acid catalyzed reactions of proton pump inhibitors in the absence of an electrophile. International journal of pharmaceutics 323(1-2):110-116 (2006).
U.S. Appl. No. 17/187,641 Office Action dated Dec. 10, 2024.
Wallach, Jason. et al. Three Birds, One Excipient: Development of an Improved pH, Isotonic, and Buffered Ketamine Formulation for Subcutaneous Injection. Pharmaceutics 14(3):556, 1-20 (2022).

* cited by examiner

COMPLEXING AGENT SALT FORMULATIONS OF PHARMACEUTICAL COMPOUNDS

CROSS REFERENCE

This application is continuation of U.S. patent application Ser. No. 17/546,880, filed on Dec. 9, 2021, which is a continuation of International Application No. PCT/US21/59760, filed on Nov. 17, 2021, which claims the benefit of U.S. Provisional Application No. 63/115,445, filed on Nov. 18, 2020, U.S. Provisional Application No. 63/115,451, filed on Nov. 18, 2020, U.S. Provisional Application No. 63/115,453, filed on Nov. 18, 2020, and U.S. Provisional Application No. 63/115,458, filed on Nov. 18, 2020, each of which is incorporated herein by reference in its entirety.

BACKGROUND

Pharmaceutical compounds and their derivatives, such as ketamine, methoxetamine, deschloroketamine, dextromethorphan, tryptamines, phenethylamines, opioid compounds, cathinones, 3,4-methylenedioxyamphetamines, alkylamino-substituted benzofurans, amphetamines, aminoindanes, and stimulants, are useful for a variety of medicinal purposes. These compounds can be used to treat, for example, pain, depression, dysthymia, PTSD, compulsivity and impulse control disorders, personality disorders, cognitive disorders, sleep, inflammatory disorders, and numerous other psychiatric and physical disorders. However, the compounds may possess many physico-chemical properties that make suitable formulations for widespread use as pharmaceutical agents difficult, including the presence of basic amines, limited solubility, hydrophobicity, and inherently ionic functional groups.

BRIEF SUMMARY OF THE INVENTION

Provided herein are formulations and salts of pharmaceutical compounds with basic nitrogen atoms. In some embodiments, a pharmaceutical compound with basic nitrogen atoms includes a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, a pharmaceutical compound with basic nitrogen atoms does not include ketamine. In some embodiments, a pharmaceutical compound with basic nitrogen atoms includes a derivative or analog of ketamine. In some embodiments, a pharmaceutical compound with basic nitrogen atoms includes methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, a pharmaceutical compound with basic nitrogen atoms has psychedelic properties and includes without limitation tryptamines, phenethylamines, and lysergamide classes of molecules. In some embodiments, a pharmaceutical compound with basic nitrogen atoms includes opioids which include an opioid receptor antagonist. In some embodiments, a pharmaceutical compound with basic nitrogen atoms has empathogenic or entactogenic properties and includes without limitation cathinones, 3,4-methylenedioxyampehtamines, aminoalkyl-substituted benzofurans, amphetamines, aminoindanes, stimulants, and other compounds. In some embodiments, the formulations and salts provided herein utilize complexing agents (e.g. cyclodextrins) with a plurality of acidic functional groups in their free acid form to create salts with pharmaceutical compounds having basic nitrogen atoms (e.g. amines). In some instances, the resulting salts have multiple molecules of protonated pharmaceutical compounds ionically associated with a single complexing agent. Such an approach can be used with any pharmaceutical compound or potential pharmaceutical compound (e.g. an existing drug comprising a basic nitrogen atom, a new chemical entity comprising a basic nitrogen atom, or any research chemical comprising a basic nitrogen atom which is of interest for medicinal purposes) to form a salt with such a complexing agent which can provide numerous advantages in a variety of formulations, including subcutaneous, sublingual, and intranasal formulations. In some instances, the compounds have dissociative properties on a subject when administered, including compounds which act on the NMDA receptor. The formulations and salts provided herein utilize complexing agents bearing deprotonated acidic functional groups as counterions to the protonated form of the basic nitrogen containing compounds, in particular cyclodextrin complexing agents such as sulfobutyl ether beta-cyclodextrin (SBEBCD). While SBEBCD and other similar such complexing agents having anionic functionalities can be used in numerous contexts to enhance solubility and stability of many formulations, traditional uses of these agents lack utility in certain contexts owing to the high levels of excess ions. In some instances, this stems from the fact that such complexing agents, with their pluralities of acidic functional groups, are commercially available primarily as their sodium or other alkali metal salts. Thus, when used in a traditional manner, a high amount of excess sodium or other unwanted or undesired component ion is added to the formulation. The instant disclosure solves this problem by pairing an pharmaceutical compound with a basic nitrogen atom in its freebase form with such a complexing agent in its free acid form, thus resulting in a salt directly between the complexing agent and the compound and eliminating the presence of substantial excess ions.

Such formulations and salts as provided herein have many advantages over others. In some instances, the solubility of either the pharmaceutical compound by itself or of the pharmaceutical compound/complexing agent salt complex is enhanced compared to a formulation utilizing a salt form of the complexing agent. Additionally, for certain compounds where the pKa of the basic nitrogen atom of the compound is at or near a physiologically tolerable pH, a formulation using the salts provided herein can achieve a desirable pH without the need for any additional buffer or excipient. Additionally, formulations using the salts provided herein may have reduced osmolality compared not only to formulations which use salts of the complexing agents and compounds, but also to formulations that utilize salts of the compounds themselves, owing to the polydentate nature of the acidic functional groups on the complexing agents provided herein. All of these benefits can also have the effect of making the compound more absorbable and bioavailable, particularly for sublingual or intranasal delivery administrations, because the increase in solubility at the pH of saliva or the nasal mucosa increases bioavailability and transmucosal absorption. Additionally, in some instances, the salts and pharmaceutical compositions can be stored as powders for long term storage, thus increasing stability of such salts and compositions. In some instances, the salts and pharmaceutical compositions are readily redissolved at the point of use, whether as an intermediate in a manufacturing process for a pharmaceutical composition or as a pharmaceutical composition to be used directly.

In one aspect, provided herein is a pharmaceutical composition, comprising: (i) a pharmaceutical compound, or an enantiomer, a mixture of enantiomers, or an isotopic variant thereof, wherein the pharmaceutical compound comprises a protonated nitrogen atom; and (ii) a complexing agent, wherein the complexing agent is an acid-substituted cyclodextrin comprising a plurality of acidic functional groups, wherein the plurality of acidic functional groups comprise an acidic group which acts as a counterion for the protonated nitrogen atom of the pharmaceutical compound. In some embodiments, the pharmaceutical compound includes a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound does not include ketamine. In some embodiments, the pharmaceutical compound includes a derivative or analog of ketamine. In some embodiments, the pharmaceutical compound includes methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound includes a tryptamine, a phenethylamine, or a lysergamide compound. In some embodiments, the pharmaceutical compound includes an opioid. In some embodiments, the pharmaceutical compound includes cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin.

In another aspect, provided herein is a pharmaceutical composition, comprising: (i) a pharmaceutical compound comprising a basic nitrogen atom, or an enantiomer, a mixture of enantiomers, or an isotopic variant thereof, or a pharmaceutically acceptable salt, solvate or hydrate thereof, wherein the pharmaceutical compound is a dissociative medication compound, a dissociative hallucinogen compound, a dissociative anesthetic compound, an arylcyclohexylamine, a 1,2-diarylethylamine, a β-keto-arylcyclohexylamine, or a compound that modulates the NMDA receptor; and (ii) a complexing agent comprising a plurality of acidic functional groups.

In another aspect, provided herein is a pharmaceutical composition, comprising: (i) a pharmaceutical compound comprising a basic nitrogen atom, or an enantiomer, a mixture of enantiomers, or an isotopic variant thereof; or a pharmaceutically acceptable salt, solvate or hydrate thereof, wherein the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine; and (ii) a complexing agent comprising a plurality of acidic functional groups.

In another aspect, provided herein is a pharmaceutical composition, comprising: (i) a pharmaceutical compound comprising a basic nitrogen atom, or an enantiomer, a mixture of enantiomers, or an isotopic variant thereof; or a pharmaceutically acceptable salt, solvate or hydrate thereof, wherein the pharmaceutical compound is a tryptamine, a phenethylamine, or a lysergamide compound; and (ii) a complexing agent comprising a plurality of acidic functional groups.

In another aspect, provided herein is a pharmaceutical composition, comprising: (i) an opioid comprising a basic nitrogen atom, or an enantiomer, a mixture of enantiomers, or an isotopic variant thereof; or a pharmaceutically acceptable salt, solvate or hydrate thereof; and (ii) a complexing agent comprising a plurality of acidic functional groups.

In another aspect, provided herein is a pharmaceutical composition, comprising: (i) a pharmaceutical compound comprising a basic nitrogen atom, or an enantiomer, a mixture of enantiomers, or an isotopic variant thereof; or a pharmaceutically acceptable salt, solvate or hydrate thereof, wherein the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin; and (ii) a complexing agent comprising a plurality of acidic functional groups.

In some embodiments, the pharmaceutical compound is a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound is not ketamine. In some embodiments, the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is a tryptamine, a phenethylamine, or a lysergamide compound. In some embodiments, the pharmaceutical compound is an opioid. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin. In some embodiments, the complexing agent is sulfobutylether-β-cyclodextrin. In some embodiments, the pharmaceutical composition has lower osmolality than a composition comprising a salt of the pharmaceutical compound and a salt of the complexing agent. In some embodiments, the pharmaceutical composition has substantially the same osmolality as a solution of the same concentration of a sodium salt of the complexing agent.

In some embodiments, the pharmaceutical composition has a lower osmolality than a solution of the same concentration of a sodium salt of the complexing agent. In some embodiments, the pharmaceutical composition is substantially free of excess ions. In some embodiments, the pharmaceutical is formulated for subcutaneous, intramuscular, sublingual, or intranasal administration. In some embodiments, the complexing agent comprises a substituted cyclodextrin.

In some embodiments, the complexing agent comprises a cyclodextrin substituted with at least one acidic functional group. In some embodiments, the cyclodextrin is substituted with 3 to 8 acidic functional groups. In some embodiments, the cyclodextrin is SBEBCD. In some embodiments, the composition has a ratio of complexing agent to the pharmaceutical compound comprising a protonated nitrogen atom that is from about 1:4 to about 1:10. In some embodiments, the pharmaceutical composition has an osmolality of no more than about 850 mOsm/kg. In some embodiments, the pharmaceutical composition has a pH of about 4 to about 7. In some embodiments, the complexing agent is present in an amount of about 10 mg/mL to about 600 mg/mL. In some embodiments, the pharmaceutical composition further comprises about 0.1 to about 20 molar equivalent of unionized pharmaceutical compound compared to the amount of complexing agent.

In one aspect, provided herein is a pharmaceutically acceptable salt of an compound pharmaceutical comprising: (i) a pharmaceutical compound, or an enantiomer, a mixture of enantiomers, or an isotopic variant thereof; or a pharmaceutically acceptable salt, solvate or hydrate thereof, wherein the pharmaceutical compound comprises a protonated nitrogen atom; and (ii) a conjugate base of a complexing agent comprising a plurality of acidic functional groups, wherein the conjugate base of the complexing agent acts as the counterion of the pharmaceutical compound. In some embodiments, the pharmaceutical compound is a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound is not ketamine. In some embodiments, the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is a tryptamine, a phenethylamine, or a lysergamide compound. In some embodiments, the pharmaceutical compound is an opioid. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin. In some embodiments, the salt is in solid form. In some embodiments, the solid form is a crystalline form. In some embodiments, wherein the solid for is an amorphous form. In some embodiments, the solid form is a lyophilized powder. In some embodiments, the salt is dissolved or suspended in an aqueous medium. In some embodiments, the salt is dissolved or suspended in an organic solvent. In some embodiments, the salt is substantially free of excess ions. In some embodiments, the complexing agent comprises a substituted cyclodextrin. In some embodiments, the complexing agent comprises a cyclodextrin substituted with at least one acidic functional group. In some embodiments, the cyclodextrin is substituted with 3 to 8 acidic functional groups. In some embodiments, the cyclodextrin is SBEBCD. In some embodiments, the composition has a ratio of complexing agent to the pharmaceutical compound comprising a protonated nitrogen atom that is from about 1:4 to about 1:10.

In another aspect, provided herein is a pharmaceutically acceptable salt of a pharmaceutical compound having the formula $$[A]_a[B]$$

wherein: A is a pharmaceutical compound comprising at least one basic nitrogen atom; B is a complexing agent comprising a plurality of acidic functional groups; and a is a number from 1-7, wherein the number is selected such that the total number of basic nitrogen atoms of A is equal to the number of acidic functional groups of B. In some embodiments, the at least one basic nitrogen atom is an amine. In some embodiments, the at least one basic nitrogen atom is comprised in a heterocycle. In some embodiments, the at least one basic nitrogen atom has a pKa value from about 4 to about 10. In some embodiments, the pharmaceutical compound comprises only a single basic nitrogen atom. In some embodiments, a is equal to the number of acidic functional groups. In some embodiments, the pharmaceutical compound comprises two or more basic nitrogen atoms. In some embodiments, the complexing agent is a cyclodextrin. In some embodiments, the complexing agent is a compound of Formula (I):

(I)

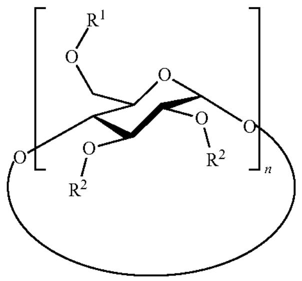

wherein: each R1 is independently H or optionally substituted alkyl; wherein at least one R1 is substituted with an acidic functional group; each R2 is independently H or optionally substituted alkyl; and n is 6, 7, or 8; or a stereoisomer, a mixture of stereoisomers, or an isotopic variant thereof; or a pharmaceutically acceptable salt, solvate or hydrate thereof.

In some embodiments, the complexing agent is SBEBCD. In some embodiments, the pharmaceutical compound is a dissociative medication, a dissociative hallucinogen compound, a dissociative anesthetic compound, an arylcyclohexylamine, a 1,2-diarylethylamine, a β-keto-arylcyclohexylamine, or a compound that modulates the NMDA receptor. In some embodiments, the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is ketamine. In some embodiments, the pharmaceutical compound is not ketamine. In some embodiments, the pharmaceutical compound is a tryptamine, a phenethylamine, or a lysergamide compound. In some embodiments, the pharmaceutical compound is a N,N-Dimethyltryptamine, a N,N-diethyltryptamine, or mescaline. In some embodiments, the pharmaceutical compound is an opioid. In some embodiments, the opioid is racemorphan, levorphanol, racemethorphan, buprenorphine, morphine, loperamide, morphine, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, 3-methylthiofentanyl, naloxone, or naltrexone. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin. In some embodiments, the pharmaceutical compound is a cathinone, an aminoalkyl-substituted benzofuran, or an aminoindane.

In one aspect, provided herein is a pharmaceutical composition, comprising: (i) a pharmaceutical compound, or an enantiomer, a mixture of enantiomers, or an isotopic variant thereof, wherein the pharmaceutical compound comprises a protonated nitrogen atom; (ii) a complexing agent, wherein the complexing agent comprises a plurality of acidic functional groups, wherein the plurality of acidic functional groups comprise a conjugate base of an acid which acts as a counterion for the protonated nitrogen atom of the pharmaceutical compound; and (iii) an additional molar equivalent of the pharmaceutical compound, wherein the additional molar equivalent of the pharmaceutical compound is unionized. In some embodiments, the pharmaceutical composition is formulated for sublingual or intranasal administration. In some embodiments, the complexing agent is a cyclodextrin. In some embodiments, the complexing agent is sulfobutylether-β-cyclodextrin. In some embodiments, the molar ratio of complexing agent to the pharmaceutical compound comprising a protonated nitrogen atom is from about 1:4 to about 1:10. In some embodiments, the additional molar equivalent of the pharmaceutical compound is from about 0.1 to about 20 moles of the pharmaceutical compound to the moles of complexing agent. In some embodiments, the pharmaceutical composition has a pH of about 4 to about 10. In some embodiments, the pharmaceutical composition has an osmolality from about 250 mOsm/kg to about 500 mOsm/kg. In some embodiments, the pharmaceutical compound is the pharmaceutical compound is a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound is ketamine. In some embodiments, the pharmaceutical compound is not ketamine. In some embodiments, the pharmaceutical compound is a tryptamine, a phenethylamine, or a lysergamide compound. In some embodiments, the pharmaceutical compound is an opioid. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin.

In one aspect is a method of preparing a pharmaceutical composition, comprising: combining in a suitable liquid medium: a) a free base form of an pharmaceutical compound, or an enantiomer, a mixture of enantiomers, or an isotopic variant thereof, wherein the pharmaceutical compound comprises at least one basic nitrogen atom, and b) a free acid form of a complexing agent comprising at least one acidic functional group. In some embodiments, the pharmaceutical compound is a dissociative medication, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is not ketamine. In some embodiments, the pharmaceutical compound is a tryptamine, a phenethylamine, or a lysergamide compound. In some embodiments, the pharmaceutical compound is a N,N-Dimethyltryptamine, a N,N-diethyltryptamine, or mescaline. In some embodiments, the pharmaceutical compound is an opioid. In some embodiments, the opioid is racemorphan, levorphanol, racemethorphan, buprenorphine, morphine, loperamide, morphine, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, 3-methylthiofentanyl, naloxone, or naltrexone. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin. In some embodiments, the pharmaceutical compound is a cathinone, an aminoalkyl-substituted benzofuran, or an aminoindane.

In one aspect is a method of preparing a pharmaceutical composition, the method comprising combining a pharmaceutically acceptable salt provided herein with an additional molar equivalent of the pharmaceutical compound disclosed herein, wherein the additional molar equivalent of the pharmaceutical compound disclosed herein is unionized.

In another aspect is a method of preparing a pharmaceutical composition, comprising: combining in a suitable liquid medium: a) a free base form of an pharmaceutical compound, or an enantiomer, a mixture of enantiomers, or an isotopic variant thereof, wherein the pharmaceutical compound comprises at least one basic nitrogen atom; and b) a free acid form of a complexing agent comprising at least one acidic functional group. In some embodiments, the pharmaceutical compound is a dissociative medication, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is not ketamine. In some embodiments, the pharmaceutical compound is a tryptamine, a phenethylamine, or a lysergamide compound. In some embodiments, the pharmaceutical compound is a N,N-Dimethyltryptamine, a N,N-diethyltryptamine, or mescaline. In some embodiments, the pharmaceutical compound is an opioid. In some embodiments, the opioid is racemorphan, levorphanol, racemethorphan, buprenorphine, morphine, loperamide, morphine, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, 3-methylthiofentanyl, naloxone, or naltrexone. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin. In some embodiments, the pharmaceutical compound is a cathinone, an aminoalkyl-substituted benzofuran, or an aminoindane. In some embodiments, the molar ratio of the pharmaceutical compound comprising at least one basic nitrogen atom to number of moles of the acidic functional groups of the free acid form of the complexing agent is from about 1:1 to about 10:1. In some embodiments, the method further comprises the step of adding an additional molar equivalent of the free base form of the pharmaceutical compound. In some embodiments, the step of adding the additional molar equivalent of the free base form of the pharmaceutical compound occurs after removing the liquid medium from the pharmaceutical composition.

In some embodiments, the pharmaceutical compound is a tryptamine. In some embodiments, the tryptamine is optionally substituted on the tryptamine ring. In some embodiments, the pharmaceutical compound is an N,N-dialkyltryptamine. In some embodiments, the pharmaceutical compound is a tryptamine selected from an N,N-Dimethyltryptamine, a N,N-diethyltryptamine, a N,N-dipropyltryptamine, a N-Methyl-N-propyltryptamine, a N-methyl-N-isopropyltryptamine, a N,N-diallyltryptamine, a N-methyl-N-allyltryptamine, N-methyl-N-ethyltryptamine, a N,N-Diisopropyltryptamine, wherein the tryptamine is optionally substituted. In some embodiments, the tryptamine is optionally substituted at the 4- or 5-position of the tryptamine ring with a substituent selected from hydroxy, acetoxy, or methoxy. In some embodiments, the tryptamine is 4-hydroxy-N-methyl-N-ethyltryptamine, 5-methoxy-N,N-diisopropyltryptamine, or O-acetylpsilocin (4-acetoxy-N,N-dimethyltryptamine). In some embodiments, the pharmaceutical compound is a lysergamide. In some embodiments, the lysergamide is methylisopropyllysergamide, ethylisopropyllysergamide, 6-allyl-6-nor-LSD, 6-ethyl-6-nor-lysergic acid diethylamide, 1-acetyl-LSD, 1-propionyl-6-ethyl-6-nor-lysergic acid diethylamide, 1-propionyl-lysergic acid diethylamide, 1-Cyclopropionyl-d-lysergic acid diethylamide, N1-butyryl-lysergic acid diethylamide, or 6-propyl-6-nor-Lysergic acid diethylamide. In some embodiments, the pharmaceutical compound is a phenethylamine. In some embodiments, the phenethylamine is mescaline, 2,5-dimethoxy-4-bromophenethylamine (2C-B), 2-(4-Iodo-2,5-dimethoxyphenyl)ethan-1-amine (2C-I), 2-(4-Chloro-2,5-dimethoxyphenyl)ethan-1-amine (2C-C), 2,5-Dimethoxy-4-iodoamphetamine, 2-[2,5-Dimethoxy-4-(propylsulfanyl) phenyl]ethan-1-amine, or 2-(4-iodo-2,5-dimethoxyphenyl)-N-[(2-methoxyphenyl)methyl]ethanamine. In some embodiments, the phenethylamine is mescaline.

In another aspect is a pharmaceutically acceptable salt of an compound pharmaceutical. In some embodiments, the compound pharmaceutical comprises: (i) a pharmaceutical compound, or an enantiomer, a mixture of enantiomers, or an isotopic variant thereof; or a pharmaceutically acceptable salt, solvate or hydrate thereof, wherein the pharmaceutical compound comprises 4 or more protonated nitrogen atoms; and (ii) a conjugate base of a complexing agent comprising a plurality of acidic functional groups, wherein the conjugate base of the complexing agent acts as the counterion of the pharmaceutical compound.

In embodiments, the pharmaceutical compound is not ketamine or a derivative thereof. In embodiments, the complexing agent acts as the counterion to between 5 to 10 pharmaceutical compounds. In embodiments, the complexing agent acts as the counterion to between 6 to 8 pharmaceutical compounds. In embodiments, the pKa of the protonated nitrogen atom is between about 4 and 12. In embodiments, the pKa of the protonated nitrogen atom is between about 8 and 10. In embodiments, the pKa of the protonated nitrogen atom is between about 7 and 9. In embodiments, the pKa of the protonated nitrogen atom is between about 9 and 11.

In embodiments, the pharmaceutical compound is selected from arylcyclo-hexylamine, 1,2-diarylethylamine, β-keto-arylcyclohexylamine, methoxetamine, deschloroketamine, N-ethyl deschloroketamine (eticyclidone), 3-methoxyphencyclidine, methoxieticyclidine, ephenidine, lanicemine, dextromethorphan, dextrorphan, methoxyketamine, a N,N-dimethyltryptamine, a N,N-diethyltryptamine, a N,N-dipropyltryptamine, a N-Methyl-N-propyltryptamine, a N-methyl-N-isopropyltryptamine, a N,N-diallyltryptamine, a N-methyl-N-allyltryptamine, N-methyl-N-ethyltryptamine, a N,N-Diisopropyltryptamine, 4-hydroxy-N-methyl-N-ethyltryptamine, 5-methoxy-N,N-diisopropyltryptamine, O-acetylpsilocin, methylisopropyllysergamide, ethylisopropyllysergamide, 6-allyl-6-nor-LSD, 6-ethyl-6-nor-lysergic acid diethylamide, 1-acetyl-LSD, 1-propionyl-6-ethyl-6-nor-lysergic acid diethylamide, 1-propionyl-lysergic acid diethylamide, 1-Cyclopropionyl-d-lysergic acid diethylamide, N1-butyryl-lysergic acid diethylamide, 6-propyl-6-nor-Lysergic acid diethylamide, mescaline, 2,5-dimethoxy-4-bromophenethylamine (2C-B), 2-(4-Iodo-2,5-dimethoxyphenyl)ethan-1-amine (2C-I), 2-(4-Chloro-2,5-dimethoxyphenyl)ethan-1-amine (2C-C), 2,5-Dimethoxy-4-iodoamphetamine, 2-[2,5-Dimethoxy-4-(propylsulfanyl)phenyl]ethan-1-amine, 2-(4-iodo-2,5-dimethoxyphenyl)-N-[(2-methoxyphenyl)methyl] ethanamine, racemorphan, levorphanol, racemethorphan, buprenorphine, morphine, loperamide, morphine, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, 3-methylthiofentanyl, naloxone, naltrexone, a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, and 6-chloro-2-aminotetralin. In embodiments, the molar ratio of complexing agent to the pharmaceutical compound is from about 1:4 to about 1:10.

In embodiments, the complexing agent is a compound of Formula (I):

(I)

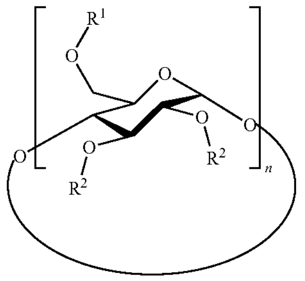

wherein:

each $R^1$ is independently H or optionally substituted alkyl; wherein at least one $R^1$ is substituted with an acidic functional group;

each $R^2$ is independently H or optionally substituted alkyl; and n is 6, 7, or 8;

or a stereoisomer, a mixture of stereoisomers, or an isotopic variant thereof; or a pharmaceutically acceptable salt, solvate or hydrate thereof. In embodiments, $R^1$ is $C_{1-8}$ alkyl substituted with one or more substituents independently selected from halogen, —C(O)OH, —N(H)C(O)OH, —$S(O)_2OH$, —$OP(O)(OH)_2$, and —OC(O)OH. In embodiments, the acidic functional group of $R^1$ is $C_{1-8}$ alkyl substituted with one or more inorganic acid. In embodiments, the acidic functional group of $R^1$ is $C_{1-8}$ alkyl substituted with one or more organic acid. In embodiments, the organic acidic is selected from malonic acid, citric acid, tartartic acid, glutamic acid, phthalic acid, benzilic acid, cinnamic acid, fumaric acid, glutaric acid, gluconic acid, hexanoic acid, lactic acid, malic acid, folic acid, propiolic acid, propionic acid, tannic acid, trifluoroacetic acid, uric acid, ascorbic acid, gallic acid, acetylsalicylic acid, and acetic acid. In embodiments, $R^2$ is H. In embodiments, $R^2$ is unsubstituted $C_{1-6}$ alkyl. In embodiments, $R^2$ is $C_{1-6}$ alkyl substituted selected from halogen, —CN, —OH, —SH, —$NO_2$, —$NH_2$, =O, =S, —O—$C_{1-6}$ alkyl, —S—$C_{1-6}$ alkyl, —$N(C_{1-6}\text{ alkyl})_2$, and —$NH(C_{1-6}\text{ alkyl})$. In embodiments, then of a compound of Formula (I) is 6. In embodiments, the n of a compound of Formula (I) is 7. In embodiments, the n of a compound of Formula (I) is 8. In embodiments, the complexing agent is sulfobutylether-β-cyclodextrin In another aspect is a method of preparing a pharmaceutical composition. The method comprises combining in a suitable liquid medium: a) a free base form of a pharmaceutical compound comprising a basic nitrogen atom, or an enantiomer, a mixture of enantiomers, or an isotopic variant thereof, wherein the pharmaceutical compound comprises at least one basic nitrogen atom, wherein the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin, and b) a free acid form of a complexing agent comprising at least one acidic functional group.

In another aspect is a method of preparing a pharmaceutical composition. The method comprises combining a pharmaceutically acceptable salt disclosed herein with an additional molar equivalent of a pharmaceutical compound disclosed herein, wherein the additional molar equivalent of the pharmaceutical compound is unionized.

In another aspect is a method of preparing a pharmaceutical composition. The method comprises combining in a suitable liquid medium: a) a free base form of an pharmaceutical compound, or an enantiomer, a mixture of enantiomers, or an isotopic variant thereof, wherein the pharmaceutical compound comprises at least one basic nitrogen atom, wherein the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin; and b) a free acid form of a complexing agent comprising at least one acidic functional group. In embodiments, the molar ratio of the pharmaceutical compound comprising at least one basic nitrogen atom to number of moles of the acidic functional groups of the free acid form of the complexing agent is from about 1:1 to about 10:1. In embodiments, the method further comprises the step of adding an additional molar equivalent of the free base form of the pharmaceutical compound. In embodiments, the step of adding the additional molar equivalent of the free base form of the pharmaceutical compound occurs after removing the liquid medium from the pharmaceutical composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
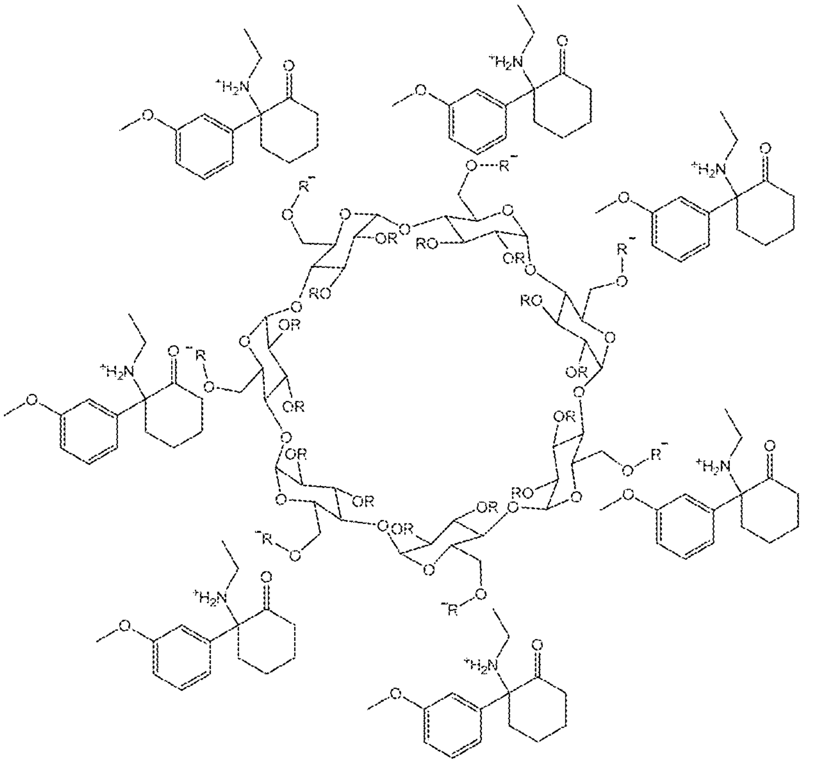
FIG. 1 shows an exemplary structure of an compound-complexing agent salt as provided herein. The compound-complexing agent salt shown is a methoxetamine-SBEBCD salt.

Provided herein are, for example, compositions comprising pharmaceutical compound salts with complexing agents as counterions. Such salts are useful in a variety of pharmaceutical compositions, including reduced irritant effect to tissues and/or dermal tissues, subcutaneous, intramuscular, intranasal, and sublingual formulations. In some aspects, use of the salts provided herein in subcutaneous, intranasal, or sublingual formulation is associated with reduced irritant effect to tissues at the administration site, as well as increased solubility and bioavailability. In certain aspects, the compositions comprising pharmaceutical compounds with basic nitrogen atoms are formulated for subcutaneous, sublingual, or intranasal administration. Also provided herein are, for example, methods of treating, preventing pain, or managing, depression or opioid overdose, psychiatric disorders, cognitive disorders, neurological disorders, and other various disorders. In some embodiments, microdoses of the pharmaceutical compounds with psychedelic properties provided herein are useful in the treatment of a variety of pain disorders and inflammatory disorders.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "about" as used herein, when referring to a numerical value or range, allows for a degree of variability in the value or range, for example, within 10%, or within 5% of a stated value or of a stated limit of a range.

The term "pharmaceutical compound" and similar such terms used herein refer to any compound which has the potential to be administered to a subject and may imbue any type of therapeutic benefit to a subject (such as treatment or prevention of a disease, mitigation of symptoms of a disease or condition, or any purpose for which a pharmaceutical or drug can be used). Generally, these compounds will be organic small molecules, though other compounds such as peptides are also considered to be pharmaceutical compounds as used herein. In preferred embodiments, the pharmaceutical compounds will comprise basic nitrogen atoms (e.g. amine groups) which can be protonated upon interaction with an acidic functional group, such as a carboxylic acid or a sulfonic acid. When referring to pharmaceutical compositions, these compounds may be referred to generally as "active pharmaceutical ingredient" or "API." In some cases, the pharmaceutical compounds herein may simply be referred to as "compounds."

The terms "opioid pharmaceutical compound," "opioid pharmaceutical," or "opioid," and similar such terms are all used interchangeably, and the same meaning is meant by each term unless otherwise specified. The term may refer to any naturally occurring opioid or any synthetic homolog or analog. Additionally, any synthetic compound which has similar bioactivity on the opioid receptors of a subject is also intended to be encompassed, as well as any compound which has an opioid antagonist activity (e.g. naltrexone or naloxone). When referring to pharmaceutical compositions, these compounds may be referred to generally as "active pharmaceutical ingredient" or "API."

As used herein, the terms "comprising," "comprises," or the like are used in their typical sense of leaving any claim or embodiment where such language is used able to accommodate additional elements, components, or features. However, it is also contemplated that in each formulation, salt, method, or other disclosure provided herein that uses the term "comprising," the formulation, salt, method or other disclosure may also be closed to other elements, components, or features as if the term "consisting of" were used in its place. Additionally, it is also contemplated the term "comprising" or similar can also be replaced in the same manner as if the term "consisting essentially of."

A "molar equivalent" as used herein refers to a comparison on the number of moles of a substance compared to the number of moles of another substance and reflects that comparison should be a moles or molarity basis (e.g. the ratio of the moles of one compound to the moles of another). The molar equivalent need not be an integer value. For example, embodiments stating that a pharmaceutical composition comprises a "molar equivalent" of a substance indicates that that the amount of the substance which is present will be measured in some kind of molarity descriptor, such as an additional equivalent of the substance from 0.001 to 100 molar equivalents, or any other range specified herein.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The terms "disease," "disorder," or "condition" refer to a state of being or health status of a patient or subject capable of being treated with the compounds or methods provided herein. The disease may be a mental or psychiatric disorder. The disease may be a mood disorder. The disease may be an inflammatory disease. The disease may be a brain tumor. The disease may be a neurological condition or disorder. In some further instances, "mental or psychiatric disorder" refers to human mental or psychiatric disorders including major depressive disorder, treatment resistant major depressive disorder, Suicidality, Suicidal Ideation, dysthymia, bipolar I disorder, bipolar II disorder, post-traumatic stress disorder (PTSD), complex trauma, anorexia nervosa, bulimia nervosa, eating disorder NOS, obsessive compulsive disorder, a substance-related disorder (e.g., cannabis dependence or withdrawal, barbiturate dependence or withdrawal, benzodiazepine dependence or withdrawal, amphetamine dependence or withdrawal, opioid dependence or withdrawal, alcohol dependence or withdrawal, cocaine dependence or withdrawal), a pain disorder and an inflammatory disorder. In some further instances, "neurological disease or disorder" refers to human neurological diseases or disorders including chronic fatigue syndrome, chronic fatigue and immunodeficiency syndrome, neuropathy, fibromyalgia, fibromyalgia syndrome, myalgic encephalomyelitis, migraine, traumatic brain injury (TBI), stroke, dementia, amyotrophic lateral sclerosis, spinal cord injury, shingles, herpes zoster, radiculopathy, polyneuropathy, dyskinesia, dystonia, tinnitus, postherpetic neuralgia, complex regional pain syndrome, central pain syndrome, chronic pain, acute pain, phantom limb syndrome with pain, phantom limb syndrome without pain, myelitis, dysthymia, complex trauma, anorexia nervosa, bulimia nervosa, eating disorder NOS, obsessive compulsive disorder, intermittent explosive disorder, a sleep disorder, a pain disorder or an inflammatory disorder. In some further instances, a brain tumor may be acoustic neuroma, astrocytoma, brain metastases, choroid plexus carcinoma, craniopharyngioma, embryonal tumors, ependymoma, glioblastoma, glioma, medulloblastoma, meningioma, oligodendroglioma, pediatric brain tumors, pineoblastoma, or pituitary tumors. In some instances, the disease, disorder, or condition is one that is associated with substantial or significant pain. In some aspects, the subject is administered the salts of formulations provided herein in order to manage pain. The pain can be associated with an suitable conditions for which an opioid pain management regiment is acceptable. In some aspects, the subject is administered the salts of formulations provided herein in order to treat a brain tumor. In some aspects, the subject is administered the following salts of formulations in order to treat a brain tumor: a pharmaceutical compound with basic nitrogen atoms including a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor, ketamine, a derivative or analog of ketamine, methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine.

The expression "effective amount," when used to describe therapy to an individual suffering from a disorder, refers to the amount of a compound described herein that is effective to inhibit or otherwise act on relevant receptors in the individual's tissues, wherein such inhibition or other action occurs to an extent sufficient to produce a beneficial therapeutic effect. The effective amount will vary based on the pharmaceutical compound, including but not limited to opioid, or other API used in the formulation and the indication intended to be treated by said compound, including but not limited to opioid, or other API.

"Substantially" as the term is used herein means completely or almost completely. For example, a composition that is "substantially free" of a component either has none of the component or contains such a trace amount that any relevant functional property of the composition is unaffected by the presence of the trace amount. For example, a compound that is "substantially pure" has only negligible traces of impurities present.

All chiral, diastereomeric, and/or racemic forms of a structure are intended, unless a particular stereochemistry or isomeric form is specifically indicated. Compounds described herein can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the present disclosure.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, e.g., protium ($^{1}H$), deuterium ($^{2}H$), or tritium ($^{3}H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^{3}H$ can be prepared using neutrons generated in a nuclear reactor. Following nuclear transformation, $^{14}C$ and $^{3}H$ are incorporated into precursor molecules, followed by further elaboration as needed.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, e.g., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, e.g., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Further examples of prodrugs include boronate esters which can be hydrolyzed under physiological conditions to afford the corresponding boronic acid. Conventional procedures for the selection and preparation of suitable prodrug derivatives are described, for example, in "Design of Prodrugs", ed. H. Bundgaard, Elsevier, 1985.

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

Isomerism in Compounds Described Herein

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, e.g., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking is A>B>C>D. The lowest ranking atom, D is oriented away from the viewer.

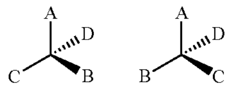

(R) Configuration (S) Configuration

The present disclosure is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound described herein, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; e.g., the R and S configurations for each asymmetric center. Therefore, single stereochemical isomers as well as enantiomeric and diastereomeric mixtures of the present compounds are within the scope of the disclosure.

"Alkyl" refers to a straight or branched hydrocarbon chain radical consisting solely of carbon and hydrogen atoms, which may optionally be unsaturated with one or more double or triple bonds, and preferably having from one to fifteen carbon atoms (i.e., $C_1$-$C_{15}$ alkyl). In certain embodiments, an alkyl comprises one to six carbon atoms (i.e., $C_1$-$C_6$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless otherwise specified, the term "alkyl" and its equivalents encompass linear, branched, and/or cyclic alkyl groups. In some instances, an "alkyl" comprises both cyclic and acyclic (linear and/or branched) alkyl components.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents may be one or more and the same or different for appropriate organic compounds.

Substituents may include any substituent, for example, a halogen, a hydroxyl, a carbonyl (such as an oxo (=O), a carboxyl, an alkoxycarbonyl, a formyl, or an acyl), a thiocarbonyl (such as a thioxo (=S), a thioester, a thioacetate, or a thioformate), an alkoxyl, a phosphoryl, a phosphate, a phosphonate, a phosphinate, an amino, an amido, an amidine, an imine, an oximo, a hydrazino, a cyano, a nitro, an azido, a sulfhydryl, an alkyl, an alkylthio, a sulfate, a sulfonate, a sulfamoyl, a sulfonamido, a sulfonyl, an aralkyl, a carbocycle, a heterocycle, a cycloalkyl, a heterocycloalkyl, an aromatic and heteroaromatic moiety.

As used herein, an "acidic functional group" or similar term (e.g. "acidic functionality") refers to a chemical moiety which contains at least one dissociable proton (or isotopic variant thereof), or the conjugate base (e.g. the deprotonated anion) of the acidic functional group. In certain embodiments, the dissociable proton dissociates from the chemical moiety at a pH common in aqueous systems (e.g. pHs from about 1 to about 14). In certain preferred embodiments, the dissociable proton dissociates from the chemical moiety in an aqueous system at a pH of less than 7 (e.g. having a pKa value of less than 7, such as a pKa of less than 6, less than 5, less than 4, less than 3, less than 2, or less than 1). As is understood by those in the art, whether an acidic functional group contains the dissociable proton will depend on the conditions of the system in which the chemical moiety is present (e.g., the pH of an aqueous system containing molecule with the acidic functional group or the presence of any base molecule). As such, the term "acidic functional group" (or reference to a specific acidic functional group such as a carboxylic acid or a sulfonic acid) as used herein is intended to cover the protonated version of the moiety, the deprotonated version of the moiety, and any salt of the moiety, unless otherwise specified.

Unless otherwise stated, structures depicted herein are also meant to include compounds which differ only in the presence of one or more isotopically enriched atoms (e.g., isotopic variant(s)). For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

A "salt," as is well known in the art, includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. The terms "pharmaceutically acceptable salts" and/or or "pharmacologically acceptable salts" are meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In certain embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, complexing agents (e.g. cyclodextrins), binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In certain embodiments, treating is preventing. In certain embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (e.g., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things. The relevant symptoms will vary depending upon the intended indication of a particular API.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In certain embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of an inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described herein. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means subcutaneous (i.e., "SC," "subQ," or "SQ") administration, oral administration, administration as a suppository, topical contact or administration, intravenous, parenteral, intraperitoneal, intramuscular, intraosseous, intralesional, intrathecal, intracranial, intranasal, epidural, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the disclosure can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation). The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, e.g., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present disclosure can also be delivered as nanoparticles.

By "co-administer" it is meant that a composition described herein is administered at the same time, just prior to, or just after the administration of one or more additional therapies. The compounds of the disclosure can be administered alone or can be coadministered to the patient. Coadministration is meant to include simultaneous or sequential administration of the compounds individually or in combination (more than one compound). The compositions of the present disclosure can be delivered transdermally, by a topical route, or formulated as applicator sticks, solutions, suspensions, emulsions, gels, creams, ointments, pastes, jellies, paints, powders, and aerosols.

Utilizing the teachings provided herein an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating a mental or psychiatric disorder, a mood disorder, a neurological condition or disorder, a metabolic disorder (e.g., type 2 diabetes mellitus and/or complications thereof), endometriosis, glaucoma, pain, or an inflammatory disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, e.g., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for infections (e.g. bacterial infections), inflammation, and/or vasodilation.

The compounds described herein can be administered to treat a metabolic disease or disorder (e.g., type 2 diabetes mellitus and/or complications thereof), a mental or psychiatric disorder, a mood disorder, a neurological condition or disorder, endometriosis, glaucoma, pain, or an inflammatory disorder. In this regard, the compounds disclosed herein may be administered either alone to treat such diseases or disorders or may be co-administered with another therapeutic agent to treat such diseases or disorders.

The compounds disclosed herein may be co-administered with other active agents including but not limited to antidepressants, antipsychotics, anti-inflammatories, anxiolytics, and/or analgesics.

The APIs (e.g., ketamine, methoxetamine, deschloroketamine, tryptamines, phenethylamines, lysergamide compounds, opioids, cathinone compounds, 3,4-methylenedioxyamphetamine compound derivatives, aminoalkyl-substituted benzofurans, substituted amphetamines, aminoindanes, stimulants, diphenhydramine, hydroxazine, phenylephrine, dopamine, adrenaline, lidocaine, oxymetazoline, clemastine, chlorpheniramine, or 6-chloro-2-aminotetralin, etc.) disclosed herein may be administered once daily until study reached endpoint. The inhibitors disclosed herein may be administered at least three times but in some studies four or more times depending on the length of the study and/or the design of the study.

The term "bioavailability (F)," as used herein, refers to the fraction of a dose of drug (e.g., epinephrine) that is absorbed from its site of administration and reaches, in an unchanged form, the systemic circulation. The term "absolute bioavailability" is used when the fraction of absorbed drug is related to its I.V. bioavailability. It may be calculated using the following formula:

$$F = \frac{AUC_{extravascular}}{AUC_{intravenous}} \times \frac{\text{Dose}_{intravenous}}{\text{Dose}_{extravascular}}$$

The term relative bioavailability ($F_{rel}$) is used to compare two different extravascular routes of drug administration and it may be calculated using the following formula:

$$F_{rel} = \frac{AUC_{extravascular\ 1}}{AUC_{extravascular\ 2}} \times \frac{\text{Dose}_{extravascular\ 2}}{\text{Dose}_{extravascular\ 1}}$$

The term "clearance (CL)," as used herein, refers to the rate at which a drug is eliminated divided by its plasma concentration, giving a volume of plasma from which drug is completely removed per unit of time. CL is equal to the elimination rate constant (λ) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Generally, dosage levels of pharmaceutical compounds (API) in the compositions can range from about 5 μg/kg to about 10 mg/kg, from about 0.5 mg/kg to about 5 mg/kg, from about 1 mg/kg to about 3 mg/kg, or a fixed dose from about 10-100 mg, or 20-75 mg, or 3-60 mg, or 10-250 mg, or 10-400 mg, or an amount greater than 400 mg.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the terms "activation," "activate," "activating," and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc., refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like.

The term "osmolality" as described herein is defined as the number of osmoles (Osm) of solute per kilogram of solvent (osmol/kg or Osm/kg).

The term "osmolarity" as described herein is defined is defined as the number of osmoles of solute per liter (L) of solution (osmol/L or Osm/L).

Osmolarity may be calculated from osmolality as follows: osmolarity=osmolality×($\rho_{sol}$−$c_a$); where $\rho_{sol}$ is the density of the solution in g/mL and $c_a$ is the (anhydrous) solute concentration in g/mL. Unless expressly stated otherwise, osmolarity is calculated using osmolality according to the preceding formula. Alternatively, osmolarity may be calculated experimentally.

II. Compositions

Complexing Agent Salts of Pharmaceutical Compounds

Provided herein are salts of conjugate acid forms of pharmaceutical compounds comprising at least one basic nitrogen and conjugate base forms of complexing agents. Such salts have advantages over other salts of compounds because they are more soluble than many other salt forms owing to the nature of the complexing agent and its ability to solubilize compounds. Additionally, in some embodiments, the preparation of such complexing agent/pharmaceutical compound salts results in a composition that will have a lower osmolality upon dissolution or otherwise in solution than a combination of individual salts of each component, or of each component individually.

In an aspect, provided herein is a pharmaceutically acceptable salt of an pharmaceutical compound comprising: (i) an pharmaceutical compound, or an enantiomer, a mixture of enantiomers, or an isotopic variant thereof; or a pharmaceutically acceptable salt, solvate or hydrate thereof, wherein the pharmaceutical compound comprises a protonated nitrogen atom; and (ii) a conjugate base of a complexing agent comprising a plurality of acidic functional groups, wherein the conjugate base of the complexing agent acts as the counterion of the pharmaceutical compound, wherein the pharmaceutical compound comprises a protonated nitrogen atom; wherein the pharmaceutical compound is a dissociative medication, a dissociative hallucinogen compound, a dissociative anesthetic compound, an arylcyclo-hexylamine, a 1,2-diarylethylamine, a β-keto-arylcyclohexylamine, an compound that modulates the NMDA receptor, a tryptamine, phenethylamine, a lysergamide compound, an opioid comprising a protonated nitrogen atom, a cathinone, a 3,4-methylenedioxyamphetamine derivative, a benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin. In some embodiments, the opioid is racemorphan, levorphanol, racemethorphan, buprenorphine, morphine, loperamide, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, 3-methylthiofentanyl, naloxone, or naltrexone. In some embodiments, the opioid is an opioid receptor antagonist. In some embodiments, the opioid receptor antagonist is naloxone, or naltrexone.

In some embodiments, the plurality of acidic functional groups comprise an acidic group which acts as a counterion for the protonated nitrogen atom of the pharmaceutical compound. In some embodiments, the acidic group is the conjugate base of the acidic group. In some embodiments, the acidic group is a carboxylic acid or carboxylate. In some embodiments, the acidic group is a carboxylate. In some embodiments, the acidic group is a sulfonic acid or sulfonate. In some embodiments, the acidic group is a sulfonate. In some embodiments, the conjugate base of the complexing agent acts as the counterion for a plurality of the pharmaceutical compound. In some embodiments, each acidic group of the plurality of acidic functional groups acts as a counterion for a plurality of the pharmaceutical compound In some embodiments, each acidic group of the plurality of acidic functional groups acts as a counterion for a protonated amine of a plurality of the pharmaceutical compound. In some embodiments, each of the plurality of acidic functional groups acts as a counterion for a pronated amine.

In some embodiments, the complexing agent is a cyclodextrin substituted with the plurality of acidic functional group. In some embodiments, the plurality of acidic functional groups is a carboxylic acid, sulfonic acid, sulfinic acid, phosphonic acid, or phosphinic acid, or any combination thereof. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the complexing agent is a substituted cyclodextrin. In some cases, substituted cyclodextrins provided herein are complex mixtures wherein individual cyclodextrin molecules may comprise different numbers of substituents from other individual cyclodextrin molecules. In such cases, the number of substituents (e.g. the number of acidic functional groups) described as being present on the cyclodextrins provided herein may refer to an average degree of substitution of the mixture. For example, when a cyclodextrin is described as substituted with 3 to 8 acidic functional groups, it is intended that a complex mixture of cyclodextrins having an average degree of substitution from 3 to 8 acidic functional groups is covered. The average degree of substitution need not be an integer value and will often be a decimal value. For example, commercially available SBEBCD has an average degree of substitution of about 6.5.

In some embodiments, the complexing agent is a substituted cyclodextrin. In some embodiments, the substituted cyclodextrin is substituted with one or more acidic functional groups, or a pharmaceutically acceptable salt thereof. In some embodiments, the substituted cyclodextrin is substituted with a plurality of carboxylic acid, sulfonic acid, sulfinic acid, phosphonic acid, or phosphinic acid functional groups. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the molar ratio of the cyclodextrin to the pharmaceutical compound comprising a protonated nitrogen atom is from about 1:4 to about 1:8. In some embodiments, the molar ratio of the cyclodextrin to the pharmaceutical compound comprising a protonated nitrogen atom is from about 1:4 to about 1:10. In some embodiments, the molar ratio of the cyclodextrin to the pharmaceutical compound comprising a protonated nitrogen atom is from about 1:5 to about 1:7. In some embodiments, the molar ratio of the cyclodextrin to the pharmaceutical compound comprising a protonated nitrogen atom is about 1:4. In some embodiments, the molar ratio of the cyclodextrin to the pharmaceutical compound comprising a protonated nitrogen atom is about 1:5. In some embodiments, the molar ratio of the cyclodextrin to the pharmaceutical compound comprising a protonated nitrogen atom is about 1:6. In some embodiments, the molar ratio of the cyclodextrin to the pharmaceutical compound comprising a protonated nitrogen atom is about 1:7. In some embodiments, the molar ratio of the cyclodextrin to the pharmaceutical compound comprising a protonated nitrogen atom is about 1:8. In some embodiments, the molar ratio of the cyclodextrin to the pharmaceutical compound comprising a protonated nitrogen atom is about 1:9. In some embodiments, the molar ratio of the cyclodextrin to the pharmaceutical compound comprising a protonated nitrogen atom is about 1:10.

In some embodiments, molar ratio of acidic functional groups of the complexing agent to the pharmaceutical compound comprising a protonated nitrogen atom is from about 2:1 to about 1:2. In some embodiments, molar ratio of acidic functional groups of the complexing agent to the pharmaceutical compound comprising a protonated nitrogen atom is from about 1.75:1 to about 1:1.75. In some embodiments, molar ratio of acidic functional groups of the complexing agent to the pharmaceutical compound comprising a protonated nitrogen atom is from about 1.5:1 to about 1:1.5. In some embodiments, molar ratio of acidic functional groups of the complexing agent to the pharmaceutical compound comprising a protonated nitrogen atom is from about 1.4:1 to about 1:1.4. In some embodiments, molar ratio of acidic functional groups of the complexing agent to the pharmaceutical compound comprising a protonated nitrogen atom is from 1.3:1 to about 1:1.3. In some embodiments, molar ratio of acidic functional groups of the complexing agent to the pharmaceutical compound comprising a protonated nitrogen atom is from about 1.25:1 to about 1:1.25. In some embodiments, molar ratio of acidic functional groups of the complexing agent to the pharmaceutical compound comprising a protonated nitrogen atom is from about 1.2:1 to about 1:1.2. In some embodiments, molar ratio of acidic functional groups of the complexing agent to the pharmaceutical compound comprising a protonated nitrogen atom is from about 1.15:1 to about 1:1.15. In some embodiments, molar ratio of acidic functional groups of the complexing agent to the pharmaceutical compound comprising a protonated nitrogen atom is from about 1.1:1 to about 1:1.1. In some embodiments, molar ratio of acidic functional groups of the complexing agent to the pharmaceutical compound comprising a protonated nitrogen atom is from about 1.05:1 to about 1:1.05. In some embodiments, molar ratio of acidic functional groups of the complexing agent to the pharmaceutical compound comprising a protonated nitrogen atom is about 1:1.

In some embodiments, the cyclodextrin is a compound of Formula (I):

(I)

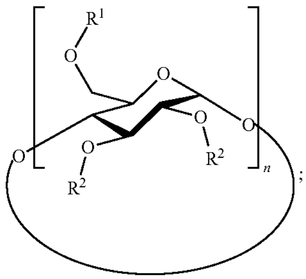

;

wherein:

each $R^1$ is independently H or optionally substituted alkyl;

each $R^2$ is independently H or optionally substituted alkyl; and n is 6, 7, or 8;

or a stereoisomer, a mixture of stereoisomers, or an isotopic variant thereof; or a pharmaceutically acceptable salt, solvate or hydrate thereof.

In some embodiments, each $R^1$ is independently H or alkyl optionally substituted with a polar functional group. In some embodiments, the polar functional group is an amido functional group, an acidic functional group, an ester functional group, a hydroxyl functional group, an alkoxy functional group, or a poly(alkylene oxide) functional group. In some embodiments, each $R^1$ is independently H or alkyl optionally substituted with an acidic functional group or a hydroxyl functional group.

In some embodiments, each $R^1$ is independently H or alkyl optionally substituted with an acidic functional group. In some embodiments, each $R^1$ is independently H or alkyl substituted with an acidic functional group. In some embodiments, each $R^1$ is independently H or $C_1$-$C_6$ alkyl substituted with an acidic functional group. In some embodiments, each $R^1$ is independently H or $C_1$-$C_6$ alkyl substituted with an acidic functional group selected from a carboxylic acid, a sulfonic acid, a sulfinic acid, a phosphonic acid, or a phosphinic acid. In some embodiments, each $R^1$ is independently H,

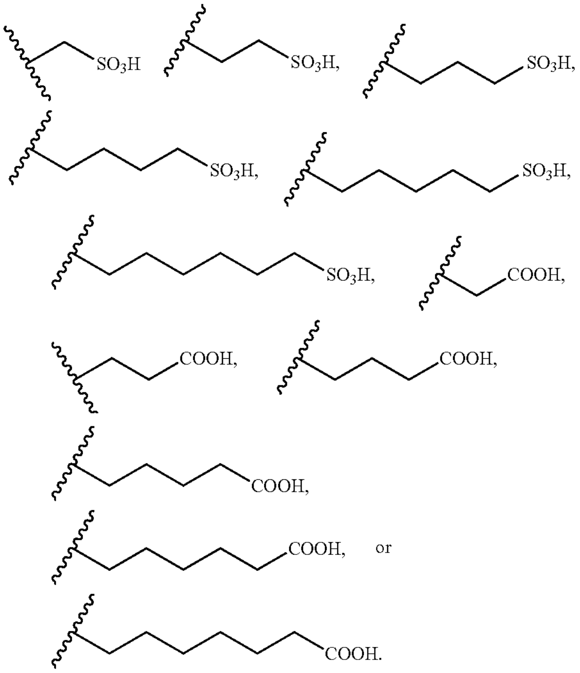

or

In some embodiments, each $R^1$ is independently H,

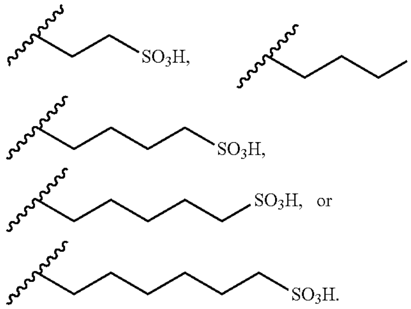

or

In some embodiments wherein $R^1$ comprises an acidic functional group, each $R^2$ is H or acetyl. In some embodiments wherein $R^1$ comprises an acidic functional group, each $R^2$ is H.

In some embodiments, each $R^1$ is independently H or alkyl optionally substituted with a hydroxyl functional group. In some embodiments, each $R^1$ is independently H or alkyl substituted with a hydroxyl functional group. In some embodiments, each $R^1$ is independently H or $C_1$-$C_6$ alkyl substituted with a hydroxyl functional group. In some embodiments, each $R^1$ is independently H or hydroxypropyl, hydroxybutyl, hydroxypentyl, or hydroxyhexyl. In some embodiments, each $R^1$ and $R^2$ is independently H or hydroxypropyl, hydroxybutyl, hydroxypentyl, or hydroxyhexyl.

In some embodiments, each $R^2$ is independently H or alkyl optionally substituted with a polar functional group. In some embodiments, each $R^2$ is independently H or alkyl optionally substituted with a hydroxyl functional group. In some embodiments, each $R^2$ is independently H or alkyl substituted with a hydroxyl functional group. In some embodiments, each $R^2$ is independently H or $C_1$-$C_6$ alkyl substituted with a hydroxyl functional group. In some embodiments, each $R^2$ is independently H or hydroxypropyl, hydroxybutyl, hydroxypentyl, or hydroxyhexyl. In some embodiments, each $R^2$ is H. In some embodiments, each $R^2$ is H or acetyl.

In some embodiments, each $R^2$ is independently H or alkyl optionally substituted with an acidic functional group. In some embodiments, each $R^2$ is independently H or $C_1$-$C_6$ alkyl optionally substituted with an acidic functional group. In some embodiments, each $R^2$ is independently H or $C_1$-$C_6$ alkyl optionally substituted with a sulfonic acid or carboxylic acid functional group.

In some embodiments, n is 6 or 7. In some embodiments, n is 7 or 8. In some embodiments, n is 6. In some embodiments, n is 7. In some embodiments, n is 8.

In some embodiments, the cyclodextrin is a SBEBCD.

In an aspect, provided herein is a pharmaceutically acceptable salt of an pharmaceutical compound having the formula $$[A]_a[B]$$

wherein:

A is an pharmaceutical compound comprising at least one basic nitrogen atom, wherein the pharmaceutical compounds is a dissociative medication, a dissociative hallucinogen compound, a dissociative anesthetic compound, an arylcyclo-hexylamine, a 1,2-diarylethylamine, a β-keto-arylcyclohexylamine, an compound that modulates the NMDA receptor, a tryptamine, a phenethylamine, a lysergamide compound, an opioid, a cathinone, a 3,4-methylenedioxyamphetamine derivative, an aminoalkyl-substituted benzofuran, a substituted amphetamine, an aminoindane, a stimulant, a diphenhydramine, a hydroxazine, a phenylephrine, a dopamine, an adrenaline, a lidocaine, an oxymetazoline, a clemastine, a chlorpheniramine, or a 6-chloro-2-aminotetralin;

B is a complexing agent comprising a plurality of acidic functional groups; and a is a number from 1-8, wherein the number is selected such that the total number of basic nitrogen atoms of A is equal to the number of acidic functional groups of B.

In some embodiments, the opioid is racemorphan, levorphanol, racemethorphan, buprenorphine, morphine, loperamide, morphine, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, or 3-methylthiofentanyl. In some embodiments, the opioid is an opioid receptor antagonist, such as naloxone or naltrexone.

B can be any of the complexing agents provided herein, including without limitations any of the cyclodextrins or compounds of Formula (I) provided herein, the number of acidic groups of such compounds influencing the value of a.

A can be any of the pharmaceutical compounds provided herein, the properties of which (e.g. the number of basic nitrogen atoms) will affect the value of a. In some cases, the pharmaceutical compound may comprise multiple basic nitrogen atoms, one or more of which (though not necessarily all) may be considered basic. However, depending on the differences in pKa value between the multiple basic nitrogen atoms, not every nitrogen atom need be protonated. In some embodiments, it is contemplated that only basic nitrogen atoms having a pKa value above a threshold pKa (e.g. a pKa of 3, 4, 5, 6, 7, 8, 9, 10, or 11) will actually be protonated in a salt provided herein, and any nitrogen atoms having a pKa below the threshold value will not. Thus, in some embodiments, the at least one basic nitrogen atom comprises any nitrogen of the pharmaceutical compound having a pKa of at least 3, at least 4, at least 5, at least 6, at least 7, at least 8, at least 9, at least 10 or at least 11.

In some embodiments, a is a number selected such that the total number of basic nitrogen atoms of A is equal to the number of acidic functional groups of B, thus resulting in a compound of neutral charge, wherein the acidic functional groups of B are deprotonated (and thus anionic) and the basic nitrogen atom or atoms of A are protonated (and thus cationic). The result is a complexing agent/pharmaceutical compound salt that is overall neutral in charge. For example, when the complexing agent of B comprises 6 acidic functional groups and the pharmaceutical compound comprises only a single basic nitrogen atom, a will be 6. Additionally, when the complexing agent of B comprises 6 acidic functional groups and the pharmaceutical compound comprises two basic nitrogen atoms that both ionize at the product pH, a will be 3.

The value of a need not be an integer value. For example, if the complexing agent of B comprises 5 acidic functional groups and the pharmaceutical compound of A comprises two basic nitrogen atoms, then a will be 2.5, and the structure of the overall salt complex will result in a charged molecule of A being effectively “shared” between two molecules of B.

Additionally, any complexing agent B need not be a uniform species of identical substitution of acidic functional groups, and it is explicitly contemplated by the instant disclosure that this will frequently not be the case. For example, commercially available SBEBCD has an average degree of substitution of about 6.5 acidic functional groups. In such a case, the compound having the formula $[A]_a[B]$ is intended to cover such a heterogenous mixture of complexing agents, and a in the case of an pharmaceutical compound with one basic nitrogen atom would be 6.5.

In some embodiments, the pharmaceutical compound of A comprises one, two, or three basic nitrogen atoms. In some embodiments, the pharmaceutical compound of A comprises one basic nitrogen atom. In some embodiments, the pharmaceutical compound of A comprises two basic nitrogen atoms. In some embodiments, the pharmaceutical compound of A comprises three basic nitrogen atoms.

In some embodiments, B comprises about 1 to about 8 acidic functional groups. In some embodiments, B comprises about 1 to about 2, about 1 to about 3, about 1 to about 4, about 1 to about 5, about 1 to about 6, about 1 to about 7, about 1 to about 8, about 2 to about 3, about 2 to about 4, about 2 to about 5, about 2 to about 6, about 2 to about 7, about 2 to about 8, about 3 to about 4, about 3 to about 5, about 3 to about 6, about 3 to about 7, about 3 to about 8, about 4 to about 5, about 4 to about 6, about 4 to about 7, about 4 to about 8, about 5 to about 6, about 5 to about 7, about 5 to about 8, about 6 to about 7, about 6 to about 8, or about 7 to about 8 acidic functional groups. In some embodiments, B comprises about 1, about 2, about 3, about 4, about 5, about 6, about 7, or about 8 acidic functional groups. In some embodiments, B comprises at least about 1, about 2, about 3, about 4, about 5, about 6, or about 7 acidic functional groups. In some embodiments, B comprises at most about 2, about 3, about 4, about 5, about 6, about 7, or about 8 acidic functional groups. In some embodiments, the acidic functional groups are strongly acidic (e.g. a pKa of <2). In some embodiments, the acidic functional groups are sulfonic acid functional groups, phosphoric acid functional groups, or carboxylic acid functional groups. In some embodiments, the acidic functional groups are sulfonic acid functional groups.

In some embodiments, the pKa of the basic nitrogen atom is about 4 to about 12. In some embodiments, the pKa of the basic nitrogen atom is about 4 to about 5, about 4 to about 6, about 4 to about 7, about 4 to about 8, about 4 to about 9, about 4 to about 10, about 4 to about 11, about 4 to about 12, about 5 to about 6, about 5 to about 7, about 5 to about 8, about 5 to about 9, about 5 to about 10, about 5 to about 11, about 5 to about 12, about 6 to about 7, about 6 to about 8, about 6 to about 9, about 6 to about 10, about 6 to about 11, about 6 to about 12, about 7 to about 8, about 7 to about 9, about 7 to about 10, about 7 to about 11, about 7 to about 12, about 8 to about 9, about 8 to about 10, about 8 to about 11, about 8 to about 12, about 9 to about 10, about 9 to about 11, about 9 to about 12, about 10 to about 11, about 10 to about 12, or about 11 to about 12. In some embodiments, the pKa of the basic nitrogen atom is about 4, about 5, about 6, about 7, about 8, about 9, about 10, about 11, or about 12. In some embodiments, the pKa of the basic nitrogen atom is at least about 4, about 5, about 6, about 7, about 8, about 9, about 10, or about 11. In some embodiments, the pKa of the basic nitrogen atom is at most about 5, about 6, about 7, about 8, about 9, about 10, about 11, or about 12.

In some embodiments, the pKa of the basic nitrogen atom is about 4 to about 7. In some embodiments, the pKa of the basic nitrogen atom is about 4 to about 4.5, about 4 to about 5, about 4 to about 5.5, about 4 to about 6, about 4 to about 6.5, about 4 to about 7, about 4.5 to about 5, about 4.5 to about 5.5, about 4.5 to about 6, about 4.5 to about 6.5, about 4.5 to about 7, about 5 to about 5.5, about 5 to about 6, about 5 to about 6.5, about 5 to about 7, about 5.5 to about 6, about 5.5 to about 6.5, about 5.5 to about 7, about 6 to about 6.5, about 6 to about 7, or about 6.5 to about 7. In some embodiments, the pKa of the basic nitrogen atom is about 4, about 4.5, about 5, about 5.5, about 6, about 6.5, or about 7. In some embodiments, the pKa of the basic nitrogen atom is at least about 4, about 4.5, about 5, about 5.5, about 6, or about 6.5. In some embodiments, the pKa of the basic nitrogen atom is at most about 4.5, about 5, about 5.5, about 6, about 6.5, or about 7.

In some embodiments, the pKa of the basic nitrogen atom is about 7 to about 11. In some embodiments, the pKa of the basic nitrogen atom is about 7 to about 7.5, about 7 to about 8, about 7 to about 8.5, about 7 to about 9, about 7 to about 9.5, about 7 to about 10, about 7 to about 10.5, about 7 to about 11, about 7.5 to about 8, about 7.5 to about 8.5, about 7.5 to about 9, about 7.5 to about 9.5, about 7.5 to about 10, about 7.5 to about 10.5, about 7.5 to about 11, about 8 to about 8.5, about 8 to about 9, about 8 to about 9.5, about 8 to about 10, about 8 to about 10.5, about 8 to about 11, about 8.5 to about 9, about 8.5 to about 9.5, about 8.5 to about 10, about 8.5 to about 10.5, about 8.5 to about 11, about 9 to about 9.5, about 9 to about 10, about 9 to about 10.5, about 9 to about 11, about 9.5 to about 10, about 9.5 to about 10.5, about 9.5 to about 11, about 10 to about 10.5, about 10 to about 11, or about 10.5 to about 11. In some embodiments, the pKa of the basic nitrogen atom is about 7, about 7.5, about 8, about 8.5, about 9, about 9.5, about 10, about 10.5, or about 11. In some embodiments, the pKa of the basic nitrogen atom is at least about 7, about 7.5, about 8, about 8.5, about 9, about 9.5, about 10, or about 10.5. In some embodiments, the pKa of the basic nitrogen atom is at most about 7.5, about 8, about 8.5, about 9, about 9.5, about 10, about 10.5, or about 11.

In some embodiments, pKa of the basic nitrogen atom is such that compound will be partially protonated at a physiologically tolerable pH. In some embodiments, the pKa is from about 4 to about 11. In some embodiments, the pKa is from about 4 to about 10. In some embodiments, the pKa is form about 4 to about 9. In some embodiments, the pKa is from about 5 to about 11. In some embodiments, the pKa is from about 5 to about 10. In some embodiments, the pKa is from about 5 to about 9. In some embodiments, the pKa is form about 6 to about 11. In some embodiments, the pKa is from about 6 to about 10. In some embodiments, the pKa is from about 6 to about 9. In some embodiments, the pKa is from about 7 to about 11. In some embodiments, the pKa is from about 7 to about 10. In some embodiments, the pKa is from about 7 to about 9. In some embodiments, the pKa is from about 8 to about 11. In some embodiments, the pKa is from about 8 to about 10. In some embodiments, the pKa is from about 8 to about 10.

In some embodiments, the basic nitrogen atom is an amine. In some embodiments, the amine is a primary amine, a secondary amine, or a tertiary amine. In some embodiments, the amine is an alkyl amine. In some embodiments, the amine is an aryl amine (e.g. an aniline).

In some embodiments, the basic nitrogen is comprised in a heterocycle. In some embodiments, the amine is comprised in an aromatic heterocycle. Non-limiting examples of such aromatic heterocycles include pyrroles, pyrazoles, imidazoles, azaindoles, indazoles, benzoxazoles, benzimidazoles, quinolines, isoquinolines, quinazolines, pyridines, pyrimidines, pyrazines, napthyridines, quinoxalines, phenazines, and the like, each of which may be substituted.

In an aspect, provided herein is a pharmaceutically acceptable salt of an pharmaceutical compound comprising: (i) an pharmaceutical compound, or an enantiomer, a mixture of enantiomers, or an isotopic variant thereof; or a pharmaceutically acceptable salt, solvate or hydrate thereof, wherein the pharmaceutical compound comprises a protonated nitrogen atom; and (ii) a conjugate base of SBEBCD, wherein the conjugate base of SBEBCD acts as the counterion of the pharmaceutical compound, wherein the pharmaceutical compound comprises a protonated nitrogen atom; wherein the pharmaceutical compound is a dissociative medication, a dissociative hallucinogen compound, a dissociative anesthetic compound, an arylcyclo-hexylamine, a 1,2-diarylethylamine, a β-keto-arylcyclohexylamine, an compound that modulates the NMDA receptor, tryptamine, a phenethylamine, a lysergamide compound, an opioid comprising a protonated nitrogen atom, a cathinone, a 3,4-methylenedioxyamphetamine derivative, an aminoalkyl-substituted benzofuran, a substituted amphetamine, an aminoindane, a stimulant, a diphenhydramine, a hydroxazine, a phenylephrine, a dopamine, an adrenaline, a lidocaine, an oxymetazoline, a clemastine, a chlorpheniramine, or a 6-chloro-2-aminotetralin. In some embodiments, the opioid is racemorphan, levorphanol, racemethorphan, buprenorphine, morphine, loperamide, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, or 3-methylthiofentanyl, naloxone, or naltrexone. In some embodiments, the opioid is an opioid receptor antagonist. In some embodiments, the opioid receptor antagonist is naloxone or naltrexone.

In some embodiments, the pharmaceutically acceptable salt provided herein consists essentially of the complexing agent and the pharmaceutical compound. In some embodiments, the pharmaceutically acceptable salt provided herein consists of the complexing agent and the pharmaceutical compound. In some embodiments, the pharmaceutically acceptable salt provided herein consists of the protonated pharmaceutical compound and the deprotonated complexing agent.

In some embodiments, the pharmaceutically acceptable salt is in a solid form. In some embodiments, the solid form is a crystalline form or an amorphous form. In some embodiments, the solid form is an amorphous powder. In some embodiments, the solid form is a lyophilized powder. In some embodiments, the solid form is a crystalline form.

In some embodiments, the pharmaceutically acceptable salt provided herein consists essentially of the complexing agent and the opioid. In some embodiments, the pharmaceutically acceptable salt provided herein consists of the complexing agent and the opioid. In some embodiments, the pharmaceutically acceptable salt provided herein consists of the protonated opioid and the deprotonated complexing agent.

In some embodiments, the pharmaceutically acceptable salt is dissolved or suspended in a liquid medium. In some embodiments, the liquid medium is an aqueous medium, an organic solvent, or a combination thereof. In some embodiments, the liquid medium is an aqueous medium. In some embodiments, the liquid medium is an organic solvent. In some embodiments, the organic solvent comprises acetic acid, acetone, acetonitrile, benzene, tert-butyl alcohol, tert-butyl methyl ether, carbon tetrachloride, chloroform, cyclohexane, 1,2-dichloroethane, dichloromethane, diethyl ether, diglyme, 1,2,-dimethoxyethane, dimethyl acetamide, dimethylformamide, dimethyl sulfoxide, dioxane, ethanol, ethyl acetate, ethyl methyl ketone, ethylene glycol, hexanes, hexamethylphosphoramide, methanol, nitromethane, pentanes, 2-proponal, pyridine, tetrahydrofuran, toluene, xylenes, or any combination thereof. In some embodiments, the pharmaceutically acceptable salt is dissolved or suspended in the liquid medium as an intermediate step in its preparation or in the preparation of a pharmaceutical composition comprising the salt.

In some embodiments, the pharmaceutically acceptable salt is substantially free of excess ions. Examples of such ions include other salts that may be left over from the preparation of the salts or byproducts of the production of the salts (e.g. sodium chloride, lithium chloride, potassium chloride, sodium bromide, and the like). In some embodiments, the excess ions are counterions to excess complexing agent or pharmaceutical compound in the salt preparation, such as excess sodium ions occupying the deprotonated acidic sites or chloride ions associated with excess protonated pharmaceutical compound.

In some embodiments, the pharmaceutically acceptable salt may comprise an excess of the pharmaceutical compound, wherein the excess pharmaceutical compound is unionized. The presence of excess pharmaceutical compound can have numerous benefits in certain contexts, including increasing the dose per unit weight or volume of the salt when the salt is used in a pharmaceutical composition. Additionally, when used in a pharmaceutical composition, the presence of free base or unionized pharmaceutical compound can be used to raise the pH of the composition as it is administered, thus potentially facilitating both bioavailability and tolerability in certain contexts (e.g. when the pKa of the pharmaceutical compound is lower than the pH at which the compound can be comfortably administered to the target tissue). Additionally, many of the complexing agents contemplated herein have an additional coordination site for unionized APIs (e.g. the middle complexing site of a cyclodextrin). Thus, in some embodiments, the complexing agents used herein can offer additional solubilization of pharmaceutical compounds beyond that accomplished merely by acid/base chemistry and ion exchange/ion pairing.

In some embodiments, the pharmaceutically acceptable salt comprises additional equivalents of the pharmaceutical compound. In some embodiments, the additional equivalents are measured as compared to the moles of complexing agent. In some embodiments, the pharmaceutically acceptable salt comprises additional molar equivalents of the pharmaceutical compound. In some embodiments, the additional molar equivalents are measured as compared to the moles of complexing agent. In some embodiments, the additional equivalents are measured as compared to the moles of the pharmaceutical compound which forms a salt with the complexing agent (e.g. the protonated pharmaceutical compound).

In some embodiments, the pharmaceutically acceptable salt comprises additional molar equivalents of unionized pharmaceutical compound compared to the protonated pharmaceutical compound of the complexing agent/protonated pharmaceutical compound salt. In some embodiments, the pharmaceutically acceptable salt comprises about 0.01 molar equivalents to about 10 molar equivalents of the unionized pharmaceutical compound. In some embodiments, the pharmaceutically acceptable salt comprises about 0.1 molar equivalents to about 1 molar equivalents of the unionized pharmaceutical compound. In some embodiments, the pharmaceutically acceptable salt comprises about 0.1 molar equivalents to about 10 molar equivalents of unionized opioid. In some embodiments, the pharmaceutically acceptable salt comprises about 0.1 molar equivalents to about 0.2 molar equivalents, about 0.1 molar equivalents to about 0.5 molar equivalents, about 0.1 molar equivalents to about 0.75 molar equivalents, about 0.1 molar equivalents to about 1 molar equivalents, about 0.2 molar equivalents to about 0.5 molar equivalents, about 0.2 molar equivalents to about 0.75 molar equivalents, about 0.2 molar equivalents to about 1 molar equivalents, about 0.5 molar equivalents to about 0.75 molar equivalents, about 0.5 molar equivalents to about 1 molar equivalents, or about 0.75 molar equivalents to about 1 molar equivalents. In some embodiments, the pharmaceutically acceptable salt comprises about 0.1 molar equivalents, about 0.2 molar equivalents, about 0.5 molar equivalents, about 0.75 molar equivalents, or about 1 molar equivalents of the unionized pharmaceutical compound. In some embodiments, the pharmaceutically acceptable salt comprises at least about 0.1 molar equivalents, about 0.2 molar equivalents, about 0.5 molar equivalents, or about 0.75 molar equivalents of the unionized pharmaceutical compound. In some embodiments, the pharmaceutically acceptable salt comprises at most about 0.2 molar equivalents, about 0.5 molar equivalents, about 0.75 molar equivalents, or about 1 molar equivalents of the unionized pharmaceutical compound. In some embodiments, the pharmaceutically acceptable salt comprises about 0.5 equivalents to about 5 equivalents of the unionized pharmaceutical compound. In some embodiments, the pharmaceutically acceptable salt comprises about 0.5 equivalents to about 1 equivalents, about 0.5 equivalents to about 2 equivalents, about 0.5 equivalents to about 3 equivalents, about 0.5 equivalents to about 4 equivalents, about 0.5 equivalents to about 5 equivalents, about 1 equivalents to about 2 equivalents, about 1 equivalents to about 3 equivalents, about 1 equivalents to about 4 equivalents, about 1 equivalents to about 5 equivalents, about 2 equivalents to about 3 equivalents, about 2 equivalents to about 4 equivalents, about 2 equivalents to about 5 equivalents, about 3 equivalents to about 4 equivalents, about 3 equivalents to about 5 equivalents, or about 4 equivalents to about 5 equivalents of the unionized pharmaceutical compound. In some embodiments, the pharmaceutically acceptable salt comprises about 0.5 equivalents, about 1 equivalents, about 2 equivalents, about 3 equivalents, about 4 equivalents, or about 5 equivalents of the unionized pharmaceutical compound. In some embodiments, the pharmaceutically acceptable salt comprises at least about 0.5 equivalents, about 1 equivalents, about 2 equivalents, about 3 equivalents, or about 4 equivalents of the unionized pharmaceutical compound. In some embodiments, the pharmaceutically acceptable salt comprises at most about 1 equivalents, about 2 equivalents, about 3 equivalents, about 4 equivalents, or about 5 equivalents of the unionized pharmaceutical compound.

In some embodiments, the pharmaceutically acceptable salt comprises additional molar equivalents of unionized pharmaceutical compound compared to complexing agent of the complexing agent/protonated pharmaceutical compound salt. In some embodiments, the pharmaceutically acceptable salt comprises about 0.01 molar equivalents to about 10 molar equivalents of unionized pharmaceutical compound. In some embodiments, the pharmaceutically acceptable salt comprises about 0.1 molar equivalents to about 10 molar equivalents of unionized opioid. In some embodiments, the pharmaceutically acceptable salt comprises about 0.1 molar equivalents to about 0.5 molar equivalents, about 0.1 molar equivalents to about 1 molar equivalents, about 0.1 molar equivalents to about 2 molar equivalents, about 0.1 molar equivalents to about 3 molar equivalents, about 0.1 molar equivalents to about 5 molar equivalents, about 0.1 molar equivalents to about 7 molar equivalents, about 0.1 molar equivalents to about 10 molar equivalents, about 0.5 molar equivalents to about 1 molar equivalents, about 0.5 molar equivalents to about 2 molar equivalents, about 0.5 molar equivalents to about 3 molar equivalents, about 0.5 molar equivalents to about 5 molar equivalents, about 0.5 molar equivalents to about 7 molar equivalents, about 0.5 molar equivalents to about 10 molar equivalents, about 1 molar equivalents to about 2 molar equivalents, about 1 molar equivalents to about 3 molar equivalents, about 1 molar equivalents to about 5 molar equivalents, about 1 molar equivalents to about 7 molar equivalents, about 1 molar equivalents to about 10 molar equivalents, about 2 molar equivalents to about 3 molar equivalents, about 2 molar equivalents to about 5 molar equivalents, about 2 molar equivalents to about 7 molar equivalents, about 2 molar equivalents to about 10 molar equivalents, about 3 molar equivalents to about 5 molar equivalents, about 3 molar equivalents to about 7 molar equivalents, about 3 molar equivalents to about 10 molar equivalents, about 5 molar equivalents to about 7 molar equivalents, about 5 molar equivalents to about 10 molar equivalents, or about 7 molar equivalents to about 10 molar equivalents of unionized pharmaceutical compound of unionized pharmaceutical compound. In some embodiments, the pharmaceutically acceptable salt comprises about 0.1 molar equivalents, about 0.5 molar equivalents, about 1 molar equivalents, about 2 molar equivalents, about 3 molar equivalents, about 5 molar equivalents, about 7 molar equivalents, or about 10 molar equivalents of unionized pharmaceutical compound. In some embodiments, the pharmaceutically acceptable salt comprises at least about 0.1 molar equivalents, about 0.5 molar equivalents, about 1 molar equivalents, about 2 molar equivalents, about 3 molar equivalents, about 5 molar equivalents, or about 7 molar equivalents of unionized pharmaceutical compound. In some embodiments, the pharmaceutically acceptable salt comprises at most about 0.5 molar equivalents, about 1 molar equivalents, about 2 molar equivalents, about 3 molar equivalents, about 5 molar equivalents, about 7 molar equivalents, or about 10 molar equivalents of unionized pharmaceutical compound. In some embodiments, the pharmaceutically acceptable salt comprises about 0.01 molar equivalents to about 20 molar equivalents of unionized pharmaceutical compound compared to the complexing agent. In some embodiments, the pharmaceutically acceptable salt comprises about 0.1 molar equivalents to about 20 molar equivalents of unionized pharmaceutical compound compared to the complexing agent. In some embodiments, the pharmaceutical composition comprises about 1 molar equivalents to about 20 molar equivalents of unionized pharmaceutical compound. compared to the complexing agent. In some embodiments, at least a portion of these additional equivalents of the unionized pharmaceutical compound relative to the complexing agent are complexed to the complexing agent. (e.g. up to about 1 molar equivalent of the unionized pharmaceutical compound relative to the moles of complexing agent).

In some embodiments, the pharmaceutical compound is a dissociative medication, a dissociative hallucinogen compound, a dissociative anesthetic compound, an arylcyclohexylamine, a 1,2-diarylethylamine, a β-keto-arylcyclohexylamine, or an compound that modulates the NMDA receptor. In some embodiments, the pharmaceutical compound is not ketamine.

In some embodiments, the pharmaceutical compound modulates the NMDA receptor. In some embodiments, the pharmaceutical compound is an NMDA receptor antagonist, an NMDA receptor agonist, a mixed NMDA receptor agonist-antagonist, or an NMDA receptor reverse agonist. In some embodiments, the pharmaceutical compound modulates the NMDA receptor at the polyamine site, the glycine binding site, the glutamate binding site, the PCP binding site, the ketamine binding site, an allosteric modulation site, the zinc binding site, or the magnesium binding site. In some embodiments, the pharmaceutical compound is not ketamine.

In some embodiments, the pharmaceutical compound does not modulate the NMDA receptor. In some embodiments, the pharmaceutical compound is not an NMDA receptor agonist. In some embodiments, the pharmaceutical compound is not ketamine.

In some embodiments, the pharmaceutical compound is methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is methoxetamine or deschloroketamine. In some embodiments, the pharmaceutical compound is methoxetamine. In some embodiments, the pharmaceutical compound is deschloroketamine.

In some embodiments, the pharmaceutical compound is ketamine, methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is methoxetamine or deschloroketamine. In some embodiments, the pharmaceutical compound is ketamine. In some embodiments, the ketamine is racemic ketamine. In some embodiments, the ketamine is stereopure or stereoenhanced ketamine. In some embodiments, the ketamine is (R)-ketamine. In some embodiments, the ketamine is (S)-ketamine.

In some embodiments, the pharmaceutical compound is tryptamine, phenethylamine, or a lysergamide compound. In some embodiments, the pharmaceutical compound is a tryptamine, a phenethylamine, or a lysergamide. In some embodiments, the pharmaceutical compound is an N,N-Dimethyltryptamine, a N,N-diethyltryptamine, a N,N-dipropyltryptamine, a N-Methyl-N-propyltryptamine, a N-methyl-N-isopropyltryptamine, a N,N-diallyltryptamine, a N-methyl-N-allyltryptamine, N-methyl-N-ethyltryptamine, a N,N-Diisopropyltryptamine, an α-ethyltryptamine, or a lysergamide.

In some embodiments, the pharmaceutical compound is an N,N-dialkyltryptamine. In some embodiments, the pharmaceutical compound is tryptamine selected from an N,N-Dimethyltryptamine, a N,N-diethyltryptamine, a N,N-dipropyltryptamine, a N-Methyl-N-propyltryptamine, a N-methyl-N-isopropyltryptamine, a N,N-diallyltryptamine, a N-methyl-N-allyltryptamine, N-methyl-N-ethyltryptamine, a N,N-Diisopropyltryptamine, wherein the tryptamine is optionally substituted. In some embodiments, the tryptamine is optionally substituted on the tryptamine ring. In some embodiments, the tryptamine is optionally substituted on the tryptamine ring with a substituent selected from hydroxy, acetoxy, alkoxy, halogen, or alkyl. In some embodiments, the tryptamine is optionally substituted at the 4- or 5-position of the tryptamine ring. In some embodiments, the tryptamine is optionally substituted at the 4- or 5-position of the tryptamine ring with a substituent selected from hydroxy, acetoxy, or methoxy.

In some embodiments, the pharmaceutical compound is a N-methyl-N-ethyltryptamine.

In some embodiments, the pharmaceutical compound is an N,N-dimethyltryptamine. In some embodiments, the pharmaceutical compound is psilocin, O-acetylpsilocin, or 5-methoxy-N,N-dimethyltryptamine.

In some embodiments, the pharmaceutical compound is a N,N-diethyltryptamine. In some embodiments, the pharmaceutical compound is N,N-diethyltryptamine, 4-hydroxy-diethyltryptamine, 4-acetoxy-N,N-diethyltryptamine, or 5-methoxy-N,N-diethyltryptamine.

In some embodiments, the pharmaceutical compound is a N,N-dipropyltryptamine. In some embodiments, the pharmaceutical compound is dipropyltryptamine, 4-hydroxy-dipropyltryptamine, 4-acetoxy-N,N-dipropyltryptamine, or 5-methoxy-N,N-dipropyltryptamine.

In some embodiments, the pharmaceutical compound is a N-methyl-N-propyltryptamine. In some embodiments, the pharmaceutical compound is N-methyl-N-propyltryptamine, 4-hydroxy-N-methyl-N-propyltryptamine, 4-acetoxy-N-methyl-N-propyltryptamine, or 5-methoxy-N-methyl-N-propyltryptamine.

In some embodiments, the pharmaceutical compound is a N-methyl-N-ethyltryptamine. In some embodiments, the pharmaceutical compound is N-methyl-N-ethyltryptamine, 4-hydroxy-N-methyl-N-ethyltryptamine, 4-acetoxy-N-methyl-N-ethyltryptamine, or 5 methoxy-N-methyl-N-ethyltryptamine.

In some embodiments, the pharmaceutical compound is a N-methyl-N-isopropyltryptamine. In some embodiments, the pharmaceutical compound is N-methyl-N-isopropyltryptamine, 4-hydroxy-N-methyl-N-isopropyltryptamine, 4-acetoxy-N-methyl-N-isopropyltryptamine, or 5 methoxy-N-methyl-N-isopropyltryptamine.

In some embodiments, the pharmaceutical compound is a N,N-diallyltryptamine. In some embodiments, the pharmaceutical compound is N,N-diallyltryptamine, 4-hydroxy-N,N-diallyltryptamine, 4-acetoxy-N,N-diallyltryptamine, or 5-methoxy-N,N-diallyltryptamine.

In some embodiments, the pharmaceutical compound is a N-methyl-N-allyl-tryptamine. In some embodiments, the pharmaceutical compound is N-methyl-N-allyl-tryptamine, 4-hydroxy-N-methyl-N-allyl-tryptamine, 4-acetoxy-N-methyl-N-allyl-tryptamine, or 5-methoxy-N-methyl-N-allyl-tryptamine.

In some embodiments, the pharmaceutical compound is a N,N-diisopropyltryptamine. In some embodiments, the pharmaceutical compound is N,N-diisopropyltryptamine, 4-hydroxy-N,N-diisopropyltryptamine, 4-acetoxy-N,N-diisopropyltryptamine, or 5-methoxy-N,N-diisopropyltryptamine. In some embodiments, the pharmaceutical compound is an α-ethyltryptamine.

In some embodiments, the pharmaceutical compound is a lysergamide. In some embodiments, the pharmaceutical compound is methylisopropyllysergamide, ethylisopropyllysergamide, 6-allyl-6-nor-LSD, 6-ethyl-6-nor-lysergic acid diethylamide, 1-acetyl-LSD, 1-propionyl-6-ethyl-6-nor-lysergic acid diethylamide, 1-propionyl-lysergic acid diethylamide, 1-Cyclopropionyl-d-lysergic acid diethylamide, N1-butyryl-lysergic acid diethylamide, or 6-propyl-6-nor-Lysergic acid diethylamide.

In some embodiments, the pharmaceutical compound is a phenethylamine. In some embodiments, the pharmaceutical compound is mescaline, 2,5-dimethoxy-4-bromophenethylamine (2C-B), 2-(4-Iodo-2,5-dimethoxyphenylethane-1-amine (2C-I), 2-(4-Chloro-2,5-dimethoxyphenyl)ethan-1-amine (2C-C), 2,5-Dimethoxy-4-iodoamphetamine, or 2-(4-iodo-2,5-dimethoxyphenyl)-N-[(2-methoxyphenyl)methyl] ethanamine. In some embodiments, the pharmaceutical compound is mescaline. In some embodiments, the pharmaceutical compound is 2,5-dimethoxy-4-bromophenethylamine (2C-B). In some embodiments, the pharmaceutical compound is 2-(4-Iodo-2,5-dimethoxyphenylethane-1-amine (2C-I).). In some embodiments, the pharmaceutical compound is 2-[2,5-Dimethoxy-4-(propylsulfanyl)phenyl] ethan-1-amine.

In some embodiments, the pharmaceutical compound is an opioid. In some embodiments, the opioid is a naturally occurring opioid. In some embodiments, the opioid is a synthetic opioid in some embodiments, the opioid is an opioid derivative. In some embodiments, the opioid is a morphine derivative. In some embodiments, the opioid is a fentanyl derivative. In some embodiments, the opioid is a semi-synthetic opioid.

In some embodiments, the opioid is racemorphan, levorphanol, racemethorphan, buprenorphine, morphine, loperamide, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, or 3-methylthiofentanyl. In some embodiments, the opioid is racemorphan, levorphanol, or racemethorphan. In some embodiments, the opioid is racemorphan. In some embodiments, the opioid is levorphanol. In some embodiments, the opioid is racemethorphan.

In some embodiments, the opioid has a pKa from about 7 to about 11. In some embodiments, the opioid is morphine, codeine, hydrocodone, oxymorphone, buprenorphine, fentanyl, methadone, tramadol, alpha-methyl acetyl fentanyl, alfentanil, butyryl fentanyl, butyrfentanyl, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, or 3-methylthiofentanyl.

In some embodiments, the opioid is an opioid receptor antagonist. In some embodiments, the opioid receptor antagonist is naloxone or naltrexone.

In some embodiments, the pharmaceutical compound is a 3-substituted methcathinone a 3-substituted ethcathinone, a 4-substituted methcathinone, a 4-substituted ethcathinone, methylone, ethylone, or butylone.

In some embodiments, the pharmaceutical compound is a 3-substituted methcathinone. In some embodiments, the pharmaceutical compound is 3-methylmethcathinone, 3-ethylmethcathinone, 3-fluoromethcathinone, 3-chloromethcathinone, or 3-bromomethcathinone. In some embodiments, the pharmaceutical compound is 3-methylmethcathinone.

In some embodiments, the pharmaceutical compound is a 3-substituted ethcathinone. In some embodiments, the pharmaceutical compound is 3-methylethcathinone, 3-ethylethcathinone, 3-fluoroethcathinone, 3-chloroethcathinone, or 3-bromoethcathinone.

In some embodiments, the pharmaceutical compound is a 4-substituted methcathinone. In some embodiments, the pharmaceutical compound is 4-methyl methcathinone, 4-ethyl methcathinone, 4-fluoromethcathinone, 4-chloromethcathinone, or 4-bromomethcathinone.

In some embodiments, the pharmaceutical compound is a 4-substituted ethcathinone. In some embodiments, the pharmaceutical compound is 4-methylethcathinone, 4-ethylethcathinone, 4-fluoroethcathinone, 4-chloroethcathinone, or 4-bromoethcathinone.

In some embodiments, the pharmaceutical compound is methylone, ethylone, or butylone. In some embodiments, the pharmaceutical compound is methylone. In some embodiments, the pharmaceutical compound is ethylone. In some embodiments, the pharmaceutical compound is butylone.

In some embodiments, the pharmaceutical compound is a 3,4-methylenedioxyamphetamine derivative. In some embodiments, the pharmaceutical compound is 1-(1,3-benzodioxol-5-yl)-2-butanamine, 1-(1,3-benzodioxol-5-yl)-N-methyl-2-butanamine, 1-(1,3-benzodioxol-5-yl)-N-ethyl-2-butanamine, 3,4-methylenedioxyamphetamine, 3,4-methylene-dioxy-N-ethyl-amphetamine, S-3,4-methylenedioxy-N-ethyl-amphetamine, 3,4-methylenedioxy-N-methylamphetamine, 5,6-methylenedioxy-2-aminoindane, 2-amino-(3,4-methylenedioxy)propiophenone, or methylenedioxypyrovalerone.

In some embodiments, the pharmaceutical compound is an aminoalkyl-substituted benzofuran. In some embodiments, the pharmaceutical compound is 5-(2-aminopropyl)-benzofuran, 2,3-dihydro isomer of 5-APB, 1-(benzofuran-5-yl)-N-methylpropan-2-amine, 6-(2-aminopropyl)-benzofuran, 2,3-dihydro isomer of 6-APB, or 1-(benzofuran-6-yl)-N-methylpropan-2-amine.

In some embodiments, the pharmaceutical compound is a substituted amphetamine. In some embodiments, the pharmaceutical compound is 4-fluoroamphetamine, 4-fluoromethamphetamine, 3-fluoroamphetamine, 3-fluoromethamphetamine, 2-fluoroamphetamine, or 2-fluoromethamphetamine.

In some embodiments, the pharmaceutical compound is an aminoindane. In some embodiments, the pharmaceutical compound is 5-iodo-2-aminoindane, 5,6-methylenedioxy-2-aminoindane, 5-methoxy-2-aminoindane (MEAI), N-acetyl-MEAI, 5-hydroxy-N-acetyl-AI, or 5-Methoxy-6-methyl-2-aminoindane.

In some embodiments, the pharmaceutical compound is a stimulant. In some embodiments, the pharmaceutical compound is ephedrine, pseudoephedrine, amphetamine, (R)-1-Phenyl-N-propylpentan-2-amine, benzofuranylpropylaminopentane, or methylphenidate.

In some embodiments, the pharmaceutical compound is diphenhydramine, hydroxazine, phenylephrine, dopamine, adrenaline, lidocaine, oxymetazoline, clemastine, chlorpheniramine, or 6-chloro-2-aminotetralin. In some embodiments, the pharmaceutical compound is diphenhydramine.

Pharmaceutical Compositions

Provided herein are pharmaceutical formulations of pharmaceutical compounds suitable for dosing or administration by a variety of routes, including subcutaneous injection, intranasal administration, and/or sublingual administration. These pharmaceutical compositions utilize the complexing agent/pharmaceutical compound salts provided herein. Such salts provide numerous advantages in each type of pharmaceutical composition, some of which are unique to the route of administration.

In an aspect provided herein is a pharmaceutical composition, comprising: (i) an pharmaceutical compound, or an enantiomer, a mixture of enantiomers, or an isotopic variant thereof, wherein the pharmaceutical compound comprises a protonated nitrogen atom; and (ii) a complexing agent, wherein the complexing agent is an acid-substituted cyclodextrin comprising a plurality of acidic functional groups, wherein the plurality of acidic functional groups comprises an acidic group which acts as a counterion for the protonated nitrogen atom of the pharmaceutical compound. In some embodiments, the pharmaceutical compound is a dissociative medication, a dissociative hallucinogen compound, a dissociative anesthetic compound, an arylcyclo-hexylamine, a 1,2-diarylethylamine, a β-keto-arylcyclohexylamine, or an compound that modulates the NMDA receptor. In some embodiments, the pharmaceutical compound is a tryptamine, a phenethylamine, or a lysergamide compound. In some embodiments, the pharmaceutical compound is an opioid. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin In another aspect, provided herein is a pharmaceutical composition comprising (i) an pharmaceutical compound, or an enantiomer, a mixture of enantiomers, or an isotopic variant thereof; or a pharmaceutically acceptable salt, solvate or hydrate thereof, wherein the pharmaceutical compound a dissociative medication, a dissociative hallucinogen compound, a dissociative anesthetic compound, an arylcyclo-hexylamine, a 1,2-diarylethylamine, a β-keto-arylcyclohexylamine, or an compound that modulates the NMDA receptor; and (ii) a complexing agent comprising a plurality of acidic functional groups.

In another aspect, provided herein, is a pharmaceutical composition comprising (i) an pharmaceutical compound, or an enantiomer, a mixture of enantiomers, or an isotopic variant thereof; or a pharmaceutically acceptable salt, solvate or hydrate thereof, wherein the pharmaceutical compound is a tryptamine, a phenethylamine, or a lysergamide compound; and (ii) a complexing agent comprising a plurality of acidic functional groups.

In another aspect, provided herein, is (i) an opioid, or an enantiomer, a mixture of enantiomers, or an isotopic variant thereof; or a pharmaceutically acceptable salt, solvate or hydrate thereof; and (ii) a complexing agent comprising a plurality of acidic functional groups.

In another aspect, provided herein, is a pharmaceutical composition comprising (i) a pharmaceutical compound, or an enantiomer, a mixture of enantiomers, or an isotopic variant thereof; or a pharmaceutically acceptable salt, solvate or hydrate thereof, wherein the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin; and (ii) a complexing agent comprising a plurality of acidic functional groups.

In another aspect, provided herein is a pharmaceutical composition, comprising: (i) a pharmaceutical compound, or an enantiomer, a mixture of enantiomers, or an isotopic variant thereof, wherein the pharmaceutical compound comprises a protonated nitrogen atom; (ii) a complexing agent, wherein the complexing agent comprises a plurality of acidic functional groups, wherein the plurality of acidic functional groups comprise a conjugate base of an acid which acts as a counterion for the protonated nitrogen atom of the pharmaceutical compound; and (iii) an additional molar equivalent of the pharmaceutical compound, wherein the additional molar equivalent of the pharmaceutical compound is unionized. In some embodiments, the additional molar equivalent of the pharmaceutical compound is from 0.01 to 20 molar equivalents. In some embodiments, the pharmaceutical compound is a dissociative medication, a dissociative hallucinogen compound, a dissociative anesthetic compound, an arylcyclo-hexylamine, a 1,2-diarylethylamine, a β-keto-arylcyclohexylamine, or an compound that modulates the NMDA receptor. In some embodiments, the pharmaceutical compound is a tryptamine, a phenethylamine, or a lysergamide compound. In some embodiments, the pharmaceutical compound is an opioid. In some embodiments, the opioid is racemorphan, levorphanol, racemethorphan, buprenorphine, morphine, loperamide, codeine, hydrocodone, oxymorphone, buprenorphine, fentanyl, methadone, tramadol, alpha-methyl acetyl fentanyl, alfentanil, butyryl fentanyl, butyrfentanil, carfentanil, 3-methylcarfentanil, 4-fluorofentanyl, beta-hydroxyfentanyl, alpha-methylfentanyl, cis-3-methylfentanyl, beta-hydroxy-3-methylfentanyl, remifentanil, sufentanil, 3-methylthiofentanyl, naloxone, or naltrexone. In some embodiments, the opioid is racemorphan, levorphanol, or racemethorphan. In some embodiments, the opioid is racemorphan. In some embodiments, the opioid is levorphanol.

In some embodiments, the opioid is racemethorphan. In some embodiments, the opioid is an opioid receptor antagonist. In some embodiments, the opioid receptor antagonist is naloxone or naltrexone. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin In some embodiments, the plurality of acidic functional groups comprise an acidic group which acts as a counterion for the protonated amine of the pharmaceutical compound. In some embodiments, the acidic group is the conjugate base of the acidic group. In some embodiments, the acidic group is a carboxylic acid or carboxylate. In some embodiments, the acidic group is a carboxylate. In some embodiments, the acidic group is a sulfonic acid or sulfonate. In some embodiments, the acidic group is a sulfonate. In some embodiments, the conjugate base of the complexing agent acts as the counterion for a plurality of the pharmaceutical compound. In some embodiments, each acidic group of the plurality of acidic functional groups acts as a counterion for a plurality of the pharmaceutical compound In some embodiments, each acidic group of the plurality of acidic functional groups acts as a counterion for a protonated amine of a plurality of the pharmaceutical compound. In some embodiments, each of the plurality of acidic functional groups acts as a counterion for a pronated amine and/or pronated nitrogen atom.

In some embodiments, the pharmaceutically composition comprises a cyclodextrin substituted with at least one acidic functional group. In some embodiments, the at least one acidic functional group is a carboxylic acid, sulfonic acid, sulfinic acid, phosphonic acid, or phosphinic acid, or any combination thereof. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the pharmaceutical composition further comprises a complexing agent.

In some embodiments, the complexing agent is a substituted or unsubstituted cyclodextrin. In some cases, substituted cyclodextrins provided herein are complex mixtures wherein individual cyclodextrin molecules may comprise different numbers of substituents from other individual cyclodextrin molecules. In such cases, the number of substituents (e.g. the number of acidic functional groups) described as being present on the cyclodextrins provided herein may refer to an average degree of substitution of the mixture. For example, when a cyclodextrin is described as substituted with 3 to 8 acidic functional groups, it is intended that a complex mixture of cyclodextrins having an average degree of substitution from 3 to 8 acidic functional groups is covered. The average degree of substitution need not be an integer value and will often be a decimal value. For example, commercially available SBEBCD has an average degree of substitution of about 6.5.

In some embodiments, the complexing agent is a substituted cyclodextrin. In some embodiments, the substituted cyclodextrin is substituted with one or more acidic functional groups, or a pharmaceutically acceptable salt thereof. In some embodiments, the substituted cyclodextrin is substituted with one or more carboxylic acid, sulfonic acid, sulfinic acid, phosphonic acid, or phosphinic acid. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the molar ratio of the cyclodextrin to the pharmaceutical compound comprising a protonated nitrogen atom is from about 1:4 to about 1:8. In some embodiments, the molar ratio of the cyclodextrin to the pharmaceutical compound comprising a protonated nitrogen atom is from about 1:4 to about 1:10. In some embodiments, the molar ratio of the cyclodextrin to the pharmaceutical compound comprising a protonated nitrogen atom is from about 1:5 to about 1:7. In some embodiments, the molar ratio of the cyclodextrin to the pharmaceutical compound comprising a protonated nitrogen atom is about 1:4. In some embodiments, the molar ratio of the cyclodextrin to the pharmaceutical compound comprising a protonated nitrogen atom is about 1:5. In some embodiments, the molar ratio of the cyclodextrin to the pharmaceutical compound comprising a protonated nitrogen atom is about 1:6. In some embodiments, the molar ratio of the cyclodextrin to the pharmaceutical compound comprising a protonated nitrogen atom is about 1:7. In some embodiments, the molar ratio of the cyclodextrin to the pharmaceutical compound comprising a protonated nitrogen atom is about 1:8. In some embodiments, the molar ratio of the cyclodextrin to the pharmaceutical compound comprising a protonated nitrogen atom is about 1:9. In some embodiments, the molar ratio of the cyclodextrin to the pharmaceutical compound comprising a protonated nitrogen atom is about 1:10. In some embodiments, the molar ratio of the cyclodextrin to the pharmaceutical compound comprising a protonated nitrogen atom is from about 1:4 to about 1:10. In some embodiments, the molar ratio of the cyclodextrin to the pharmaceutical compound comprising a protonated nitrogen atom is from about 1:5 to about 1:7. In some embodiments, the molar ratio of the cyclodextrin to the pharmaceutical compound comprising a protonated nitrogen atom is about 1:4. In some embodiments, the molar ratio of the cyclodextrin to the pharmaceutical compound comprising a protonated nitrogen atom is about 1:5. In some embodiments, the molar ratio of the cyclodextrin to the pharmaceutical compound comprising a protonated nitrogen atom is about 1:6. In some embodiments, the molar ratio of the cyclodextrin to the pharmaceutical compound comprising a protonated nitrogen is about 1:7.

In some embodiments, molar ratio of acidic functional groups of the complexing agent to the pharmaceutical compound comprising a protonated nitrogen atom is from about 2:1 to about 1:2. In some embodiments, molar ratio of acidic functional groups of the complexing agent to the pharmaceutical compound comprising a protonated nitrogen atom is from about 1.75:1 to about 1:1.75. In some embodiments, molar ratio of acidic functional groups of the complexing agent to the pharmaceutical compound comprising a protonated nitrogen atom is from about 1.5:1 to about 1:1.5. In some embodiments, molar ratio of acidic functional groups of the complexing agent to the pharmaceutical compound comprising a protonated nitrogen atom is from about 1.4:1 to about 1:1.4. In some embodiments, molar ratio of acidic functional groups of the complexing agent to the pharmaceutical compound comprising a protonated nitrogen atom is from 1.3:1 to about 1:1.3. In some embodiments, molar ratio of acidic functional groups of the complexing agent to the pharmaceutical compound comprising a protonated nitrogen atom is from about 1.25:1 to about 1:1.25. In some embodiments, molar ratio of acidic functional groups of the complexing agent to the pharmaceutical compound comprising a protonated nitrogen atom is from about 1.2:1 to about 1:1.2. In some embodiments, molar ratio of acidic functional groups of the complexing agent to the pharmaceutical compound comprising a protonated nitrogen atom is from about 1.15:1 to about 1:1.15. In some embodiments, molar ratio of acidic functional groups of the complexing agent to the pharmaceutical compound comprising a protonated nitrogen atom is from about 1.1:1 to about 1:1.1. In some embodiments, molar ratio of acidic functional groups of the complexing agent to the pharmaceutical compound comprising a protonated nitrogen atom is from about 1.05:1 to about 1:1.05. In some embodiments, molar ratio of acidic functional groups of the complexing agent to the pharmaceutical compound comprising a protonated nitrogen atom is about 1:1.

In some embodiments, molar ratio of acidic functional groups of the complexing agent to the pharmaceutical compound comprising a protonated nitrogen atom is from about 2:1 to about 1:2. In some embodiments, molar ratio of acidic functional groups of the complexing agent to the pharmaceutical compound comprising a protonated nitrogen atom is from about 1.75:1 to about 1:1.75. In some embodiments, molar ratio of acidic functional groups of the complexing agent to the pharmaceutical compound comprising a protonated nitrogen is from about 1.5:1 to about 1:1.5. In some embodiments, molar ratio of acidic functional groups of the complexing agent to the pharmaceutical compound comprising a protonated nitrogen atom is from about 1.4:1 to about 1:1.4. In some embodiments, molar ratio of acidic functional groups of the complexing agent to the pharmaceutical compound comprising a protonated nitrogen atom is from about 1.3:1 to about 1:1.3. In some embodiments, molar ratio of acidic functional groups of the complexing agent to the pharmaceutical compound comprising a protonated nitrogen atom is from about 1.25:1 to about 1:1.25. In some embodiments, molar ratio of acidic functional groups of the complexing agent to the pharmaceutical compound comprising a protonated nitrogen atom is from about 1.2:1 to about 1:1.2. In some embodiments, molar ratio of acidic functional groups of the complexing agent to the pharmaceutical compound comprising a protonated nitrogen atom is from about 1.15:1 to about 1:1.15. In some embodiments, molar ratio of acidic functional groups of the complexing agent to the pharmaceutical compound comprising a protonated nitrogen atom is from about 1.1:1 to about 1:1.1. In some embodiments, molar ratio of acidic functional groups of the complexing agent to the pharmaceutical compound comprising a protonated nitrogen atom is from about 1.05:1 to about 1:1.05. In some embodiments, molar ratio of acidic functional groups of the complexing agent to the pharmaceutical compound comprising a protonated nitrogen is about 1:1.

In some embodiments, the cyclodextrin is a compound of Formula (I):

(I)

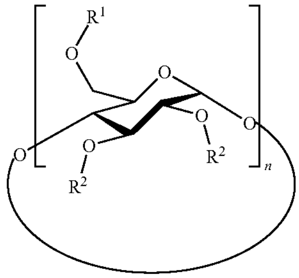

;

wherein:

each $R^1$ is independently H or optionally substituted alkyl;

each $R^2$ is independently H or optionally substituted alkyl; and n is 6, 7, or 8;

or a stereoisomer, a mixture of stereoisomers, or an isotopic variant thereof; or a pharmaceutically acceptable salt, solvate or hydrate thereof.

In some embodiments, each $R^1$ is independently H or alkyl optionally substituted with a polar functional group. In some embodiments, the polar functional group is an amido functional group, an acidic functional group, an ester functional group, a hydroxyl functional group, an alkoxy functional group, or a poly(alkylene oxide) functional group. In some embodiments, each $R^1$ is independently H or alkyl optionally substituted with an acidic functional group or a hydroxyl functional group.

In some embodiments, each $R^1$ is independently H or alkyl optionally substituted with an acidic functional group. In some embodiments, each $R^1$ is independently H or alkyl substituted with an acidic functional group. In some embodiments, each $R^1$ is independently H or $C_1$-$C_6$ alkyl substituted with an acidic functional group. In some embodiments, each $R^1$ is independently H or $C_1$-$C_6$ alkyl substituted with an acidic functional group selected from a carboxylic acid, a sulfonic acid, a sulfinic acid, a phosphonic acid, or a phosphinic acid. In some embodiments, each $R^1$ is independently H,

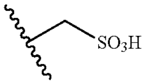

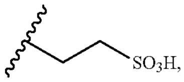

,

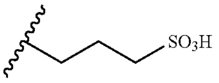

,

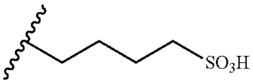

,

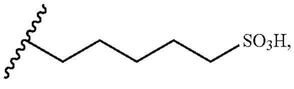

,

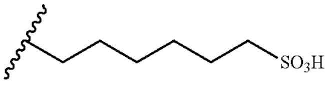

,

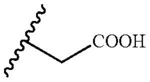

,

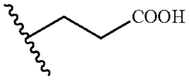

,

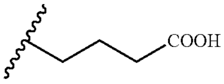

,

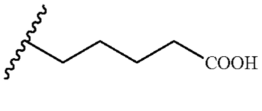

,

-continued

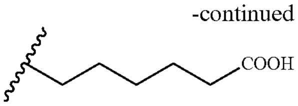

, or

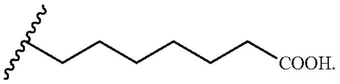

In some embodiments, each $R^1$ is independently H,

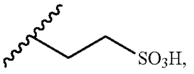

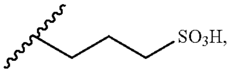

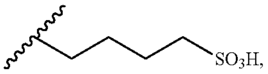

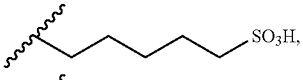

or

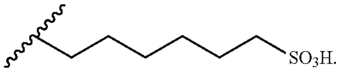

In some embodiments wherein $R^1$ comprises an acidic functional group, each $R^2$ is H or acetyl. In some embodiments wherein $R^1$ comprises an acidic functional group, each $R^2$ is H.

In some embodiments, each $R^1$ is independently H or alkyl optionally substituted with a hydroxyl functional group. In some embodiments, each $R^1$ is independently H or alkyl substituted with a hydroxyl functional group. In some embodiments, each $R^1$ is independently H or $C_1$-$C_6$ alkyl substituted with a hydroxyl functional group. In some embodiments, each $R^1$ is independently H or hydroxypropyl, hydroxybutyl, hydroxypentyl, or hydroxyhexyl. In some embodiments, each $R^1$ and $R^2$ is independently H or hydroxypropyl, hydroxybutyl, hydroxypentyl, or hydroxyhexyl.

In some embodiments, each $R^2$ is independently H or alkyl optionally substituted with a polar functional group. In some embodiments, each $R^2$ is independently H or alkyl optionally substituted with a hydroxyl functional group. In some embodiments, each $R^2$ is independently H or alkyl substituted with a hydroxyl functional group. In some embodiments, each $R^2$ is independently H or $C_1$-$C_6$ alkyl substituted with a hydroxyl functional group. In some embodiments, each $R^2$ is independently H or hydroxypropyl, hydroxybutyl, hydroxypentyl, or hydroxyhexyl. In some embodiments, each $R^2$ is H. In some embodiments, each $R^2$ is H or acetyl.

In some embodiments, each $R^2$ is independently H or alkyl optionally substituted with an acidic functional group. In some embodiments, each $R^2$ is independently H or $C_1$-$C_6$ alkyl optionally substituted with an acidic functional group. In some embodiments, each $R^2$ is independently H or $C_1$-$C_6$ alkyl optionally substituted with a sulfonic acid or carboxylic acid functional group.

In some embodiments, n is 6 or 7. In some embodiments, n is 7 or 8. In some embodiments, n is 6. In some embodiments, n is 7. In some embodiments, n is 8.

In some embodiments, the cyclodextrin is a sulfobutylether-beta-cyclodextrin (SBEBCD) or a hydroxypropyl-beta-cyclodextrin (HPBCD).

In some embodiments, the cyclodextrin is a SBEBCD. In some embodiments, the SBEBCD is the free acid form of SBEBCD.

In some embodiments, the molar ratio of SBEBCD to the pharmaceutical compound comprising a protonated nitrogen atom is from about 1:4 to about 1:8. In some embodiments, the molar ratio of SBEBCD to the pharmaceutical compound comprising a protonated nitrogen atom is from about 1:4 to about 1:10. In some embodiments, the molar ratio of SBEBCD to the pharmaceutical compound comprising a protonated nitrogen atom is from about 1:4 to about 1:8. In some embodiments, the molar ratio of SBEBCD to the pharmaceutical compound comprising a protonated nitrogen atom is from about 1:4 to about 1:10. In some embodiments, the molar ratio of SBEBCD to the pharmaceutical compound comprising a protonated nitrogen atom is from about 1:5 to about 1:7. In some embodiments, the molar ratio of SBEBCD to the pharmaceutical compound comprising a protonated nitrogen atom is about 1:4. In some embodiments, the molar ratio of SBEBCD to the pharmaceutical compound comprising a protonated nitrogen atom is about 1:5. In some embodiments, the molar ratio of SBEBCD to the pharmaceutical compound comprising a protonated nitrogen atom is about 1:6. In some embodiments, the molar ratio of SBEBCD to the pharmaceutical compound comprising a protonated nitrogen atom is about 1:7. In some embodiments, the molar ratio of SBEBCD to the pharmaceutical compound comprising a protonated nitrogen atom is about 1:8. In some embodiments, the molar ratio of SBEBCD to the pharmaceutical compound comprising a protonated nitrogen atom is about 1:9. In some embodiments, the molar ratio of SBEBCD to the pharmaceutical compound comprising a protonated nitrogen atom is about 1:10. In some embodiments, the molar ratio of SBEBCD to the pharmaceutical compound comprising a protonated nitrogen atom is about 1:2 to about 1:10. In some embodiments, the molar ratio of SBEBCD to the pharmaceutical compound comprising a protonated nitrogen atom is about 1:2 to about 1:3, about 1:2 to about 1:4, about 1:2 to about 1:5, about 1:2 to about 1:6, about 1:2 to about 1:7, about 1:2 to about 1:8, about 1:2 to about 1:9, about 1:2 to about 1:10, about 1:3 to about 1:4, about 1:3 to about 1:5, about 1:3 to about 1:6, about 1:3 to about 1:7, about 1:3 to about 1:8, about 1:3 to about 1:9, about 1:3 to about 1:10, about 1:4 to about 1:5, about 1:4 to about 1:6, about 1:4 to about 1:7, about 1:4 to about 1:8, about 1:4 to about 1:9, about 1:4 to about 1:10, about 1:5 to about 1:6, about 1:5 to about 1:7, about 1:5 to about 1:8, about 1:5 to about 1:9, about 1:5 to about 1:10, about 1:6 to about 1:7, about 1:6 to about 1:8, about 1:6 to about 1:9, about 1:6 to about 1:10, about 1:7 to about 1:8, about 1:7 to about 1:9, about 1:7 to about 1:10, about 1:8 to about 1:9, about 1:8 to about 1:10, or about 1:9 to about 1:10. In some embodiments, the molar ratio of SBEBCD to the pharmaceutical compound comprising a protonated nitrogen atom is about 1:2, about 1:3, about 1:4, about 1:5, about 1:6, about 1:7, about 1:8, about 1:9, or about 1:10. In some embodiments, the molar ratio of SBEBCD to the pharmaceutical compound comprising a protonated nitrogen atom is at least about 1:2, about 1:3, about 1:4, about 1:5, about 1:6, about 1:7, about 1:8, or about 1:9. In some embodiments, the molar ratio of SBEBCD to the pharmaceutical compound comprising a protonated nitrogen atom is at most about 1:3, about 1:4, about 1:5, about 1:6, about 1:7, about 1:8, about 1:9, or about 1:10.

In some embodiments, the pharmaceutically acceptable salt or pharmaceutical composition provided herein consists essentially of the complexing agent and the pharmaceutical compound. In some embodiments, the pharmaceutically acceptable salt or pharmaceutical composition provided herein consists of the complexing agent and the pharmaceutical compound. In some embodiments, the pharmaceutically acceptable salt or pharmaceutical composition provided herein consists of the protonated pharmaceutical compound and the deprotonated complexing agent.

In some embodiments, the pharmaceutical composition further comprises a base, a buffer, or a combination thereof.

In some embodiments, the pharmaceutical composition does not comprise a base, a buffer, or a combination thereof.

In some embodiments, the co-solvent is ethanol, propylene glycol, tween 20, tween 80, glycerin, or a combination thereof.

In some embodiments, the complexing agent is a substituted or unsubstituted cyclodextrin. In some cases, substituted cyclodextrins provided herein are complex mixtures wherein individual cyclodextrin molecules may comprise different numbers of substituents from other individual cyclodextrin molecules. In such cases, the number of substituents (e.g. the number of acidic functional groups) described as being present on the cyclodextrins provided herein may refer to an average degree of substitution of the mixture. For example, when a cyclodextrin is described as substituted with 3 to 8 acidic functional groups, it is intended that a complex mixture of cyclodextrins having an average degree of substitution from 3 to 8 acidic functional groups is covered.

In some embodiments, the complexing agent is a substituted cyclodextrin. In some embodiments, the substituted cyclodextrin is substituted with one or more acidic functional groups, or a pharmaceutically acceptable salt thereof. In some embodiments, the substituted cyclodextrin is substituted with one or more carboxylic acid, sulfonic acid, sulfinic acid, phosphonic acid, or phosphonic acid. In some embodiments, the cyclodextrin is substituted with at least 1, at least 2, at least 3, at least 4, at least 5, or at least 6 acidic functional groups. In some embodiments, the cyclodextrin is substituted with 3 to 8 acidic functional groups, 3 to 7 acidic functional groups, 4 to 8 acidic functional groups, 4 to 7 acidic functional groups, 5 to 8 acidic functional groups, 6 to 8 acidic functional groups, or 7 to 8 acidic functional groups.

In some embodiments, the cyclodextrin is a compound of Formula (I).

In some embodiments, the cyclodextrin is a sulfobutylether-beta-cyclodextrin (SBEBCD).

In some embodiments, the SBEBCD is the free acid form of SBEBCD.

In some embodiments, the pharmaceutically acceptable salt is formulated in an aqueous medium, either as a solution or a suspension. Such solutions or suspensions can be used in a variety of formulations, such as formulations for subcutaneous administration, intranasal administration, or sublingual administration. In some embodiments, when formulated in an aqueous medium, the pharmaceutical compositions provided herein will have lowered osmolality compared to other formulations having the same concentration of complexing agent and pharmaceutical compound which utilize salts of the complexing agent, the pharmaceutical compound, or both.

In some embodiments, the pharmaceutical composition has lower osmolality than a composition comprising a salt of the pharmaceutical compound and a salt of the complexing agent. In some embodiments, In some embodiments, the pharmaceutical composition has lower osmolality than a composition comprising a salt of the pharmaceutical compound. In some embodiments, In some embodiments, the pharmaceutical composition has lower osmolality than a composition comprising a salt of the complexing agent (e.g. a sodium salt). the pharmaceutical composition has substantially the same osmolality as a solution of the same concentration of a salt of the complexing agent. In some embodiments, the pharmaceutical composition has substantially the same osmolality as a solution of the same concentration of a sodium salt of the complexing agent. In some embodiments, the comparison of osmolality of the pharmaceutical composition is compared to one in which the concentration of the pharmaceutical compound and the complexing agent is the same. In some embodiments, the salt of the complexing agent used for the comparison is the sodium salt. In some embodiments, the salt of the pharmaceutical compound is the HCl salt.

In some embodiments, the pharmaceutical composition has an osmolality that is about 10% to about 50% less than a corresponding pharmaceutical composition prepared from a salt of the complexing agent. In some embodiments, the pharmaceutical composition has an osmolality that is about 10% to about 20%, about 10% to about 30%, about 10% to about 40%, about 10% to about 50%, about 20% to about 30%, about 20% to about 40%, about 20% to about 50%, about 30% to about 40%, about 30% to about 50%, or about 40% to about 50% less than a corresponding pharmaceutical composition prepared from a salt of the complexing agent. In some embodiments, the pharmaceutical composition has an osmolality that is about 10%, about 20%, about 30%, about 40%, or about 50% less than a corresponding pharmaceutical composition prepared from a salt of the complexing agent. In some embodiments, the pharmaceutical composition has an osmolality that is at least about 10%, about 20%, about 30%, or about 40% less than a corresponding pharmaceutical composition prepared from a salt of the complexing agent.

In some embodiments, the pharmaceutical composition has an osmolality that is about 10% to about 50% less than a corresponding pharmaceutical composition prepared from a salt of the pharmaceutical compound. In some embodiments, the pharmaceutical composition has an osmolality that is about 10% to about 20%, about 10% to about 30%, about 10% to about 40%, about 10% to about 50%, about 20% to about 30%, about 20% to about 40%, about 20% to about 50%, about 30% to about 40%, about 30% to about 50%, or about 40% to about 50% less than a corresponding pharmaceutical composition prepared from a salt of the pharmaceutical compound. In some embodiments, the pharmaceutical composition has an osmolality that is about 10%, about 20%, about 30%, about 40%, or about 50% less than a corresponding pharmaceutical composition prepared from a salt of the pharmaceutical compound. In some embodiments, the pharmaceutical composition has an osmolality that is at least about 10%, about 20%, about 30%, or about 40% less than a corresponding pharmaceutical composition prepared from a salt of the pharmaceutical compound.

In some embodiments, the pharmaceutical composition has an osmolality that is about 50 mOsm/kg to about 500 mOsm/kg less than a corresponding pharmaceutical composition prepared from a salt of the complexing agent. In some embodiments, the pharmaceutical composition has an osmolality that is about 50 mOsm/kg to about 100 mOsm/kg, about 50 mOsm/kg to about 150 mOsm/kg, about 50 mOsm/kg to about 200 mOsm/kg, about 50 mOsm/kg to about 250 mOsm/kg, about 50 mOsm/kg to about 300 mOsm/kg, about 50 mOsm/kg to about 400 mOsm/kg, about 50 mOsm/kg to about 500 mOsm/kg, about 100 mOsm/kg to about 150 mOsm/kg, about 100 mOsm/kg to about 200 mOsm/kg, about 100 mOsm/kg to about 250 mOsm/kg, about 100 mOsm/kg to about 300 mOsm/kg, about 100 mOsm/kg to about 400 mOsm/kg, about 100 mOsm/kg to about 500 mOsm/kg, about 150 mOsm/kg to about 200 mOsm/kg, about 150 mOsm/kg to about 250 mOsm/kg, about 150 mOsm/kg to about 300 mOsm/kg, about 150 mOsm/kg to about 400 mOsm/kg, about 150 mOsm/kg to about 500 mOsm/kg, about 200 mOsm/kg to about 250 mOsm/kg, about 200 mOsm/kg to about 300 mOsm/kg, about 200 mOsm/kg to about 400 mOsm/kg, about 200 mOsm/kg to about 500 mOsm/kg, about 250 mOsm/kg to about 300 mOsm/kg, about 250 mOsm/kg to about 400 mOsm/kg, about 250 mOsm/kg to about 500 mOsm/kg, about 300 mOsm/kg to about 400 mOsm/kg, about 300 mOsm/kg to about 500 mOsm/kg, or about 400 mOsm/kg to about 500 mOsm/kg less than a corresponding pharmaceutical composition prepared from a salt of the complexing agent. In some embodiments, the pharmaceutical composition has an osmolality that is about 50 mOsm/kg, about 100 mOsm/kg, about 150 mOsm/kg, about 200 mOsm/kg, about 250 mOsm/kg, about 300 mOsm/kg, about 400 mOsm/kg, or about 500 mOsm/kg less than a corresponding pharmaceutical composition prepared from a salt of the complexing agent. In some embodiments, the pharmaceutical composition has an osmolality that is at least about 50 mOsm/kg, about 100 mOsm/kg, about 150 mOsm/kg, about 200 mOsm/kg, about 250 mOsm/kg, about 300 mOsm/kg, or about 400 mOsm/kg less than a corresponding pharmaceutical composition prepared from a salt of the complexing agent.

In some embodiments, the pharmaceutical composition has an osmolality that is about 50 mOsm/kg to about 500 mOsm/kg less than a corresponding pharmaceutical composition prepared from a salt of the pharmaceutical compound. In some embodiments, the pharmaceutical composition has an osmolality that is about 50 mOsm/kg to about 100 mOsm/kg, about 50 mOsm/kg to about 150 mOsm/kg, about 50 mOsm/kg to about 200 mOsm/kg, about 50 mOsm/kg to about 250 mOsm/kg, about 50 mOsm/kg to about 300 mOsm/kg, about 50 mOsm/kg to about 400 mOsm/kg, about 50 mOsm/kg to about 500 mOsm/kg, about 100 mOsm/kg to about 150 mOsm/kg, about 100 mOsm/kg to about 200 mOsm/kg, about 100 mOsm/kg to about 250 mOsm/kg, about 100 mOsm/kg to about 300 mOsm/kg, about 100 mOsm/kg to about 400 mOsm/kg, about 100 mOsm/kg to about 500 mOsm/kg, about 150 mOsm/kg to about 200 mOsm/kg, about 150 mOsm/kg to about 250 mOsm/kg, about 150 mOsm/kg to about 300 mOsm/kg, about 150 mOsm/kg to about 400 mOsm/kg, about 150 mOsm/kg to about 500 mOsm/kg, about 200 mOsm/kg to about 250 mOsm/kg, about 200 mOsm/kg to about 300 mOsm/kg, about 200 mOsm/kg to about 400 mOsm/kg, about 200 mOsm/kg to about 500 mOsm/kg, about 250 mOsm/kg to about 300 mOsm/kg, about 250 mOsm/kg to about 400 mOsm/kg, about 250 mOsm/kg to about 500 mOsm/kg, about 300 mOsm/kg to about 400 mOsm/kg, about 300 mOsm/kg to about 500 mOsm/kg, or about 400 mOsm/kg to about 500 mOsm/kg less than a corresponding pharmaceutical composition prepared from a salt of the pharmaceutical compound. In some embodiments, the pharmaceutical composition has an osmolality that is about 50 mOsm/kg, about 100 mOsm/kg, about 150 mOsm/kg, about 200 mOsm/kg, about 250 mOsm/kg, about 300 mOsm/kg, about 400 mOsm/kg, or about 500 mOsm/kg less than a corresponding pharmaceutical composition prepared from a salt of the pharmaceutical compound. In some embodiments, the pharmaceutical composition has an osmolality that is at least about 50 mOsm/kg, about 100 mOsm/kg, about 150 mOsm/kg, about 200 mOsm/kg, about 250 mOsm/kg, about 300 mOsm/kg, or about 400 mOsm/kg less than a corresponding pharmaceutical composition prepared from a salt of the pharmaceutical compound.

In some embodiments, the pharmaceutical composition has an osmolality that is about 50 mOsm/kg to about 500 mOsm/kg less than a corresponding pharmaceutical composition prepared from a salt of the pharmaceutical compound and a salt of the complexing agent. In some embodiments, the pharmaceutical composition has an osmolality that is about 50 mOsm/kg to about 100 mOsm/kg, about 50 mOsm/kg to about 150 mOsm/kg, about 50 mOsm/kg to about 200 mOsm/kg, about 50 mOsm/kg to about 250 mOsm/kg, about 50 mOsm/kg to about 300 mOsm/kg, about 50 mOsm/kg to about 400 mOsm/kg, about 50 mOsm/kg to about 500 mOsm/kg, about 100 mOsm/kg to about 150 mOsm/kg, about 100 mOsm/kg to about 200 mOsm/kg, about 100 mOsm/kg to about 250 mOsm/kg, about 100 mOsm/kg to about 300 mOsm/kg, about 100 mOsm/kg to about 400 mOsm/kg, about 100 mOsm/kg to about 500 mOsm/kg, about 150 mOsm/kg to about 200 mOsm/kg, about 150 mOsm/kg to about 250 mOsm/kg, about 150 mOsm/kg to about 300 mOsm/kg, about 150 mOsm/kg to about 400 mOsm/kg, about 150 mOsm/kg to about 500 mOsm/kg, about 200 mOsm/kg to about 250 mOsm/kg, about 200 mOsm/kg to about 300 mOsm/kg, about 200 mOsm/kg to about 400 mOsm/kg, about 200 mOsm/kg to about 500 mOsm/kg, about 250 mOsm/kg to about 300 mOsm/kg, about 250 mOsm/kg to about 400 mOsm/kg, about 250 mOsm/kg to about 500 mOsm/kg, about 300 mOsm/kg to about 400 mOsm/kg, about 300 mOsm/kg to about 500 mOsm/kg, or about 400 mOsm/kg to about 500 mOsm/kg less than a corresponding pharmaceutical composition prepared from a salt of the pharmaceutical compound and a salt of the complexing agent. In some embodiments, the pharmaceutical composition has an osmolality that is about 50 mOsm/kg, about 100 mOsm/kg, about 150 mOsm/kg, about 200 mOsm/kg, about 250 mOsm/kg, about 300 mOsm/kg, about 400 mOsm/kg, or about 500 mOsm/kg less than a corresponding pharmaceutical composition prepared from a salt of the pharmaceutical compound and a salt of the complexing agent. In some embodiments, the pharmaceutical composition has an osmolality that is at least about 50 mOsm/kg, about 100 mOsm/kg, about 150 mOsm/kg, about 200 mOsm/kg, about 250 mOsm/kg, about 300 mOsm/kg, or about 400 mOsm/kg less than a corresponding pharmaceutical composition prepared from a salt of the pharmaceutical compound and a salt of the complexing agent Subcutaneous Formulations In some aspects, the pharmaceutical composition provided herein is formulated for subcutaneous administration. Subcutaneously deliverable compounds have the advantage over other forms of compounds (e.g. IV or IM delivery) in that it can be used outside of a hospital or clinical setting, such as at home by the subject. Other formulations of compounds suitable for at home use, such as oral or nasal delivery formulations, tend to require higher doses to achieve comparable clinical effects, which carries risks, including bladder dysfunction due to the higher dosing and dissociative effects. Additionally, oral or sublingual administration is sometimes unreliable due to the presence of food or chyme in the stomach or proximal small intestines and substantial first pass metabolism. Intranasal administration can cause allergic or irritation rhinitis, epistaxis (nosebleeds), or bacterial or viral sinusitis in certain contexts.

In some embodiments, the pharmaceutical formulation provided herein are able to combine a high concentration of compound (e.g. >20 mg/mL) with additional characteristics of the formulation making it ideally suited to subcutaneous injection. These additional characteristics may include osmolality and pH closer to physiological levels than is possible with a composition prepared exclusively or partially with a salt of the compound and/or complexing agent while still maintaining stability of the formulation and solubility of compound. In some embodiments, these desired properties are achieved through use of a complexing agent, particularly cyclodextrins, which act enhance the solubility of the compound at elevated pHs (e.g. pHs as high as about 5.5, or another pH near the low end of the buffering capacity of the particular compound of interest). In some embodiments, these attributes are further enhanced through the use modified cyclodextrins, particularly cyclodextrins modified by sulfonate functional groups (e.g. a sulfobutylether-beta-cyclodextrin (SBEBCD). In some embodiments, use of a cyclodextrin modified to replace the sodium in the sodium sulfonate salt functional groups to form sulfonic acid functional groups (e.g. SBEBCD) is particularly advantageous, as the sulfonic acidic functional groups can act as the counter-anion to protonate the non-ionized or freebase form of the compound. In such embodiments, a low osmolality in a high concentration pharmaceutical compound formulation is achieved because additional salts and counterions can be omitted from the formulation. Thus, high concentrations of compounds at pH levels compatible with subcutaneous injection can be achieved at osmolalities comparable to physiological levels (~300 mOsm/kg), thus enabling the subcutaneous administration of compounds without side effects such as pain or injection site irritation.

In some embodiments, the pharmaceutical composition is a solution. In some embodiments, the pharmaceutical composition is a solid. In some embodiments, the pharmaceutical composition has a pH >about 4.

In some embodiments, the pharmaceutical composition has a pH of about 4 to about 7. In some embodiments, the pharmaceutical composition has a pH of about 4 to about 7. In some embodiments, the pharmaceutical composition has a pH of about 4 to about 4.5, about 4 to about 5, about 4 to about 5.5, about 4 to about 6, about 4 to about 6.5, about 4 to about 7, about 4.5 to about 5, about 4.5 to about 5.5, about 4.5 to about 6, about 4.5 to about 6.5, about 4.5 to about 7, about 5 to about 5.5, about 5 to about 6, about 5 to about 6.5, about 5 to about 7, about 5.5 to about 6, about 5.5 to about 6.5, about 5.5 to about 7, about 6 to about 6.5, about 6 to about 7, or about 6.5 to about 7. In some embodiments, the pharmaceutical composition has a pH of about 4, about 4.5, about 5, about 5.5, about 6, about 6.5, or about 7. In some embodiments, the pharmaceutical composition has a pH of at least about 4, about 4.5, about 5, about 5.5, about 6, or about 6.5. In some embodiments, the pharmaceutical composition has a pH of at most about 4.5, about 5, about 5.5, about 6, about 6.5, or about 7.

In some embodiments, the pharmaceutical composition has a pH of about 4.5 to about 6.5.

In some embodiments, the pharmaceutical composition has an osmolality of from about 250 mOsm/kg to about 850 mOsm/kg. In some embodiments, the pharmaceutical composition has an osmolality of from about 275 mOsm/kg to about 850 mOsm/kg. In some embodiments, the pharmaceutical composition has an osmolality of from about 300 mOsm/kg to about 850 mOsm/kg. In some embodiments, the pharmaceutical composition has an osmolality of from about 325 mOsm/kg to about 850 mOsm/kg. In some embodiments, the pharmaceutical composition has an osmolality of from about 350 mOsm/kg to about 850 mOsm/kg. In some embodiments, the pharmaceutical composition has an osmolality of from about 375 mOsm/kg to about 850 mOsm/kg. In some embodiments, the pharmaceutical composition has an osmolality of from about 400 mOsm/kg to about 850 mOsm/kg. In some embodiments, the pharmaceutical composition has an osmolality of from about 300 mOsm/kg to about 450 mOsm/kg. In some embodiments, the pharmaceutical composition has an osmolality of from about 475 mOsm/kg to about 850 mOsm/kg. In some embodiments, the pharmaceutical composition has an osmolality of from about 500 mOsm/kg to about 850 mOsm/kg.

In some embodiments, the pharmaceutical composition has an osmolality of at least about 250 mOsm/kg. In some embodiments, the pharmaceutical composition has an osmolality of at least about 275 mOsm/kg. In some embodiments, the pharmaceutical composition has an osmolality of at least about 300 mOsm/kg. In some embodiments, the pharmaceutical composition has an osmolality of at least about 325 mOsm/kg. In some embodiments, the pharmaceutical composition has an osmolality of at least about 350 mOsm/kg. In some embodiments, the pharmaceutical composition has an osmolality of at least about 375 mOsm/kg. In some embodiments, the pharmaceutical composition has an osmolality of at least about 400 mOsm/kg. In some embodiments, the pharmaceutical composition has an osmolality of at least about 425 mOsm/kg. In some embodiments, the pharmaceutical composition has an osmolality of at least about 450 mOsm/kg. In some embodiments, the pharmaceutical composition has an osmolality of at least about 475 mOsm/kg. In some embodiments, the pharmaceutical composition has an osmolality of at least about 500 mOsm/kg.

In some embodiments, the pharmaceutical composition has an osmolality of about <850 mOsm/kg. In some embodiments, the pharmaceutical composition has an osmolality of about <825 mOsm/kg. In some embodiments, the pharmaceutical composition has an osmolality of about <800 mOsm/kg. In some embodiments, the pharmaceutical composition has an osmolality of about <775 mOsm/kg. In some embodiments, the pharmaceutical composition has an osmolality of about <750 mOsm/kg. In some embodiments, the pharmaceutical composition has an osmolality of about <725 mOsm/kg. In some embodiments, the pharmaceutical composition has an osmolality of about <700 mOsm/kg. In some embodiments, the pharmaceutical composition has an osmolality of about <675 mOsm/kg. In some embodiments, the pharmaceutical composition has an osmolality of about <650 mOsm/kg. In some embodiments, the pharmaceutical composition has an osmolality of about <625 mOsm/kg. In some embodiments, the pharmaceutical composition has an osmolality of about <600 mOsm/kg. In some embodiments, the pharmaceutical composition has an osmolality of about <575 mOsm/kg. In some embodiments, the pharmaceutical composition has an osmolality of about <550 mOsm/kg. In some embodiments, the pharmaceutical composition has an osmolality of about <525 mOsm/kg. In some embodiments, the pharmaceutical composition has an osmolality of about <500 mOsm/kg. In some embodiments, the pharmaceutical composition has an osmolality of about <450 mOsm/kg. In some embodiments, the pharmaceutical composition has an osmolality of about <400 mOsm/kg. In some embodiments, the pharmaceutical composition has an osmolality of about <350 mOsm/kg.

In some embodiments, the pharmaceutical composition has an osmolality of about 300 mOsm/kg to about 850 mOsm/kg. In some embodiments, the pharmaceutical composition has an osmolality of about 300 mOsm/kg to about 350 mOsm/kg, about 300 mOsm/kg to about 400 mOsm/kg, about 300 mOsm/kg to about 450 mOsm/kg, about 300 mOsm/kg to about 500 mOsm/kg, about 300 mOsm/kg to about 550 mOsm/kg, about 300 mOsm/kg to about 600 mOsm/kg, about 300 mOsm/kg to about 650 mOsm/kg, about 300 mOsm/kg to about 700 mOsm/kg, about 300 mOsm/kg to about 750 mOsm/kg, about 300 mOsm/kg to about 800 mOsm/kg, about 300 mOsm/kg to about 850 mOsm/kg, about 350 mOsm/kg to about 400 mOsm/kg, about 350 mOsm/kg to about 450 mOsm/kg, about 350 mOsm/kg to about 500 mOsm/kg, about 350 mOsm/kg to about 550 mOsm/kg, about 350 mOsm/kg to about 600 mOsm/kg, about 350 mOsm/kg to about 650 mOsm/kg, about 350 mOsm/kg to about 700 mOsm/kg, about 350 mOsm/kg to about 750 mOsm/kg, about 350 mOsm/kg to about 800 mOsm/kg, about 350 mOsm/kg to about 850 mOsm/kg, about 400 mOsm/kg to about 450 mOsm/kg, about 400 mOsm/kg to about 500 mOsm/kg, about 400 mOsm/kg to about 550 mOsm/kg, about 400 mOsm/kg to about 600 mOsm/kg, about 400 mOsm/kg to about 650 mOsm/kg, about 400 mOsm/kg to about 700 mOsm/kg, about 400 mOsm/kg to about 750 mOsm/kg, about 400 mOsm/kg to about 800 mOsm/kg, about 400 mOsm/kg to about 850 mOsm/kg, about 450 mOsm/kg to about 500 mOsm/kg, about 450 mOsm/kg to about 550 mOsm/kg, about 450 mOsm/kg to about 600 mOsm/kg, about 450 mOsm/kg to about 650 mOsm/kg, about 450 mOsm/kg to about 700 mOsm/kg, about 450 mOsm/kg to about 750 mOsm/kg, about 450 mOsm/kg to about 800 mOsm/kg, about 450 mOsm/kg to about 850 mOsm/kg, about 500 mOsm/kg to about 550 mOsm/kg, about 500 mOsm/kg to about 600 mOsm/kg, about 500 mOsm/kg to about 650 mOsm/kg, about 500 mOsm/kg to about 700 mOsm/kg, about 500 mOsm/kg to about 750 mOsm/kg, about 500 mOsm/kg to about 800 mOsm/kg, about 500 mOsm/kg to about 850 mOsm/kg, about 550 mOsm/kg to about 600 mOsm/kg, about 550 mOsm/kg to about 650 mOsm/kg, about 550 mOsm/kg to about 700 mOsm/kg, about 550 mOsm/kg to about 750 mOsm/kg, about 550 mOsm/kg to about 800 mOsm/kg, about 550 mOsm/kg to about 850 mOsm/kg, about 600 mOsm/kg to about 650 mOsm/kg, about 600 mOsm/kg to about 700 mOsm/kg, about 600 mOsm/kg to about 750 mOsm/kg, about 600 mOsm/kg to about 800 mOsm/kg, about 600 mOsm/kg to about 850 mOsm/kg, about 650 mOsm/kg to about 700 mOsm/kg, about 650 mOsm/kg to about 750 mOsm/kg, about 650 mOsm/kg to about 800 mOsm/kg, about 650 mOsm/kg to about 850 mOsm/kg, about 700 mOsm/kg to about 750 mOsm/kg, about 700 mOsm/kg to about 800 mOsm/kg, about 700 mOsm/kg to about 850 mOsm/kg, about 750 mOsm/kg to about 800 mOsm/kg, about 750 mOsm/kg to about 850 mOsm/kg, or about 800 mOsm/kg to about 850 mOsm/kg. In some embodiments, the pharmaceutical composition has an osmolality of about 300 mOsm/kg, about 350 mOsm/kg, about 400 mOsm/kg, about 450 mOsm/kg, about 500 mOsm/kg, about 550 mOsm/kg, about 600 mOsm/kg, about 650 mOsm/kg, about 700 mOsm/kg, about 750 mOsm/kg, about 800 mOsm/kg, or about 850 mOsm/kg. In some embodiments, the pharmaceutical composition has an osmolality of at least about 300 mOsm/kg, about 350 mOsm/kg, about 400 mOsm/kg, about 450 mOsm/kg, about 500 mOsm/kg, about 550 mOsm/kg, about 600 mOsm/kg, about 650 mOsm/kg, about 700 mOsm/kg, about 750 mOsm/kg, or about 800 mOsm/kg. In some embodiments, the pharmaceutical composition has an osmolality of at most about 350 mOsm/kg, about 400 mOsm/kg, about 450 mOsm/kg, about 500 mOsm/kg, about 550 mOsm/kg, about 600 mOsm/kg, about 650 mOsm/kg, about 700 mOsm/kg, about 750 mOsm/kg, about 800 mOsm/kg, or about 850 mOsm/kg.

In some embodiments, the pharmaceutical composition is isotonic.

In some embodiments, the pharmaceutical composition has an osmolality of about 500 mOsm/kg.

In some embodiments, the pharmaceutical compound or an enantiomer, a mixture of enantiomers, or an isotopic variant thereof; or solvate or hydrate thereof, has a concentration of about 20 mg/mL to about 150 mg/mL. In some embodiments, the pharmaceutical compound or an enantiomer, a mixture of enantiomers, or an isotopic variant thereof; or solvate or hydrate thereof, has a concentration up to about 150 mg/mL. In some embodiments, the pharmaceutical compound or an enantiomer, a mixture of enantiomers, or an isotopic variant thereof; or solvate or hydrate thereof, has a concentration at least about 20 mg/mL.

In some embodiments, the pharmaceutical compound, or an enantiomer, a mixture of enantiomers, or an isotopic variant thereof; or solvate or hydrate thereof, has a concentration of about 80 mg/mL to about 120 mg/mL.

In some embodiments, the pharmaceutical compound, or an enantiomer, a mixture of enantiomers, or an isotopic variant thereof; or solvate or hydrate thereof, has a concentration of about 95 mg/mL to about 105 mg/mL.

In some embodiments, the pharmaceutical compound, or an enantiomer, a mixture of enantiomers, or an isotopic variant thereof; or solvate or hydrate thereof, has a concentration of about 20 mg/mL. In some embodiments, the pharmaceutical compound, or an enantiomer, a mixture of enantiomers, or an isotopic variant thereof; or solvate or hydrate thereof, has a concentration of about 25 mg/mL. In some embodiments, the pharmaceutical compound, or an enantiomer, a mixture of enantiomers, or an isotopic variant thereof; or solvate or hydrate thereof, has a concentration of about 30 mg/mL. In some embodiments, the pharmaceutical compound, or an enantiomer, a mixture of enantiomers, or an isotopic variant thereof; or solvate or hydrate thereof, has a concentration of about 35 mg/mL. In some embodiments, the pharmaceutical compound, or an enantiomer, a mixture of enantiomers, or an isotopic variant thereof; or solvate or hydrate thereof, has a concentration of about 40 mg/mL. In some embodiments, the pharmaceutical compound, or an enantiomer, a mixture of enantiomers, or an isotopic variant thereof; or solvate or hydrate thereof, has a concentration of about 45 mg/mL. In some embodiments, the pharmaceutical compound, or an enantiomer, a mixture of enantiomers, or an isotopic variant thereof; or solvate or hydrate thereof, has a concentration of about 50 mg/mL. In some embodiments, the pharmaceutical compound, or an enantiomer, a mixture of enantiomers, or an isotopic variant thereof; or solvate or hydrate thereof, has a concentration of about 55 mg/mL. In some embodiments, the pharmaceutical compound, or an enantiomer, a mixture of enantiomers, or an isotopic variant thereof; or solvate or hydrate thereof, has a concentration of about 60 mg/mL. In some embodiments, the pharmaceutical compound, or an enantiomer, a mixture of enantiomers, or an isotopic variant thereof; or solvate or hydrate thereof, has a concentration of about 65 mg/mL. In some embodiments, the pharmaceutical compound, or an enantiomer, a mixture of enantiomers, or an isotopic variant thereof; or solvate or hydrate thereof, has a concentration of about 70 mg/mL. In some embodiments, the pharmaceutical compound, or an enantiomer, a mixture of enantiomers, or an isotopic variant thereof; or solvate or hydrate thereof, has a concentration of about 75 mg/mL. In some embodiments, the pharmaceutical compound, or an enantiomer, a mixture of enantiomers, or an isotopic variant thereof; or solvate or hydrate thereof, has a concentration of about 80 mg/mL. In some embodiments, the pharmaceutical compound, or an enantiomer, a mixture of enantiomers, or an isotopic variant thereof; or solvate or hydrate thereof, has a concentration of about 85 mg/mL. In some embodiments, the pharmaceutical compound, or an enantiomer, a mixture of enantiomers, or an isotopic variant thereof; or solvate or hydrate thereof, has a concentration of about 90 mg/mL. In some embodiments, the pharmaceutical compound, or an enantiomer, a mixture of enantiomers, or an isotopic variant thereof; or solvate or hydrate thereof, has a concentration of about 95 mg/mL. In some embodiments, the pharmaceutical compound, or an enantiomer, a mixture of enantiomers, or an isotopic variant thereof; or solvate or hydrate thereof, has a concentration of about 100 mg/mL. In some embodiments, the pharmaceutical compound, or an enantiomer, a mixture of enantiomers, or an isotopic variant thereof; or solvate or hydrate thereof, has a concentration of about 105 mg/mL. In some embodiments, the pharmaceutical compound, or an enantiomer, a mixture of enantiomers, or an isotopic variant thereof; or solvate or hydrate thereof, has a concentration of about 110 mg/mL. In some embodiments, the pharmaceutical compound, or an enantiomer, a mixture of enantiomers, or an isotopic variant thereof; or solvate or hydrate thereof, has a concentration of about 115 mg/mL. In some embodiments, the pharmaceutical compound, or an enantiomer, a mixture of enantiomers, or an isotopic variant thereof; or solvate or hydrate thereof, has a concentration of about 120 mg/mL. In some embodiments, the pharmaceutical compound, or an enantiomer, a mixture of enantiomers, or an isotopic variant thereof; or solvate or hydrate thereof, has a concentration of about 125 mg/mL. In some embodiments, the pharmaceutical compound, or an enantiomer, a mixture of enantiomers, or an isotopic variant thereof; or solvate or hydrate thereof, has a concentration of about 130 mg/mL. In some embodiments, the pharmaceutical compound, or an enantiomer, a mixture of enantiomers, or an isotopic variant thereof; or solvate or hydrate thereof, has a concentration of about 135 mg/mL. In some embodiments, the pharmaceutical compound, or an enantiomer, a mixture of enantiomers, or an isotopic variant thereof; or solvate or hydrate thereof, has a concentration of about 140 mg/mL. In some embodiments, the pharmaceutical compound, or an enantiomer, a mixture of enantiomers, or an isotopic variant thereof; or solvate or hydrate thereof, has a concentration of about 145 mg/mL. In some embodiments, the pharmaceutical compound, or an enantiomer, a mixture of enantiomers, or an isotopic variant thereof; or solvate or hydrate thereof, has a concentration of about 150 mg/mL.

In some embodiments, the pharmaceutical compound, or an enantiomer, a mixture of enantiomers, or an isotopic variant thereof; or solvate or hydrate thereof, has a concentration of about 95 mg/mL, about 96 mg/mL, about 97 mg/mL, about 98 mg/mL, about 99 mg/mL, about 100 mg/mL, about 101 mg/mL, 102 mg/mL, about 103 mg/mL, about 104 mg/mL, or about 105 mg/mL.

In some embodiments, the pharmaceutical compound or an enantiomer, a mixture of enantiomers, or an isotopic variant thereof; or solvate or hydrate thereof, has a concentration of about 20 mg/mL to about 150 mg/mL. In some embodiments, the pharmaceutical compound or an enantiomer, a mixture of enantiomers, or an isotopic variant thereof; or solvate or hydrate thereof, has a concentration of about 20 mg/mL to about 40 mg/mL, about 20 mg/mL to about 60 mg/mL, about 20 mg/mL to about 80 mg/mL, about 20 mg/mL to about 100 mg/mL, about 20 mg/mL to about 120 mg/mL, about 20 mg/mL to about 140 mg/mL, about 20 mg/mL to about 150 mg/mL, about 40 mg/mL to about 60 mg/mL, about 40 mg/mL to about 80 mg/mL, about 40 mg/mL to about 100 mg/mL, about 40 mg/mL to about 120 mg/mL, about 40 mg/mL to about 140 mg/mL, about 40 mg/mL to about 150 mg/mL, about 60 mg/mL to about 80 mg/mL, about 60 mg/mL to about 100 mg/mL, about 60 mg/mL to about 120 mg/mL, about 60 mg/mL to about 140 mg/mL, about 60 mg/mL to about 150 mg/mL, about 80 mg/mL to about 100 mg/mL, about 80 mg/mL to about 120 mg/mL, about 80 mg/mL to about 140 mg/mL, about 80 mg/mL to about 150 mg/mL, about 100 mg/mL to about 120 mg/mL, about 100 mg/mL to about 140 mg/mL, about 100 mg/mL to about 150 mg/mL, about 120 mg/mL to about 140 mg/mL, about 120 mg/mL to about 150 mg/mL, or about 140 mg/mL to about 150 mg/mL. In some embodiments, the pharmaceutical compound or an enantiomer, a mixture of enantiomers, or an isotopic variant thereof; or solvate or hydrate thereof, has a concentration of about 20 mg/mL, about 40 mg/mL, about 60 mg/mL, about 80 mg/mL, about 100 mg/mL, about 120 mg/mL, about 140 mg/mL, or about 150 mg/mL. In some embodiments, the pharmaceutical compound or an enantiomer, a mixture of enantiomers, or an isotopic variant thereof; or solvate or hydrate thereof, has a concentration of at least about 20 mg/mL, about 40 mg/mL, about 60 mg/mL, about 80 mg/mL, about 100 mg/mL, about 120 mg/mL, or about 140 mg/mL. In some embodiments, the pharmaceutical compound or an enantiomer, a mixture of enantiomers, or an isotopic variant thereof; or solvate or hydrate thereof, has a concentration of at most about 40 mg/mL, about 60 mg/mL, about 80 mg/mL, about 100 mg/mL, about 120 mg/mL, about 140 mg/mL, or about 150 mg/mL.

In some embodiments, the cyclodextrin is present in an amount of about 50 mg/mL to about 600 mg/mL. In some embodiments, the cyclodextrin is present in an amount of about 10 mg/mL to about 600 mg/mL. In some embodiments, the cyclodextrin is present in an amount of about 50 mg/mL to about 600 mg/mL. In some embodiments, the cyclodextrin is present in an amount of about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 200 mg/mL to about 300 mg/mL, about 200 mg/mL to about 400 mg/mL, about 200 mg/mL to about 500 mg/mL, about 200 mg/mL to about 600 mg/mL, about 300 mg/mL to about 400 mg/mL, about 300 mg/mL to about 500 mg/mL, about 300 mg/mL to about 600 mg/mL, about 400 mg/mL to about 500 mg/mL, about 400 mg/mL to about 600 mg/mL, or about 500 mg/mL to about 600 mg/mL. In some embodiments, the cyclodextrin is present in an amount of about 50 mg/mL, about 100 mg/mL, about 200 mg/mL, about 300 mg/mL, about 400 mg/mL, about 500 mg/mL, or about 600 mg/mL. In some embodiments, the cyclodextrin is present in an amount of at least about 50 mg/mL, about 100 mg/mL, about 200 mg/mL, about 300 mg/mL, about 400 mg/mL, or about 500 mg/mL. In some embodiments, the cyclodextrin is present in an amount of at most about 100 mg/mL, about 200 mg/mL, about 300 mg/mL, about 400 mg/mL, about 500 mg/mL, or about 600 mg/mL.

In some embodiments, the pharmaceutical composition further comprises a preservative. In some embodiments, the preservative is benzethonium chloride. In some embodiments, the benzethonium chloride is present in an amount of about 0.1 mg/mL to about 0.5 mg/mL. In some embodiments, the preservative is benzethonium chloride, benzalkonium chloride, or chloroxylenol. Other preservatives include benzyl alcohol, methyl parabens, ethyl or n-propyl, and p-hydroxybenzoate. In some embodiments, preservatives are antimicrobial agents, including, but not limited to: Phenol, Meta-cresol, Benzyl alcohol, parabens (methyl, propyl, or butyl), benzalkonium chloride, benzethonium chloride, chlorobutanol, Myristyl gamma picolinium chloride, 2-phenoxyethanol, Phenethyl alcohol, Sorbates (sorbic acid, sodium sorbate), Ethanol, and/or Propylene glycol. In some embodiments, the preservative is present in an amount of about 0.1 mg/mL to about 1 mg/mL. In some embodiments, the preservative is present in an amount of about 0.1 mg/mL to about 0.2 mg/mL, about 0.1 mg/mL to about 0.3 mg/mL, about 0.1 mg/mL to about 0.4 mg/mL, about 0.1 mg/mL to about 0.5 mg/mL, about 0.1 mg/mL to about 0.6 mg/mL, about 0.1 mg/mL to about 0.7 mg/mL, about 0.1 mg/mL to about 0.8 mg/mL, about 0.1 mg/mL to about 0.9 mg/mL, about 0.1 mg/mL to about 1 mg/mL, about 0.2 mg/mL to about 0.3 mg/mL, about 0.2 mg/mL to about 0.4 mg/mL, about 0.2 mg/mL to about 0.5 mg/mL, about 0.2 mg/mL to about 0.6 mg/mL, about 0.2 mg/mL to about 0.7 mg/mL, about 0.2 mg/mL to about 0.8 mg/mL, about 0.2 mg/mL to about 0.9 mg/mL, about 0.2 mg/mL to about 1 mg/mL, about 0.3 mg/mL to about 0.4 mg/mL, about 0.3 mg/mL to about 0.5 mg/mL, about 0.3 mg/mL to about 0.6 mg/mL, about 0.3 mg/mL to about 0.7 mg/mL, about 0.3 mg/mL to about 0.8 mg/mL, about 0.3 mg/mL to about 0.9 mg/mL, about 0.3 mg/mL to about 1 mg/mL, about 0.4 mg/mL to about 0.5 mg/mL, about 0.4 mg/mL to about 0.6 mg/mL, about 0.4 mg/mL to about 0.7 mg/mL, about 0.4 mg/mL to about 0.8 mg/mL, about 0.4 mg/mL to about 0.9 mg/mL, about 0.4 mg/mL to about 1 mg/mL, about 0.5 mg/mL to about 0.6 mg/mL, about 0.5 mg/mL to about 0.7 mg/mL, about 0.5 mg/mL to about 0.8 mg/mL, about 0.5 mg/mL to about 0.9 mg/mL, about 0.5 mg/mL to about 1 mg/mL, about 0.6 mg/mL to about 0.7 mg/mL, about 0.6 mg/mL to about 0.8 mg/mL, about 0.6 mg/mL to about 0.9 mg/mL, about 0.6 mg/mL to about 1 mg/mL, about 0.7 mg/mL to about 0.8 mg/mL, about 0.7 mg/mL to about 0.9 mg/mL, about 0.7 mg/mL to about 1 mg/mL, about 0.8 mg/mL to about 0.9 mg/mL, about 0.8 mg/mL to about 1 mg/mL, or about 0.9 mg/mL to about 1 mg/mL. In some embodiments, the preservative is present in an amount of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL. In some embodiments, the preservative is present in an amount of about at least about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, or about 0.9 mg/mL. In some embodiments, the preservative is present in an amount of about at most about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, or about 1 mg/mL.

In some embodiments of the pharmaceutical compositions disclosed herein, the form is a subcutaneous (e.g., infusion or bolus) dosage form. In some embodiments of the pharmaceutical composition, wherein the form is a subcutaneous dosage form, the pH is from about 3.0 to about 7.0. In some embodiments of the pharmaceutical composition, wherein the form is a subcutaneous dosage form, the pH is from about 4.0 to about 5.0. In some embodiments of the pharmaceutical composition, wherein the form is a subcutaneous dosage form, the pH is from about 4.5 to about 5.5. In some embodiments of the pharmaceutical composition, wherein the form is a subcutaneous dosage form, the pH is from about 5.0 to about 6.0. In some embodiments of the pharmaceutical composition, wherein the form is a subcutaneous dosage form, the pH is from about 5.5 to about 6.5. In some embodiments of the pharmaceutical composition, wherein the form is a subcutaneous dosage form, the pH is from about 6.0 to about 7.0. In some embodiments of the pharmaceutical composition, wherein the form is a subcutaneous dosage form, the pH is about 3.0. In some embodiments of the pharmaceutical composition, wherein the form is a subcutaneous dosage form, the pH is about 3.5. In some embodiments of the pharmaceutical composition, wherein the form is a subcutaneous dosage form, the pH is about 4.0. In some embodiments of the pharmaceutical composition, wherein the form is a subcutaneous dosage form, the pH is about 4.5. In some embodiments of the pharmaceutical composition, wherein the form is a subcutaneous dosage form, the pH is about 5.0. In some embodiments of the pharmaceutical composition, wherein the form is a subcutaneous dosage form, the pH is about 5.1. In some embodiments of the pharmaceutical composition, wherein the form is a subcutaneous dosage form, the pH is about 5.2. In some embodiments of the pharmaceutical composition, wherein the form is a subcutaneous dosage form, the pH is about 5.3. In some embodiments of the pharmaceutical composition, wherein the form is a subcutaneous dosage form, the pH is about 5.4. In some embodiments of the pharmaceutical composition, wherein the form is a subcutaneous dosage form, the pH is about 5.5. In some embodiments of the pharmaceutical composition, wherein the form is a subcutaneous dosage form, the pH is about 5.6. In some embodiments of the pharmaceutical composition, wherein the form is a subcutaneous dosage form, the pH is about 5.7. In some embodiments of the pharmaceutical composition, wherein the form is a subcutaneous dosage form, the pH is about 5.8. In some embodiments of the pharmaceutical composition, wherein the form is a subcutaneous dosage form, the pH is about 5.9. In some embodiments of the pharmaceutical composition, wherein the form is a subcutaneous dosage form, the pH is about 6.0. In some embodiments of the pharmaceutical composition, wherein the form is a subcutaneous dosage form, the pH is about 6.5. In some embodiments of the pharmaceutical composition, wherein the form is a subcutaneous dosage form, the pH is about 7.0.

Intranasal Formulations

In some aspects, the pharmaceutical composition comprising the pharmaceutical compound provided herein is formulated for intranasal administration. While many traditional approaches to intranasal administration of pharmaceutical compounds face distinct challenges due to poor tissue tolerability (e.g. burning, nosebleeds, infections), bioavailability, and rate of tissue uptake, the pharmaceutical compositions comprising the complexing agent salts provided herein overcome many of these difficulties. In some cases, the complexing agent/pharmaceutical compound salts allow for delivery of the selected compound at a targeted pH to match natural tissue conditions while maintaining an osmolality that is also compatible with the nasal tissue. Additionally, in some cases, the presence of the complexing agent ionically associated with the pharmaceutical compound helps to solubilize the non-ionized compound component as the pharmaceutical composition is deposited in the nasal tissue and ions and other compounds exchange with the components of nasal mucosa to allow uptake of the compounds. In some cases, the presence of the complexing agent in the formulation also allows enhanced solubility of the pharmaceutical compound at the pH of the surrounding nasal mucosa after delivery.

Additionally, in some embodiments, a pharmaceutical composition comprising the complexing agent/pharmaceutical compound salts provided herein comprise additional equivalents of the pharmaceutical compound that is not ionically associated with the complexing agent, such as unionized pharmaceutical compound or ionized with a different counterion. When additional unionized pharmaceutical compound is used, the complexing agent (e.g., a cyclodextrin such as SBEBCD) may complex with this additional pharmaceutical compound through non-ionic interactions. Additionally, the pharmaceutical composition may further comprise additional equivalents unionized pharmaceutical compound relative to the amount complexing agent present (e.g. up to 20 or more molar equivalents of free base pharmaceutical compound). When a substantial excess of pharmaceutical compound is present, the cyclodextrin can deliver and solubilize one equivalent of the pharmaceutical compound at a time through complexation interactions with the core of the cyclodextrin, and can further act in a shuttle-like mechanism to further solubilize the additional molar equivalents of free base pharmaceutical compound which may also be present. When such a formulation is administered, bioavailability and tolerability may be increased due to the presence of an amount of unionized pharmaceutical compound. This may occur for multiple reasons, including that free base (unionized) pharmaceutical compound is more readily uptaken by the pertinent cells and distributed to the targeted tissue in the body (e.g. by passive diffusion). Additionally, the presence of additional unionized pharmaceutical compound can act as a buffer to aid in achieving the desired pH of the localized tissue (depending on the amount of unionized pharmaceutical compound added and the pKa of the pharmaceutical compound). In some embodiments, the desired pH can thus be achieved without the presence of additional base or buffer.

In some embodiments, the pharmaceutical composition comprising the complexing agent/pharmaceutical compound salt is formulated for intranasal administration. In some embodiments, the pharmaceutical composition is formulated as an inhalable powder for intranasal administration. In some embodiments, the pharmaceutical composition is formulated as a liquid suspension for intranasal administration. In some embodiments, the pharmaceutical composition is formulated as a liquid solution for intranasal administration. In some embodiments, the liquid suspension is an aqueous suspension. In some embodiments, the liquid solution is an aqueous solution.

In some embodiments, the pharmaceutical composition comprises additional equivalents of the pharmaceutical compound. In some embodiments, the pharmaceutical composition comprises additional molar equivalents of the pharmaceutical compound. In some embodiments, the additional equivalents are measured as compared to the moles of complexing agent. In some embodiments, the additional equivalents are measured as compared to the moles of the pharmaceutical compound which forms a salt with the complexing agent.

In some embodiments, the pharmaceutical composition comprises additional equivalents of unionized pharmaceutical compound compared to the protonated pharmaceutical compound of the complexing agent/protonated pharmaceutical compound salt. In some embodiments, the pharmaceutical composition comprises about 0.01 molar equivalents to about 10 molar equivalents of the unionized pharmaceutical compound. In some embodiments, the pharmaceutical composition comprises about 0.1 molar equivalents to about 1 molar equivalents of the unionized pharmaceutical compound. In some embodiments, the pharmaceutical composition comprises about 0.01 molar equivalents to about 1 molar equivalents of the unionized pharmaceutical compound. In some embodiments, the pharmaceutical composition comprises about 0.1 molar equivalents to about 0.2 molar equivalents, about 0.1 molar equivalents to about 0.5 molar equivalents, about 0.1 molar equivalents to about 0.75 molar equivalents, about 0.1 molar equivalents to about 1 molar equivalents, about 0.2 molar equivalents to about 0.5 molar equivalents, about 0.2 molar equivalents to about 0.75 molar equivalents, about 0.2 molar equivalents to about 1 molar equivalents, about 0.5 molar equivalents to about 0.75 molar equivalents, about 0.5 molar equivalents to about 1 molar equivalents, or about 0.75 molar equivalents to about 1 molar equivalents of the unionized pharmaceutical compound. In some embodiments, the pharmaceutical composition comprises about 0.1 molar equivalents, about 0.2 molar equivalents, about 0.5 molar equivalents, about 0.75 molar equivalents, or about 1 molar equivalents of the unionized pharmaceutical compound. In some embodiments, the pharmaceutical composition comprises at least about 0.1 molar equivalents, about 0.2 molar equivalents, about 0.5 molar equivalents, or about 0.75 molar equivalents of the unionized pharmaceutical compound. In some embodiments, the pharmaceutical composition comprises at most about 0.2 molar equivalents, about 0.5 molar equivalents, about 0.75 molar equivalents, or about 1 molar equivalents of the unionized pharmaceutical compound. In some embodiments, the pharmaceutical composition comprises about 0.5 equivalents to about 5 equivalents of the unionized pharmaceutical compound. In some embodiments, the pharmaceutical composition comprises about 0.5 equivalents to about 1 equivalents, about 0.5 equivalents to about 2 equivalents, about 0.5 equivalents to about 3 equivalents, about 0.5 equivalents to about 4 equivalents, about 0.5 equivalents to about 5 equivalents, about 1 equivalents to about 2 equivalents, about 1 equivalents to about 3 equivalents, about 1 equivalents to about 4 equivalents, about 1 equivalents to about 5 equivalents, about 2 equivalents to about 3 equivalents, about 2 equivalents to about 4 equivalents, about 2 equivalents to about 5 equivalents, about 3 equivalents to about 4 equivalents, about 3 equivalents to about 5 equivalents, or about 4 equivalents to about 5 equivalents of the unionized pharmaceutical compound. In some embodiments, the pharmaceutical composition comprises about 0.5 equivalents, about 1 equivalents, about 2 equivalents, about 3 equivalents, about 4 equivalents, or about 5 equivalents of the unionized pharmaceutical compound. In some embodiments, the pharmaceutical composition comprises at least about 0.5 equivalents, about 1 equivalents, about 2 equivalents, about 3 equivalents, or about 4 equivalents of the unionized pharmaceutical compound. In some embodiments, the pharmaceutical composition comprises at most about 1 equivalents, about 2 equivalents, about 3 equivalents, about 4 equivalents, or about 5 equivalents of the unionized pharmaceutical compound.

In some embodiments, the pharmaceutical composition comprises a sufficient amount of unionized pharmaceutical compound to form a buffering system with the ionized pharmaceutical compound in the composition. In some embodiments, the buffering system is at a desired pH. In some embodiments, the buffering system results in a desired pH when administered to nasal tissue.

In some embodiments, the buffering system results in a pH within a target range of the pKa value of the pharmaceutical compound. In some embodiments, the target pH is within about 0.2 pH units to about 2 pH units of the pKa value. In some embodiments, the target pH is within about 0.2 pH units to about 0.5 pH units, about 0.2 pH units to about 1 pH units, about 0.2 pH units to about 1.5 pH units, about 0.2 pH units to about 2 pH units, about 0.5 pH units to about 1 pH units, about 0.5 pH units to about 1.5 pH units, about 0.5 pH units to about 2 pH units, about 1 pH units to about 1.5 pH units, about 1 pH units to about 2 pH units, or about 1.5 pH units to about 2 pH units of the pKa value. In some embodiments, the target pH is within about 0.2 pH units, about 0.5 pH units, about 1 pH units, about 1.5 pH units, or about 2 pH units of the pKa value. In some embodiments, the target pH is within at least about 0.2 pH units, about 0.5 pH units, about 1 pH units, or about 1.5 pH units of the pKa value. In some embodiments, the target pH is within at most about 0.5 pH units, about 1 pH units, about 1.5 pH units, or about 2 pH units of the pKa value.

In some embodiments, the buffering system results in a pH wherein a certain percentage of the pharmaceutical compound is ionized upon administration. In some embodiments, the buffering system results in a pH wherein about 1% to about 99% of the pharmaceutical compound is ionized. In some embodiments, the buffering system results in a pH wherein about 1% to about 5%, about 1% to about 10%, about 1% to about 25%, about 1% to about 50%, about 1% to about 70%, about 1% to about 90%, about 1% to about 95%, about 1% to about 99%, about 5% to about 10%, about 5% to about 25%, about 5% to about 50%, about 5% to about 70%, about 5% to about 90%, about 5% to about 95%, about 5% to about 99%, about 10% to about 25%, about 10% to about 50%, about 10% to about 70%, about 10% to about 90%, about 10% to about 95%, about 10% to about 99%, about 25% to about 50%, about 25% to about 70%, about 25% to about 90%, about 25% to about 95%, about 25% to about 99%, about 50% to about 70%, about 50% to about 90%, about 50% to about 95%, about 50% to about 99%, about 70% to about 90%, about 70% to about 95%, about 70% to about 99%, about 90% to about 95%, about 90% to about 99%, or about 95% to about 99% of the pharmaceutical compound is ionized. In some embodiments, the buffering system results in a pH wherein about 1%, about 5%, about 10%, about 25%, about 50%, about 70%, about 90%, about 95%, or about 99% of the pharmaceutical compound is ionized. In some embodiments, the buffering system results in a pH wherein at least about 1%, about 5%, about 10%, about 25%, about 50%, about 70%, about 90%, or about 95% of the pharmaceutical compound is ionized. In some embodiments, the buffering system results in a pH wherein at most about 5%, about 10%, about 25%, about 50%, about 70%, about 90%, about 95%, or about 99% of the pharmaceutical compound is ionized. In some embodiments, the percent ionization is measured immediately after administration.

In some embodiments, the pharmaceutical composition comprises additional molar equivalents of unionized pharmaceutical compound compared to complexing agent of the complexing agent/protonated pharmaceutical compound salt. In some embodiments, the pharmaceutical composition comprises about 0.01 molar equivalents to about 10 molar equivalents of unionized pharmaceutical compound compared to the complexing agent. In some embodiments, the pharmaceutical composition comprises about 0.1 molar equivalents to about 10 molar equivalents of unionized pharmaceutical compound. In some embodiments, the pharmaceutical composition comprises about 0.01 molar equivalents to about 1 molar equivalents of the unionized pharmaceutical compound. In some embodiments, the pharmaceutical composition comprises about 0.1 molar equivalents to about 0.5 molar equivalents, about 0.1 molar equivalents to about 1 molar equivalents, about 0.1 molar equivalents to about 2 molar equivalents, about 0.1 molar equivalents to about 3 molar equivalents, about 0.1 molar equivalents to about 5 molar equivalents, about 0.1 molar equivalents to about 7 molar equivalents, about 0.1 molar equivalents to about 10 molar equivalents, about 0.5 molar equivalents to about 1 molar equivalents, about 0.5 molar equivalents to about 2 molar equivalents, about 0.5 molar equivalents to about 3 molar equivalents, about 0.5 molar equivalents to about 5 molar equivalents, about 0.5 molar equivalents to about 7 molar equivalents, about 0.5 molar equivalents to about 10 molar equivalents, about 1 molar equivalents to about 2 molar equivalents, about 1 molar equivalents to about 3 molar equivalents, about 1 molar equivalents to about 5 molar equivalents, about 1 molar equivalents to about 7 molar equivalents, about 1 molar equivalents to about 10 molar equivalents, about 2 molar equivalents to about 3 molar equivalents, about 2 molar equivalents to about 5 molar equivalents, about 2 molar equivalents to about 7 molar equivalents, about 2 molar equivalents to about 10 molar equivalents, about 3 molar equivalents to about 5 molar equivalents, about 3 molar equivalents to about 7 molar equivalents, about 3 molar equivalents to about 10 molar equivalents, about 5 molar equivalents to about 7 molar equivalents, about 5 molar equivalents to about 10 molar equivalents, or about 7 molar equivalents to about 10 molar equivalents of unionized pharmaceutical compound of unionized pharmaceutical compound. In some embodiments, the pharmaceutical composition comprises about 0.1 molar equivalents, about 0.5 molar equivalents, about 1 molar equivalents, about 2 molar equivalents, about 3 molar equivalents, about 5 molar equivalents, about 7 molar equivalents, or about 10 molar equivalents of unionized pharmaceutical compound. In some embodiments, the pharmaceutical composition comprises at least about 0.1 molar equivalents, about 0.5 molar equivalents, about 1 molar equivalents, about 2 molar equivalents, about 3 molar equivalents, about 5 molar equivalents, or about 7 molar equivalents of unionized pharmaceutical compound. In some embodiments, the pharmaceutical composition comprises at most about 0.5 molar equivalents, about 1 molar equivalents, about 2 molar equivalents, about 3 molar equivalents, about 5 molar equivalents, about 7 molar equivalents, or about 10 molar equivalents of unionized pharmaceutical compound. In some embodiments, the pharmaceutical composition comprises about 0.01 molar equivalents to about 20 molar equivalents of unionized pharmaceutical compound compared to the complexing agent. In some embodiments, the pharmaceutical composition comprises about 1 molar equivalents to about 20 molar equivalents of unionized pharmaceutical compound compared to the complexing agent. In some embodiments, at least a portion these additional equivalents of the unionized pharmaceutical compound relative to the complexing agent are complexed to the complexing agent (e.g. up to about 1 molar equivalent of the unionized pharmaceutical compound).

In some embodiments, the pharmaceutical composition comprises a suitable carrier for intranasal administration. Carriers are usually inert and frequently function as a diluent for dispensing the therapeutic agent into a storage container like a capsule or in a device, or aid in the intranasal administration of the pharmaceutical compound. In some embodiments, a pharmaceutically acceptable carrier for the present compositions include but are not limited to amino acids, peptides, proteins, non-biological polymers, biological polymers, simple sugars, carbohydrates, gums, inorganic salts and metal compounds which may be present singularly or in combination. In some embodiments, the pharmaceutically acceptable carrier comprises native, derivatized, modified forms, or combinations thereof.

In some embodiments, useful proteins include, but are not limited to, gelatin or albumin. In some embodiments, useful sugars that can serve as pharmaceutically acceptable carriers include, but are not limited to fructose, galactose, glucose, lactitol, lactose, maltitol, maltose, mannitol, melezitose, myoinositol, palatinite, raffinose, stachyose, sucrose, trehalose, xylitol, hydrates thereof, and combinations of thereof.

In some embodiments, useful carbohydrates that can serve as pharmaceutically acceptable carriers include, but are not limited to starches such as corn starch, potato starch, amylose, amylopectin, pectin, hydroxypropyl starch, carboxymethyl starch, and cross-linked starch. In other embodiments, useful carbohydrates that can serve as pharmaceutically acceptable carriers include, but are not limited to cellulose, crystalline cellulose, microcrystalline cellulose, α-cellulose, methylcellulose, hydroxypropyl cellulose, carboxymethyl cellulose, ethyl cellulose, hydroxypropyl methyl cellulose, and cellulose acetate.

In another embodiment, useful inorganic salts or metal compounds include, but are not limited to aluminum, calcium, magnesium, silicon, and zinc salts. In some embodiments, the aluminum salts include for example, aluminum hydroxychloride, aluminum magnesium hydroxide, aluminum hydroxide, aluminum sulfate, aluminum stearate, aluminum monostearate and potassium aluminum sulfate. In other embodiments, the calcium salts include for example, apatite, hydroxyapatite, calcium carbonate, calcium chloride, calcium citrate, calcium silicate, calcium oxide, calcium hydroxide, calcium stearate, calcium phosphate tribasic, calcium lactate, calcium oleate, calcium palmirate, calcium hydrogenphosphate, calcium primary phosphate, calcium acetate, and calcium sulfate. In some embodiments, the magnesium compounds include, for example, magnesium chloride, magnesium aluminate silicate, magnesium silicate, magnesium oxide, magnesium hydroxide, magnesium stearate, magnesium carbonate, magnesium sulfate, and sodium magnesium silicate.

In some embodiments, the carrier is substantially water insoluble. In further embodiments, the substantially water insoluble carrier is selected from the group consisting of peptides, proteins, non-biological polymers, biological polymers, carbohydrates, gums, inorganic salts and metal compounds. In some embodiments, substantially water insoluble carbohydrates include cellulose, crystalline cellulose, and microcrystalline cellulose.

In some embodiments, the carrier is substantially water soluble. In further embodiments, the substantially water soluble carrier is selected from the group consisting of polysaccharides, sugars, salts, peptides, proteins, carbohydrates, non-biological polymers, biological polymers, gums, inorganic salts and metal compounds. In some embodiments, the substantially water soluble polysaccharide is cellulose. In some embodiments, the cellulose is hydroxypropyl cellulose, carboxymethyl cellulose, ethyl cellulose, hydroxypropyl methyl cellulose, or cellulose acetate. In other embodiments, the substantially water soluble polysaccharide is a starch. In some embodiments, the substantially water soluble starch is hydroxypropyl starch, carboxymethyl starch, cross-linked starch, amylose, amylopectin, or pectin and combinations of thereof. In some embodiments, the substantially water soluble sugar includes fructose, galactose, glucose, lactitol, lactose, maltitol, maltose, mannitol, melezitose, myoinositol, palatinite, raffinose, stachyose, sucrose, trehalose, xylitol, hydrates thereof, and combinations of thereof.

Usually, carriers have a mean particle size and/or particle size distribution that is substantially larger than that of the drug. The small particle size of therapeutic agents frequently exhibit very poor flow properties that compromise the filling accuracy of the dispensed agent when it is loaded into storage containers like capsules or into devices. The same poor flow properties will also impede aerosolisation or spray characteristics and compromise the intended amount of therapeutic agent to be delivered to the patient. By blending a microtine therapeutic agent with an excess of carrier that has a substantially larger median particle size, the flow properties of the composition will essentially determine the properties of the carrier thereby improving the handling characteristics required for accurate dispensing and administration.

For some formulations herein, the carrier particles have a mean particle size of at least 1 μm, at least 2 μm, at least 3 μm, at least 4 μm, at least 5 μm, at least 10 μm, at least 15 μm, at least 20 μm, at least, 25 μm, at least 30 μm, at least 40 μm, at least 50 μm, at least 60 μm, at least 70 μm, at least 80 μm, at least 90 μm, at least 100 μm, at least 150 μm, at least 200 μm, or at least 250 μm.

The intranasal pharmaceutical compositions may also comprise any of the other excipients provided herein, including without limitation any lubricant, fluidizer, surfactant, buffer, preservative, anti-oxidant, wetting agent, or any other such suitable excipient which is compatible with an intranasal formulation.

Sublingual Formulations

In some aspects, the pharmaceutical composition provided herein is formulated for sublingual administration. In some embodiments, pharmaceutical compounds with low bioavailability, slow onset of physiological effect, and compounds with substantial non-target effects on the gastrointestinal tract or liver are ideal compounds for use with sublingual formulations comprising the complexing agent/pharmaceutical compound salts as provided herein. As with the intranasal formulations provided herein, traditional sublingual approaches to formulations of pharmaceutical compounds suffer from drawbacks of poor bioavailability (in some cases due, at least in part, to poor solubility) as well as tissue irritation (e.g. burning or stinging sensations) in the mouth. The instant salts remedy this by enhancing solubility of the compounds at relatively high doses at tolerable pHs and concentrations without a substantial increase in osmolality compared to formulations made from salts of the complexing agents or the compounds, thus minimizing tissue irritation while also maximizing bioavailability and absorption.

Additionally, in some embodiments, a pharmaceutical composition comprising the complexing agent/pharmaceutical compound salts provided herein comprise additional equivalents of the pharmaceutical compound that is not ionically associated with the complexing agent, such as unionized pharmaceutical compound or ionized with a different counterion. When additional unionized pharmaceutical compound is used, the complexing agent (e.g., a cyclodextrin such as SBEBCD) may complex with this additional pharmaceutical compound through non-ionic interactions. When such a formulation is administered, bioavailability and tolerability may be increased due to the presence of an amount of unionized pharmaceutical compound. This may occur for multiple reasons, including that free base (unionized) pharmaceutical compound is more readily uptaken by the pertinent cells and distributed to the targeted tissue in the body (e.g. by passive diffusion). Additionally, the presence of additional unionized pharmaceutical compound, even beyond a 1:1 molar ratio of pharmaceutical compound: complexing agent (e.g., a ratio up to 20:1 or even higher) that would be expected to be complexed inside the complexing agent (e.g., a cyclodextrin such as SBEBCD) can act to improve the sublingual formulation. For example, the additional equivalents of free base compound can simultaneously act as a buffer, as an aid in achieving the desired pH of the localized tissue (depending on the amount of unionized pharmaceutical compound added and the pKa of the pharmaceutical compound), and as a source of unionized or free base drug product for absorption and update by the tissue (e.g. by mucosal absorption). In some embodiments, the desired pH can thus be achieved without the presence of additional base or buffer.

In some embodiments, the pharmaceutical composition comprising the complexing agent/pharmaceutical compound salt is formulated for sublingual administration. In some embodiments, the pharmaceutical composition is formulated as a sublingual tablet, a sublingual strip, a sublingual drop, a sublingual spray, a sublingual troche, or a lozenge.

In some embodiments, the pharmaceutical composition comprises additional equivalents of unionized pharmaceutical compound compared to the protonated pharmaceutical compound of the complexing agent/protonated pharmaceutical compound salt. In some embodiments, the pharmaceutical composition comprises about 0.01 molar equivalents to about 5 molar equivalents of the unionized pharmaceutical compound. In some embodiments, the pharmaceutical composition comprises about 0.1 molar equivalents to about 1 molar equivalents of the unionized pharmaceutical compound. In some embodiments, the pharmaceutical composition comprises about 0.1 molar equivalents to about 0.2 molar equivalents, about 0.1 molar equivalents to about 0.5 molar equivalents, about 0.1 molar equivalents to about 0.75 molar equivalents, about 0.1 molar equivalents to about 1 molar equivalents, about 0.2 molar equivalents to about 0.5 molar equivalents, about 0.2 molar equivalents to about 0.75 molar equivalents, about 0.2 molar equivalents to about 1 molar equivalents, about 0.5 molar equivalents to about 0.75 molar equivalents, about 0.5 molar equivalents to about 1 molar equivalents, or about 0.75 molar equivalents to about 1 molar equivalents. In some embodiments, the pharmaceutical composition comprises about 0.1 molar equivalents, about 0.2 molar equivalents, about 0.5 molar equivalents, about 0.75 molar equivalents, or about 1 molar equivalents of the unionized pharmaceutical compound. In some embodiments, the pharmaceutical composition comprises at least about 0.1 molar equivalents, about 0.2 molar equivalents, about 0.5 molar equivalents, or about 0.75 molar equivalents of the unionized pharmaceutical compound. In some embodiments, the pharmaceutical composition comprises at most about 0.2 molar equivalents, about 0.5 molar equivalents, about 0.75 molar equivalents, or about 1 molar equivalents of the unionized pharmaceutical compound. In some embodiments, the pharmaceutical composition comprises about 0.5 equivalents to about 5 equivalents of the unionized pharmaceutical compound. In some embodiments, the pharmaceutical composition comprises about 0.5 equivalents to about 1 equivalents, about 0.5 equivalents to about 2 equivalents, about 0.5 equivalents to about 3 equivalents, about 0.5 equivalents to about 4 equivalents, about 0.5 equivalents to about 5 equivalents, about 1 equivalents to about 2 equivalents, about 1 equivalents to about 3 equivalents, about 1 equivalents to about 4 equivalents, about 1 equivalents to about 5 equivalents, about 2 equivalents to about 3 equivalents, about 2 equivalents to about 4 equivalents, about 2 equivalents to about 5 equivalents, about 3 equivalents to about 4 equivalents, about 3 equivalents to about 5 equivalents, or about 4 equivalents to about 5 equivalents of the unionized pharmaceutical compound. In some embodiments, the pharmaceutical composition comprises about 0.5 equivalents, about 1 equivalents, about 2 equivalents, about 3 equivalents, about 4 equivalents, or about 5 equivalents of the unionized pharmaceutical compound. In some embodiments, the pharmaceutical composition comprises at least about 0.5 equivalents, about 1 equivalents, about 2 equivalents, about 3 equivalents, or about 4 equivalents of the unionized pharmaceutical compound. In some embodiments, the pharmaceutical composition comprises at most about 1 equivalents, about 2 equivalents, about 3 equivalents, about 4 equivalents, or about 5 equivalents of the unionized pharmaceutical compound.

In some embodiments, the pharmaceutical composition comprises a sufficient amount of unionized pharmaceutical compound to form a buffering system with the ionized pharmaceutical compound in the composition. In some embodiments, the buffering system is at a desired pH. In some embodiments, the buffering system results in a desired pH when administered to sublingual tissue.

In some embodiments, the buffering system results in a pH within a target range of the pKa value of the pharmaceutical compound. In some embodiments, the target pH is within about 0.2 pH units to about 2 pH units of the pKa value. In some embodiments, the target pH is within about 0.2 pH units to about 0.5 pH units, about 0.2 pH units to about 1 pH units, about 0.2 pH units to about 1.5 pH units, about 0.2 pH units to about 2 pH units, about 0.5 pH units to about 1 pH units, about 0.5 pH units to about 1.5 pH units, about 0.5 pH units to about 2 pH units, about 1 pH units to about 1.5 pH units, about 1 pH units to about 2 pH units, or about 1.5 pH units to about 2 pH units of the pKa value. In some embodiments, the target pH is within about 0.2 pH units, about 0.5 pH units, about 1 pH units, about 1.5 pH units, or about 2 pH units of the pKa value. In some embodiments, the target pH is within at least about 0.2 pH units, about 0.5 pH units, about 1 pH units, or about 1.5 pH units of the pKa value. In some embodiments, the target pH is within at most about 0.5 pH units, about 1 pH units, about 1.5 pH units, or about 2 pH units of the pKa value.

In some embodiments, the buffering system results in a pH wherein a certain percentage of the pharmaceutical compound is ionized upon administration. In some embodiments, the buffering system results in a pH wherein about 1% to about 99% of the pharmaceutical compound is ionized. In some embodiments, the buffering system results in a pH wherein about 1% to about 5%, about 1% to about 10%, about 1% to about 25%, about 1% to about 50%, about 1% to about 70%, about 1% to about 90%, about 1% to about 95%, about 1% to about 99%, about 5% to about 10%, about 5% to about 25%, about 5% to about 50%, about 5% to about 70%, about 5% to about 90%, about 5% to about 95%, about 5% to about 99%, about 10% to about 25%, about 10% to about 50%, about 10% to about 70%, about 10% to about 90%, about 10% to about 95%, about 10% to about 99%, about 25% to about 50%, about 25% to about 70%, about 25% to about 90%, about 25% to about 95%, about 25% to about 99%, about 50% to about 70%, about 50% to about 90%, about 50% to about 95%, about 50% to about 99%, about 70% to about 90%, about 70% to about 95%, about 70% to about 99%, about 90% to about 95%, about 90% to about 99%, or about 95% to about 99% of the pharmaceutical compound is ionized. In some embodiments, the buffering system results in a pH wherein about 1%, about 5%, about 10%, about 25%, about 50%, about 70%, about 90%, about 95%, or about 99% of the pharmaceutical compound is ionized. In some embodiments, the buffering system results in a pH wherein at least about 1%, about 5%, about 10%, about 25%, about 50%, about 70%, about 90%, or about 95% of the pharmaceutical compound is ionized. In some embodiments, the buffering system results in a pH wherein at most about 5%, about 10%, about 25%, about 50%, about 70%, about 90%, about 95%, or about 99% of the pharmaceutical compound is ionized. In some embodiments, the percent ionization is measured immediately after administration.

In some embodiments, the pharmaceutical composition comprises additional molar equivalents of unionized pharmaceutical compound compared to complexing agent of the complexing agent/protonated pharmaceutical compound salt. In some embodiments, the pharmaceutical composition comprises about 0.01 molar equivalents to about 10 molar equivalents of unionized pharmaceutical compound. In some embodiments, the pharmaceutical composition comprises about 0.1 molar equivalents to about 10 molar equivalents of unionized pharmaceutical compound. In some embodiments, the pharmaceutical composition comprises about 0.1 molar equivalents to about 0.5 molar equivalents, about 0.1 molar equivalents to about 1 molar equivalents, about 0.1 molar equivalents to about 2 molar equivalents, about 0.1 molar equivalents to about 3 molar equivalents, about 0.1 molar equivalents to about 5 molar equivalents, about 0.1 molar equivalents to about 7 molar equivalents, about 0.1 molar equivalents to about 10 molar equivalents, about 0.5 molar equivalents to about 1 molar equivalents, about 0.5 molar equivalents to about 2 molar equivalents, about 0.5 molar equivalents to about 3 molar equivalents, about 0.5 molar equivalents to about 5 molar equivalents, about 0.5 molar equivalents to about 7 molar equivalents, about 0.5 molar equivalents to about 10 molar equivalents, about 1 molar equivalents to about 2 molar equivalents, about 1 molar equivalents to about 3 molar equivalents, about 1 molar equivalents to about 5 molar equivalents, about 1 molar equivalents to about 7 molar equivalents, about 1 molar equivalents to about 10 molar equivalents, about 2 molar equivalents to about 3 molar equivalents, about 2 molar equivalents to about 5 molar equivalents, about 2 molar equivalents to about 7 molar equivalents, about 2 molar equivalents to about 10 molar equivalents, about 3 molar equivalents to about 5 molar equivalents, about 3 molar equivalents to about 7 molar equivalents, about 3 molar equivalents to about 10 molar equivalents, about 5 molar equivalents to about 7 molar equivalents, about 5 molar equivalents to about 10 molar equivalents, or about 7 molar equivalents to about 10 molar equivalents of unionized pharmaceutical compound of unionized pharmaceutical compound. In some embodiments, the pharmaceutical composition comprises about 0.1 molar equivalents, about 0.5 molar equivalents, about 1 molar equivalents, about 2 molar equivalents, about 3 molar equivalents, about 5 molar equivalents, about 7 molar equivalents, or about 10 molar equivalents of unionized pharmaceutical compound. In some embodiments, the pharmaceutical composition comprises at least about 0.1 molar equivalents, about 0.5 molar equivalents, about 1 molar equivalents, about 2 molar equivalents, about 3 molar equivalents, about 5 molar equivalents, or about 7 molar equivalents of unionized pharmaceutical compound. In some embodiments, the pharmaceutical composition comprises at most about 0.5 molar equivalents, about 1 molar equivalents, about 2 molar equivalents, about 3 molar equivalents, about 5 molar equivalents, about 7 molar equivalents, or about 10 molar equivalents of unionized pharmaceutical compound. In some embodiments, the pharmaceutical composition comprises about 0.01 molar equivalents to about 20 molar equivalents of unionized pharmaceutical compound compared to the complexing agent. In some embodiments, the pharmaceutical composition comprises about 1 molar equivalents to about 20 molar equivalents of unionized pharmaceutical compound compared to the complexing agent. In some embodiments, at least a portion these additional equivalents of the unionized pharmaceutical compound relative to the complexing agent are complexed to the complexing agent (e.g. up to about 1 molar equivalent of the unionized pharmaceutical compound).

In some embodiments, the pharmaceutical composition comprises additional components to improve properties specific to sublingual administration. Non-limiting examples of such additional excipients or components include permeation enhancers, stabilizers, lyophilization excipients, disintegrants, masking agents, flavors, binders, sweeteners, bittering agents, texturing agents, wetting agents, dispersing agents, additional buffers, and other such excipients.

Additional Formulation Components

The compounds (e.g., ketamine, methoxetamine, deschloroketamine, mescaline, tryptamines, phenethylamines, lysergamides, racemorphan, levorphanol, racemethorphan, 3-methylmethcathinone, ethylone, diphenhydramine, etc.) of the present disclosure may be in the form of compositions suitable for administration to a subject. In general, such compositions are "pharmaceutical compositions" comprising a compound (e.g., ketamine, methoxetamine, deschloroketamine, mescaline, tryptamines, phenethylamines, lysergamides, racemorphan, levorphanol, racemethorphan, 3-methylmethcathinone, ethylone, diphenhydramine, etc.) and one or more pharmaceutically acceptable or physiologically acceptable diluents, carriers or excipients. In some embodiments, the compounds (e.g., ketamine, methoxetamine, deschloroketamine, mescaline, tryptamines, phenethylamines, lysergamides, racemorphan, levorphanol, racemethorphan, 3-methylmethcathinone, ethylone, diphenhydramine, etc.) are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

In certain embodiments of the pharmaceutical compositions described herein, the co-solvent comprises PEG200, PEG300, PEG400, PEG600, propylene glycol, ethanol, polysorbate 20, polysorbate 80, cremophor, glycerin, benzyl alcohol, dimethylacetamide (DMA), N-methyl-2-pyrrolidone (NMP), tert-butanol, or combinations thereof.

In certain embodiments, the dosage form or pharmaceutical composition comprises a surface-active agent.

In certain embodiments of the pharmaceutical compositions described herein, the surface-active agent comprises polyoxyethylene sorbitan monooleate (Tween 80), sorbitan monooleate, polyoxyethylene sorbitan monolaurate (Tween 20), lecithin, polyoxyethylene-polyoxypropylene copolymers (Pluronics1), or combinations thereof.

In certain embodiments, the dosage form or pharmaceutical composition comprises a non-ionic surfactant.

In certain embodiments of the pharmaceutical compositions described herein, the non-ionic surfactant comprises Cremophor RH40, Cremophor RH60, d-alpha-topopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, or combinations thereof.

In some embodiments, the pharmaceutical composition comprises one or more co-solvents, solubilization/solubilizing agents, stabilization agents, antioxidants, preservatives, cryoprotectants, lyoprotectants, bulking agents, tonicity-adjusting agents, or antimicrobial agents. In some embodiments, the pharmaceutical composition comprises at least one co-solvent. In some embodiments, the pharmaceutical composition comprises at least one solubilizing agent. In some embodiments, the pharmaceutical composition comprises at least one stabilization agent. In some embodiments, the pharmaceutical composition comprises at least one antioxidant. In some embodiments, the pharmaceutical composition comprises at least one preservative. In some embodiments, the pharmaceutical composition comprises at least one cryoprotectant. In some embodiments, the pharmaceutical composition comprises at least one lyoprotectant. In some embodiments, the pharmaceutical composition comprises at least one bulking agent. In some embodiments, the pharmaceutical composition comprises at least one tonicity-adjusting agent. In some embodiments, the pharmaceutical composition comprises at least one antimicrobial agent.

In some embodiments, the formulation or pharmaceutical composition is a pharmaceutical composition. In some embodiments, the formulation is in the form of a sterile injectable aqueous or oleaginous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin). In some embodiments, the formulation comprises a co-solvent. In some embodiments, a suitable co-solvent is propylene glycol, glycerin, ethanol, polyethylene glycol (300 and 400), Sorbitol, dimethylacetamide, Cremophor EL, or N-methyl-2-pyrrolidone, or dimethylsulfoxide.

In some embodiments, the formulation or pharmaceutical composition is an aqueous suspension. Aqueous suspensions contain active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives (e.g. benzethonium chloride).

In some embodiments, the formulation or pharmaceutical composition comprises a stabilization agent. In some embodiments, the formulation comprises a surface-active solubilization agent. Surface-active solubilization agents include, but are not limited to: polyoxyethylene sorbitan monooleate (Tween 80), sorbitan monooleate, polyoxyethylene sorbitan monolaurate (Tween 20), lecithin, and Polyoxyethylene-polyoxypropylene copolymers (Pluronics1). In some embodiments, the formulation comprises a non-ionic surfactant solubilization agent. Non-ionic surfactants include, but are not limited: Cremophor RH 40, Cremophor RH 60, d-alpha-tocopherol polyethylene glycol 1000 succinate, polysorbate 20, polysorbate 80, Solutol HS 1, sorbitan monooleate, poloxamer 407, Labrafil M-1944CS, Labrafil M-2125CS, Labrasol, Gellucire 44/14, Softigen 767, and mono-fatty esters and di-fatty acid esters of PEG 300, 400, and 1750. In some embodiments, the formulation comprises a phospholipid solubilizing agent such as, hydrogenated soy phosphatidylcholine, phosphatidylcholine, distearoylphosphatidylglycerol, L-alpha-dimyristoylphosphatidylcholine, or L-alpha-dimyristoylphosphatidylglycerol.

In some embodiments, the formulation or pharmaceutical composition comprises a complexation agent. In some embodiments, the complexation agent is hydroxypropyl-b-cyclodextrin, bulfobutylether-b-cyclodextrin (Captisol1), or polyvinylpyrrolidone. In some embodiments, the complexation agent is an amino acid such as, arginine, lysine, or histidine. In some embodiments, the formulation or pharmaceutical composition comprises a cyclodextrin excipient. Cyclodextrin excipients are used to enhance the stability, tolerability and absorption of compounds in parenteral aqueous solutions. Common cyclodextrin excipients include but are not limited to: alpha-Cyclodextrin (alpha-CD), beta-Cyclodextrin (beta-CD), gamma-Cyclodextrin (gamma-CD), Diethyl-ethyl-beta-cyclodextrin (DE-beta-CD), Dimethyl-ethyl-beta-cyclodextrin (DM-beta-CD), Hydroxypropyl-beta-cyclodextrin (HP-beta-CD), Hydroxypropyl-gamma-cyclodextrin (HP-gamma-CD), Methyl-b-cyclodextrin (M-beta-CD), Sulfobutylether-beta-cyclodextrin (SBE-beta-CD), Randomly methylated-beta-CD (RM-beta-CD), Maltosyl-beta-CD (mal-beta-CD), Hydroxypropyl-alpha-CD.

The formulations or pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The formulation or pharmaceutical composition typically comprises a therapeutically effective amount of an active compound (e.g., ketamine, methoxetamine, deschloroketamine, mescaline, tryptamines, phenethylamines, lysergamides, racemorphan, levorphanol, or racemethorphan, 3-methylmethcathinone, ethylone, diphenhydramine, etc.), or a hydrate, solvate, tautomer, or pharmaceutically acceptable salt thereof, and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a triethanolamine (Tris) buffer, histidine, bicarbonate; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

Many active pharmaceutical ingredients (APIs), including pharmaceutical compounds, are weak acids or weak bases. Weak acids or weak bases can exist in an un-ionized form or as an ionized complex prepared by the addition of a base or acid respectively. The resultant complex is stabilized by ionic interactions and is known as a salt. This complex exists via an ionic bond between an ionized API and an oppositely charged counterion. Salts offer a number of advantages over their un-ionized counterparts. The choice of counterion can have a large influence on the salts properties and the use of a given salt form of a given API in a pharmaceutical product is influenced and guided by a number of factors for example stability (photo, hydrolytic and thermal), solubility, physicochemical properties, solid state properties (crystallinity, polymorphism, particle size, crystal morphology, melting point, compactability), production considerations (e.g., ease of handling and processing), dissolution rate, modulation of drug release, compatibility with excipients and containers, ease and consistency of production, desired route of administration, and organoleptic factors (e.g., taste). Furthermore, with respect to injection, salt can influence pain and irritation at the injection site.

APIs that are weak acids or weak bases can act as their own buffers at pH's near the pKa of the API. For example, an compound which comprises an amino functionality with a pKa of ~7.5, and can thus serve as a buffer in the region of about ±2 pH units from the pKa (e.g. from pHs of about 5.5 to about 9.5). When the formulation has a target pH within this range, an additional buffer may not be required. In some embodiments, the pharmaceutical composition provided herein does not comprise an additional buffer.

With regard to cyclodextrin solubilization, specific salts of various APIs have been found to form multicomponent complexes/systems or ternary systems which can have distinct desirable properties as compared to their standard binary complexes/systems counterparts prepared between the cyclodextrin and the un-ionized API, as well as compared to other multicomponent ternary complexes/systems involving different salt forms of that API. These multicomponent complexes/systems can thus dramatically influence solubility of the API in aqueous solutions, dissolution rates, can influence product stability, and pharmacokinetic properties of the pharmaceutical preparation.

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations or pharmaceutical compositions can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver an pharmaceutical compound, including implants (e.g., implantable pumps) and catheter systems, slow injection pumps and devices, all of which are well known to the skilled artisan.

In some embodiments, the formulation or pharmaceutical composition is stored in a reservoir of the drug delivery device. In some embodiments, the formulation is stored in a cartridge that is insertable and/or attachable to the drug delivery device. In some embodiments, the cartridge and/or drug delivery device comprises a product label for intramuscular injection. In some embodiments, the cartridge and/or drug delivery device comprises a product label for subcutaneous injection. In some embodiments, the cartridge and/or drug delivery device comprises a product label for intravenous injection. In some embodiments, disclosed herein is a kit comprising a product label for intramuscular injection. In some embodiments, disclosed herein is a kit comprising a product label for subcutaneous injection. In some embodiments, disclosed herein is a kit comprising a product label for intravenous injection.

In some embodiments, the formulation or pharmaceutical composition is a liquid formulation comprising an pharmaceutical compound.

It is frequently beneficial to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity. Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

The pharmaceutical compound of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the compound of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the dosage of the compound is contained in a "unit dosage form." The phrase "unit dosage form" refers to physically discrete units, each unit including a predetermined amount of the compound (e.g., ketamine, methoxetamine, deschloroketamine, mescaline, tryptamines, phenethylamines, lysergamides, racemorphan, levorphanol, or racemethorphan, 3-methylmethcathinone, ethylone, diphenhydramine, etc.), or a hydrate, solvate, or pharmaceutically acceptable salt thereof), sufficient to produce the desired effect. It will be appreciated that the parameters of a unit dosage form will depend on the particular agent and the effect to be achieved.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

Depot injections, which are generally administered subcutaneously or intramuscularly, may also be utilized to release the compound (e.g., ketamine, methoxetamine, deschloroketamine, mescaline, tryptamines, phenethylamines, lysergamides, racemorphan, levorphanol, or racemethorphan, 3-methylmethcathinone, ethylone, diphenhydramine, etc.) disclosed herein over a defined period of time. Depot injections are usually either solid- or oil-based and generally comprise at least one of the formulation components set forth herein. One of ordinary skill in the art is familiar with possible formulations and uses of depot injections.

Some formulations include one or more stabilization agents. Potential stabilization agents that are contemplated include buffers: Acetate, Citrate, Sodium Citrate, Tartrate, Phosphate, histidine, bicarbonate, Triethanolamine (TRIS) and their salts. In some formulations, the potential stabilization agents might include antioxidants and preservatives such as: Ascorbic acid, Acetylcysteine (NAC), Sulfurous acid salts (bisulfite, metabisulfite), Monothioglyercol. Butylated hydroxyanisole (BHA), Butylated hydroxytoluene (BHT), Tert-butylhydroquinone (TBHQ), 2',4',5'-Trihydroxybutyrophenone phenylhydrazone (THBP), Ethylenediaminetetraacetic acid (EDTA), Sodium formaldehyde sulfoxylate (SFS), Tocopherol (Vitamin E), Ascorbyl palmitate, Gallates (e.g., propyl gallate, octyl gallate, lauryl gallate), Cysteine ethyl ether, Tartaric acid, Phosphoric acid, Thiourea, Sodium thioglycolate, Nitrogen, and/or Argon.

In some formulations, the potential stabilization agents might include bulking agents, cryoprotectants, and lyoprotectants. Agents that were considered include: Mannitol, Glycine, Sucrose, Lactose, Trehalose, Dextran, Povidone, Sorbitol and/or Polydextrose. In some formulations potential stabilization agents might include tonicity-adjusting agents. Agents that were considered include: sodium chloride, Glycerin, Mannitol, Dextrose, and/or glycerol. In some formulations the potential stabilization agents might include antimicrobial agents including, but not limited to: Phenol, Meta-cresol, Benzyl alcohol, parabens (methyl, propyl, or butyl), benzalkonium chloride, benzethonium chloride, chlorobutanol, Myristyl gamma picolinium chloride, 2-phenoxyethanol, Phenethyl alcohol, Sorbates (sorbic acid, sodium sorbate), Ethanol, and/or Propylene glycol.

In some formulations, soothing agents might include topical analgesics such as: lidocaine, benzocaine, tetracaine, bupivacaine, ropivacaine, and/or levobupivacaine.

In some formulations, emulsion stabilizers include hydroxyethyl cellulose, hydroxypropylcellulose, and/or hydroxypropyl methyl cellulose (hypromellose).

The compound (e.g., ketamine, methoxetamine, deschloroketamine) contemplated by the present disclosure may be in the form of any other suitable pharmaceutical composition currently known or developed in the future.

III. Methods

Methods of Treatment Using Pharmaceutical Compositions

In an aspect, provided herein is a method of treating a disease or condition in a subject, the method comprising administering to the subject a pharmaceutical composition provided herein. The disease or condition will depend on the particular compound selected in the pharmaceutical composition.

Dissociative Compounds

Generally, the dissociative compounds provided herein (e.g. ketamine or analogs or derivatives thereof) will be useful for all of the listed indications. In some embodiments, formulations and methods disclosed herein are used to treat pain or a pain disorder. In some embodiments, chronic pain refers to pain having a duration of greater than 3 months. Examples of pain and pain disorders include pain that is not otherwise specified (NOS) such as acute pain, body aches, buttock muscular pain, lower back pain, chronic back pain, chronic coccygeal pain, chronic low back pain, chronic malignant pain, chronic neck pain, chronic nonmalignant pain, chronic pain, and generalized pain. In some embodiments, the pain can include pain crisis, pain in buttocks, pain of coccyx (chronic or acute), or neoplasm related pain (chronic or acute). In some embodiments, the pain is chronic pain. In some embodiments, the pain is acute pain.

In some embodiments, the pain is chronic post-procedural and/or post-surgical pain. Examples of post-procedural pain include chronic pain due to bilateral total hip arthroplasty, chronic pain due to bilateral total knee arthroplasty, chronic pain due to left total hip arthroplasty, chronic pain due to left total knee replacement, chronic pain due to right total hip arthroplasty, chronic pain due to right total knee replacement, chronic pain following bilateral partial hip arthroplasty, chronic pain following bilateral partial knee arthroplasty, chronic pain following left partial hip arthroplasty, chronic pain following left partial knee arthroplasty, chronic pain following right partial hip arthroplasty, chronic pain following right partial knee arthroplasty, pain due to bilateral total hip arthroplasty, pain due to bilateral total knee arthroplasty, pain due to left total hip arthroplasty, pain due to left total knee replacement, pain due to right total hip arthroplasty, pain due to right total knee replacement, pain following bilateral partial hip arthroplasty, pain following bilateral partial knee arthroplasty, pain following left partial hip arthroplasty, pain following left partial knee arthroplasty, pain following right partial hip arthroplasty, pain following right partial knee arthroplasty, chronic post-mastectomy pain, chronic post-mastectomy pain, and chronic postoperative pain.

In some embodiments, the pain is chronic pain due to trauma or injury. In some embodiments, the pain is a chronic pain syndrome, also referred to as chronic pain associated with psychosocial dysfunction or psychosocial dysfunction due to chronic pain. In some embodiments, the pain is a neoplasm related pain or pain due to neoplastic disease (chronic or acute). In some embodiments, the pain is causalgia (lower limb and/or upper limb).

In some embodiments, the pain is central pain syndrome, complex regional pain syndrome I, complex regional pain syndrome II (lower limb), or complex regional pain syndrome II (upper limb).

In some embodiments, the disease or disorder is a psychiatric disorder. In some embodiments, the psychiatric disorder is major depressive disorder, treatment resistant major depressive disorder, suicidality, suicidal ideation, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, complex regional pain syndrome, reflex sympathetic dystrophy, or any combination thereof.

In some embodiments, the disease or disorder is a cognitive or neurological disorder. In some embodiments, the cognitive or neurological disorder is Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, Rett syndrome, dyskinesia, unspecified dystonia, or pseudobulbar affect.

In some embodiments, formulations and methods disclosed herein are used to treat one or more personality disorders. Examples of personality disorders include avoidant personality disorder, dependent personality disorder, antisocial personality disorder, histrionic personality disorder, borderline personality disorder, obsessive-compulsive personality disorder, cyclothymic personality disorder, obsessive compulsive disorder, and impulse control disorder (NOS).

In some embodiments, formulations and methods disclosed herein are used to treat one or more of major depressive disorder, treatment resistant major depressive disorder, suicidality, suicidal ideation, dysthymia, bipolar disorder (Type I-Depressed), bipolar disorder (Type II-Depressed), post-traumatic stress disorder (PTSD), panic disorder, generalized anxiety disorder, and substance abuse induced mood disorder.

In some embodiments, formulations and methods disclosed herein are used to treat drug dependence. Examples of drug dependence include opiate dependence, benzodiazepine dependence, sedative (hypnotic or anxiolytic) dependence, alcohol dependence, stimulant dependence, cocaine dependence, cannabis detoxification, opiate dependence (with withdrawal), benzodiazepine dependence (with withdrawal), sedative (with withdrawal) dependence, alcohol dependence (with withdrawal), stimulant dependence (with withdrawal), cocaine dependence (with withdrawal), and cannabis detoxification (with withdrawal).

In another aspect is provided a method of treating, preventing, or ameliorating at least one symptom of a disorder, disease, or condition with the pharmaceutical compositions disclosed herein, including embodiments, wherein the disorder, disease, or condition is a mental or psychiatric disorder, a mood disorder, a neurological condition or disorder, type 2 diabetes mellitus and/or complications thereof, endometriosis, glaucoma, pain, or an inflammatory disorder.

Psychedelic Compounds

Generally, the psychedelic compounds provided herein (e.g. mescaline, etc.) will be useful for all of the listed indications.

In some embodiments, the disease or disorder is a psychiatric disorder. In some embodiments, the psychiatric disorder is major depressive disorder, treatment resistant major depressive disorder, dysthymia, suicidality, suicidal ideation, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, personality disorders, complex regional pain syndrome, reflex sympathetic dystrophy, post-concussive memory disorders and cognitive disorders, traumatic brain injury, post-chemotherapy cognitive dysfunction and memory disorders, inflammatory disorders, cognitive disorders, memory disorders, dementia NOS, fatigue or any combination thereof. In some embodiments, the psychiatric disorder is major depressive disorder, treatment resistant major depressive disorder, Suicidality, Suicidal Ideation, dysthymia, bipolar I disorder, bipolar II disorder, post-traumatic stress disorder (PTSD), complex trauma, anorexia nervosa, bulimia nervosa, eating disorder NOS, obsessive compulsive disorder, a substance-related disorder (e.g., cannabis dependence or withdrawal, barbiturate dependence or withdrawal, benzodiazepine dependence or withdrawal, amphetamine dependence or withdrawal, opioid dependence or withdrawal, alcohol dependence or withdrawal, cocaine dependence or withdrawal).

In some embodiments, formulations and methods disclosed herein are used to treat one or more personality disorders. Examples of personality disorders include avoidant personality disorder, dependent personality disorder, antisocial personality disorder, histrionic personality disorder, borderline personality disorder, obsessive-compulsive personality disorder, cyclothymic personality disorder, obsessive compulsive disorder, and impulse control disorder (NOS).

In some embodiments, formulations and methods disclosed herein are used to treat one or more of major depressive disorder, treatment resistant major depressive disorder, suicidality, suicidal ideation, dysthymia, bipolar disorder (Type I-Depressed), bipolar disorder (Type II-Depressed), post-traumatic stress disorder (PTSD), panic disorder, generalized anxiety disorder, and substance abuse induced mood disorder.

In some embodiments, formulations and methods disclosed herein are used to treat drug dependence. Examples of drug dependence include opiate dependence, benzodiazepine dependence, sedative (hypnotic or anxiolytic) dependence, alcohol dependence, stimulant dependence, cocaine dependence, cannabis detoxification, opiate dependence (with withdrawal), benzodiazepine dependence (with withdrawal), sedative (with withdrawal) dependence, alcohol dependence (with withdrawal), stimulant dependence (with withdrawal), cocaine dependence (with withdrawal), and cannabis detoxification (with withdrawal).

In some embodiments, formulations and methods disclosed herein are used to treat pain or a pain disorder. In some embodiments, when the embodiments, formulations, and methods provided herein are used to treat pain, the pharmaceutical compounds provided herein are administered as microdoses (e.g., doses below the threshold which induce psychedelic effects). In some embodiments, chronic pain refers to pain having a duration of greater than 3 months. Examples of pain and pain disorders include pain that is not otherwise specified (NOS) such as acute pain, body aches, buttock muscular pain, lower back pain, chronic back pain, chronic coccygeal pain, chronic low back pain, chronic malignant pain, chronic neck pain, chronic nonmalignant pain, chronic pain, and generalized pain. In some embodiments, the pain can include pain crisis, pain in buttocks, pain of coccyx (chronic or acute), or neoplasm related pain (chronic or acute). In some embodiments, the pain is chronic pain. In some embodiments, the pain is acute pain.

In some embodiments, the pain is chronic post-procedural and/or post-surgical pain. Examples of post-procedural pain include chronic pain due to bilateral total hip arthroplasty, chronic pain due to bilateral total knee arthroplasty, chronic pain due to left total hip arthroplasty, chronic pain due to left total knee replacement, chronic pain due to right total hip arthroplasty, chronic pain due to right total knee replacement, chronic pain following bilateral partial hip arthroplasty, chronic pain following bilateral partial knee arthroplasty, chronic pain following left partial hip arthroplasty, chronic pain following left partial knee arthroplasty, chronic pain following right partial hip arthroplasty, chronic pain following right partial knee arthroplasty, pain due to bilateral total hip arthroplasty, pain due to bilateral total knee arthroplasty, pain due to left total hip arthroplasty, pain due to left total knee replacement, pain due to right total hip arthroplasty, pain due to right total knee replacement, pain following bilateral partial hip arthroplasty, pain following bilateral partial knee arthroplasty, pain following left partial hip arthroplasty, pain following left partial knee arthroplasty, pain following right partial hip arthroplasty, pain following right partial knee arthroplasty, chronic post-mastectomy pain, chronic post-mastectomy pain, and chronic postoperative pain.

In some embodiments, the pain is chronic pain due to trauma or injury. In some embodiments, the pain is a chronic pain syndrome, also referred to as chronic pain associated with psychosocial dysfunction or psychosocial dysfunction due to chronic pain. In some embodiments, the pain is a neoplasm related pain or pain due to neoplastic disease (chronic or acute). In some embodiments, the pain is causalgia (lower limb and/or upper limb).

In some embodiments, the pain is central pain syndrome, complex regional pain syndrome I, complex regional pain syndrome II (lower limb), or complex regional pain syndrome II (upper limb).

In some embodiments, the disease or disorder is an inflammatory disorder or disease associated with inflammation. Non-limiting examples of inflammatory disorders and diseases associated with inflammation include asthma, atherosclerosis, autoimmune diseases, autoinflammatory diseases, celiac disease, chronic prostatis, colitis, diverticulitis, glomerulonephritis, inflammatory bowel disease, interstitial cystitis, mastocytosis, pelvic inflammatory disease, reperfusion injury, rheumatic fever, rheumatoid arthritis, rhinitis, sarcoidosis, transplant rejection, and vasculitis.

Opioids

In an aspect, provided herein is a method of treating pain in a subject, the method comprising administering to the subject a pharmaceutical composition provided herein.

In some embodiments, the pain is acute or chronic pain. In some embodiments, the pain is chronic pain.

In some embodiments, the pain is complex regional pain syndrome, central pain syndrome, chronic pain, acute pain, or phantom limb syndrome with pain. In some embodiments, the pain is acute pain. In some embodiments, the pain is post-operative pain. In some embodiments, the pain is from a traumatic injury, such as a battlefield wound. In some embodiments, the pain is cancer pain.

In some embodiments, formulations and methods disclosed herein are used to treat pain or a pain disorder. In some embodiments, chronic pain refers to pain having a duration of greater than 3 months. Examples of pain and pain disorders include pain that is not otherwise specified (NOS) such as acute pain, body aches, buttock muscular pain, lower back pain, chronic back pain, chronic coccygeal pain, chronic low back pain, chronic malignant pain, chronic neck pain, chronic nonmalignant pain, chronic pain, and generalized pain. In some embodiments, the pain can include pain crisis, pain in buttocks, pain of coccyx (chronic or acute), or neoplasm related pain (chronic or acute). In some embodiments, the pain is chronic pain. In some embodiments, the pain is acute pain.

In some embodiments, the pain is chronic post-procedural and/or post-surgical pain. Examples of post-procedural pain include chronic pain due to bilateral total hip arthroplasty, chronic pain due to bilateral total knee arthroplasty, chronic pain due to left total hip arthroplasty, chronic pain due to left total knee replacement, chronic pain due to right total hip arthroplasty, chronic pain due to right total knee replacement, chronic pain following bilateral partial hip arthroplasty, chronic pain following bilateral partial knee arthroplasty, chronic pain following left partial hip arthroplasty, chronic pain following left partial knee arthroplasty, chronic pain following right partial hip arthroplasty, chronic pain following right partial knee arthroplasty, pain due to bilateral total hip arthroplasty, pain due to bilateral total knee arthroplasty, pain due to left total hip arthroplasty, pain due to left total knee replacement, pain due to right total hip arthroplasty, pain due to right total knee replacement, pain following bilateral partial hip arthroplasty, pain following bilateral partial knee arthroplasty, pain following left partial hip arthroplasty, pain following left partial knee arthroplasty, pain following right partial hip arthroplasty, pain following right partial knee arthroplasty, chronic post-mastectomy pain, chronic post-mastectomy pain, and chronic postoperative pain.

In some embodiments, the pain is chronic pain due to trauma or injury. In some embodiments, the pain is a chronic pain syndrome, also referred to as chronic pain associated with psychosocial dysfunction or psychosocial dysfunction due to chronic pain. In some embodiments, the pain is a neoplasm related pain or pain due to neoplastic disease (chronic or acute). In some embodiments, the pain is causalgia (lower limb and/or upper limb).

In some embodiments, the pain is central pain syndrome, complex regional pain syndrome I, complex regional pain syndrome II (lower limb), or complex regional pain syndrome II (upper limb).

In an aspect, provided herein, is a method of treating a disease or condition in a subject, the method comprising administering to the subject a pharmaceutical composition provided herein, wherein the disease or condition is depression or opioid overdose. In some embodiments, the disease or condition is opioid overdose and the opioid of the pharmaceutical composition is an opioid receptor antagonist, such as naloxone or naltrexone.

Empathogenic and Entactogenic Compounds

In an aspect, provided herein is a method of treating a disease or disorder in a subject, the method comprising administering to the subject a pharmaceutical composition provided herein.

In some embodiments, the disease or disorder is acute pain or chronic pain. In some embodiments, the pain is acute pain. In some embodiments, the pain is post-operative pain. In some embodiments, the pain is from a traumatic injury, such as a battlefield wound. In some embodiments, the pain is cancer pain.

In some embodiments, formulations and methods disclosed herein are used to treat pain or a pain disorder. In some embodiments, chronic pain refers to pain having a duration of greater than 3 months. Examples of pain and pain disorders include pain that is not otherwise specified (NOS) such as acute pain, body aches, buttock muscular pain, lower back pain, chronic back pain, chronic coccygeal pain, chronic low back pain, chronic malignant pain, chronic neck pain, chronic nonmalignant pain, chronic pain, and generalized pain. In some embodiments, the pain can include pain crisis, pain in buttocks, pain of coccyx (chronic or acute), or neoplasm related pain (chronic or acute).

In some embodiments, the disease or disorder is a sleep disorder.

In some embodiments, the disease or disorder is an inflammatory disorder or disease associated with inflammation. Non-limiting examples of inflammatory disorders and diseases associated with inflammation include asthma, atherosclerosis, autoimmune diseases, autoinflammatory diseases, celiac disease, chronic prostatis, colitis, diverticulitis, glomerulonephritis, inflammatory bowel disease, interstitial cystitis, mastocytosis, pelvic inflammatory disease, reperfusion injury, rheumatic fever, rheumatoid arthritis, rhinitis, sarcoidosis, transplant rejection, and vasculitis.

In some embodiments, the disease or disorder is a psychiatric disorder. In some embodiments, the psychiatric disorder is major depressive disorder, treatment resistant major depressive disorder, suicidality, suicidal ideation, complex trauma, dysthymia or persistent depressive disorder, bipolar depressive disorder type I, bipolar depressive disorder type II, chronic pain, eating disorder NOS, pain disorder NOS, panic disorder, post-traumatic stress disorder, obsessive-compulsive disorder, complex regional pain syndrome, reflex sympathetic dystrophy, intermittent explosive disorder, or any combination thereof.

In some embodiments, the disease or disorder is a cognitive disorder or a neurological disorder. In some embodiments, the cognitive disorder, or a neurological disorder is Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, Rett syndrome, dyskinesia, unspecified dystonia, or pseudobulbar affect.

In some embodiments, formulations and methods disclosed herein are used to treat one or more personality disorders. Examples of personality disorders include avoidant personality disorder, dependent personality disorder, antisocial personality disorder, histrionic personality disorder, borderline personality disorder, obsessive-compulsive personality disorder, cyclothymic personality disorder, obsessive compulsive disorder, and impulse control disorder (NOS).

In some embodiments, formulations and methods disclosed herein are used to treat one or more eating disorders. Examples of eating disorders include anorexia nervosa and bulimia disorder, as well as other eating disorders not otherwise specified (NOS).

In some embodiments, formulations and methods disclosed herein are used to treat one or more of major depressive disorder, treatment resistant major depressive disorder, suicidality, suicidal ideation, dysthymia, bipolar disorder (Type I-Depressed), bipolar disorder (Type II-Depressed), post-traumatic stress disorder (PTSD), panic disorder, generalized anxiety disorder, and substance abuse induced mood disorder.

In some embodiments, formulations and methods disclosed herein are used to treat a cognitive or neurological disorder or condition such as Huntington's disease, Parkinson's disease, frontotemporal dementia, dementia, Alzheimer's disease, amyotrophic lateral sclerosis, spinal cord trauma, stroke, diffuse traumatic brain injury, HIV-associated dementia, epilepsy, suicidal ideation, Rett syndrome, dyskinesia, dystonia (unspecified), or pseudobulbar affect.

In some embodiments, formulations and methods disclosed herein are used to treat drug dependence. Examples of drug dependence include opiate dependence, benzodiazepine dependence, sedative (hypnotic or anxiolytic) dependence, alcohol dependence, stimulant dependence, cocaine dependence, cannabis detoxification, opiate dependence (with withdrawal), benzodiazepine dependence (with withdrawal), sedative (with withdrawal) dependence, alcohol dependence (with withdrawal), stimulant dependence (with withdrawal), cocaine dependence (with withdrawal), and cannabis detoxification (with withdrawal).

Methods of Formulating Pharmaceutical Compounds and Preparing Complexing Agent Salts of Pharmaceutical Compounds In one aspect, provided herein is a method of preparing a pharmaceutical composition, comprising: mixing a free acid form of a complexing agent comprising a plurality of acidic functional groups and a freebase form of an pharmaceutical compound, wherein the pharmaceutical compound comprises a basic nitrogen atom. In some embodiments, the pharmaceutical compound includes a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound does not include ketamine. In some embodiments, the pharmaceutical compound includes methoxetamine, deschloroketamine, N-ethyl deschloroketamine (eticyclidone), 3-methoxyphencyclidine, methoxieticyclidine, ephenidine, lanicemine, dextromethorphan, dextrorphan, or methoxyketamine. In some embodiments, the pharmaceutical compound is a tryptamine, a phenethylamine, or a lysergamide compound. In some embodiments, the pharmaceutical compound is an opioid. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin.

In another aspect, provided herein is a method of preparing a pharmaceutical composition, comprising mixing a free acid form of a complexing agent comprising a plurality of acidic functional groups and a freebase form of an pharmaceutical compound, wherein the pharmaceutical compound comprises a basic nitrogen atom, and adding an additional molar equivalent of the pharmaceutical compound, wherein the additional molar equivalent is unionized and does not ionize after addition. In some embodiments, the pharmaceutical compound includes a dissociative medication compound, a dissociative hallucinogen compound, a dissociative anesthetic compound, an arylcyclo-hexylamine, a 1,2-diarylethylamine, a β-keto-arylcyclohexylamine, or a compound that modulates the NMDA receptor. In some embodiments, the pharmaceutical compound does not include ketamine. In some embodiments, the pharmaceutical compound is a tryptamine, a phenethylamine, or a lysergamide compound. In some embodiments, the pharmaceutical compound is an opioid. In some embodiments, the pharmaceutical compound is a cathinone, a 3,4-methylenedioxyamphetamine derivative, an aminoalkyl-substituted benzofuran, a substituted amphetamine, an aminoindane, a stimulant, diphenhydramine, hydroxazine, phenylephrine, dopamine, adrenaline, lidocaine, oxymetazoline, clemastine, chlorpheniramine, or 6-chloro-2-aminotetralin.

In some embodiments, the mixing occurs in a suitable medium. In some embodiments, the suitable medium is an aqueous medium. In some embodiments, the suitable medium is an organic solvent. In some embodiments, the mixing occurs in a solution. In some embodiments, the mixing occurs when the complexing agent and the pharmaceutical compound are in powder form.

In some embodiments, the mixing occurs by portion-wise addition of one of the reagents. In some embodiments, the pharmaceutical compound is added portion wise to a solution comprising the complexing agent.

In some embodiments, the pharmaceutical composition is in a form for dosing or administration by subcutaneous injection.

In some embodiments, the complexing agent comprising at least one acidic functional group is a cyclodextrin. Any of the cyclodextrins provided in the "Compositions" section can be used. The cyclodextrin or other complexing agent may also be added at any amount provided in the "Compositions" section or at any molar ratio provided therein, including ratios of acidic functional groups to the pharmaceutical compound.

In some embodiments, the method further comprises adjusting the pH of the pharmaceutical composition. In some embodiments, only a minimal adjustment of the pH is necessary. In some embodiments, the pH is adjusted with a strong base. In some embodiments, the pH is adjusted with sodium hydroxide, potassium hydroxide, barium hydroxide, cesium hydroxide, strontium hydroxide magnesium hydroxide, calcium hydroxide, lithium hydroxide, or rubidium hydroxide. In some embodiments, the pH is adjusted with sodium hydroxide. In some embodiments, the pH is adjusted to a desired pH. In some embodiments, the desired pH is any of the pH values provided herein in the "Compositions" section.

In some embodiments, the pharmaceutical composition has a pH >about 4. The pH of the pharmaceutical composition can be any of the pH values provided in the "Compositions" section, such as a pH from about 4 to about 7, or any other of the pH values or ranges provided therein.

In some embodiments, the method further comprises adding a preservative to the composition. The preservative may be added to the composition at any time or in any order. In some embodiments, the preservative is added after the complexing agent and the pharmaceutical compound have been added. In some embodiments, the preservative is added prior to adding the pharmaceutical compound. In some embodiments, the preservative is benzethonium chloride. The preservative may also be any of the preservatives provided in the "Compositions" section and may be added at any concentration provided therein.

In some embodiments, the method further comprises adding a base, a buffer, an emulsifying agent, a surfactant, a solubilizing agent, an emulsifying agent, a co-solvent, or any combination thereof. The method may also further comprise adding any of the additional components provided herein in the "Compositions" section, including without limitation bases, buffers, co-solvents, preservatives, surface-active agents, surfactants, solubilizing agents, stabilization agents, antioxidants, cryoprotectants, lyoprotectants, bulking agents, tonicity-adjusting agents, antimicrobial agents, diluents, soothing agents, and/or emulsion stabilizers.

In some embodiments, the method further comprises adjusting the osmolality of the pharmaceutical composition. In some embodiments, the adjusting the osmolality of the pharmaceutical comprises diluting the pharmaceutical composition. Diluting the pharmaceutical composition may comprise diluting with water or other physiologically acceptable buffer, such as phosphate buffered saline, or any of the buffers provided in the "Compositions" section. In some embodiments, adjusting the osmolality of the pharmaceutical composition comprises adding a tonicity modifying agent. The tonicity modifying reagent may be any pharmaceutically acceptable reagent, such as sodium chloride, or any of the reagents provided in the "Compositions" section. In some embodiments, there is no need to adjust the osmolality of the pharmaceutical composition after mixing the pharmaceutical compound or the compound of structural Formula (I) and the complexing agent.

The final osmolality of the pharmaceutical composition may be any of the osmolalities provided in the "Compositions" section, such an osmolality from about 250 mOsm/kg to about 850 mOsm/kg, or any other range or value provided therein.

The final concentration of the compound of structural Formula (I) of the pharmaceutical composition may be any of the concentrations provided in the "Compositions" section, including values over 10 or 20 mg/mL or any of the other values or ranges provided therein.

In some embodiments, the molar ratio of the pharmaceutical compound comprising the at least one basic nitrogen atom to the number of moles of the acidic functional groups of the free acid form of the complexing agent is such that there is a molar excess of the pharmaceutical compound. In such a case, the resulting formulation retains a portion of the pharmaceutical compound in free base form. In some embodiments, the molar ratio of the pharmaceutical compound to the number of moles of acidic functional groups of the complexing agent is about 1:1, in which case all or substantially all of the pharmaceutical compound becomes protonated. In some embodiments, the molar ratio of the pharmaceutical compound to the number of moles of acidic functional groups of the complexing agent is greater than 1:1 (e.g., 2:1, 3:1, 4:1, 5:1, 6:1, 7:1, 8:1, 9:1, or 10:1 or greater), in which case a portion of the pharmaceutical compound will remain unionized.

In some embodiments, all or a portion of the pharmaceutical compound becomes protonated in the liquid medium upon addition of the free acid form of the complexing agent. At this point, in some embodiments, a molar excess of the free base form of the pharmaceutical compound is then added. In some embodiments, the liquid medium is first removed by a suitable method (e.g. evaporation, lyophilization, etc.) before the molar excess of the free base form of the pharmaceutical compound is added. In such cases, any of the ratios of molar equivalents of unionized pharmaceutical compound provided herein may be used.

Also provided herein are methods of generating the free acid form of complexing agents comprising at least one acidic functional group. In some cases, complexing agents comprising acidic functional groups are commercially available only as salts of the complexing agents, such as sodium salts. For example, SBEBCD is sold commercially as the sodium salt.

The free acid form of such complexing agents can be generated by any number of methods. For example, the salts of complexing agents comprising acidic functional groups can be bound to a suitable acidic cation exchange resin (e.g. Amberlite® IR120 Hydrogen form resin, available from commercial vendors such as Sigma Aldrich) and then eluted to yield the desired free acid form of the complexing agent.

An additional method potentially suitable for this purpose could involve treating the sodium salt of the complexing agent (e.g. SBEBCD) with a hydrochloric acid or other suitable acid in a suitable organic solvent. Ideally, the organic solvent is selected such the resulting sodium chloride will precipitate out of solution and leave the complexing agent free acid in solution. The sodium chloride salt could then be removed by filtration, and the filtrate could then be concentrated or the solvent removed to yield the free acid. Conversely, the filtrate could be solvent exchanged with water for injection using standard azeotropic distillation under vacuum. Alternatively, the filtrate could be used to prepare the formulation as is and removed at a later stage.

EXAMPLES

Example 1. Preparation of a Methoxetamine-SBEBCD Salt

A methoxetamine-SBEBCD salt is prepared according to the general protocol shown in Scheme 1. The protocol provided herein is used to prepare a stable, high concentration methoxetamine solution. This solution can be adjusted to an osmolality near physiological levels (~300 mOsm/kg) and a pH near the bottom range of the buffering capacity of the methoxetamine's pKa value (~2 pH units below) for use in a subcutaneous formulation. Alternatively, the aqueous solution can be lyophilized to remove the liquid and leave behind the methoxetamine-SBEBCD salt in solid form, which can then be used in any subsequent formulation desired.

Scheme 1

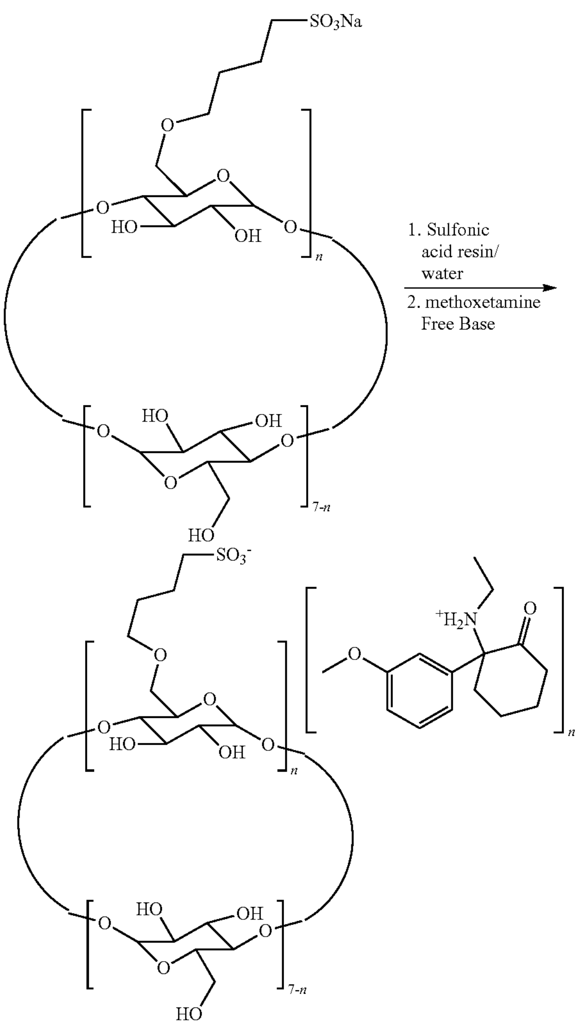

Experimental Procedure for the Preparation of Methoxetamine SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol®: Can be purchased from Ligand Pharmaceuticals, Inc. (Ligand) (pharmaceutical grade). The moisture content is verified by Karl Fisher analysis. Captisol® is a polysulfobutylated β-cyclodextrin sodium form, with an average of 6.5 sulfobutyl groups per molecule and an average MW of 2,163.

Methoxetamine HCl: Purchased from desired manufacturer and can be used without further purification. Free base methoxetamine is prepared from the HCl salt with concentrated sodium hydroxide and isolated by vacuum filtration.

Synthesis of Captisol® Acid. Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and was completely dried by applying compressed air for 10 minutes before the sample was applied. A solution of 15% Captisol® (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

Methoxetamine Freebase: Methoxetamine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Synthesis of Methoxetamine-Captisol® Salt: Captisol® acid prepared above (moisture corrected to ascertain actual concentration) is dissolved in HPLC grade water in a test tube with a teflon stirbar. The solution is stirred vigorously and methoxetamine freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of methoxetamine, at which point nearly all (~99%) of the methoxetamine will be protonated. The solution is syringe filtered with a 0.45 μM nylon filter and is stored in a test tube under ambient air and wrapped in aluminum foil. Part of the volume is lyophilized to produce a powder of the methoxetamine-Captisol® salt. This resulting powder is observed under ambient conditions to observe for any wetting, discoloration, or other observable change. The remaining volume of solution containing the methoxetamine-Captisol® salt is similarly monitored for visible changes. The sample is also periodically monitored by HPLC to ascertain stability over time. The structure of the resulting methoxetamine-Captisol® salt is shown in FIG. 1.

Figure 2:
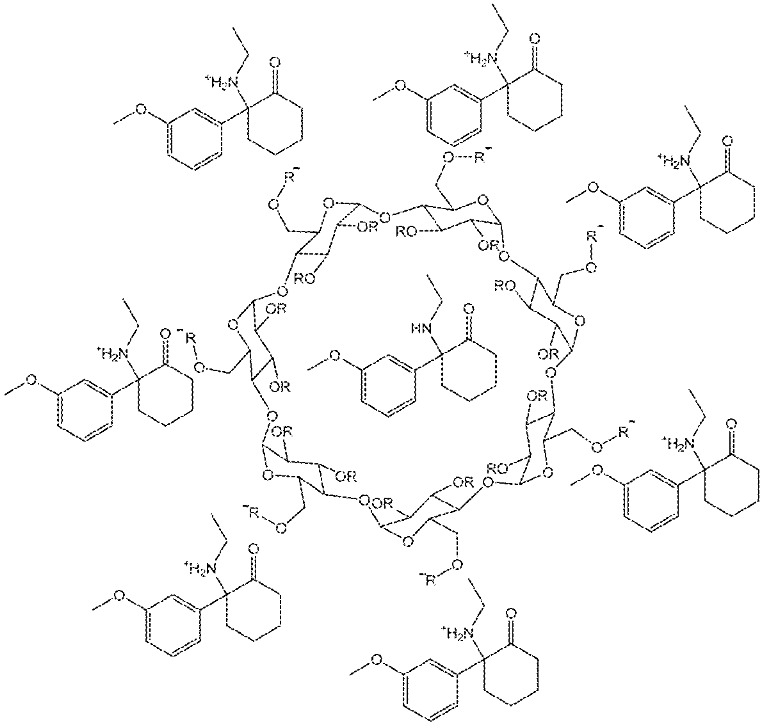
FIG. 2 shows an exemplary structure of a methoxetamine-SBEBCD salt which is also acting as an inclusion complex for an additional equivalent of free base methoxetamine.

Example 2. Preparation of a Methoxetamine-SBEBCD Salt with Free Base Methoxetamine Complexed within the SBEBCD The salt forms of the complexing agent/pharmaceutical compounds provided herein can also be adapted to incorporate additional molar equivalents of free base compound. For example, in instances where the complexing agent is a cyclodextrin such as SBEBCD, the interior portion of the cyclodextrin can incorporate an additional molecule of compound. An exemplary illustration of such a complex can be seen in FIG. 2, which shows the methoxetamine/SBEBCD salt complex described in Example 1 which has been modified to incorporate an additional uncharged molecule of methoxetamine on the interior of the cyclodextrin. Such complexes can have additional benefits when used in pharmaceutical compositions, including increased solubility of the compounds upon administration, increased bioavailability of the compounds, and the presence of free base compound can act to create a buffering system that allows for a more biocompatible pH to be achieved upon delivery of the pharmaceutical composition as the free base compound neutralizes some of the acidic functionalities of the protonated compounds of the salt complex.

Such complexes can be created in a variety of ways, several of which are shown by example below. In order to ascertain the proper ratio of salt complex to free base compound to add to prepare a mixture with an additional molecule of compound incorporated into the center of the cyclodextrin, it is necessary to determine the molecular weight of the salt complex. This can be readily calculated from the known molecular weight of the starting materials and stoichiometry of the complexing agent and compound. For example, as the SBEBCD used to prepare the methoxetamine-SBEBCD salt in Example 1 has an average of 6.5 sulfobutyl groups per molecule, the resulting salt has an average of 6.5 methoxetamine molecules for every cyclodextrin molecule, resulting in the salt having an average molecular weight of 3630 Daltons. This value can be calculated as follows: From the average molecular weight of the SBEBCD (average MW of 2,163) is subtracted the weight of sodium atoms which have been removed (6.5 times 22.99 Daltons), and the weight of methoxetamine molecules (6.5 times 247.33 Daltons) and additional hydrogen atoms (6.5 times 1.01 Daltons) is added, yielding an average molecule weight of about 3630 Daltons. Additionally, any residual water in the resulting salt can be measured by an appropriate procedure, such as Karl Fischer analysis.

The complexes described in this example can be prepared by any suitable method, including without limitation the procedures described below.

Physical mixture method—The required molar quantities (1:1) of free base methoxetamine (68 mg) and the lyophilized methoxetamine-SBEBCD salt (1.0 g) prepared in Example 1 are weighed accurately and mixed together thoroughly in a mortar with vigorous trituration for about three hours. The mixture is then passed through a sieve and stored in an airtight container until further use.

Kneading Method—The required quantities of free base methoxetamine (68 mg) and the lyophilized methoxetamine-SBEBCD salt (1.0 g) prepared in Example 1 are accurately weighed (resulting molar ratio of 1:1). A homogenous paste of lyophilized methoxetamine-SBEBCD salt is prepared in a mortar by adding water:methanol (1:1) to the mixture in small quantities. Free base methoxetamine powder is then added to the paste in portions with continuous kneading for three hours. An appropriate quantity of water:methanol mixture is added to maintain suitable consistency of the paste. This paste is then dried in a hot air oven for 24 hours. The dried complex is then powdered and sieved, then stored in an airtight container until further use.

Co-Precipitation Method—Quantities of free base methoxetamine (68 mg) and lyophilized methoxetamine-SBEBCD salt (1.0 g) prepared in Example 1 are dissolved separately in methanol and water, respectively. The solution of free base methoxetamine is added dropwise to the cyclodextrin containing solution. The contents are stirred continuously for 6 hours, at which point they are dried at elevated temperature for 48 hours, collected, and stored in airtight containers until further use.

Solvent Evaporation Method—Free base methoxetamine (68 mg) is dissolved in a suitable organic solvent (e.g. methanol) at room temperature. The required amount of lyophilized methoxetamine-SBEBCD salt (1.0 g) prepared in Example 1 is dissolved in hot water and is added dropwise into the solution with continuous stirring over one hour. The resulting complexes are then filtered and dried under a vacuum. The resulting solid mass is then stored in a desiccator under vacuum to a constant weight. The dried product is removed, sieved, then stored in a closed airtight container.

Characterization of Resulting Inclusion Complexes

The resulting salt/inclusion complexes are then characterized for drug content, solubility, and stability. The samples are analyzed by appropriate analytical techniques (e.g. co-precipitation of drug in the complex, scanning electron microscopy of the physical mixtures, IR spectral analysis, differential scanning calorimetry, nuclear magnetic resonance (NMR) spectroscopy, and dissolution/HPLC analysis) at various timepoints in order to ensure the resulting inclusion complexes have the desired amount of methoxetamine and are suitably stable for later use. Such inclusion complexes can be directly administered or used in a further formulation.

Alternative Preparation Methods

In addition to the methods described above, alternative methods for the preparation of the salt-inclusion complexes described herein are available. For example, the preparation of an inclusion complex could be prepared prior to forming the free-acid complexing agent, which is then used to neutralize excess free base pharmaceutical compound in a later step. Alternatively, it is contemplated that the preparation of the salt and the complex could be formed simultaneously in a one-pot reaction scheme.

Example 3. Preparation of a Deschloroketamine-SBEBCD Salt

A deschloroketamine-SBEBCD salt is prepared according to the general protocol shown in Scheme 2. The protocol provided herein is used to prepare a stable, high concentration deschloroketamine solution. This solution can be adjusted to an osmolality near physiological levels (~300 mOsm/kg) and a pH near the bottom range of the buffering capacity of the deschloroketamine's pKa value (~2 pH units below) for use in a subcutaneous formulation. Alternatively, the aqueous solution can be lyophilized to remove the liquid and leave behind the deschloroketamine-SBEBCD salt in solid form, which can then be used in any subsequent formulation desired.

Scheme 2

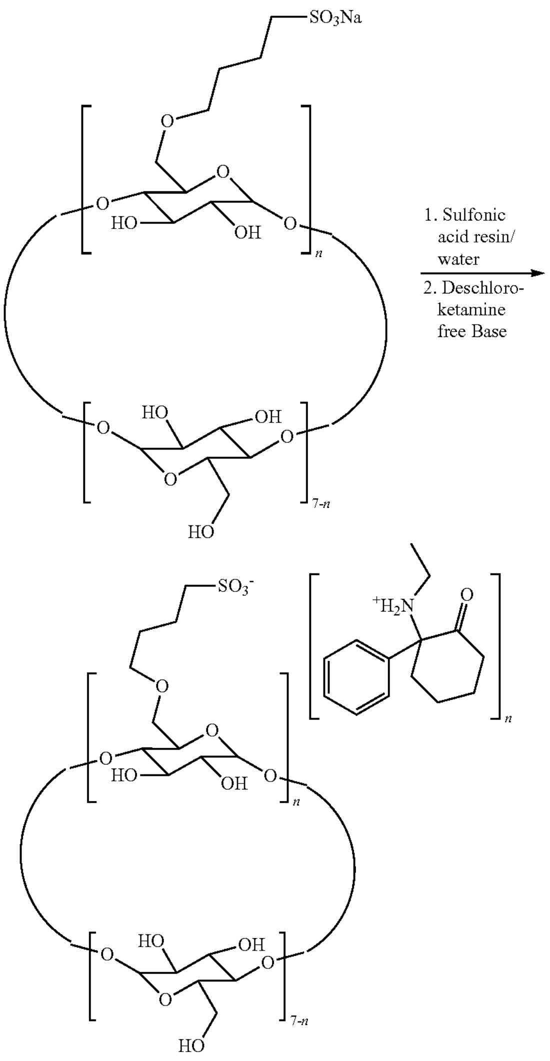

Experimental Procedure for the Preparation of Deschloroketamine SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 1.

Deschloroketamine HCl: Purchased from desired manufacturer and can be used without further purification. Free base deschloroketamine is prepared from the HCl salt with concentrated sodium hydroxide and isolated by vacuum filtration.

Deschloroketamine Freebase: Deschloroketamine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 3:
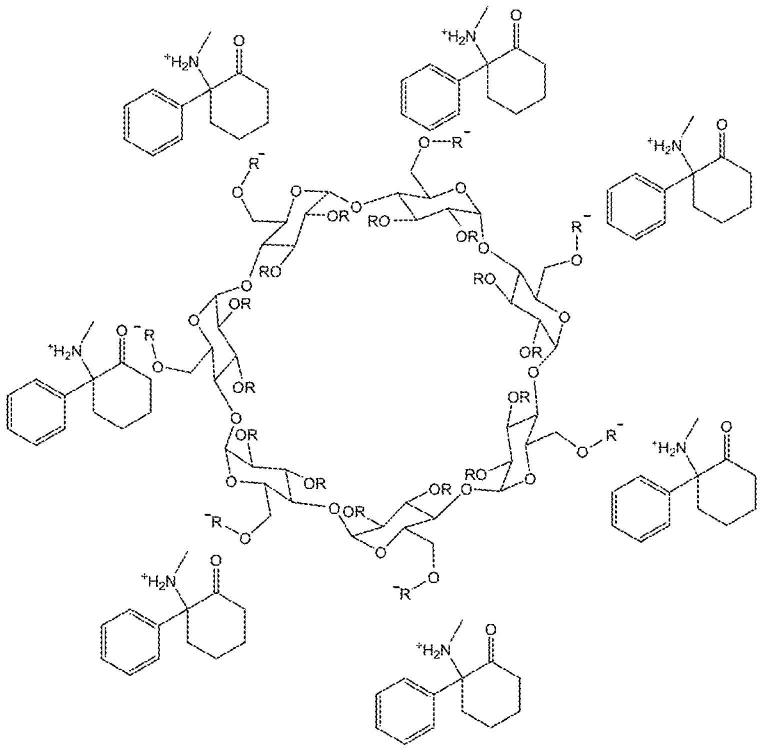
FIG. 3 shows an exemplary structure of a deschloroketamine-SBEBCD salt.

Synthesis of Deschloroketamine-Captisol® Salt: Captisol® acid prepared above (moisture corrected to ascertain actual concentration) is dissolved in HPLC grade water in a test tube with a teflon stirbar. The solution is stirred vigorously and deschloroketamine freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of deschloroketamine, at which point nearly all (~99%) of the deschloroketamine will be protonated. The solution is syringe filtered with a 0.45 μM nylon filter and is stored in a test tube under ambient air and wrapped in aluminum foil. Part of the volume is lyophilized to produce a powder of the deschloroketamine-Captisol® salt. This resulting powder is observed under ambient conditions to observe for any wetting, discoloration, or other observable change. The remaining volume of solution containing the deschloroketamine-Captisol® salt is similarly monitored for visible changes. The sample is also periodically monitored by HPLC to ascertain stability over time. The structure of the resulting deschloroketamine-Captisol® salt is shown in FIG. 3.

Example 4. Preparation of a 3-Methoxyphencyclidine-SBEBCD Salt

A 3-methoxyphencyclidine-SBEBCD salt is prepared according to the general protocol shown in Scheme 3. The protocol provided herein is used to prepare a stable, high concentration 3-methoxyphencyclidine solution. This solution can be adjusted to an osmolality near physiological levels (~300 mOsm/kg) and a pH near the bottom range of the buffering capacity of the 3-methoxyphencyclidine's pKa value (~2 pH units below) for use in a subcutaneous formulation. Alternatively, the aqueous solution can be lyophilized to remove the liquid and leave behind the 3-methoxyphencyclidine-SBEBCD salt in solid form, which can then be used in any subsequent formulation desired.

Scheme 3

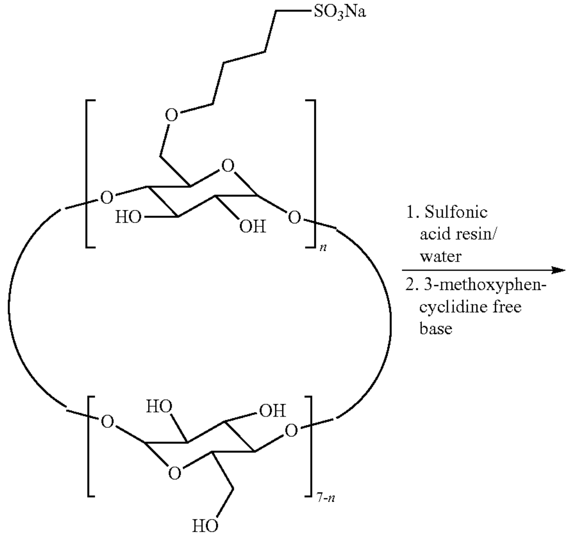

-continued

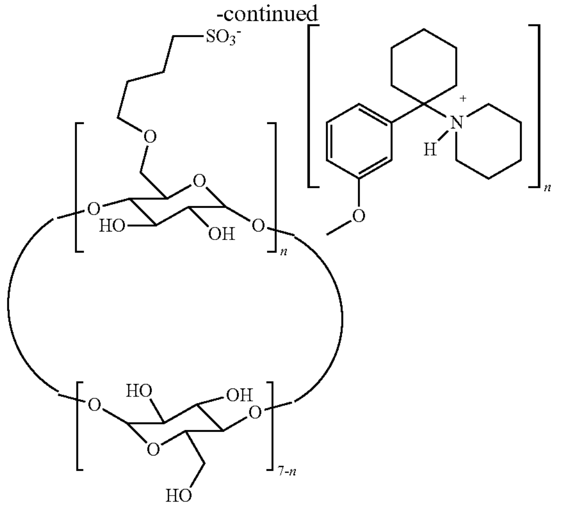

Experimental Procedure for the Preparation of 3-Methoxyphencyclidine SBEBCD Salt HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 1.

3-methoxyphencyclidine HCl: Purchased from desired manufacturer and can be used without further purification. Free base 3-methoxyphencyclidine is prepared from the HCl salt with concentrated sodium hydroxide and isolated by vacuum filtration.

3-methoxyphencyclidine Freebase: 3-methoxyphencyclidine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Synthesis of 3-methoxyphencyclidine-Captisol® Salt: Captisol® acid prepared above (moisture corrected to ascertain actual concentration) is dissolved in HPLC grade water in a test tube with a teflon stirbar. The solution is stirred vigorously and 3-methoxyphencyclidine freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of 3-methoxyphencyclidine, at which point nearly all (~99%) of the 3-methoxyphencyclidine will be protonated. The solution is syringe filtered with a 0.45 μM nylon filter and is stored in a test tube under ambient air and wrapped in aluminum foil. Part of the volume is lyophilized to produce a powder of the 3-methoxyphencyclidine-Captisol® salt. This resulting powder is observed under ambient conditions to observe for any wetting, discoloration, or other observable change. The remaining volume of solution containing the 3-methoxyphencyclidine-Captisol® salt is similarly monitored for visible changes. The sample is also periodically monitored by HPLC to ascertain stability over time.

Figure 4:
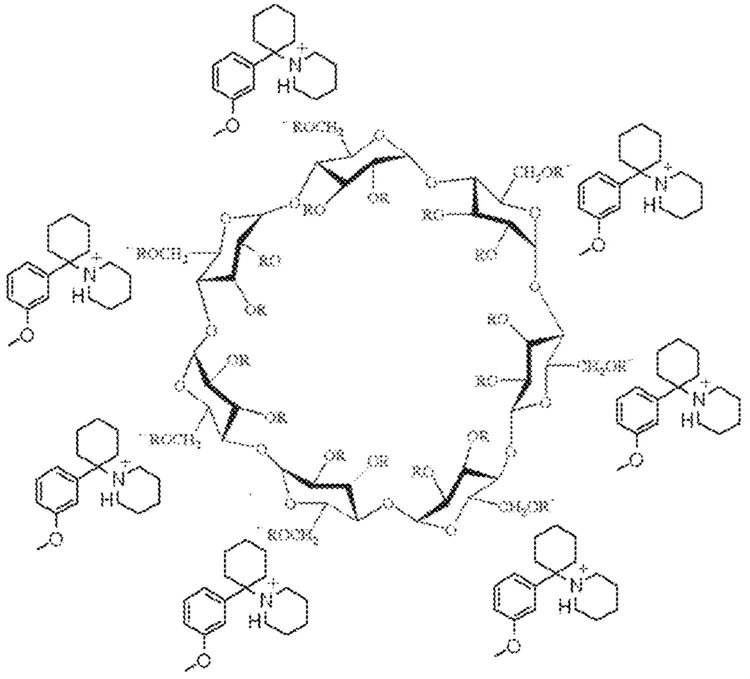
FIG. 4 shows an exemplary structure of a 3-methoxy-phencyclidine-SBEBCD salt.

The structure of the resulting 3-methoxyphencyclidine-Captisol® salt is shown in FIG. 4.

Example 5. Preparation of a 3-Methoxieticyclidine-SuACD Salt

A 3-methoxyphencyclidine-Succinated alpha-cyclodextrin (SuACD) salt is prepared according to the general protocol shown in Scheme 4. The protocol provided herein is used to prepare a stable, high concentration 3-methoxieticyclidine solution. This solution can be adjusted to an osmolality near physiological levels (~300 mOsm/kg) and a pH near the bottom range of the buffering capacity of the 3-methoxyphencyclidine's pKa value (~2 pH units below) for use in a subcutaneous formulation. Alternatively, the aqueous solution can be lyophilized to remove the liquid and leave behind the 3-methoxieticyclidine-SuACD salt in solid form, which can then be used in any subsequent formulation desired.

Scheme 4

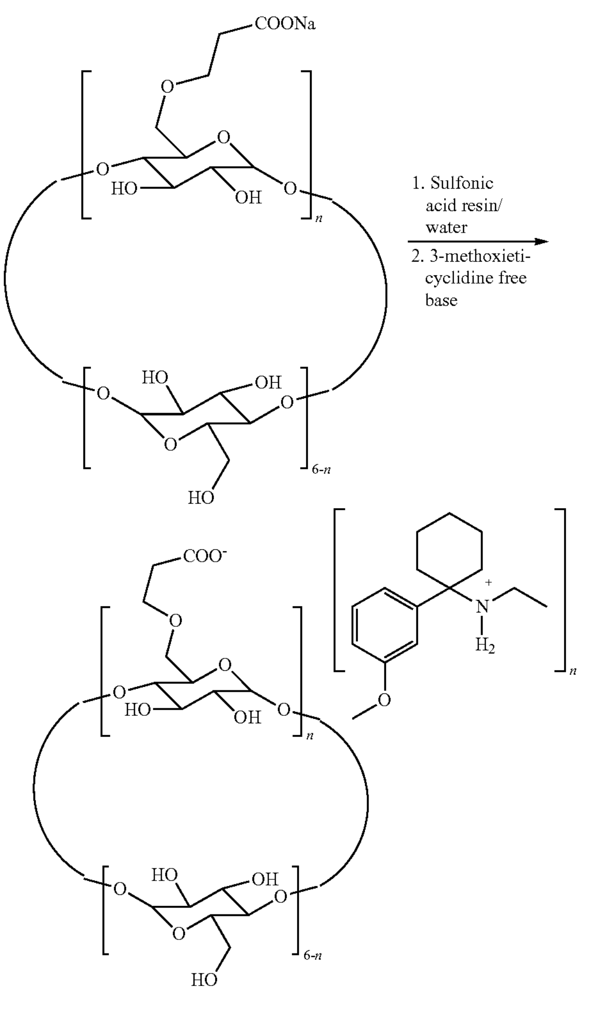

Experimental Procedure for the Preparation of 3-Methoxieticyclidine SuACD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

SuACD—Can be purchased from Arachem (M) Sdn Bhd. (Arachem) (pharmaceutical grade). The moisture content is verified by Karl Fisher analysis. SuACD is a polysuccinylated α-cyclodextrin sodium form, with an average of ~4 succinyl groups per molecule and an average MW of ~1300

SuACD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% SuACD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

3-methoxieticyclidine HCl: Purchased from desired manufacturer and can be used without further purification. Free base 3-methoxieticyclidine is prepared from the HCl salt with concentrated sodium hydroxide and isolated by vacuum filtration.

3-methoxieticyclidine Freebase: 3-methoxieticyclidine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 5:
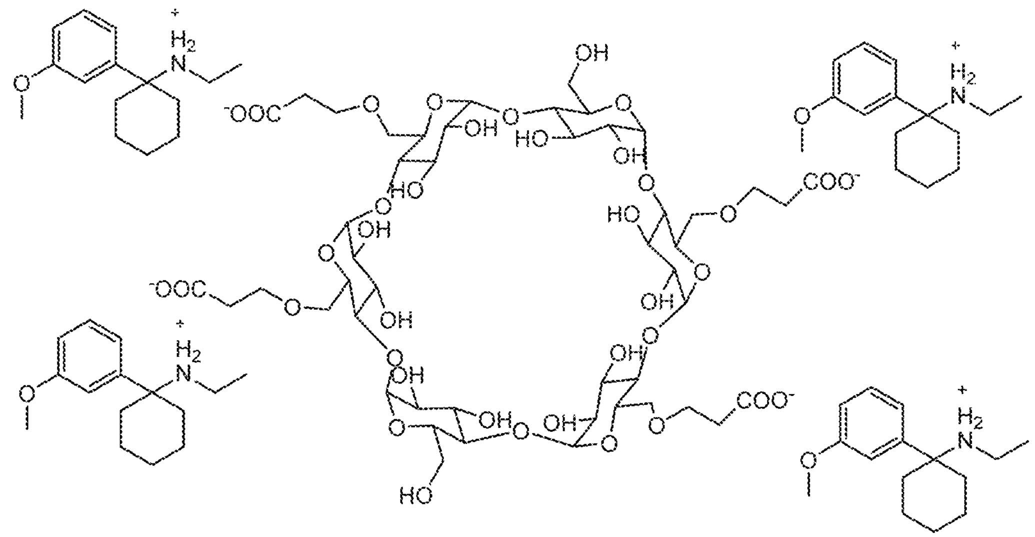
FIG. 5 shows an exemplary structure of a methoxieticyclidine-SuACD salt.

Synthesis of 3-methoxieticyclidine-SuACD Salt: SuACD acid prepared above (moisture corrected to ascertain actual concentration) is dissolved in HPLC grade water in a test tube with a teflon stirbar. The solution is stirred vigorously and 3-methoxieticyclidine freebase (1 equivalent per acidic functional group of SuACD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of 3-methoxieticyclidine, at which point nearly all (~99%) of the 3-methoxyphencyclidine will be protonated. The solution is syringe filtered with a 0.45 μM nylon filter and is stored in a test tube under ambient air and wrapped in aluminum foil. Part of the volume is lyophilized to produce a powder of the 3-methoxieticyclidine-SuACD salt. This resulting powder is observed under ambient conditions to observe for any wetting, discoloration, or other observable change. The remaining volume of solution containing the 3-methoxieticyclidine-SuACD salt is similarly monitored for visible changes. The sample is also periodically monitored by HPLC to ascertain stability over time. The structure of the resulting 3-methoxieticyclidine-SuACD salt is shown in FIG. 5

Example 6. Preparation of a Dextromethorphan-CMGCD Salt

A dextromethorphan-carboxymethyl-gamma-cyclodextrin (CMGCD) salt is prepared according to the general protocol shown in Scheme 5. The protocol provided herein is used to prepare a stable, high concentration dextromethorphan solution. This solution can be adjusted to an osmolality near physiological levels (~300 mOsm/kg) and a pH near the bottom range of the buffering capacity of the 3-methoxyphencyclidine's pKa value (~2 pH units below) for use in a subcutaneous formulation. Alternatively, the aqueous solution can be lyophilized to remove the liquid and leave behind the dextromethorphan-CMGCD salt in solid form, which can then be used in any subsequent formulation desired.

Scheme 5

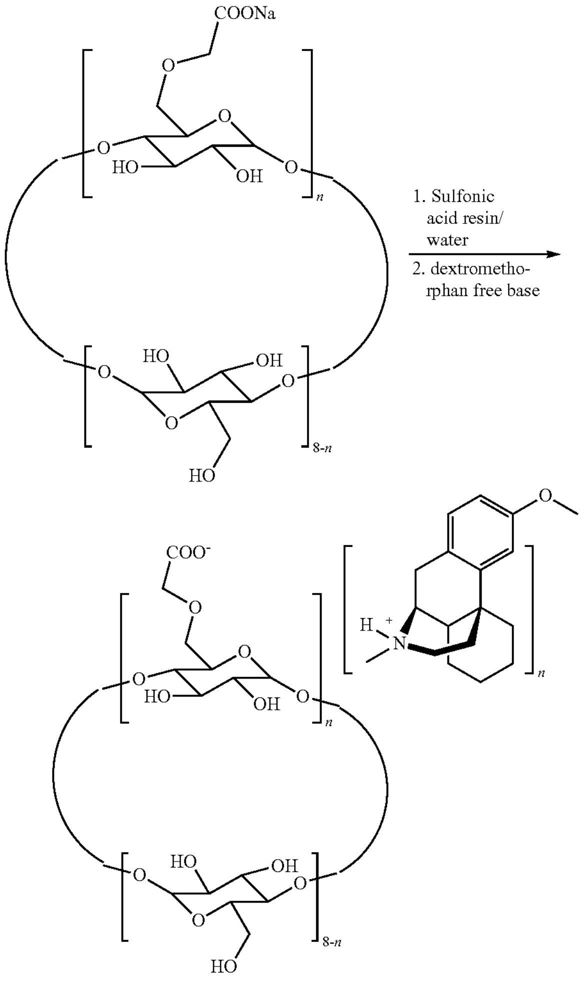

Experimental Procedure for the Preparation of Dextromethorphan-CMGCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

CMGCD—Can be purchased from Arachem (M) Sdn Bhd (Arachem). The moisture content is verified by Karl Fisher analysis. CMGCD is a carboxymethylated γ-cyclodextrin sodium form, with an average of ~4 carboxymethyl groups per molecule and an average MW of ~1600.

CMGCD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% CMGCD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting solid is stored in a foil-wrapped scintillation vial at −20° C.

Dextromethorphan HBr: Purchased from desired manufacturer and can be used without further purification. Free base dextromethorphan is prepared from the HBr salt with concentrated sodium hydroxide and isolated by vacuum filtration.

Dextromethorphan Freebase: Dextromethorphan hydrobromide is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 6:
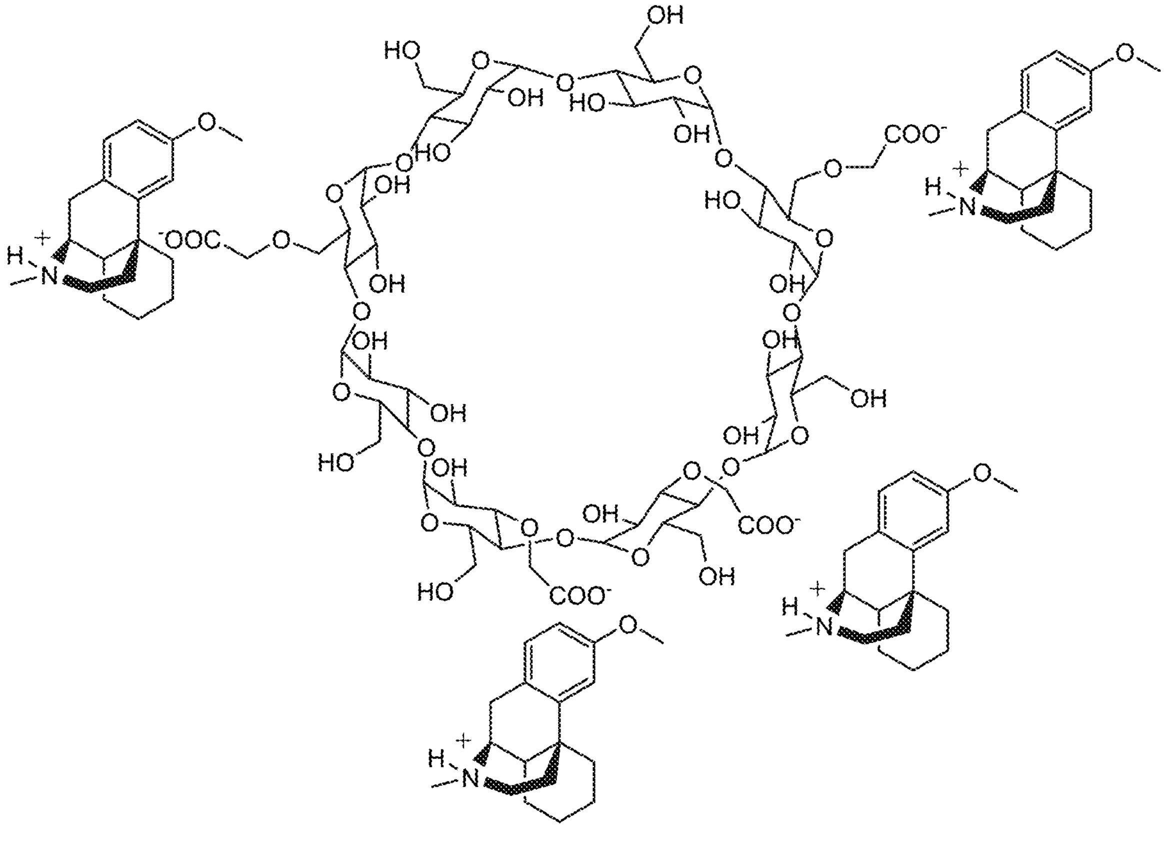
FIG. 6 shows an exemplary structure of a dextromethorphan-CMGCD salt.

Synthesis of Dextromethorphan CMGCD Salt: CMGCD acid prepared above (moisture corrected to ascertain actual concentration) is dissolved in HPLC grade water in a test tube with a teflon stirbar. The solution is stirred vigorously and dextromethorphan freebase (1 equivalent per acidic functional group of CMGCD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of dextromethorphan, at which point nearly all (~99%) of the dextromethorphan will be protonated. The solution is syringe filtered with a 0.45 μM nylon filter and is stored in a test tube under ambient air and wrapped in aluminum foil. Part of the volume is lyophilized to produce a powder of the dextromethorphan-CMGCD salt. This resulting powder is observed under ambient conditions to observe for any wetting, discoloration, or other observable change. The remaining volume of solution containing the dextromethorphan-CMGCD salt is similarly monitored for visible changes. The sample is also periodically monitored by HPLC to ascertain stability over time. The structure of the resulting dextromethorphan-CMGCD salt is shown in FIG. 6.

Example 7. Sublingual Formulation of Ketamine Comprising Ketamine-SBEBCD Salt and Free Base Ketamine A composition is prepared as in Example 2 utilizing a ketamine-SBEBCD salt (1.0 g, prepared using an analogous method to that shown in Example 1) with an additional molar equivalent of free-base ketamine (67 mg) is further formulated for sublingual formulation in unit dose form as a sublingual troche. An example protocol for preparation of such a formulation is as follows:

A 400 mL beaker is placed on the scales and tared. The active ingredient ketamine-SBEBCD salt/free base mixture is added. A polyethylene glycol (PEG) base (e.g. PEG 1450) is prepared in a separate beaker by melting in a water bath placed over a hotplate. The melted PEG base is then added to the 400 mL beaker containing the ketamine-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, buttering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the ketamine is released into the saliva of the subject. The additional free base ketamine acts to modulate the pH of the composition upon dissolution to closely match the pH of the saliva (~pH 7). In the saliva, soluble freebase ketamine liberates for mucosal absorption from center of cyclodextrin and from ketamine salts to increase bioavailability. Solubilized non-ionized ketamine in equilibrium with the dynamic buffering of two mechanisms of effect from the captisol acid (e.g. protonation/salt formation of ketamine and complexation of free base ketamine) helps keep pH higher than ketamine HCl allowing a higher proportion and more rapid mucosal absorption of drug product.

Figure 7:
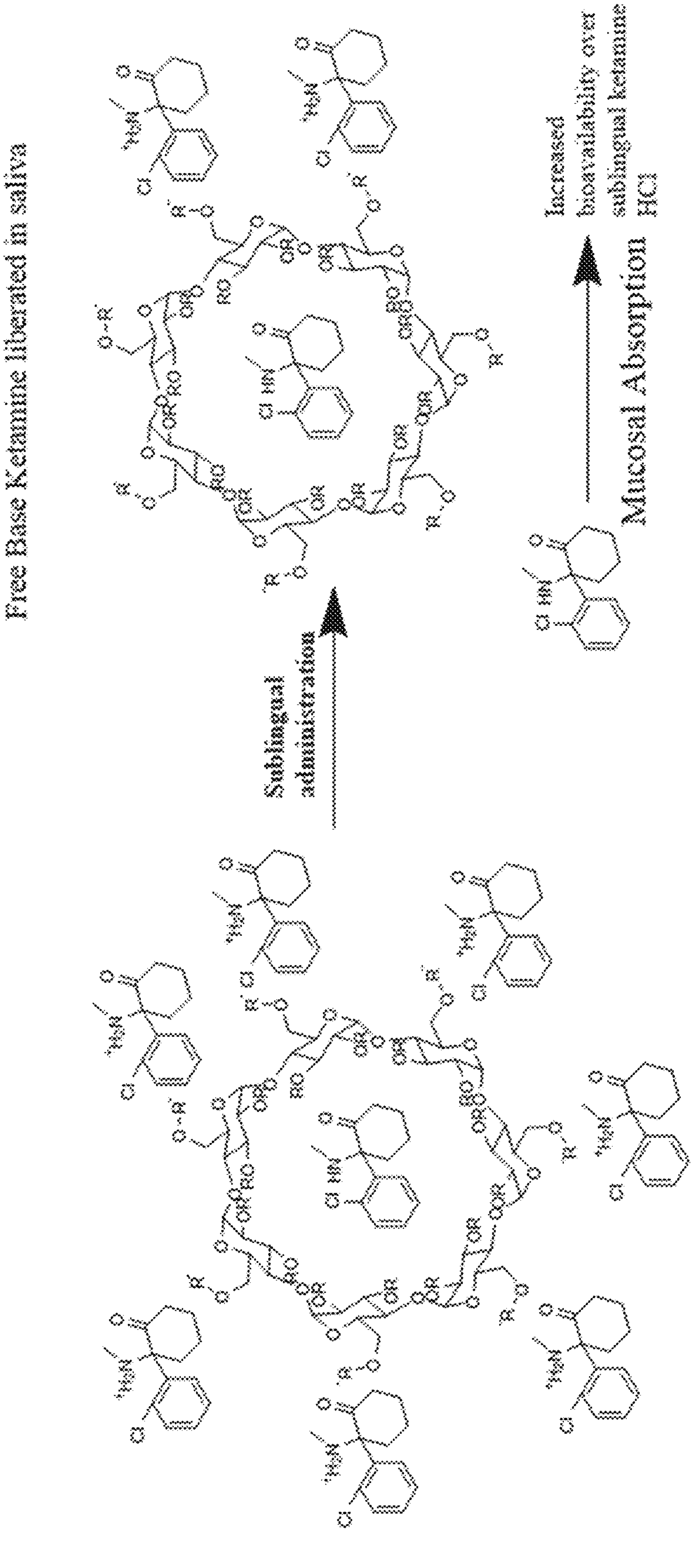
FIG. 7 shows a schematic of sublingual administration of a ketamine-SBEBCD salt formulation.

This two-mechanism effect resulting in increased bioavailability is illustrated in FIG. 7, which shows non-ionized ketamine within the cyclodextrin core of the SBEBCD. This is non-ionized ketamine is released into the saliva which is then absorbed via mucosal absorption. Buffering effects within the saliva then convert the protonated ketamine to the non-ionized state, which can be complexed with the now unoccupied cyclodextrin core to aid solubilization of the poorly soluble free base form. This process then repeats until all of the ketamine is absorbed, resulting in a successful sublingual administration that is painless and prevents crashing out of the drug molecule during administration. This also produces a form of dynamic buffering that can keep the pH higher to allow the ionized ketamine molecules complexed in the ketamine-SBEBCD salt to become deprotonated or unionized even while in a highly solubilized state, increasing submucosal absorption capacity are rate. Compared with a similar dose in a similar troche formulation made from ketamine HCl, tolerability, bioavailability, and solubility are all enhanced due to the SBECD-salt complex and free base ketamine complexed within the cyclodextrin core.

Example 8. Sublingual Formulation of Ketamine Comprising Ketamine-SBEBCD Salt and High Molar Equivalent Free Base Ketamine A ketamine-SBSBCD salt is prepared analogously to the salt prepared in Example 1 and is further processed into a sublingual formulation in unit dose form as a sublingual troche. The sublingual formulation here utilizes a substantial excess of free base ketamine in the formulation (10× molar equivalents compared to the ketamine-SBEBCD salt in the formulation). The substantial excess of free base ketamine provides numerous advantages over other formulations using compound-complexing agents salts as provided herein.

One advantage is that the presence of excess free base compound allows for pH adjustment and buffering in situ upon administration to closely match the tissue pH. The presence of excess free base molecules allows the compound to act as its own buffer, thus raising the pH compared to administration of the salt complex alone. By using the compound as its own buffer, a larger dose of the compound of interest can be applied without reaching excessive osmolality as additional base components may be omitted.

Additionally, using the compound as a buffer allows the total dosage unit (in this case a sublingual dose, but the concept is equally applicable to other dosage forms, particularly intranasal administration) to maintain the desired pH even as the material is absorbed by the relevant tissues after administration. As the compound is absorbed by the tissues, other free base molecules remain present to continue buffering the pH to a physically tolerable level. In some instances, a substantial portion of the excess of free base compound may only dissolve after administration after a certain amount of the compound has been absorbed into the mucosa, particularly when the free base compound is only sparingly soluble. In such a case, the absorption of the compound drives the equilibrium of the dissolution of the compound as it is absorbed, thus ensuring that only a desirable amount of free base compound is present at any time to act as an appropriate buffer to maintain the desired physiologically tolerable pH.

Finally, the presence of excess free base compound has the advantage of providing a consistent source of active compound, which can continuously occupy the complexing site within the cyclodextrin as the drug product compound is absorbed over time. The cyclodextrins in the formulation act as a shuttle for compound, helping to solubilize the compound, which can then be absorbed by the body. The cyclodextrin can then repeat this complexing/solubilization process with additional molecules of the compound to help solubilize the remaining excess free base.

Example Protocol The required quantities of free base ketamine (670 mg, 10× molar excess compared to the amount of SBEBCD) and the lyophilized ketamine-SBEBCD salt (1.0 g) prepared analogously to the salt in Example 1 are accurately weighed (resulting molar ratio of 10:1 free base ketamine:SBEBCD). A homogenous paste of lyophilized ketamine-SBEBCD salt is prepared in a mortar by adding water: ethanol (1:1) to the mixture in small quantities. Free base ketamine powder is then added to the paste in portions with continuous kneading for three hours. An appropriate quantity of water:ethanol mixture is added to maintain suitable consistency of the paste. This paste is then dried in a hot air oven for 24 hours. The dried complex is then powdered and sieved, then stored in an airtight container until further use.

The dried complex comprising excess free base ketamine is then formulated for sublingual formulation in unit dose form as a sublingual troche. An example protocol for preparation of such a formulation is as follows:

A 400 mL beaker is placed on the scales and tared. The active ingredient ketamine-SBEBCD salt/free base mixture prepared above is added. A polyethylene glycol (PEG) base (e.g. PEG 1450) is prepared in a separate beaker by melting in a water bath placed over a hotplate. The melted PEG base is then added to the 400 mL beaker containing the ketamine- SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, buttering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the ketamine is released into the saliva of the subject. The additional free base ketamine acts to modulate the pH of the composition upon dissolution to closely match the pH of the saliva (~pH 7). The excess free base ketamine successfully counteracts the acidic nature of the protonated ketamine from the SBEBCD salt. In the saliva, soluble amounts of freebase ketamine dissolve for mucosal absorption, both by eluting from the cyclodextrin and to a lesser extent by direct dissolution of the free base ketamine. Solubilized non-ionized ketamine is then absorbed into the nasal mucosa. This shifts the equilibrium of solubilization such that more free base ketamine becomes solubilized, both in solution and through complexation with the interior of the cyclodextrin. This dynamic buffering and solubilization process is driven through two mechanisms of effect: protonation/salt formation of ketamine (solubilization through forming an ion) and complexation of free base ketamine. These continuous effects driven by equilibrium thus increase absorption of the compound, allowing for a high concentration of drug product to be delivered in a formulation densely populated with drug product.

Figure 8:
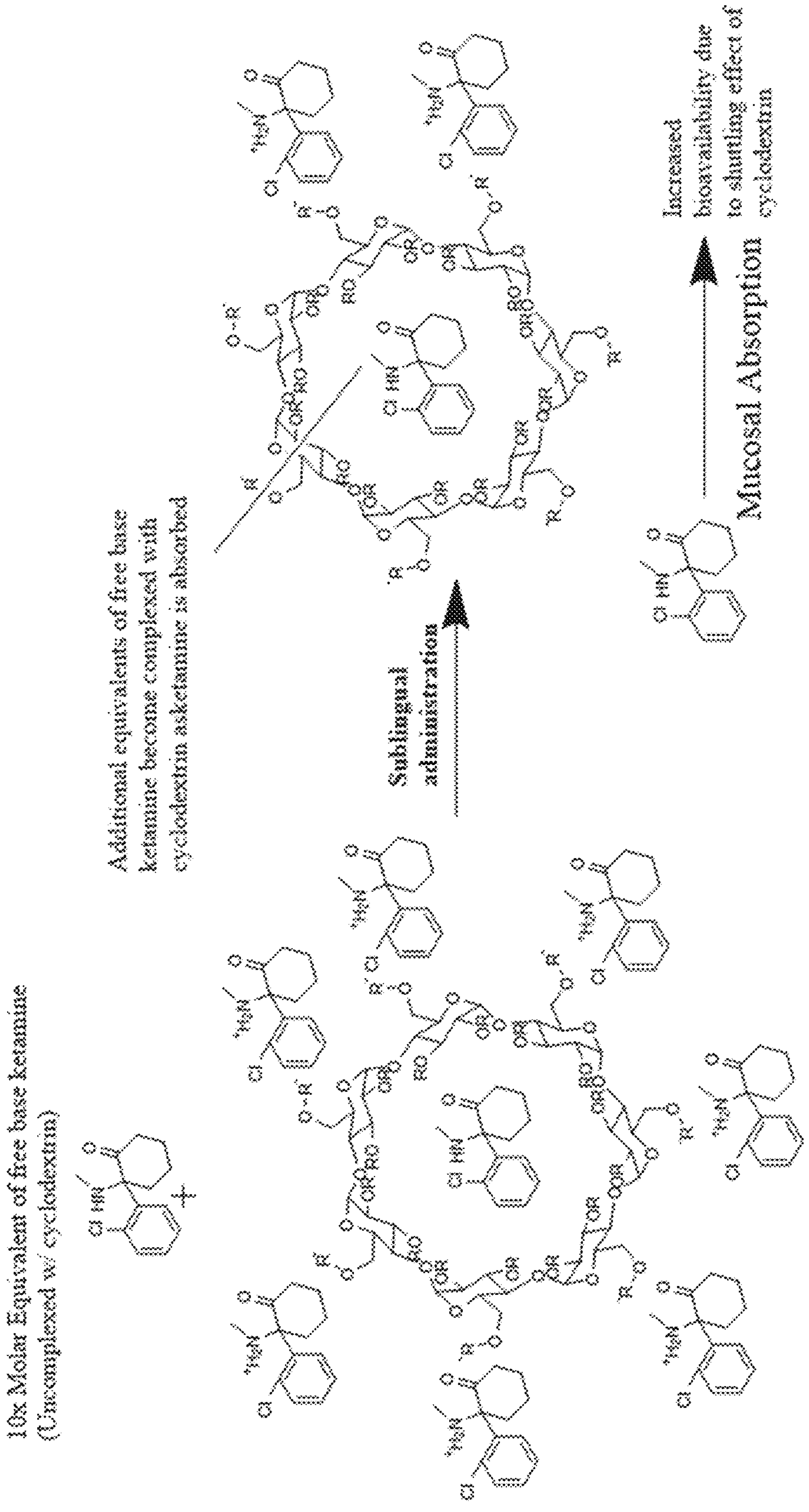
FIG. 8 shows a schematic of sublingual administration of a ketamine-SBEBCD salt formulation comprising an excess of free base ketamine.

The mechanism underling these effect resulting in increased bioavailability and enhanced buffering capacity of the system is illustrated in FIG. 8, which shows non-ionized ketamine within the cyclodextrin core of the SBEBCD and excess free base ketamine also present. The non-ionized ketamine is first released into the saliva from the cyclodextrin and then absorbed via mucosal absorption. Once absorbed, the equilibrium of the system shifts and allows more free base ketamine to become dissolved in the saliva, either directly or, more substantially, through additional complexation with the now unoccupied cyclodextrin core in a shuttle-like mechanism. As the additional free base ketamine solubilizes in the system, the desired physiologically tolerable pH of the formulation is maintained as the acidity of the protonated ketamine molecules present in the salt form continue to be neutralized as more free base compound solubilizes. This process then repeats until all of the ketamine is absorbed, resulting in a successful sublingual administration that is painless and effective. This also produces a form of dynamic buffering that can keep the pH elevated relative to a dose form without excess free base drug compound, thus allowing the ionized ketamine molecules associated with the ketamine-SBEBCD salt to become deprotonated or unionized even while in a highly solubilized state, increasing submucosal absorption capacity and rate. Compared with a similar dose in a similar troche formulation made from ketamine HCl, tolerability, bioavailability, and solubility are all enhanced due to the SBECD-salt complex and free base ketamine complexed within the cyclodextrin core.

Example 9. Preparation of a Mescaline-SBEBCD Salt

A mescaline-SBEBCD salt is prepared according to the general protocol shown in Scheme 6. The protocol provided herein is used to prepare a stable, high concentration mescaline solution. This solution can be adjusted to an osmolality near physiological levels (~300 mOsm/kg) and a pH near the bottom range of the buffering capacity of the mescaline's pKa value (~2 pH units below) for use in a subcutaneous formulation. Alternatively, the aqueous solution can be lyophilized to remove the liquid and leave behind the mescaline-SBEBCD salt in solid form, which can then be used in any subsequent formulation desired.

Scheme 6

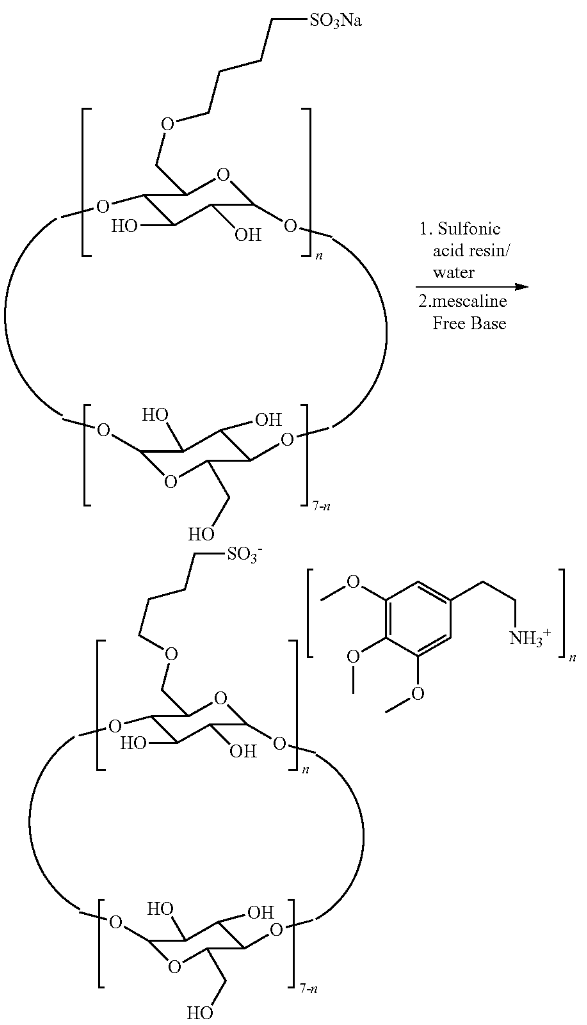

Experimental Procedure for the Preparation of Mescaline SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol®: Can be purchased from Ligand Pharmaceuticals, Inc. (Ligand) (pharmaceutical grade). The moisture content is verified by Karl Fisher analysis. Captisol® is a polysulfobutylated β-cyclodextrin sodium form, with an average of 6.5 sulfobutyl groups per molecule and an average MW of 2,163.

Mescaline HCl: Purchased from desired manufacturer and can be used without further purification. Free base mescaline is prepared from the HCl salt with concentrated sodium hydroxide and isolated by vacuum filtration.

Synthesis of Captisol® Acid. Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and was completely dried by applying compressed air for 10 minutes before the sample was applied. A solution of 15% Captisol® (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

Mescaline Freebase: Mescaline hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 9:
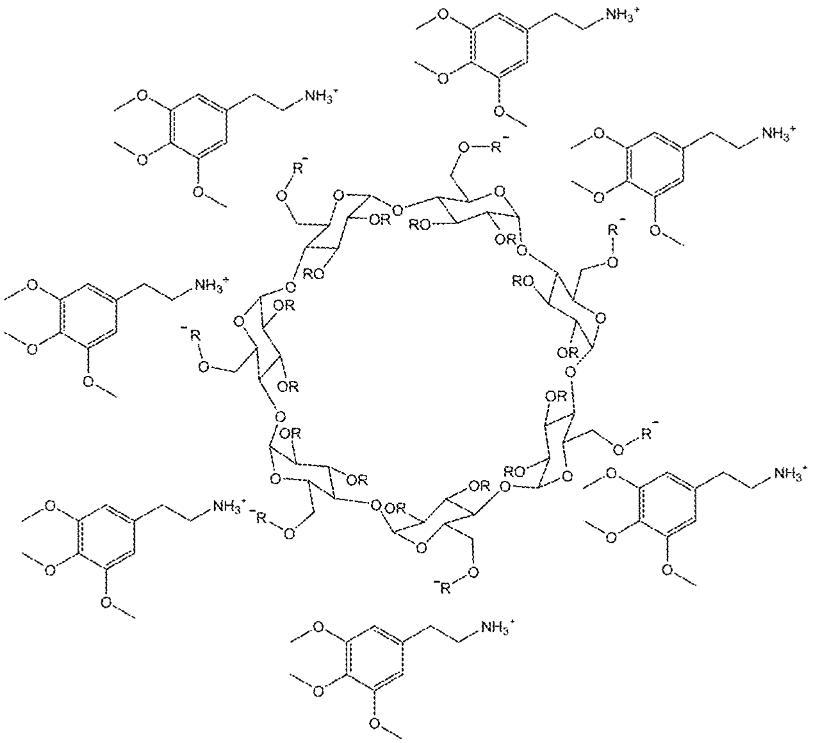
FIG. 9 shows an exemplary structure of an compound-complexing agent salt as provided herein. The compound-complexing agent salt shown is a mescaline-SBEBCD salt.

Synthesis of Mescaline-Captisol® Salt: Captisol® acid prepared above (moisture corrected to ascertain actual concentration) is dissolved in HPLC grade water in a test tube with a teflon stirbar. The solution is stirred vigorously and mescaline freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of mescaline, at which point nearly all (~99%) of the mescaline will be protonated. The solution is syringe filtered with a 0.45 μM nylon filter and is stored in a test tube under ambient air and wrapped in aluminum foil. Part of the volume is lyophilized to produce a powder of the mescaline-Captisol® salt. This resulting powder is observed under ambient conditions to observe for any wetting, discoloration, or other observable change. The remaining volume of solution containing the mescaline-Captisol® salt is similarly monitored for visible changes. The sample is also periodically monitored by HPLC to ascertain stability over time. The structure of the resulting mescaline-Captisol® salt is shown in FIG. 9.

Figure 10:
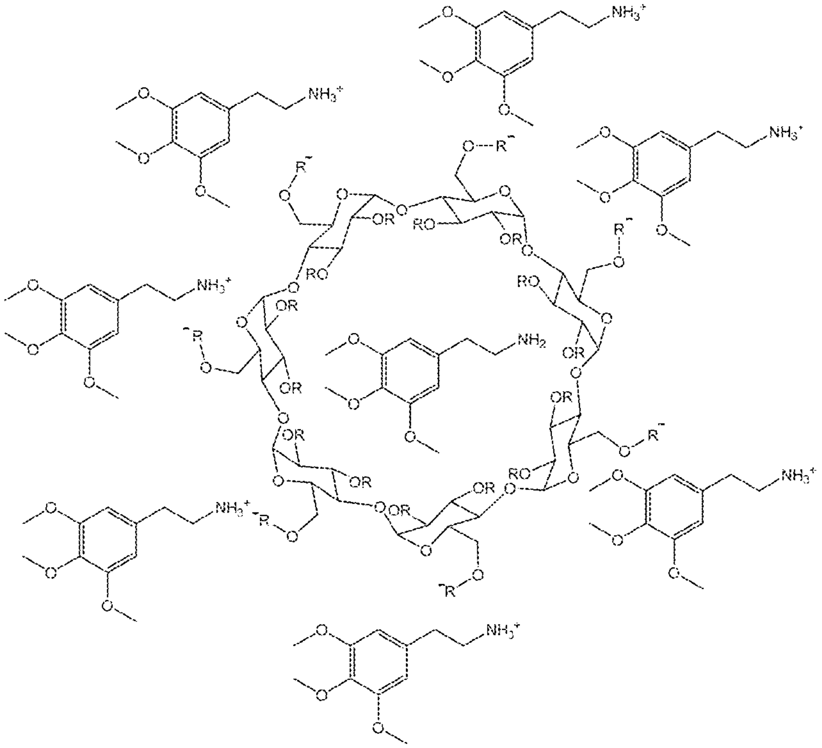
FIG. 10 shows an exemplary structure of a mescaline-SBEBCD salt which is also acting as an inclusion complex for an additional equivalent of free base mescaline.

Example 10. Preparation of a Mescaline-SBEBCD Salt with Free Base Mescaline Complexed within the SBEBCD The salt forms of the complexing agent/pharmaceutical compounds provided herein can also be adapted to incorporate additional molar equivalents of free base compound. For example, in instances where the complexing agent is a cyclodextrin such as SBEBCD, the interior portion of the cyclodextrin can incorporate an additional molecule of compound. An exemplary illustration of such a complex can be seen in FIG. 10, which shows the mescaline/SBEBCD salt complex described in Example 9 which has been modified to incorporate an additional uncharged molecule of mescaline on the interior of the cyclodextrin. Such complexes can have additional benefits when used in pharmaceutical compositions, including increased solubility of the compounds upon administration, increased bioavailability of the compounds, and the presence of free base compound can act to create a buffering system that allows for a more biocompatible pH to be achieved upon delivery of the pharmaceutical composition as the free base compound neutralizes some of the acidic functionalities of the protonated compounds of the salt complex.

Such complexes can be created in a variety of ways, several of which are shown by example below. In order to ascertain the proper ratio of salt complex to free base compound to add to prepare a mixture with an additional molecule of compound incorporated into the center of the cyclodextrin, it is necessary to determine the molecular weight of the salt complex. This can be readily calculated from the known molecular weight of the starting materials and stoichiometry of the complexing agent and compound. For example, as the SBEBCD used to prepare the mescaline-SBEBCD salt in Example 9 has an average of 6.5 sulfobutyl groups per molecule, the resulting salt has an average of 6.5 mescaline molecules for every cyclodextrin molecule, resulting in the salt having an average molecular weight of ~3630 Daltons. This value can be calculated as follows: From the average molecular weight of the SBEBCD (average MW of 2,163) is subtracted the weight of sodium atoms which have been removed (6.5 times 22.99 Daltons), and the weight of mescaline molecules (6.5 times 211.26 Daltons) and additional hydrogen atoms (6.5 times 1.01 Daltons) is added, yielding an average molecule weight of about 3400 Daltons. Additionally, any residual water in the resulting salt can be measured by an appropriate procedure, such as Karl Fischer analysis.

The complexes described in this example can be prepared by any suitable method, including without limitation the procedures described below.

Physical mixture method—The required molar quantities (1:1) of free base mescaline (62 mg) and the lyophilized mescaline-SBEBCD salt (1.0 g) prepared in Example 9 are weighed accurately and mixed together thoroughly in a mortar with vigorous trituration for about three hours. The mixture is then passed through a sieve and stored in an airtight container until further use.

Kneading Method—The required quantities of free base mescaline (62 mg) and the lyophilized mescaline-SBEBCD salt (1.0 g) prepared in Example 9 are accurately weighed (resulting molar ratio of 1:1). A homogenous paste of lyophilized mescaline-SBEBCD salt is prepared in a mortar by adding water:methanol (1:1) to the mixture in small quantities. Free base mescaline powder is then added to the paste in portions with continuous kneading for three hours. An appropriate quantity of water:methanol mixture is added to maintain suitable consistency of the paste. This paste is then dried in a hot air oven for 24 hours. The dried complex is then powdered and sieved, then stored in an airtight container until further use.

Co-Precipitation Method—Quantities of free base mescaline (62 mg) and lyophilized mescaline-SBEBCD salt (1.0 g) prepared in Example 9 are dissolved separately in methanol and water, respectively. The solution of free base mescaline is added dropwise to the cyclodextrin containing solution. The contents are stirred continuously for 6 hours, at which point they are dried at elevated temperature for 48 hours, collected, and stored in airtight containers until further use.

Solvent Evaporation Method—Free base mescaline (62 mg) is dissolved in a suitable organic solvent (e.g. methanol) at room temperature. The required amount of lyophilized mescaline-SBEBCD salt (1.0 g) prepared in Example 9 is dissolved in hot water and is added dropwise into the solution with continuous stirring over one hour. The resulting complexes are then filtered and dried under a vacuum. The resulting solid mass is then stored in a desiccator under vacuum to a constant weight. The dried product is removed, sieved, then stored in a closed airtight container.

Characterization of Resulting Inclusion Complexes

The resulting salt/inclusion complexes are then characterized for drug content, solubility, and stability. The samples are analyzed by appropriate analytical techniques (e.g. co-precipitation of drug in the complex, scanning electron microscopy of the physical mixtures, IR spectral analysis, differential scanning calorimetry, X-ray diffraction or X-ray powder diffraction, and dissolution/HPLC analysis) at various timepoints in order to ensure the resulting inclusion complexes have the desired amount of mescaline and are suitably stable for later use. Such inclusion complexes can be directly administered or used in a further formulation.

Alternative Preparation Methods

In addition to the methods described above, alternative methods for the preparation of the salt-inclusion complexes described herein are available. For example, the preparation of an inclusion complex could be prepared prior to forming the free-acid complexing agent, which is then used to neutralize excess free base pharmaceutical compound in a later step. Alternatively, it is contemplated that the preparation of the salt and the complex could be formed simultaneously in a one-pot reaction scheme.

Example 11. Preparation of a N,N-Dimethyltryptamine-SBEBCD Salt

A N,N-dimethyltryptamine-SBEBCD salt is prepared according to the general protocol shown in Scheme 7. The protocol provided herein is used to prepare a stable, high concentration N,N-dimethyltryptamine solution. This solution can be adjusted to an osmolality near physiological levels (~300 mOsm/kg) and a pH near the bottom range of the buffering capacity of the N,N-dimethyltryptamine's pKa value (~2 pH units below) for use in a subcutaneous formulation. Alternatively, the aqueous solution can be lyophilized to remove the liquid and leave behind the N,N-dimethyltryptamine-SBEBCD salt in solid form, which can then be used in any subsequent formulation desired.

Scheme 7

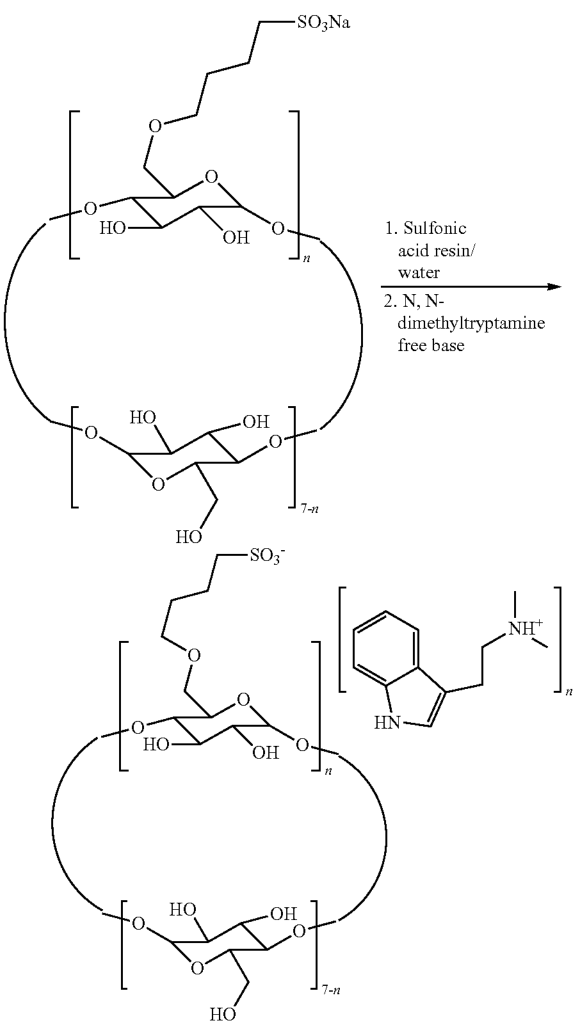

Experimental Procedure for the Preparation of N,N-Dimethyltryptamine SBEBCD Salt HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 1.

N,N-dimethyltryptamine HCl: Purchased from desired manufacturer and can be used without further purification. Free base N,N-dimethyltryptamine is prepared from the HCl salt with concentrated sodium hydroxide and isolated by vacuum filtration.

N,N-dimethyltryptamine Freebase: N,N-dimethyltryptamine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 11:
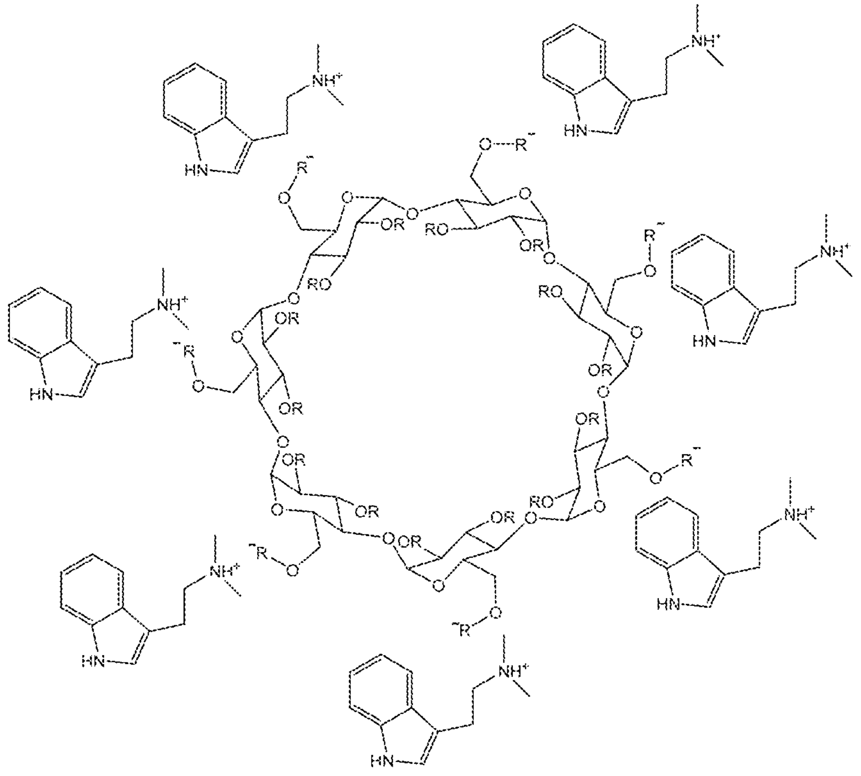
FIG. 11 shows an exemplary structure of a N,N-dimethyltryptamine-SBEBCD salt.

Synthesis of N,N-dimethyltryptamine-Captisol® Salt: Captisol® acid prepared above (moisture corrected to ascertain actual concentration) is dissolved in HPLC grade water in a test tube with a teflon stirbar. The solution is stirred vigorously and N,N-dimethyltryptamine freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of N,N-dimethyltryptamine, at which point nearly all (~99%) of the N,N-dimethyltryptamine will be protonated. The solution is syringe filtered with a 0.45 μM nylon filter and is stored in a test tube under ambient air and wrapped in aluminum foil. Part of the volume is lyophilized to produce a powder of the N,N-dimethyltryptamine-Captisol® salt. This resulting powder is observed under ambient conditions to observe for any wetting, discoloration, or other observable change. The remaining volume of solution containing the N,N-dimethyltryptamine-Captisol® salt is similarly monitored for visible changes. The sample is also periodically monitored by HPLC to ascertain stability over time. The structure of the resulting N,N-dimethyltryptamine-Captisol® salt is shown in FIG. 11.

Example 12. Preparation of a 4-hydroxy-N-methyl-N-isopropyl-tryptamine-SBEBCD Salt A 4-hydroxy-N-methyl-N-isopropyl-tryptamine-SBEBCD salt is prepared according to the general protocol shown in Scheme 8. The protocol provided herein is used to prepare a stable, high concentration 4-hydroxy-N-methyl-N-isopropyl-tryptamine solution. This solution can be adjusted to an osmolality near physiological levels (~300 mOsm/kg) and a pH near the bottom range of the buffering capacity of the 4-hydroxy-N-methyl-N-isopropyl-tryptamine's pKa value (~2 pH units below) for use in a subcutaneous formulation. Alternatively, the aqueous solution can be lyophilized to remove the liquid and leave behind the 4-hydroxy-N-methyl-N-isopropyl-tryptamine-SBEBCD salt in solid form, which can then be used in any subsequent formulation desired.

Scheme 8

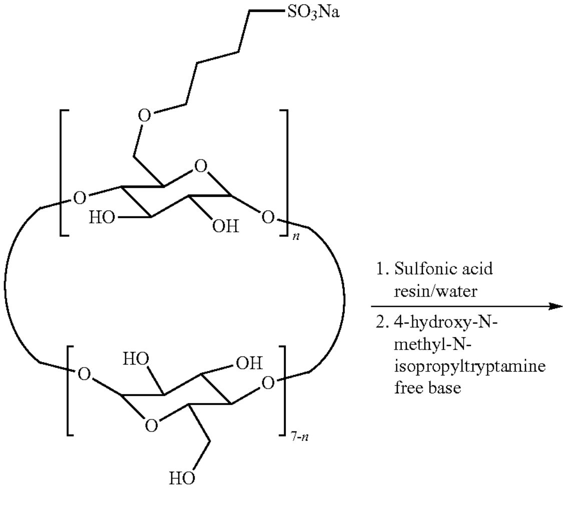

-continued

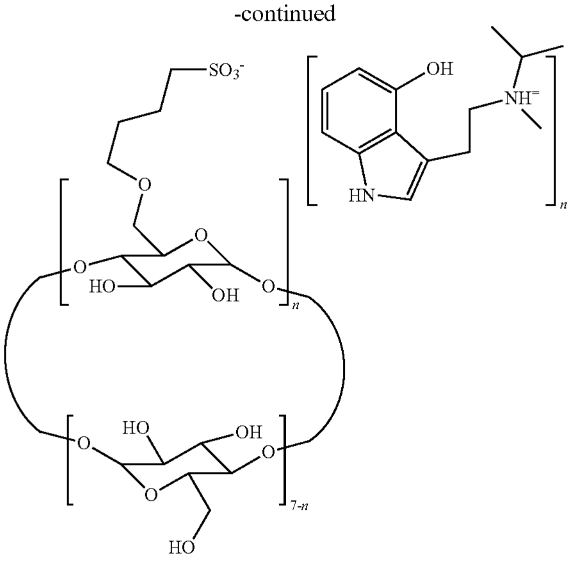

Experimental Procedure for the Preparation of 4-Hydroxy-N-Methyl-N-Isopropyl-Tryptamine SBEBCD Salt HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 9.

4-hydroxy-N-methyl-N-isopropyl-tryptamine HCl: Purchased from desired manufacturer and can be used without further purification. Free base 4-hydroxy-N-methyl-N-isopropyl-tryptamine is prepared from the HCl salt with concentrated sodium hydroxide and isolated by vacuum filtration.

4-hydroxy-N-methyl-N-isopropyl-tryptamine Freebase: 4-hydroxy-N-methyl-N-isopropyl-tryptamine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 12:
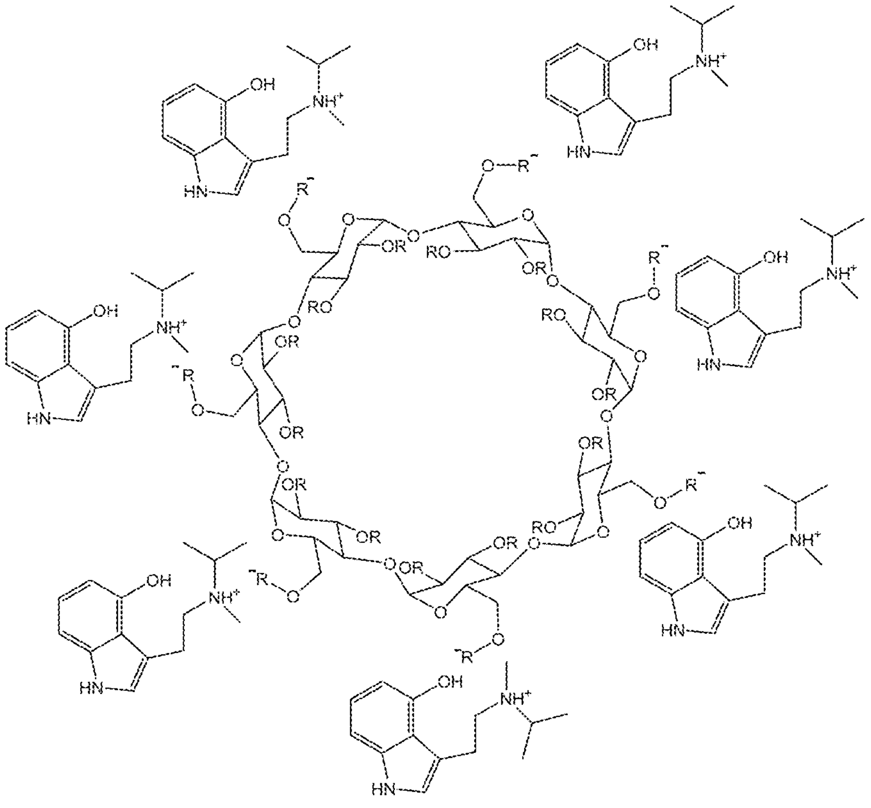
FIG. 12 shows an exemplary structure of a 4-hydroxy-N-methyl-N-isopropyl-tryptamine-SBEBCD salt.

Synthesis of 4-hydroxy-N-methyl-N-isopropyl-tryptamine-Captisol® Salt: Captisol® acid prepared above (moisture corrected to ascertain actual concentration) is dissolved in HPLC grade water in a test tube with a teflon stirbar. The solution is stirred vigorously and 4-hydroxy-N-methyl-N-isopropyl-tryptamine freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to −2 pH units below the pKa of 4-hydroxy-N-methyl-N-isopropyl-tryptamine, at which point nearly all (~99%) of the 4-hydroxy-N-methyl-N-isopropyl-tryptamine will be protonated. The solution is syringe filtered with a 0.45 μM nylon filter and is stored in a test tube under ambient air and wrapped in aluminum foil. Part of the volume is lyophilized to produce a powder of the 4-hydroxy-N-methyl-N-isopropyl-tryptamine-Captisol® salt. This resulting powder is observed under ambient conditions to observe for any wetting, discoloration, or other observable change. The remaining volume of solution containing the 4-hydroxy-N-methyl-N-isopropyl-tryptamine-Captisol® salt is similarly monitored for visible changes. The sample is also periodically monitored by HPLC to ascertain stability over time. The structure of the resulting 4-hydroxy-N-methyl-N-isopropyl-tryptamine-Captisol® salt is shown in FIG. 12.

Example 13. Preparation of a 4-acetoxy-N-methyl-N-ethyl-tryptamine-SuACD Salt A 4-hydroxy-N-methyl-N-isopropyl-tryptamine-Succinated alpha-cyclodextrin (SuACD) salt is prepared according to the general protocol shown in Scheme 9. The protocol provided herein is used to prepare a stable, high concentration 4-acetoxy-N-methyl-N-ethyl-tryptamine solution. This solution can be adjusted to an osmolality near physiological levels (~300 mOsm/kg) and a pH near the bottom range of the buffering capacity of the 4-hydroxy-N-methyl-N-isopropyl-tryptamine's pKa value (~2 pH units below) for use in a subcutaneous formulation. Alternatively, the aqueous solution can be lyophilized to remove the liquid and leave behind the 4-acetoxy-N-methyl-N-ethyl-tryptamine-SuACD salt in solid form, which can then be used in any subsequent formulation desired.

Scheme 9

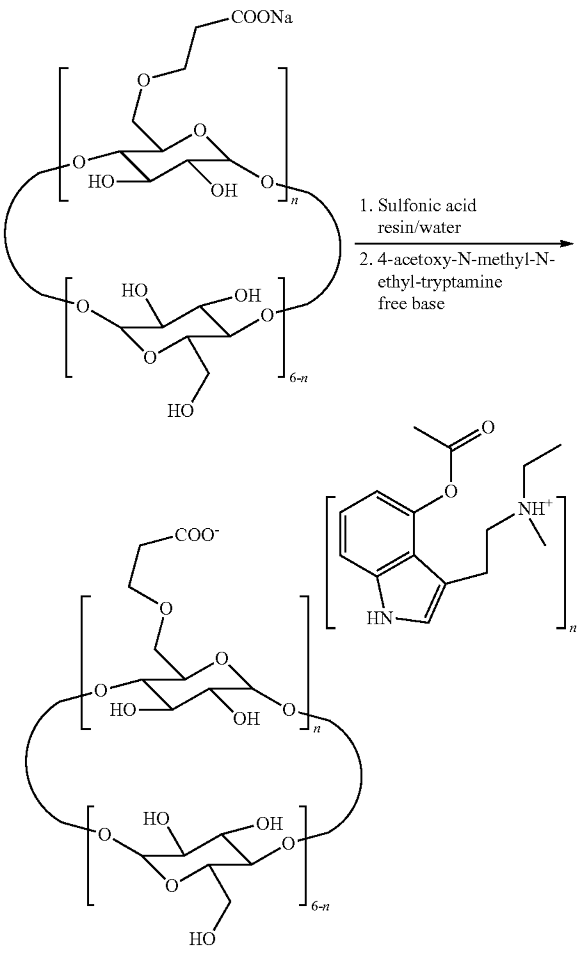

Experimental Procedure for the Preparation of 4-Acetoxy-N-Methyl-N-Ethyl-Tryptamine SuACD Salt HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

SuACD—Can be purchased from Arachem (M) Sdn Bhd. (Arachem) (pharmaceutical grade). The moisture content is verified by Karl Fisher analysis. SuACD is a polysuccinylated α-cyclodextrin sodium form, with an average of ~4 succinyl groups per molecule and an average MW of ~1300

SuACD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% SuACD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

4-acetoxy-N-methyl-N-ethyl-tryptamine HCl: Purchased from desired manufacturer and can be used without further purification. Free base 4-acetoxy-N-methyl-N-ethyl-tryptamine is prepared from the HCl salt with concentrated sodium hydroxide and isolated by vacuum filtration.

4-acetoxy-N-methyl-N-ethyl-tryptamine Freebase: 4-acetoxy-N-methyl-N-ethyl-tryptamine hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 13:
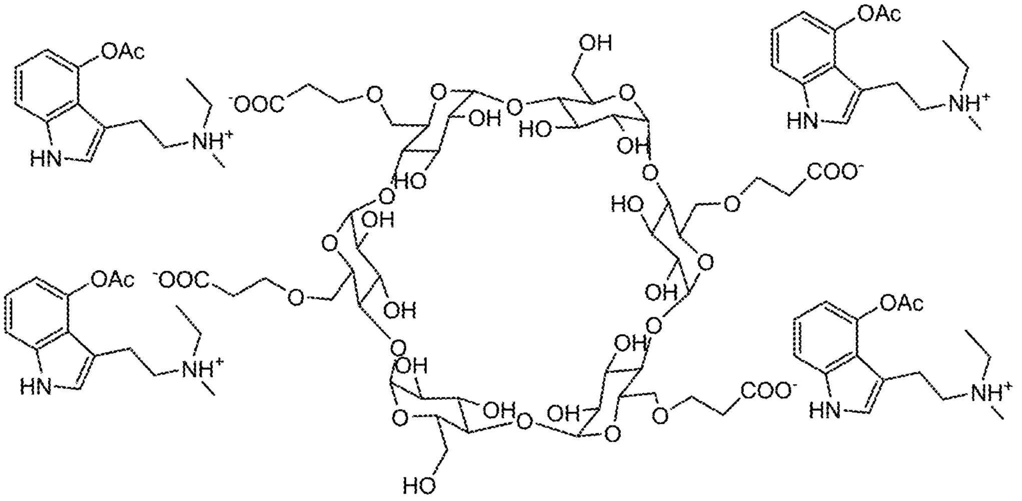
FIG. 13 shows an exemplary structure of a 4-acetoxy-N-methyl-N-ethyl-tryptamine-SuACD salt.

Synthesis of 4-acetoxy-N-methyl-N-ethyl-tryptamine-SuACD Salt: SuACD acid prepared above (moisture corrected to ascertain actual concentration) is dissolved in HPLC grade water in a test tube with a teflon stirbar. The solution is stirred vigorously and 4-acetoxy-N-methyl-N-ethyl-tryptamine freebase (1 equivalent per acidic functional group of SuACD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of 4-acetoxy-N-methyl-N-ethyl-tryptamine, at which point nearly all (~99%) of the 4-hydroxy-N-methyl-N-isopropyl-tryptamine will be protonated. The solution is syringe filtered with a 0.45 μM nylon filter and is stored in a test tube under ambient air and wrapped in aluminum foil. Part of the volume is lyophilized to produce a powder of the 4-acetoxy-N-methyl-N-ethyl-tryptamine-SuACD salt. This resulting powder is observed under ambient conditions to observe for any wetting, discoloration, or other observable change. The remaining volume of solution containing the 4-acetoxy-N-methyl-N-ethyl-tryptamine-SuACD salt is similarly monitored for visible changes. The sample is also periodically monitored by HPLC to ascertain stability over time. The structure of the resulting 4-acetoxy-N-methyl-N-ethyl-tryptamine-SuACD salt is shown in FIG. 13

Example 14. Preparation of a Methylisopropyllysergamide-CMGCD Salt

A methylisopropyllysergamide-carboxymethyl-gamma-cyclodextrin (CMGCD) salt is prepared according to the general protocol shown in Scheme 10. The protocol provided herein is used to prepare a stable, high concentration methylisopropyllysergamide solution. This solution can be adjusted to an osmolality near physiological levels (~300 mOsm/kg) and a pH near the bottom range of the buffering capacity of the methylisopropyllysergamide's pKa value (~2 pH units below) for use in a subcutaneous formulation. Alternatively, the aqueous solution can be lyophilized to remove the liquid and leave behind the methylisopropyllysergamide-CMGCD salt in solid form, which can then be used in any subsequent formulation desired.

Scheme 10

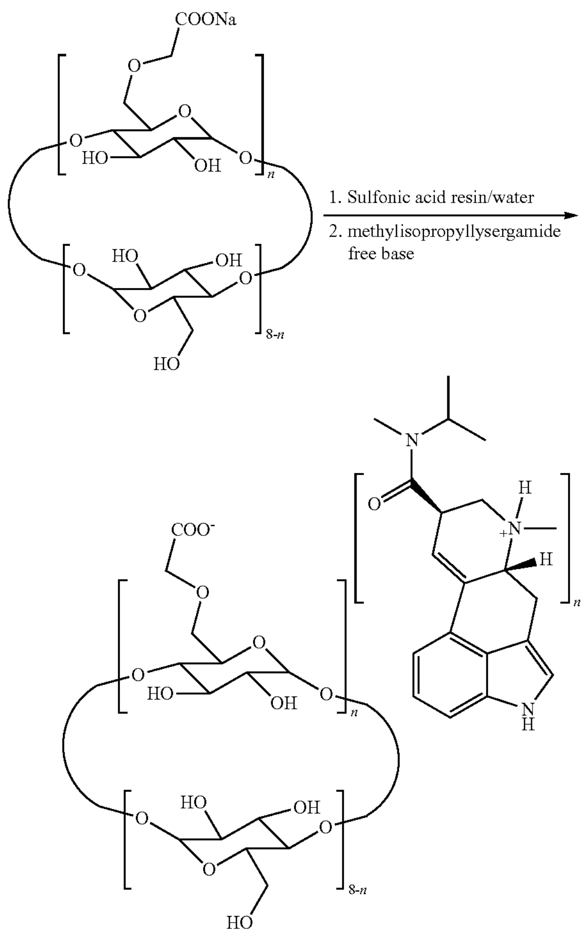

Experimental Procedure for the Preparation of Methylisopropyllysergamide-CMGCD Salt HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

CMGCD—Can be purchased from Arachem (M) Sdn Bhd (Arachem). The moisture content is verified by Karl Fisher analysis. CMGCD is a carboxymethylated γ-cyclodextrin sodium form, with an average of ~4 carboxymethyl groups per molecule and an average MW of ~1600.

CMGCD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% CMGCD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting solid is stored in a foil-wrapped scintillation vial at −20° C.

Methylisopropyllysergamide HCl: Purchased from desired manufacturer and can be used without further purification. Free base methylisopropyllysergamide is prepared from the HBr salt with concentrated sodium hydroxide and isolated by vacuum filtration.

Methylisopropyllysergamide Freebase: Methylisopropyllysergamide hydrochloride is dissolved in $dH_2O$ (100 mL). 2M NaOH was added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 14:
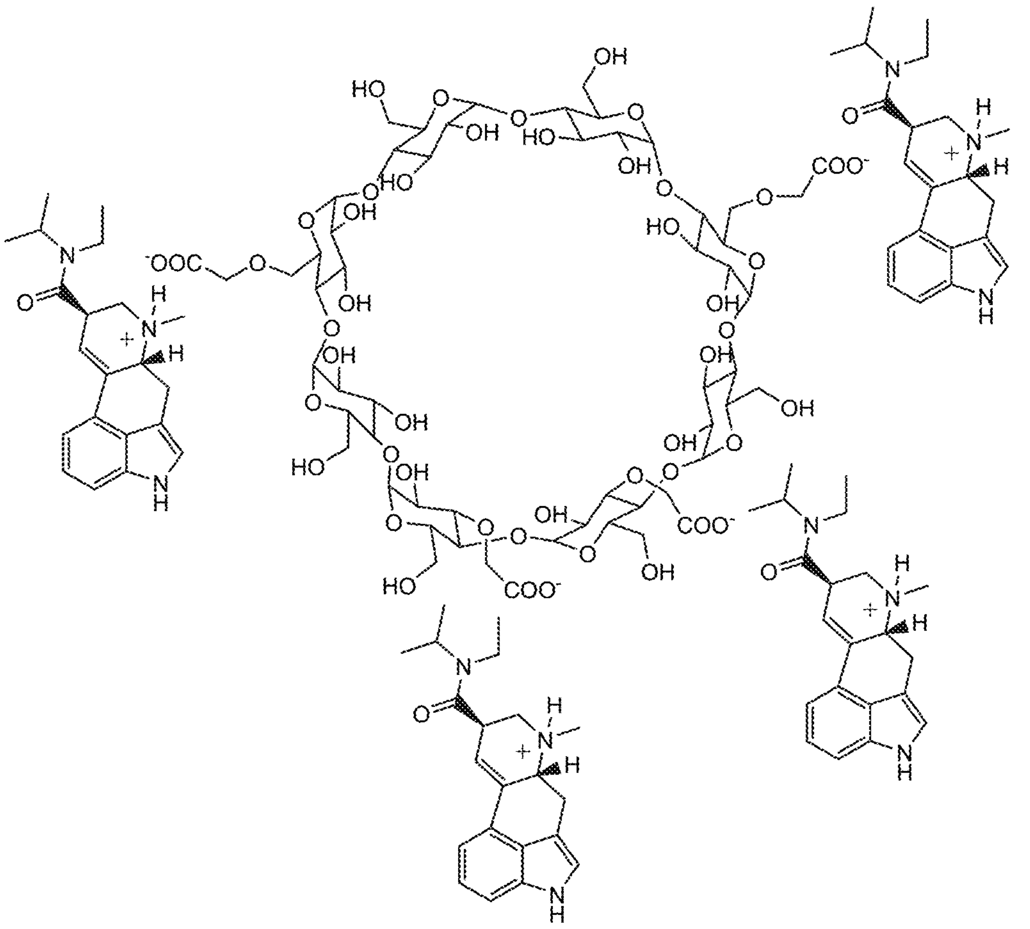
FIG. 14 shows an exemplary structure of a methylisopropyllysergamide-CMGCD salt.

Synthesis of Methylisopropyllysergamide CMGCD Salt: CMGCD acid prepared above (moisture corrected to ascertain actual concentration) is dissolved in HPLC grade water in a test tube with a teflon stirbar. The solution is stirred vigorously and methylisopropyllysergamide freebase (1 equivalent per acidic functional group of CMGCD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of methylisopropyllysergamide, at which point nearly all (~99%) of the methylisopropyllysergamide will be protonated. The solution is syringe filtered with a 0.45 μM nylon filter and is stored in a test tube under ambient air and wrapped in aluminum foil. Part of the volume is lyophilized to produce a powder of the methylisopropyllysergamide-CMGCD salt. This resulting powder is observed under ambient conditions to observe for any wetting, discoloration, or other observable change. The remaining volume of solution containing the methylisopropyllysergamide-CMGCD salt is similarly monitored for visible changes. The sample is also periodically monitored by HPLC to ascertain stability over time. The structure of the resulting methylisopropyllysergamide-CMGCD salt is shown in FIG. 14.

Example 15. Sublingual Formulation of Mescaline Comprising Mescaline-SBEBCD Salt and Free Base Mescaline A composition is prepared as in Example 10 utilizing a mescaline-SBEBCD salt (1.0 g, prepared using an analogous method to that shown in Example 9) with an additional molar equivalent of free-base mescaline (62 mg) is further formulated for sublingual formulation in unit dose form as a sublingual troche. An example protocol for preparation of such a formulation is as follows:

A 400 mL beaker is placed on the scales and tared. The active ingredient mescaline-SBEBCD salt/free base mixture is added. A polyethylene glycol (PEG) base (e.g. PEG 1450) is prepared in a separate beaker by melting in a water bath placed over a hotplate. The melted PEG base is then added to the 400 mL beaker containing the mescaline-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, bittering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the mescaline is released into the saliva of the subject. The additional free base mescaline acts to modulate the pH of the composition upon dissolution to closely match the pH of the saliva (~pH 7). In the saliva, soluble freebase mescaline liberates for mucosal absorption from center of cyclodextrin and from mescaline salts to increase bioavailability. Solubilized non-ionized mescaline in equilibrium with the dynamic buffering of two mechanisms of effect from the captisol acid (e.g. protonation/salt formation of mescaline and complexation of free base mescaline) helps keep pH higher than mescaline HCl allowing a higher proportion and more rapid mucosal absorption of drug product.

Figure 15:
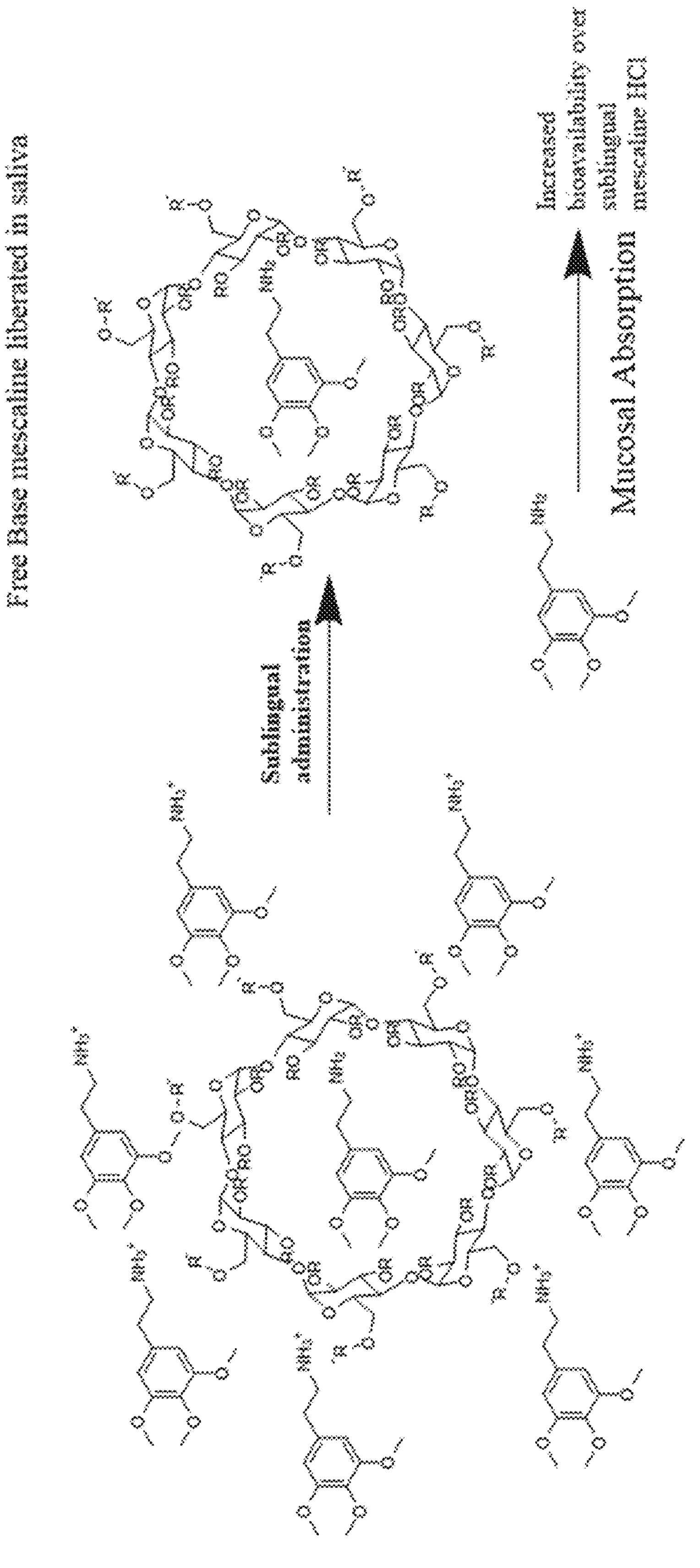
FIG. 15 shows a schematic of sublingual administration of a mescaline-SBEBCD salt formulation.

This two-mechanism effect resulting in increased bioavailability is illustrated in FIG. 15, which shows non-ionized mescaline within the cyclodextrin core of the SBEBCD. This is non-ionized mescaline is released into the saliva which is then absorbed via mucosal absorption. Buffering effects within the saliva then convert the protonated mescaline to the non-ionized state, which can be complexed with the now unoccupied cyclodextrin core to aid solubilization of the poorly soluble free base form. This process then repeats until all of the mescaline is absorbed, resulting in a successful sublingual administration that is painless and prevents crashing out of the drug molecule during administration. This also produces a form of dynamic buffering that can keep the pH higher to allow the ionized mescaline molecules complexed in the mescaline-SBEBCD salt to become deprotonated or unionized even while in a highly solubilized state, increasing submucosal absorption capacity are rate. Compared with a similar dose in a similar troche formulation made from mescaline HCl, tolerability, bioavailability, and solubility are all enhanced due to the SBECD-salt complex and free base mescaline complexed within the cyclodextrin core.

Example 16. Sublingual Formulation of Mescaline Comprising Mescaline-SBEBCD Salt and High Molar Equivalent Free Base Mescaline A mescaline-SBSBCD salt is prepared analogously to the salt prepared in Example 9 and is further processed into a sublingual formulation in unit dose form as a sublingual troche. The sublingual formulation here utilizes a substantial excess of free base mescaline in the formulation (10× molar equivalents compared to the mescaline-SBEBCD salt in the formulation). The substantial excess of free base mescaline provides numerous advantages over other formulations using compound-complexing agents salts as provided herein.

One advantage is that the presence of excess free base compound allows for pH adjustment and buffering in situ upon administration to closely match the tissue pH. The presence of excess free base molecules allows the compound to act as its own buffer, thus raising the pH compared to administration of the salt complex alone. By using the compound as its own buffer, a larger dose of the compound of interest can be applied without reaching excessive osmolality as additional base components may be omitted.

Additionally, using the compound as a buffer allows the total dosage unit (in this case a sublingual dose, but the concept is equally applicable to other dosage forms, particularly intranasal administration) to maintain the desired pH even as the material is absorbed by the relevant tissues after administration. As the compound is absorbed by the tissues, other free base molecules remain present to continue buffering the pH to a physically tolerable level. In some instances, a substantial portion of the excess of free base compound may only dissolve after administration after a certain amount of the compound has been absorbed into the mucosa, particularly when the free base compound is only sparingly soluble. In such a case, the absorption of the compound drives the equilibrium of the dissolution of the compound as it is absorbed, thus ensuring that only a desirable amount of free base compound is present at any time to act as an appropriate buffer to maintain the desired physiologically tolerable pH.

Finally, the presence of excess free base compound has the advantage of providing a consistent source of active compound, which can continuously occupy the complexing site within the cyclodextrin as the drug product compound is absorbed over time. The cyclodextrins in the formulation act as a shuttle for compound, helping to solubilize the compound, which can then be absorbed by the body. The cyclodextrin can then repeat this complexing/solubilization process with additional molecules of the compound to help solubilize the remaining excess free base.

Example Protocol The required quantities of free base mescaline (620 mg, 10× molar excess compared to the amount of SBEBCD) and the lyophilized mescaline-SBEBCD salt (1.0 g) prepared analogously to the salt in Example 1 are accurately weighed (resulting molar ratio of 10:1 free base mescaline:SBEBCD). A homogenous paste of lyophilized mescaline-SBEBCD salt is prepared in a mortar by adding water: ethanol (1:1) to the mixture in small quantities. Free base mescaline powder is then added to the paste in portions with continuous kneading for three hours. An appropriate quantity of water:ethanol mixture is added to maintain suitable consistency of the paste. This paste is then dried in a hot air oven for 24 hours. The dried complex is then powdered and sieved, then stored in an airtight container until further use.

The dried complex comprising excess free base mescaline is then formulated for sublingual formulation in unit dose form as a sublingual troche. An example protocol for preparation of such a formulation is as follows:

A 400 mL beaker is placed on the scales and tared. The active ingredient mescaline-SBEBCD salt/free base mixture prepared above is added. A polyethylene glycol (PEG) base (e.g. PEG 1450) is prepared in a separate beaker by melting in a water bath placed over a hotplate. The melted PEG base is then added to the 400 mL beaker containing the mescaline-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, buttering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the mescaline is released into the saliva of the subject. The additional free base mescaline acts to modulate the pH of the composition upon dissolution to closely match the pH of the saliva (~pH 7). The excess free base mescaline successfully counteracts the acidic nature of the protonated mescaline from the SBEBCD salt. In the saliva, soluble amounts of freebase mescaline dissolve for mucosal absorption, both by eluting from the cyclodextrin and to a lesser extent by direct dissolution of the free base mescaline. Solubilized non-ionized mescaline is then absorbed into the nasal mucosa. This shifts the equilibrium of solubilization such that more free base mescaline becomes solubilized, both in solution and through complexation with the interior of the cyclodextrin. This dynamic buffering and solubilization process is driven through two mechanisms of effect: protonation/salt formation of mescaline (solubilization through forming an ion) and complexation of free base mescaline. These continuous effects driven by equilibrium thus increase absorption of the compound, allowing for a high concentration of drug product to be delivered in a formulation densely populated with drug product.

Figure 16:
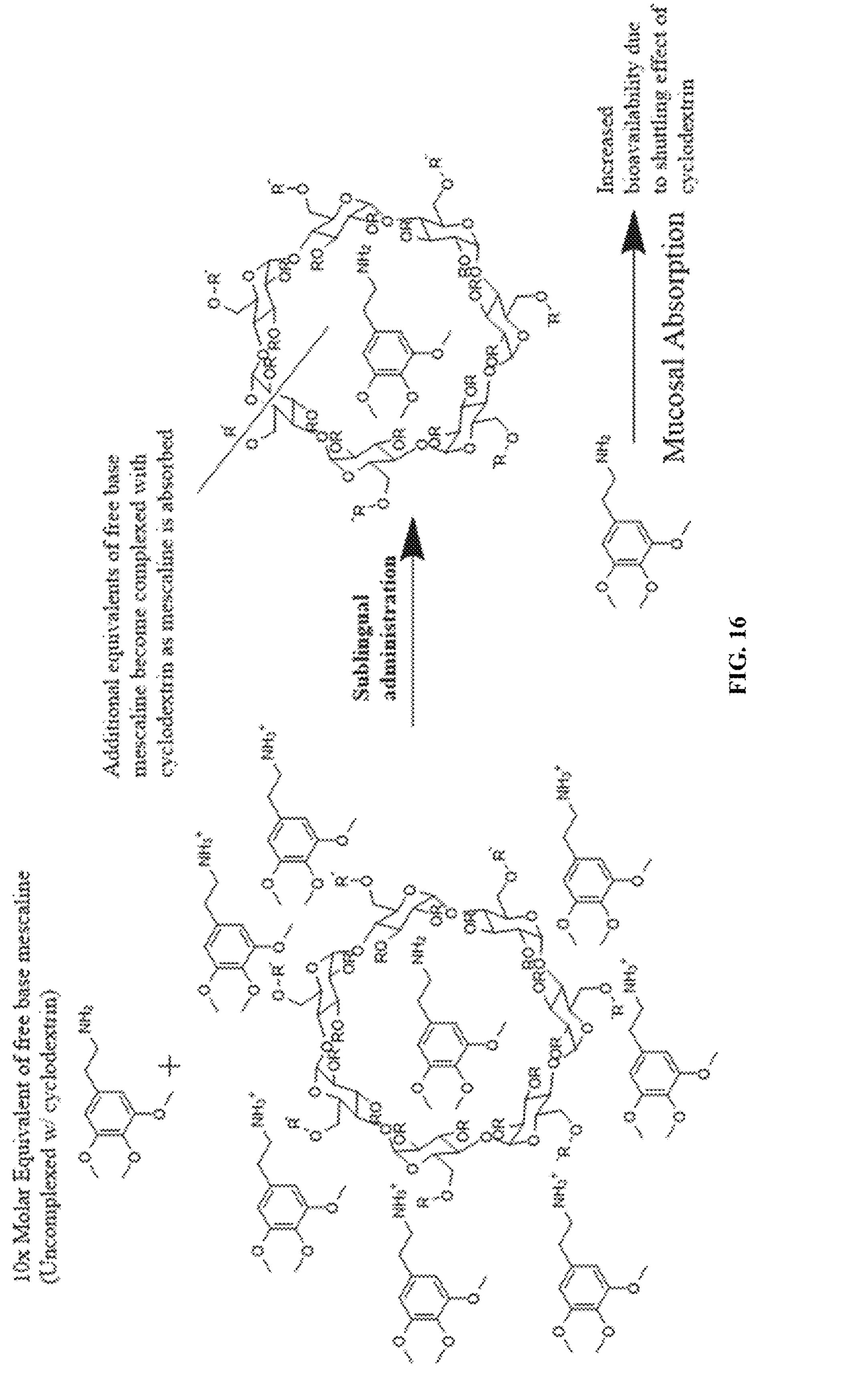
FIG. 16 shows a schematic of sublingual administration of a mescaline-SBEBCD salt formulation comprising an excess of free base mescaline.

The mechanism underling these effect resulting in increased bioavailability and enhanced buffering capacity of the system is illustrated in FIG. 16, which shows non-ionized mescaline within the cyclodextrin core of the SBEBCD and excess free base mescaline also present. The non-ionized mescaline is first released into the saliva from the cyclodextrin and then absorbed via mucosal absorption. Once absorbed, the equilibrium of the system shifts and allows more free base mescaline to become dissolved in the saliva, either directly or, more substantially, through additional complexation with the now unoccupied cyclodextrin core in a shuttle-like mechanism. As the additional free base mescaline solubilizes in the system, the desired physiologically tolerable pH of the formulation is maintained as the acidity of the protonated mescaline molecules present in the salt form continue to be neutralized as more free base compound solubilizes. This process then repeats until all of the mescaline is absorbed, resulting in a successful sublingual administration that is painless and effective. This also produces a form of dynamic buffering that can keep the pH elevated relative to a dose form without excess free base drug compound, thus allowing the ionized mescaline molecules associated with the mescaline-SBEBCD salt to become deprotonated or unionized even while in a highly solubilized state, increasing submucosal absorption capacity and rate. Compared with a similar dose in a similar troche formulation made from mescaline HCl, tolerability, bioavailability, and solubility are all enhanced due to the SBECD-salt complex and free base mescaline complexed within the cyclodextrin core.

Example 17. Preparation of a Racemorphan-SBEBCD Salt

A racemorphan-SBEBCD salt is prepared according to the general protocol shown in Scheme 11. The protocol provided herein is used to prepare a stable, high concentration racemorphan solution. This solution can be adjusted to an osmolality near physiological levels (~300 mOsm/kg) and a pH near the bottom range of the buffering capacity of the racemorphan's pKa value (~2 pH units below) for use in a subcutaneous formulation. Alternatively, the aqueous solution can be lyophilized to remove the liquid and leave behind the racemorphan-SBEBCD salt in solid form, which can then be used in any subsequent formulation desired.

Scheme 11

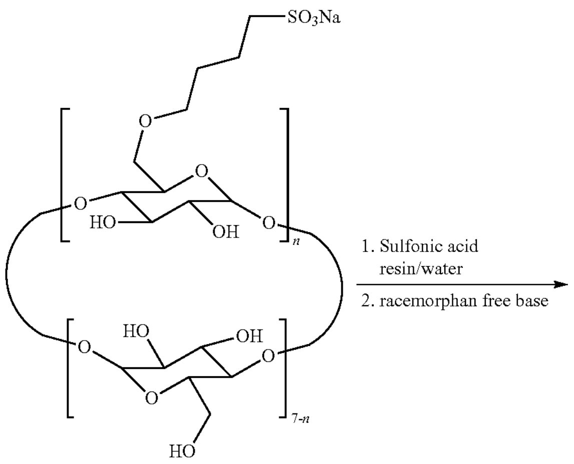

-continued

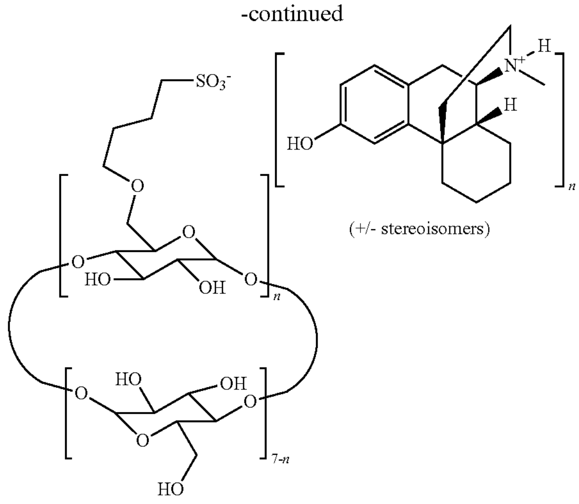

(+/- stereoisomers)

Experimental Procedure for the Preparation of Racemorphan SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol®: Can be purchased from Ligand Pharmaceuticals, Inc. (Ligand) (pharmaceutical grade). The moisture content is verified by Karl Fisher analysis. Captisol® is a polysulfobutylated β-cyclodextrin sodium form, with an average of 6.5 sulfobutyl groups per molecule and an average MW of 2,163.

Racemorphan HCl: Purchased from desired manufacturer and can be used without further purification. Free base racemorphan is prepared from the HCl salt with concentrated sodium hydroxide and isolated by vacuum filtration.

Synthesis of Captisol® Acid. Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and was completely dried by applying compressed air for 10 minutes before the sample was applied. A solution of 15% Captisol® (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

Racemorphan Freebase: Racemorphan hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 17:
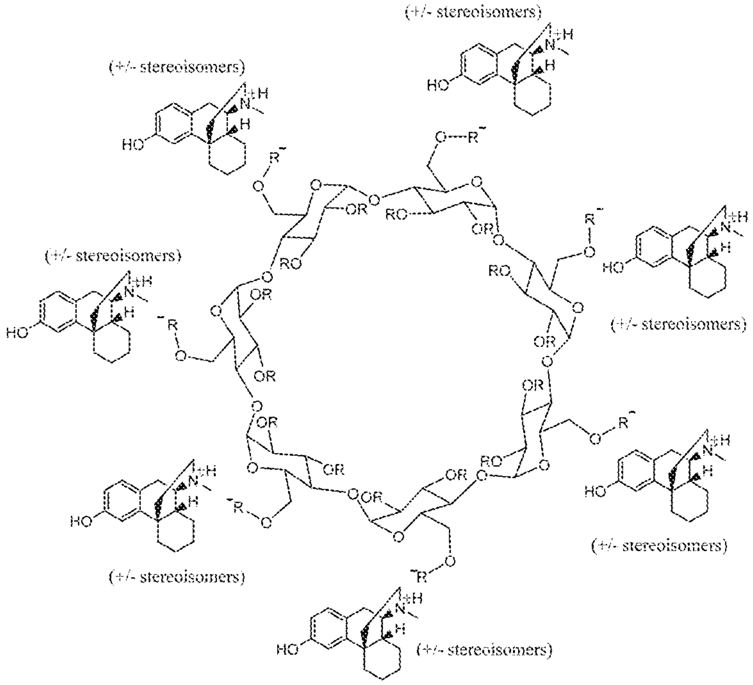
FIG. 17 shows an exemplary structure of an opioid-complexing agent salt as provided herein. The opioid-complexing agent salt shown is a racemorphan-SBEBCD salt.

Synthesis of Racemorphan-Captisol® Salt: Captisol® acid prepared above (moisture corrected to ascertain actual concentration) is dissolved in HPLC grade water in a test tube with a teflon stirbar. The solution is stirred vigorously and racemorphan freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of racemorphan, at which point nearly all (~99%) of the racemorphan will be protonated. The solution is syringe filtered with a 0.45 μM nylon filter and is stored in a test tube under ambient air and wrapped in aluminum foil. Part of the volume is lyophilized to produce a powder of the racemorphan-Captisol® salt. This resulting powder is observed under ambient conditions to observe for any wetting, discoloration, or other observable change. The remaining volume of solution containing the racemorphan-Captisol® salt is similarly monitored for visible changes. The sample is also periodically monitored by HPLC to ascertain stability over time. The structure of the resulting racemorphan-Captisol® salt is shown in FIG. 17.

Figure 18:
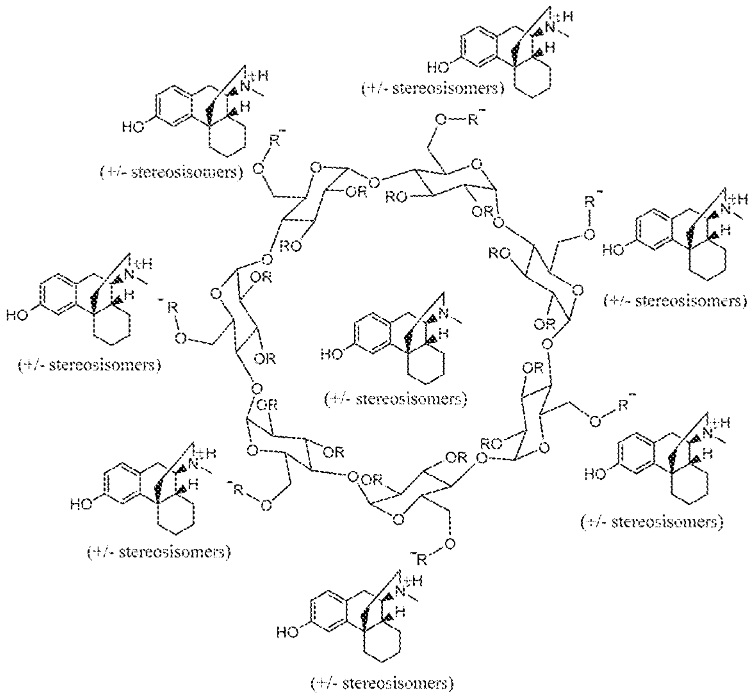
FIG. 18 shows an exemplary structure of a racemorphan-SBEBCD salt which is also acting as an inclusion complex for an additional equivalent of free base racemorphan.

Example 18. Preparation of a Racemorphan-SBEBCD Salt with Free Base Racemorphan Complexed within the SBEBCD The salt forms of the complexing agent/opioids provided herein can also be adapted to incorporate additional molar equivalents of free base opioid. For example, in instances where the complexing agent is a cyclodextrin such as SBEBCD, the interior portion of the cyclodextrin can incorporate an additional molecule of opioid. An exemplary illustration of such a complex can be seen in FIG. 18, which shows the racemorphan/SBEBCD salt complex described in Example 1 which has been modified to incorporate an additional uncharged molecule of racemorphan on the interior of the cyclodextrin. Such complexes can have additional benefits when used in pharmaceutical compositions, including increased solubility of the opioids upon administration, increased bioavailability of the opioids, and the presence of free base opioid can act to create a buffering system that allows for a more biocompatible pH to be achieved upon delivery of the pharmaceutical composition as the free base opioid neutralizes some of the acidic functionalities of the protonated opioids of the salt complex.

Such complexes can be created in a variety of ways, several of which are shown by example below. In order to ascertain the proper ratio of salt complex to free base opioid to add to prepare a mixture with an additional molecule of opioid incorporated into the center of the cyclodextrin, it is necessary to determine the molecular weight of the salt complex. This can be readily calculated from the known molecular weight of the starting materials and stoichiometry of the complexing agent and opioid. For example, as the SBEBCD used to prepare the racemorphan-SBEBCD salt in Example 1 has an average of 6.5 sulfobutyl groups per molecule, the resulting salt has an average of 6.5 racemorphan molecules for every cyclodextrin molecule, resulting in the salt having an average molecular weight of ~3630 Daltons. This value can be calculated as follows: From the average molecular weight of the SBEBCD (average MW of 2,163) is subtracted the weight of sodium atoms which have been removed (6.5 times 22.99 Daltons), and the weight of racemorphan molecules (6.5 times 257.37 Daltons) and additional hydrogen atoms (6.5 times 1.01 Daltons) is added, yielding an average molecule weight of about 3690

Daltons. Additionally, any residual water in the resulting salt can be measured by an appropriate procedure, such as Karl Fischer analysis.

The complexes described in this example can be prepared by any suitable method, including without limitation the procedures described below.

Physical mixture method—The required molar quantities (1:1) of free base racemorphan (70 mg) and the lyophilized racemorphan-SBEBCD salt (1.0 g) prepared in Example 1 are weighed accurately and mixed together thoroughly in a mortar with vigorous trituration for about three hours. The mixture is then passed through a sieve and stored in an airtight container until further use.

Kneading Method—The required quantities of free base racemorphan (70 mg) and the lyophilized racemorphan-SBEBCD salt (1.0 g) prepared in Example 17 are accurately weighed (resulting molar ratio of 1:1). A homogenous paste of lyophilized racemorphan-SBEBCD salt is prepared in a mortar by adding water:methanol (1:1) to the mixture in small quantities. Free base racemorphan powder is then added to the paste in portions with continuous kneading for three hours. An appropriate quantity of water:methanol mixture is added to maintain suitable consistency of the paste. This paste is then dried in a hot air oven for 24 hours. The dried complex is then powdered and sieved, then stored in an airtight container until further use.

Co-Precipitation Method—Quantities of free base racemorphan (70 mg) and lyophilized racemorphan-SBEBCD salt (1.0 g) prepared in Example 17 are dissolved separately in methanol and water, respectively. The solution of free base racemorphan is added dropwise to the cyclodextrin containing solution. The contents are stirred continuously for 6 hours, at which point they are dried at elevated temperature for 48 hours, collected, and stored in airtight containers until further use.

Solvent Evaporation Method—Free base racemorphan (70 mg) is dissolved in a suitable organic solvent (e.g. methanol) at room temperature. The required amount of lyophilized racemorphan-SBEBCD salt (1.0 g) prepared in Example 1 is dissolved in hot water and is added dropwise into the solution with continuous stirring over one hour. The resulting complexes are then filtered and dried under a vacuum. The resulting solid mass is then stored in a desiccator under vacuum to a constant weight. The dried product is removed, sieved, then stored in a closed airtight container.

Characterization of Resulting Inclusion Complexes

The resulting salt/inclusion complexes are then characterized for drug content, solubility, and stability. The samples are analyzed by appropriate analytical techniques (e.g. co-precipitation of drug in the complex, scanning electron microscopy of the physical mixtures, IR spectral analysis, differential scanning calorimetry, X-ray diffraction or X-ray powder diffraction, and dissolution/HPLC analysis) at various timepoints in order to ensure the resulting inclusion complexes have the desired amount of racemorphan and are suitably stable for later use. Such inclusion complexes can be directly administered or used in a further formulation.

Alternative Preparation Methods

In addition to the methods described above, alternative methods for the preparation of the salt-inclusion complexes described herein are available. For example, the preparation of an inclusion complex could be prepared prior to forming the free-acid complexing agent, which is then used to neutralize excess free base opioid in a later step. Alternatively, it is contemplated that the preparation of the salt and the complex could be formed simultaneously in a one-pot reaction scheme.

Example 19. Preparation of a Levorphanol-SBEBCD Salt

A levorphanol-SBEBCD salt is prepared according to the general protocol shown in Scheme 12. The protocol provided herein is used to prepare a stable, high concentration Levorphanol solution. This solution can be adjusted to an osmolality near physiological levels (~300 mOsm/kg) and a pH near the bottom range of the buffering capacity of the levorphanol's pKa value (~2 pH units below) for use in a subcutaneous formulation. Alternatively, the aqueous solution can be lyophilized to remove the liquid and leave behind the levorphanol-SBEBCD salt in solid form, which can then be used in any subsequent formulation desired.

Scheme 12

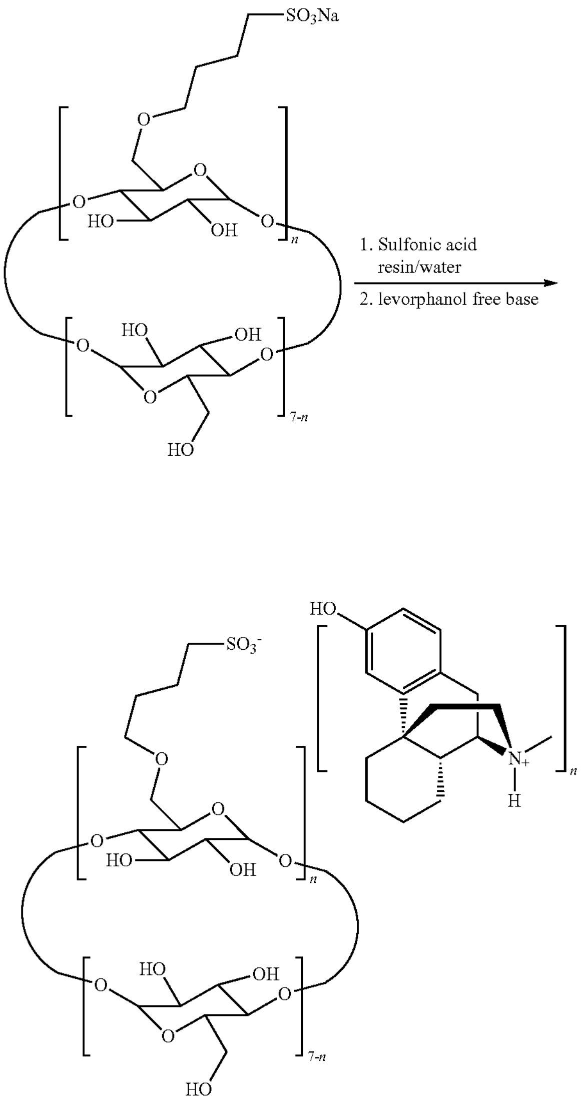

Experimental Procedure for the Preparation of Levorphanol SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 17.

Levorphanol HCl: Purchased from desired manufacturer and can be used without further purification. Free base levorphanol is prepared from the HCl salt with concentrated sodium hydroxide and isolated by vacuum filtration.

Levorphanol Freebase: Levorphanol hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 19:
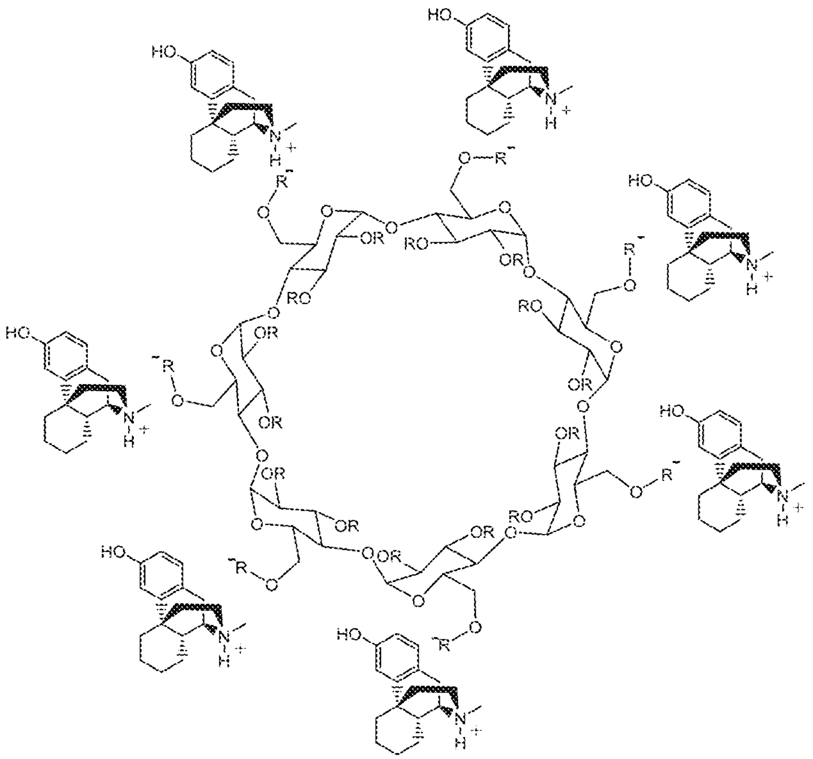
FIG. 19 shows an exemplary structure of a levorphanol-SBEBCD salt.

Synthesis of Levorphanol-Captisol® Salt: Captisol® acid prepared above (moisture corrected to ascertain actual concentration) is dissolved in HPLC grade water in a test tube with a teflon stirbar. The solution is stirred vigorously and levorphanol freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of levorphanol, at which point nearly all (~99%) of the levorphanol will be protonated. The solution is syringe filtered with a 0.45 μM nylon filter and is stored in a test tube under ambient air and wrapped in aluminum foil. Part of the volume is lyophilized to produce a powder of the levorphanol-Captisol® salt. This resulting powder is observed under ambient conditions to observe for any wetting, discoloration, or other observable change. The remaining volume of solution containing the levorphanol-Captisol® salt is similarly monitored for visible changes. The sample is also periodically monitored by HPLC to ascertain stability over time. The structure of the resulting levorphanol-Captisol® salt is shown in FIG. 19.

Example 20. Preparation of a Racemethorphan-SBEBCD Salt

A racemethorphan-SBEBCD salt is prepared according to the general protocol shown in Scheme 13. The protocol provided herein is used to prepare a stable, high concentration racemethorphan solution. This solution can be adjusted to an osmolality near physiological levels (~300 mOsm/kg) and a pH near the bottom range of the buffering capacity of the racemethorphan's pKa value (~2 pH units below) for use in a subcutaneous formulation. Alternatively, the aqueous solution can be lyophilized to remove the liquid and leave behind the racemethorphan-SBEBCD salt in solid form, which can then be used in any subsequent formulation desired.

Scheme 13

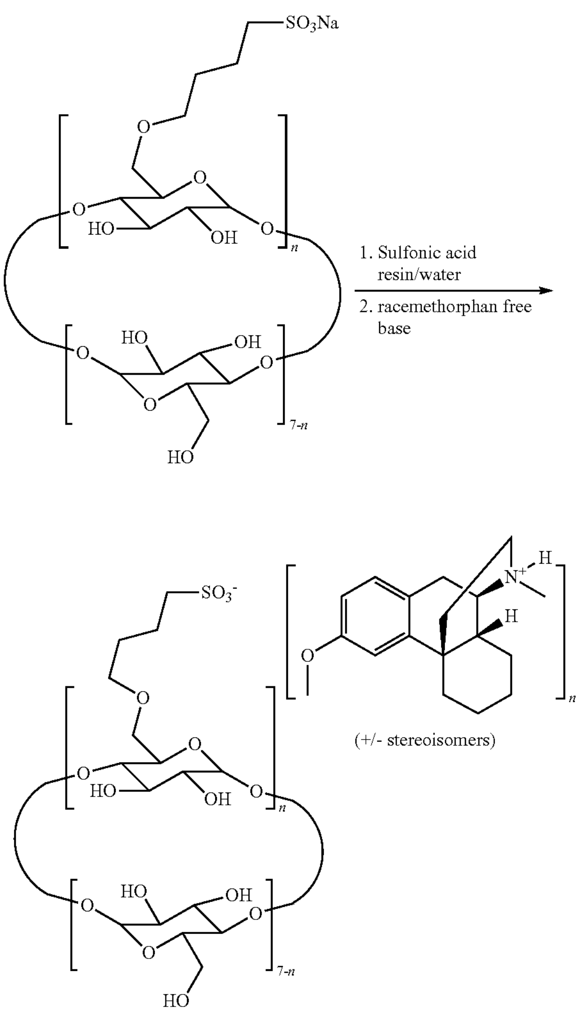

Experimental Procedure for the Preparation of Racemethorphan SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 1.

Racemethorphan HCl: Purchased from desired manufacturer and can be used without further purification. Free base racemethorphan is prepared from the HCl salt with concentrated sodium hydroxide and isolated by vacuum filtration.

Racemethorphan Freebase: Racemethorphan hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 20:
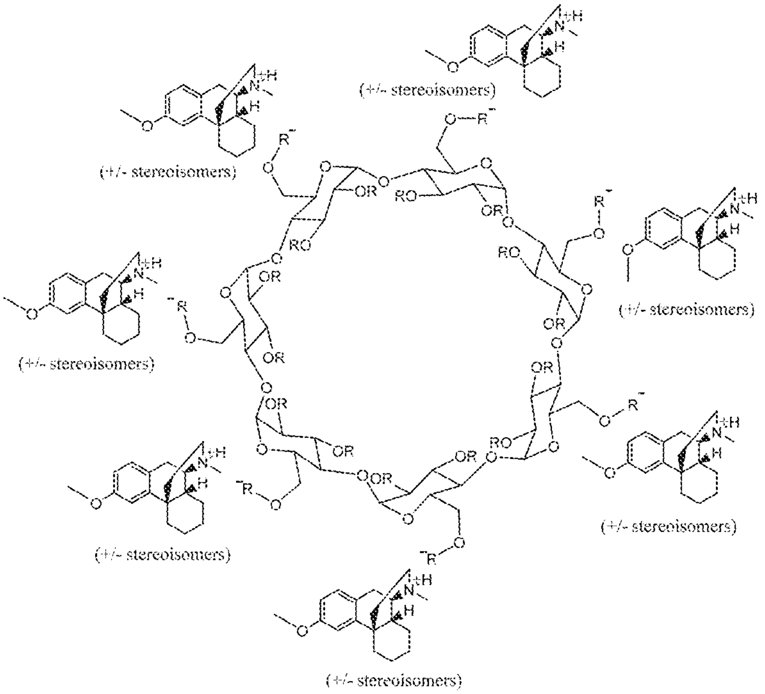
FIG. 20 shows an exemplary structure of a racemethorphan-SBEBCD salt.

Synthesis of Racemethorphan-Captisol® Salt: Captisol® acid prepared above (moisture corrected to ascertain actual concentration) is dissolved in HPLC grade water in a test tube with a teflon stirbar. The solution is stirred vigorously and racemethorphan freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of racemethorphan, at which point nearly all (~99%) of the racemethorphan will be protonated. The solution is syringe filtered with a 0.45 μM nylon filter and is stored in a test tube under ambient air and wrapped in aluminum foil. Part of the volume is lyophilized to produce a powder of the racemethorphan-Captisol® salt. This resulting powder is observed under ambient conditions to observe for any wetting, discoloration, or other observable change. The remaining volume of solution containing the racemethorphan-Captisol® salt is similarly monitored for visible changes. The sample is also periodically monitored by HPLC to ascertain stability over time. The structure of the resulting racemethorphan-Captisol® salt is shown in FIG. 20.

Example 21. Preparation of a Fentanyl-SuACD Salt

A racemethorphan-succinated alpha-cyclodextrin (SuACD) salt is prepared according to the general protocol shown in Scheme 14. The protocol provided herein is used to prepare a stable, high concentration fentanyl solution. This solution can be adjusted to an osmolality near physiological levels (~300 mOsm/kg) and a pH near the bottom range of the buffering capacity of the fentanyl's pKa value (~2 pH units below) for use in a subcutaneous formulation. Alternatively, the aqueous solution can be lyophilized to remove the liquid and leave behind the fentanyl-SuACD salt in solid form, which can then be used in any subsequent formulation desired.

Scheme 14

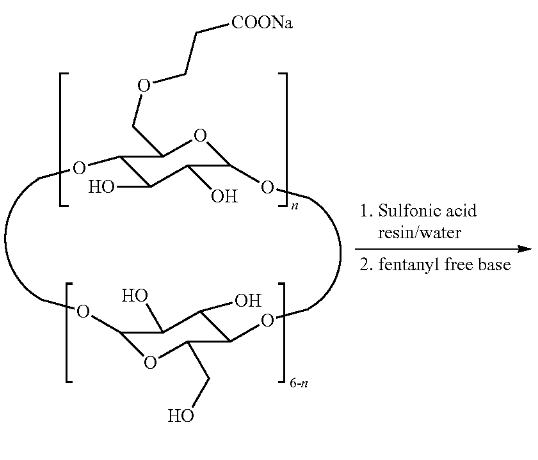

-continued

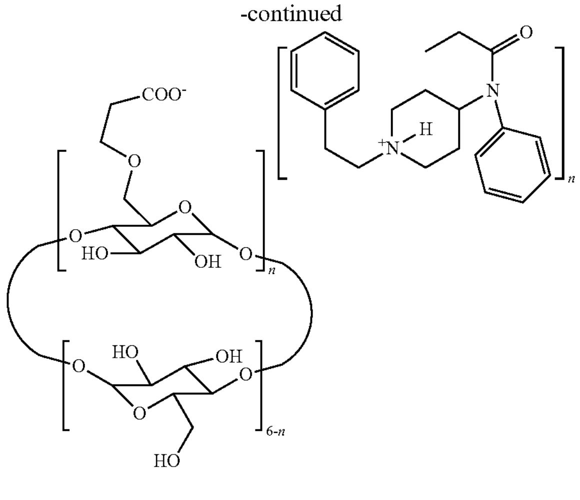

Experimental Procedure for the Preparation of Fentanyl SuACD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

SuACD—Can be purchased from Arachem (M) Sdn Bhd. (Arachem) (pharmaceutical grade). The moisture content is verified by Karl Fisher analysis. SuACD is a polysuccinylated α-cyclodextrin sodium form, with an average of ~4 succinyl groups per molecule and an average MW of ~1300

SuACD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% SuACD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

fentanyl HCl: Purchased from desired manufacturer and can be used without further purification. Free base fentanyl is prepared from the HCl salt with concentrated sodium hydroxide and isolated by vacuum filtration.

fentanyl Freebase: fentanyl hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 21:
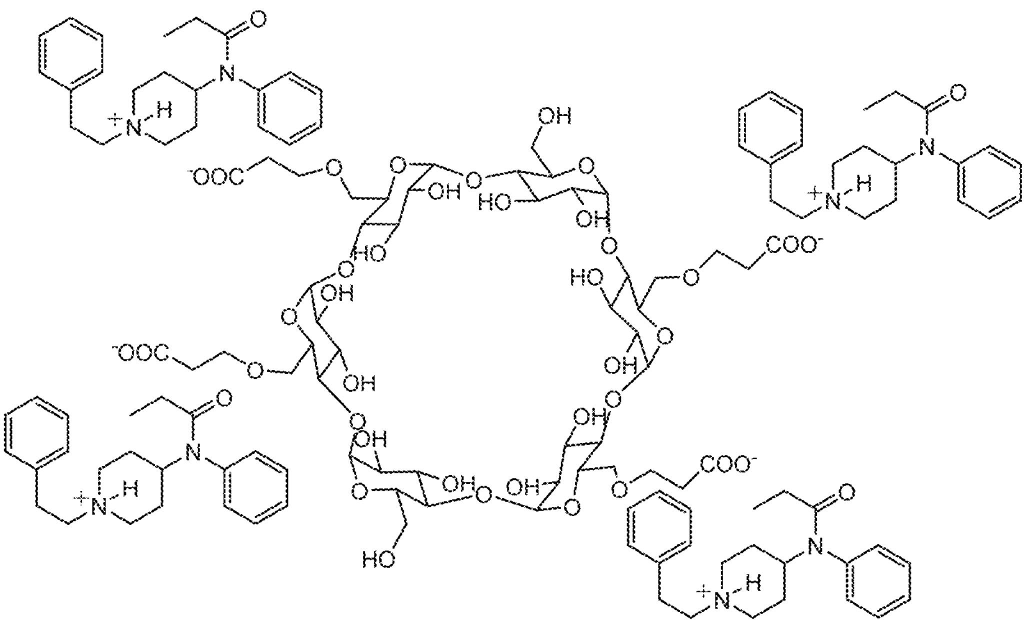
FIG. 21 shows an exemplary structure of a fentanyl-SuACD salt.

Synthesis of fentanyl-SuACD Salt: SuACD acid prepared above (moisture corrected to ascertain actual concentration) is dissolved in HPLC grade water in a test tube with a teflon stirbar. The solution is stirred vigorously and fentanyl freebase (1 equivalent per acidic functional group of SuACD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of fentanyl, at which point nearly all (~99%) of the racemethorphan will be protonated. The solution is syringe filtered with a 0.45 μM nylon filter and is stored in a test tube under ambient air and wrapped in aluminum foil. Part of the volume is lyophilized to produce a powder of the fentanyl-SuACD salt. This resulting powder is observed under ambient conditions to observe for any wetting, discoloration, or other observable change. The remaining volume of solution containing the fentanyl-SuACD salt is similarly monitored for visible changes. The sample is also periodically monitored by HPLC to ascertain stability over time. The structure of the resulting fentanyl-SuACD salt is shown in FIG. 21

Example 22. Preparation of a Buprenorphine-CMGCD Salt

A buprenorphine-carboxymethyl-gamma-cyclodextrin (CMGCD) salt is prepared according to the general protocol shown in Scheme 15. The protocol provided herein is used to prepare a stable, high concentration buprenorphine solution. This solution can be adjusted to an osmolality near physiological levels (~300 mOsm/kg) and a pH near the bottom range of the buffering capacity of the buprenorphine's pKa value (~2 pH units below) for use in a subcutaneous formulation. Alternatively, the aqueous solution can be lyophilized to remove the liquid and leave behind the buprenorphine-CMGCD salt in solid form, which can then be used in any subsequent formulation desired.

Scheme 15

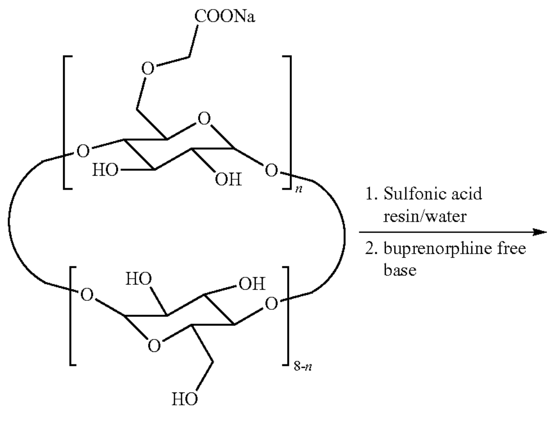

-continued

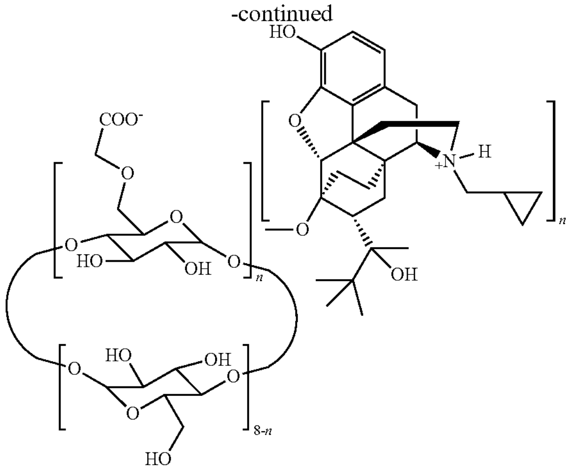

Experimental Procedure for the Preparation of Buprenorphine-CMGCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

CMGCD—Can be purchased from Arachem (M) Sdn Bhd (Arachem). The moisture content is verified by Karl Fisher analysis. CMGCD is a carboxymethylated γ-cyclodextrin sodium form, with an average of ~4 carboxymethyl groups per molecule and an average MW of ~1600.

CMGCD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% CMGCD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting solid is stored in a foil-wrapped scintillation vial at −20° C.

Buprenorphine HCl: Purchased from desired manufacturer and can be used without further purification. Free base buprenorphine is prepared from the HBr salt with concentrated sodium hydroxide and isolated by vacuum filtration.

Buprenorphine Freebase: Buprenorphine hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 22:
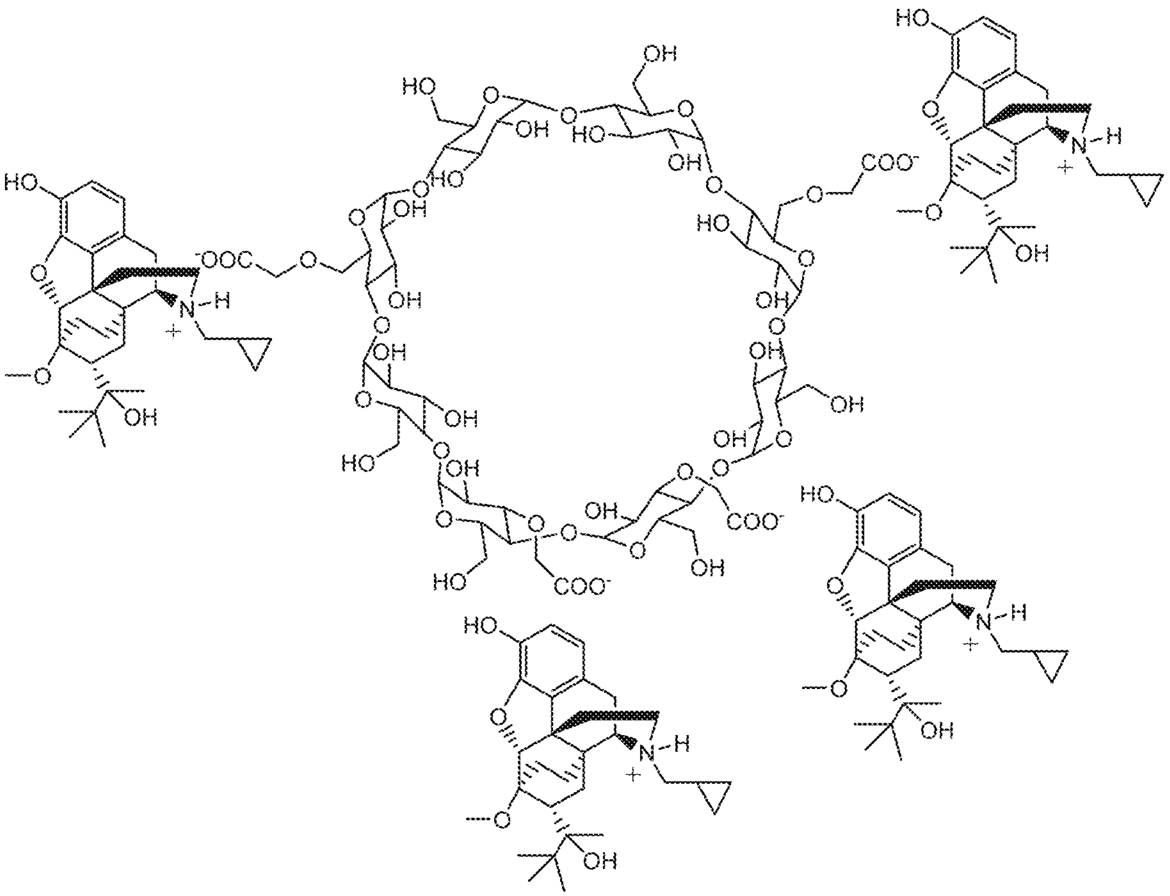
FIG. 22 shows an exemplary structure of a buprenorphine-CMGCD salt.

Synthesis of Buprenorphine CMGCD Salt: CMGCD acid prepared above (moisture corrected to ascertain actual concentration) is dissolved in HPLC grade water in a test tube with a teflon stirbar. The solution is stirred vigorously and buprenorphine freebase (1 equivalent per acidic functional group of CMGCD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of buprenorphine, at which point nearly all (~99%) of the buprenorphine will be protonated. The solution is syringe filtered with a 0.45 μM nylon filter and is stored in a test tube under ambient air and wrapped in aluminum foil. Part of the volume is lyophilized to produce a powder of the buprenorphine-CMGCD salt. This resulting powder is observed under ambient conditions to observe for any wetting, discoloration, or other observable change. The remaining volume of solution containing the buprenorphine-CMGCD salt is similarly monitored for visible changes. The sample is also periodically monitored by HPLC to ascertain stability over time. The structure of the resulting buprenorphine-CMGCD salt is shown in FIG. 22.

Example 23. Sublingual Formulation of Racemorphan Comprising Racemorphan-SBEBCD Salt and Free Base Racemorphan A composition is prepared as in Example 18 utilizing a racemorphan-SBEBCD salt (1.0 g, prepared using an analogous method to that shown in Example 17) with an additional molar equivalent of free-base racemorphan (70 mg) is further formulated for sublingual formulation in unit dose form as a sublingual troche. An example protocol for preparation of such a formulation is as follows:

A 400 mL beaker is placed on the scales and tared. The active ingredient racemorphan-SBEBCD salt/free base mixture is added. A polyethylene glycol (PEG) base (e.g. PEG 1450) is prepared in a separate beaker by melting in a water bath placed over a hotplate. The melted PEG base is then added to the 400 mL beaker containing the racemorphan-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, bittering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the racemorphan is released into the saliva of the subject. The additional free base racemorphan acts to modulate the pH of the composition upon dissolution to closely match the pH of the saliva (~pH 7). In the saliva, soluble freebase racemorphan liberates for mucosal absorption from center of cyclodextrin and from racemorphan salts to increase bioavailability. Solubilized non-ionized racemorphan in equilibrium with the dynamic buffering of two mechanisms of effect from the captisol acid (e.g. protonation/salt formation of racemorphan and complexation of free base racemorphan) helps keep pH higher than racemorphan HCl allowing a higher proportion and more rapid mucosal absorption of drug product.

Figure 23:
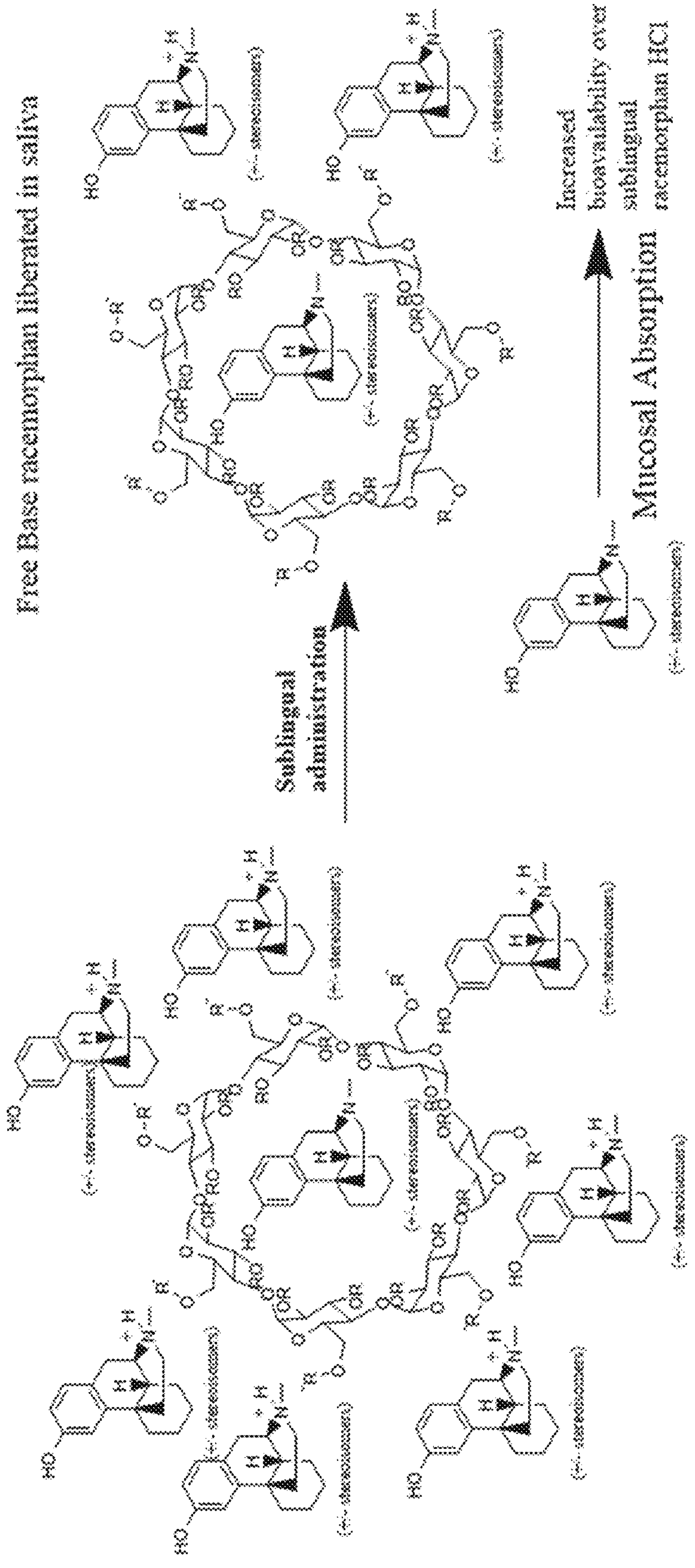
FIG. 23 shows a schematic of sublingual administration of a racemorphan-SBEBCD salt formulation.

This two-mechanism effect resulting in increased bioavailability is illustrated in FIG. 23, which shows non-ionized racemorphan within the cyclodextrin core of the SBEBCD. This is non-ionized racemorphan is released into the saliva which is then absorbed via mucosal absorption. Buffering effects within the saliva then convert the protonated racemorphan to the non-ionized state, which can be complexed with the now unoccupied cyclodextrin core to aid solubilization of the poorly soluble free base form. This process then repeats until all of the racemorphan is absorbed, resulting in a successful sublingual administration that is painless and prevents crashing out of the drug molecule during administration. This also produces a form of dynamic buffering that can keep the pH higher to allow the ionized racemorphan molecules complexed in the racemorphan-SBEBCD salt to become deprotonated or unionized even while in a highly solubilized state, increasing submucosal absorption capacity are rate. Compared with a similar dose in a similar troche formulation made from racemorphan HCl, tolerability, bioavailability, and solubility are all enhanced due to the SBECD-salt complex and free base racemorphan complexed within the cyclodextrin core.

Example 24. Sublingual Formulation of Racemorphan Comprising Racemorphan-SBEBCD Salt and High Molar Equivalent Free Base Racemorphan A racemorphan-SBSBCD salt is prepared analogously to the salt prepared in Example 17 and is further processed into a sublingual formulation in unit dose form as a sublingual troche. The sublingual formulation here utilizes a substantial excess of free base racemorphan in the formulation (10× molar equivalents compared to the racemorphan-SBEBCD salt in the formulation). The substantial excess of free base racemorphan provides numerous advantages over other formulations using compound-complexing agents salts as provided herein.

One advantage is that the presence of excess free base compound allows for pH adjustment and buffering in situ upon administration to closely match the tissue pH. The presence of excess free base molecules allows the compound to act as its own buffer, thus raising the pH compared to administration of the salt complex alone. By using the compound as its own buffer, a larger dose of the compound of interest can be applied without reaching excessive osmolality as additional base components may be omitted.

Additionally, using the compound as a buffer allows the total dosage unit (in this case a sublingual dose, but the concept is equally applicable to other dosage forms, particularly intranasal administration) to maintain the desired pH even as the material is absorbed by the relevant tissues after administration. As the compound is absorbed by the tissues, other free base molecules remain present to continue buffering the pH to a physically tolerable level. In some instances, a substantial portion of the excess of free base compound may only dissolve after administration after a certain amount of the compound has been absorbed into the mucosa, particularly when the free base compound is only sparingly soluble. In such a case, the absorption of the compound drives the equilibrium of the dissolution of the compound as it is absorbed, thus ensuring that only a desirable amount of free base compound is present at any time to act as an appropriate buffer to maintain the desired physiologically tolerable pH.

Finally, the presence of excess free base compound has the advantage of providing a consistent source of active compound, which can continuously occupy the complexing site within the cyclodextrin as the drug product compound is absorbed over time. The cyclodextrins in the formulation act as a shuttle for compound, helping to solubilize the compound, which can then be absorbed by the body. The cyclodextrin can then repeat this complexing/solubilization process with additional molecules of the compound to help solubilize the remaining excess free base.

Example Protocol The required quantities of free base racemorphan (700 mg, 10× molar excess compared to the amount of SBEBCD) and the lyophilized racemorphan-SBEBCD salt (1.0 g) prepared analogously to the salt in Example 17 are accurately weighed (resulting molar ratio of 10:1 free base racemorphan:SBEBCD). A homogenous paste of lyophilized racemorphan-SBEBCD salt is prepared in a mortar by adding water: ethanol (1:1) to the mixture in small quantities. Free base racemorphan powder is then added to the paste in portions with continuous kneading for three hours. An appropriate quantity of water:ethanol mixture is added to maintain suitable consistency of the paste. This paste is then dried in a hot air oven for 24 hours. The dried complex is then powdered and sieved, then stored in an airtight container until further use.

The dried complex comprising excess free base racemorphan is then formulated for sublingual formulation in unit dose form as a sublingual troche. An example protocol for preparation of such a formulation is as follows:

A 400 mL beaker is placed on the scales and tared. The active ingredient racemorphan-SBEBCD salt/free base mixture prepared above is added. A polyethylene glycol (PEG) base (e.g. PEG 1450) is prepared in a separate beaker by melting in a water bath placed over a hotplate. The melted PEG base is then added to the 400 mL beaker containing the racemorphan-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, buttering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the racemorphan is released into the saliva of the subject. The additional free base racemorphan acts to modulate the pH of the composition upon dissolution to closely match the pH of the saliva (~pH 7). The excess free base racemorphan successfully counteracts the acidic nature of the protonated racemorphan from the SBEBCD salt. In the saliva, soluble amounts of freebase racemorphan dissolve for mucosal absorption, both by eluting from the cyclodextrin and to a lesser extent by direct dissolution of the free base racemorphan. Solubilized non-ionized racemorphan is then absorbed into the nasal mucosa. This shifts the equilibrium of solubilization such that more free base racemorphan becomes solubilized, both in solution and through complexation with the interior of the cyclodextrin. This dynamic buffering and solubilization process is driven through two mechanisms of effect: protonation/salt formation of racemorphan (solubilization through forming an ion) and complexation of free base racemorphan. These continuous effects driven by equilibrium thus increase absorption of the compound, allowing for a high concentration of drug product to be delivered in a formulation densely populated with drug product.

Figure 24:
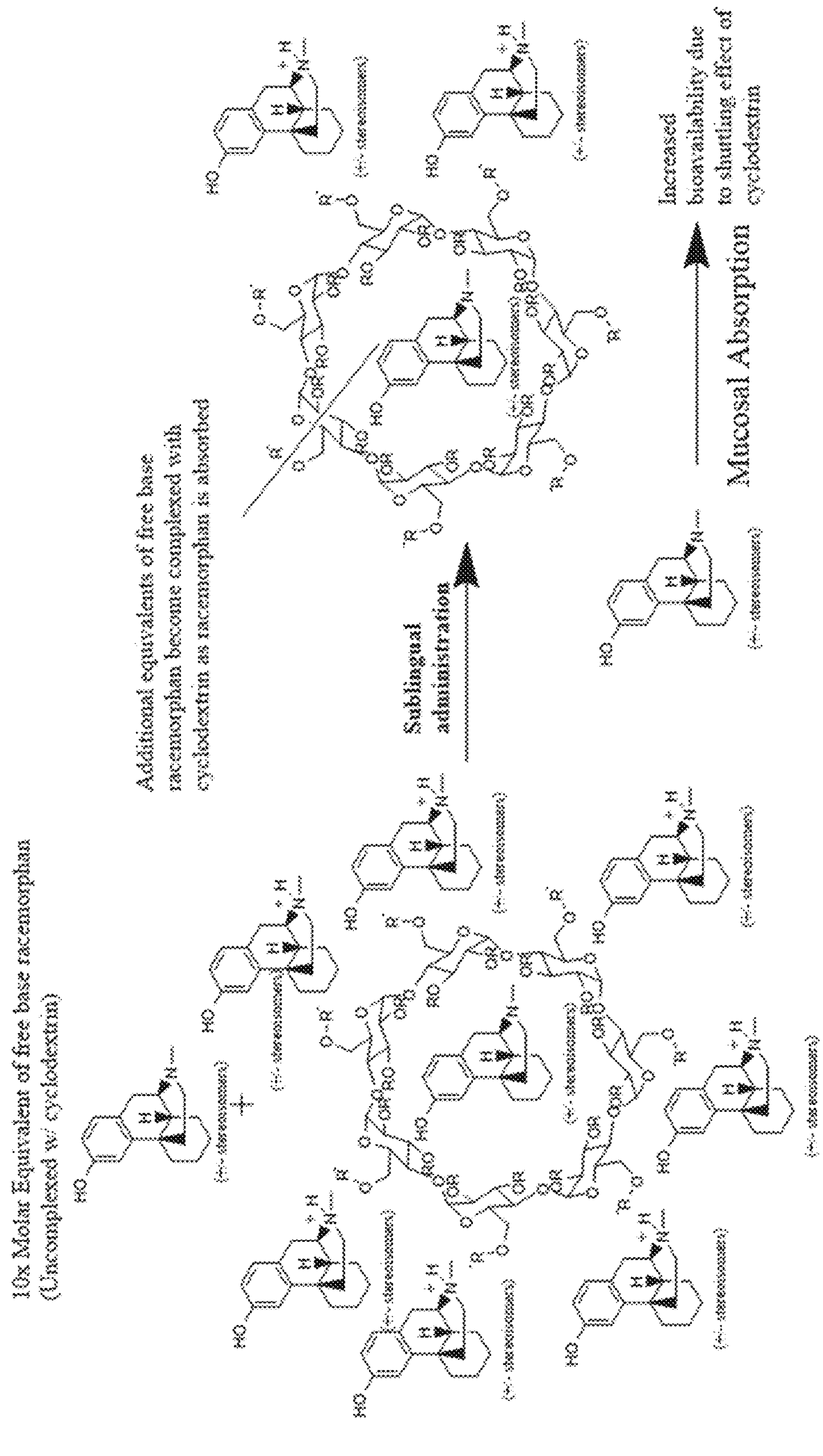
FIG. 24 shows a schematic of sublingual administration of a racemorphan-SBEBCD salt formulation comprising an excess of free base racemorphan

The mechanism underling these effect resulting in increased bioavailability and enhanced buffering capacity of the system is illustrated in FIG. 24, which shows non-ionized racemorphan within the cyclodextrin core of the SBEBCD and excess free base racemorphan also present. The non-ionized racemorphan is first released into the saliva from the cyclodextrin and then absorbed via mucosal absorption. Once absorbed, the equilibrium of the system shifts and allows more free base racemorphan to become dissolved in the saliva, either directly or, more substantially, through additional complexation with the now unoccupied cyclodextrin core in a shuttle-like mechanism. As the additional free base racemorphan solubilizes in the system, the desired physiologically tolerable pH of the formulation is maintained as the acidity of the protonated racemorphan molecules present in the salt form continue to be neutralized as more free base compound solubilizes. This process then repeats until all of the racemorphan is absorbed, resulting in a successful sublingual administration that is painless and effective. This also produces a form of dynamic buffering that can keep the pH elevated relative to a dose form without excess free base drug compound, thus allowing the ionized racemorphan molecules associated with the racemorphan-SBEBCD salt to become deprotonated or unionized even while in a highly solubilized state, increasing submucosal absorption capacity and rate. Compared with a similar dose in a similar troche formulation made from racemorphan HCl, tolerability, bioavailability, and solubility are all enhanced due to the SBECD-salt complex and free base racemorphan complexed within the cyclodextrin core.

Example 25. Preparation of a 3-Methylmethcathinone-SBEBCD Salt

A 3-methylmethcathinone-SBEBCD salt is prepared according to the general protocol shown in Scheme 16. The protocol provided herein is used to prepare a stable, high concentration 3-methylmethcathinone solution. This solution can be adjusted to an osmolality near physiological levels (~300 mOsm/kg) and a pH near the bottom range of the buffering capacity of the 3-methylmethcathinone's pKa value (~2 pH units below) for use in a subcutaneous formulation. Alternatively, the aqueous solution can be lyophilized to remove the liquid and leave behind the 3-methylmethcathinone-SBEBCD salt in solid form, which can then be used in any subsequent formulation desired.

Scheme 16

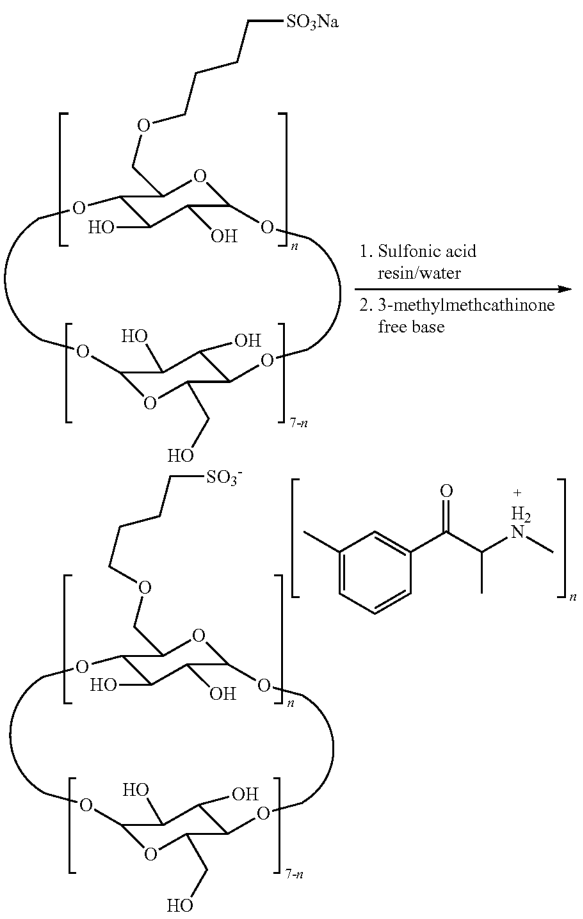

Experimental Procedure for the Preparation of 3-Methylmethcathinone SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol®: Can be purchased from Ligand Pharmaceuticals, Inc. (Ligand) (pharmaceutical grade). The moisture content is verified by Karl Fisher analysis. Captisol® is a polysulfobutylated β-cyclodextrin sodium form, with an average of 6.5 sulfobutyl groups per molecule and an average MW of 2,163.

3-methylmethcathinone HCl: Purchased from desired manufacturer and can be used without further purification. Free base 3-methylmethcathinone is prepared from the HCl salt with concentrated sodium hydroxide and isolated by vacuum filtration.

Synthesis of Captisol® Acid. Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and was completely dried by applying compressed air for 10 minutes before the sample was applied. A solution of 15% Captisol® (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

3-methylmethcathinone Freebase: 3-methylmethcathinone hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 25:
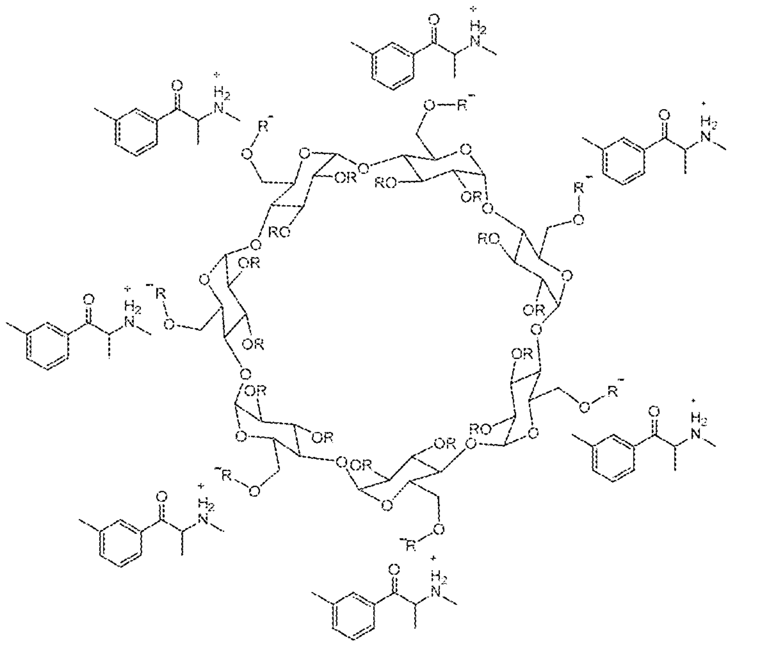
FIG. 25 shows an exemplary structure of an compound-complexing agent salt as provided herein. The compound-complexing agent salt shown is a 3-methylmethcathinone-SBEBCD salt.

Synthesis of 3-methylmethcathinone-Captisol® Salt: Captisol® acid prepared above (moisture corrected to ascertain actual concentration) is dissolved in HPLC grade water in a test tube with a teflon stirbar. The solution is stirred vigorously and 3-methylmethcathinone freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to −2 pH units below the pKa of 3-methylmethcathinone, at which point nearly all (~99%) of the 3-methylmethcathinone will be protonated. The solution is syringe filtered with a 0.45 μM nylon filter and is stored in a test tube under ambient air and wrapped in aluminum foil. Part of the volume is lyophilized to produce a powder of the 3-methylmethcathinone-Captisol® salt. This resulting powder is observed under ambient conditions to observe for any wetting, discoloration, or other observable change. The remaining volume of solution containing the 3-methylmethcathinone-Captisol® salt is similarly monitored for visible changes. The sample is also periodically monitored by HPLC to ascertain stability over time. The structure of the resulting 3-methylmethcathinone-Captisol® salt is shown in FIG. 25.

Figure 26:
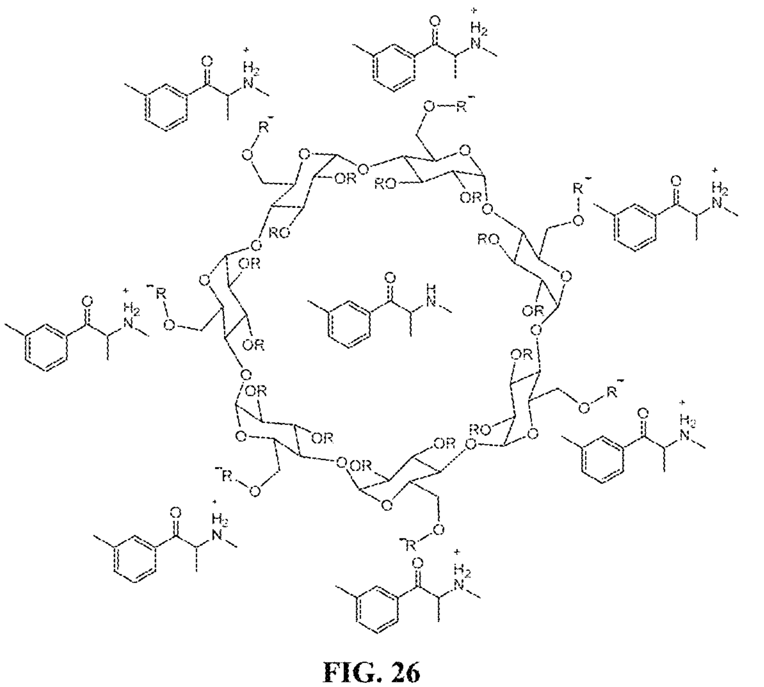
FIG. 26 shows an exemplary structure of a 3-methylmethcathinone-SBEBCD salt which is also acting as an inclusion complex for an additional equivalent of free base 3-methylmethcathinone.

Example 26. Preparation of a 3-Methylmethcathinone-SBEBCD Salt with Free Base 3-Methylmethcathinone Complexed within the SBEBCD The salt forms of the complexing agent/pharmaceutical compounds provided herein can also be adapted to incorporate additional molar equivalents of free base compound. For example, in instances where the complexing agent is a cyclodextrin such as SBEBCD, the interior portion of the cyclodextrin can incorporate an additional molecule of pharmaceutical compound. An exemplary illustration of such a complex can be seen in FIG. 26, which shows the 3-methylmethcathinone/SBEBCD salt complex described in Example 1 which has been modified to incorporate an additional uncharged molecule of 3-methylmethcathinone on the interior of the cyclodextrin. Such complexes can have additional benefits when used in pharmaceutical compositions, including increased solubility of the compounds upon administration, increased bioavailability of the compounds, and the presence of free base compound can act to create a buffering system that allows for a more biocompatible pH to be achieved upon delivery of the pharmaceutical composition as the free base compound neutralizes some of the acidic functionalities of the protonated compounds of the salt complex.

Such complexes can be created in a variety of ways, several of which are shown by example below. In order to ascertain the proper ratio of salt complex to free base compound to add to prepare a mixture with an additional molecule of compound incorporated into the center of the cyclodextrin, it is necessary to determine the molecular weight of the salt complex. This can be readily calculated from the known molecular weight of the starting materials and stoichiometry of the complexing agent and compound. For example, as the SBEBCD used to prepare the 3-methylmethcathinone-SBEBCD salt in Example 25 has an average of 6.5 sulfobutyl groups per molecule, the resulting salt has an average of 6.5 3-methylmethcathinone molecules for every cyclodextrin molecule, resulting in the salt having an average molecular weight of 3170 Daltons. This value can be calculated as follows: From the average molecular weight of the SBEBCD (average MW of 2,163) is subtracted the weight of sodium atoms which have been removed (6.5 times 22.99 Daltons), and the weight of 3-methylmethcathinone molecules (6.5 times 177.25 Daltons) and additional hydrogen atoms (6.5 times 1.01 Daltons) is added, yielding an average molecule weight of about 3170 Daltons. Additionally, any residual water in the resulting salt can be measured by an appropriate procedure, such as Karl Fischer analysis.

The complexes described in this example can be prepared by any suitable method, including without limitation the procedures described below.

Physical mixture method—The required molar quantities (1:1) of free base 3-methylmethcathinone (70 mg) and the lyophilized 3-methylmethcathinone-SBEBCD salt (1.0 g) prepared in Example 1 are weighed accurately and mixed together thoroughly in a mortar with vigorous trituration for about three hours. The mixture is then passed through a sieve and stored in an airtight container until further use.

Kneading Method—The required quantities of free base 3-methylmethcathinone (56 mg) and the lyophilized 3-methylmethcathinone-SBEBCD salt (1.0 g) prepared in Example 1 are accurately weighed (resulting molar ratio of 1:1). A homogenous paste of lyophilized 3-methylmethcathinone-SBEBCD salt is prepared in a mortar by adding water: ethanol (1:1) to the mixture in small quantities. Free base 3-methylmethcathinone powder is then added to the paste in portions with continuous kneading for three hours. An appropriate quantity of water:ethanol mixture is added to maintain suitable consistency of the paste. This paste is then dried in a hot air oven for 24 hours. The dried complex is then powdered and sieved, then stored in an airtight container until further use.

Co-Precipitation Method—Quantities of free base 3-methylmethcathinone (56 mg) and lyophilized 3-methylmethcathinone-SBEBCD salt (1.0 g) prepared in Example 1 are dissolved separately in ethanol and water, respectively. The solution of free base 3-methylmethcathinone is added dropwise to the cyclodextrin containing solution. The contents are stirred continuously for 6 hours, at which point they are dried at elevated temperature for 48 hours, collected, and stored in airtight containers until further use.

Solvent Evaporation Method—Free base 3-methylmethcathinone (56 mg) is dissolved in a suitable organic solvent (e.g. ethanol) at room temperature. The required amount of lyophilized 3-methylmethcathinone-SBEBCD salt (1.0 g) prepared in Example 25 is dissolved in hot water and is added dropwise into the solution with continuous stirring over one hour. The resulting complexes are then filtered and dried under a vacuum. The resulting solid mass is then stored in a desiccator under vacuum to a constant weight. The dried product is removed, sieved, then stored in a closed airtight container.

Characterization of Resulting Inclusion Complexes

The resulting salt/inclusion complexes are then characterized for drug content, solubility, and stability. The samples are analyzed by appropriate analytical techniques (e.g. co-precipitation of drug in the complex, scanning electron microscopy of the physical mixtures, IR spectral analysis, differential scanning calorimetry, nuclear magnetic resonance (NMR) spectroscopy, and dissolution/HPLC analysis) at various timepoints in order to ensure the resulting inclusion complexes have the desired amount of 3-methylmethcathinone and are suitably stable for later use. Such inclusion complexes can be directly administered or used in a further formulation.

Alternative Preparation Methods

In addition to the methods described above, alternative methods for the preparation of the salt-inclusion complexes described herein are available. For example, the preparation of an inclusion complex could be prepared prior to forming the free-acid complexing agent, which is then used to neutralize excess free base compound in a later step. Alternatively, it is contemplated that the preparation of the salt and the complex could be formed simultaneously in a one-pot reaction scheme.

Advantages of Inclusion Complexes

The resulting 3-methylmethcathinone-SBEBCD salt/3-methylmethcathinone free base mixture contains approximately 6-7 protonated 3-methylmethcathinone molecules bonded to every molecule of SBEBCD with an additional free base molecule of 3-methylmethcathinone also present (e.g. complexed within the cyclodextrin core of the SBEBCD). The additional unionized 3-methylmethcathinone provides improved drug product absorption and pH adjustment for improved tolerance upon administration. Such complexes provide several advantages over other preparations. One notable advantage of this preparation over other possible preparations of 3-methylmethcathinone is the presence of highly soluble ionized 3-methylmethcathinone complexed to an SBEBCD molecule modified to be its conjugate acid in the simultaneous presence of added 1 molar equivalent of non-ionized 3-methylmethcathinone that can raise the pH on the dry powder formulation for sublingual or intranasal delivery to a more closely match the pH of saliva (approximately 7.0) or nasal mucosal secretions. This also produces a form of dynamic buffering that can keep the pH higher to allow the ionized 3-methylmethcathinone molecules complexed in the 3-methylmethcathinone-captisol salt to become deprotonated or unionized even while in a highly solubilized state, increasing submucosal absorption capacity are rate.

Example 27. Preparation of a Diphenhydramine-SBEBCD Salt

A diphenhydramine-SBEBCD salt is prepared according to the general protocol shown in Scheme 17. The protocol provided herein is used to prepare a stable, high concentration Diphenhydramine solution. This solution can be adjusted to an osmolality near physiological levels (~300 mOsm/kg) and a pH near the bottom range of the buffering capacity of the diphenhydramine's pKa value (~2 pH units below) for use in a subcutaneous formulation. Alternatively, the aqueous solution can be lyophilized to remove the liquid and leave behind the diphenhydramine-SBEBCD salt in solid form, which can then be used in any subsequent formulation desired.

Scheme 17

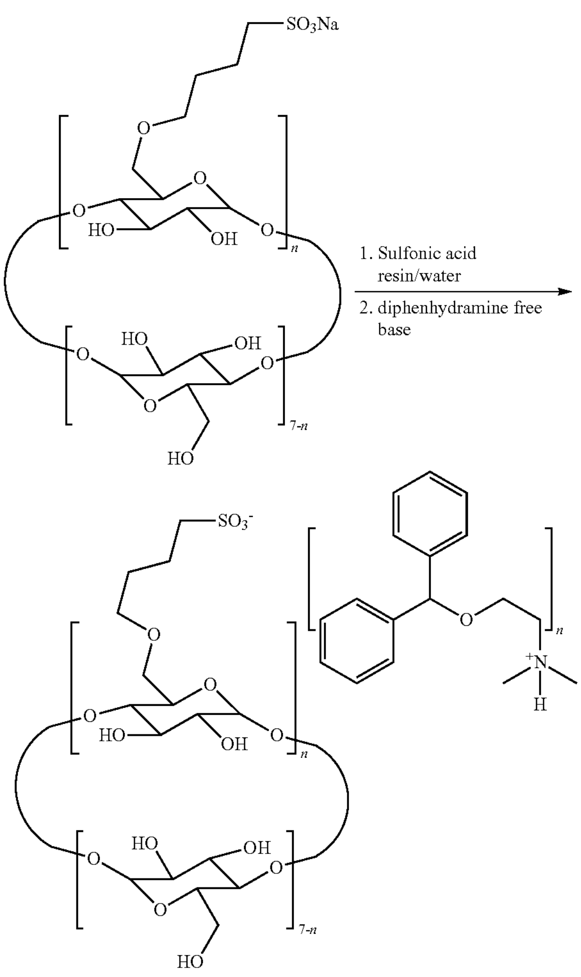

Experimental Procedure for the Preparation of Diphenhydramine SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 1.

Diphenhydramine HCl: Purchased from desired manufacturer and can be used without further purification. Free base diphenhydramine is prepared from the HCl salt with concentrated sodium hydroxide and isolated by vacuum filtration.

Diphenhydramine Freebase: Diphenhydramine hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 27:
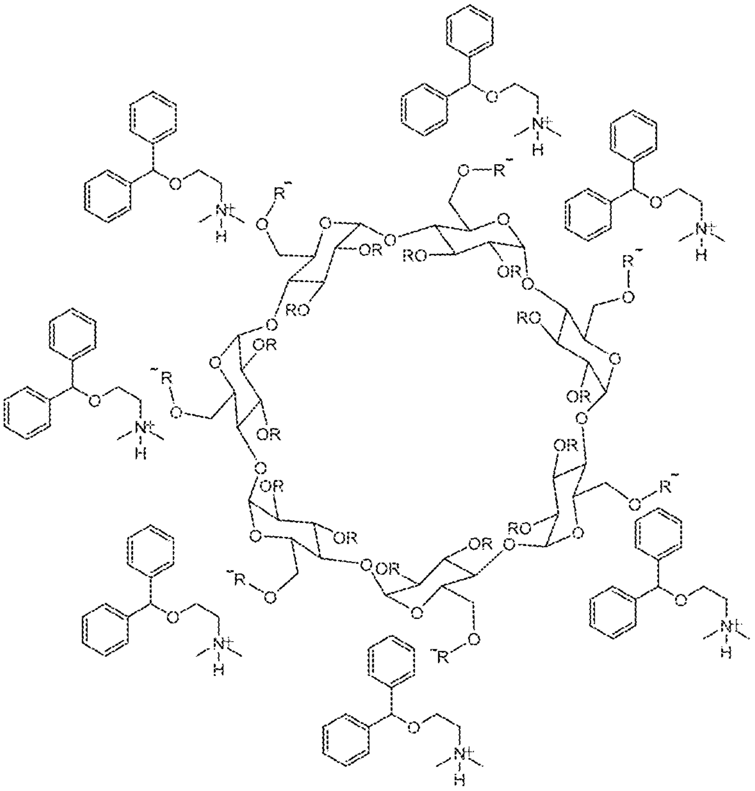
FIG. 27 shows an exemplary structure of a diphenhydramine-SBEBCD salt.

Synthesis of Diphenhydramine-Captisol® Salt: Captisol® acid prepared above (moisture corrected to ascertain actual concentration) is dissolved in HPLC grade water in a test tube with a teflon stirbar. The solution is stirred vigorously and diphenhydramine freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of diphenhydramine, at which point nearly all (~99%) of the diphenhydramine will be protonated. The solution is syringe filtered with a 0.45 μM nylon filter and is stored in a test tube under ambient air and wrapped in aluminum foil. Part of the volume is lyophilized to produce a powder of the diphenhydramine-Captisol® salt. This resulting powder is observed under ambient conditions to observe for any wetting, discoloration, or other observable change. The remaining volume of solution containing the diphenhydramine-Captisol® salt is similarly monitored for visible changes. The sample is also periodically monitored by HPLC to ascertain stability over time. The structure of the resulting diphenhydramine-Captisol® salt is shown in FIG. 27.

Example 28. Preparation of a 1-(1,3-benzodioxol-5-yl)-N-methyl-2-butanamine (MBDB)-SBEBCD Salt A MBDB-SBEBCD salt is prepared according to the general protocol shown in Scheme 18. The protocol provided herein is used to prepare a stable, high concentration MBDB solution. This solution can be adjusted to an osmolality near physiological levels (~300 mOsm/kg) and a pH near the bottom range of the buffering capacity of the MBDB's pKa value (~2 pH units below) for use in a subcutaneous formulation. Alternatively, the aqueous solution can be lyophilized to remove the liquid and leave behind the MBDB-SBEBCD salt in solid form, which can then be used in any subsequent formulation desired.

Scheme 18

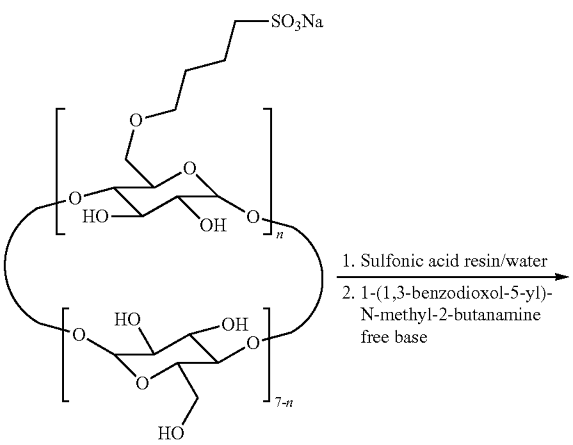

-continued

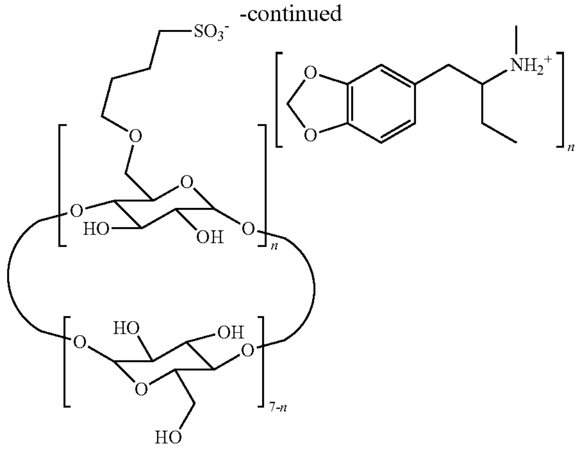

Experimental Procedure for the Preparation of MBDB SBEBCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

Captisol® Acid—Prepared as described in Example 1.

MBDB HCl: Purchased from desired manufacturer and can be used without further purification. Free base MBDB is prepared from the HCl salt with concentrated sodium hydroxide and isolated by vacuum filtration.

MBDB Freebase: MBDB hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 28:
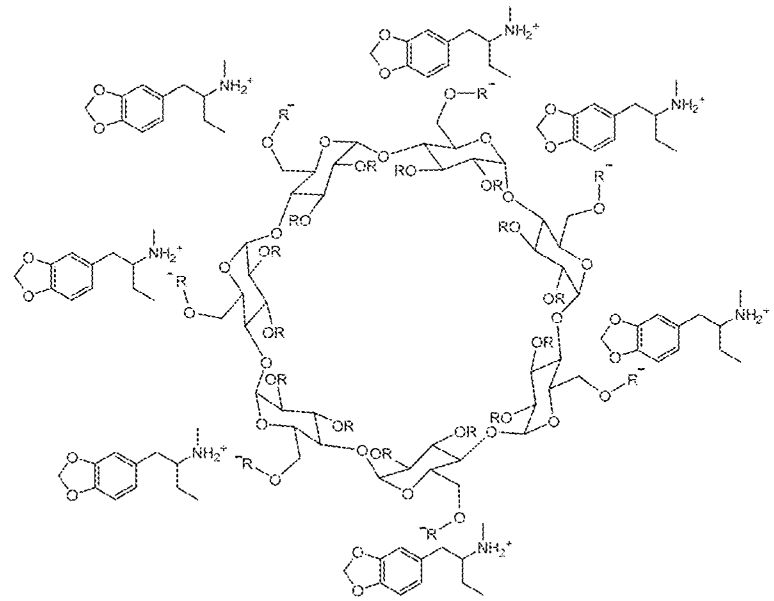
FIG. 28 shows an exemplary structure of a 1-(1,3-benzodioxol-5-yl)-N-methyl-2-butanamine (MBDB)-SBEBCD salt.

Synthesis of MBDB-Captisol® Salt: Captisol® acid prepared above (moisture corrected to ascertain actual concentration) is dissolved in HPLC grade water in a test tube with a teflon stirbar. The solution is stirred vigorously and MBDB freebase (1 equivalent per acidic functional group of Captisol® acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of MBDB, at which point nearly all (~99%) of the MBDB will be protonated. The solution is syringe filtered with a 0.45 μM nylon filter and is stored in a test tube under ambient air and wrapped in aluminum foil. Part of the volume is lyophilized to produce a powder of the MBDB-Captisol® salt. This resulting powder is observed under ambient conditions to observe for any wetting, discoloration, or other observable change. The remaining volume of solution containing the MBDB-Captisol® salt is similarly monitored for visible changes. The sample is also periodically monitored by HPLC to ascertain stability over time. The structure of the resulting MBDB-Captisol® salt is shown in FIG. 28.

Example 29. Preparation of a 5-(2-aminopropyl)-benzofuran (5-APB)-SuACD Salt

A 5-APB-Succinated alpha-cyclodextrin (SuACD) salt is prepared according to the general protocol shown in Scheme 19. The protocol provided herein is used to prepare a stable, high concentration 5-APB solution. This solution can be adjusted to an osmolality near physiological levels (~300 mOsm/kg) and a pH near the bottom range of the buffering capacity of the 5-APB's pKa value (~2 pH units below) for use in a subcutaneous formulation. Alternatively, the aqueous solution can be lyophilized to remove the liquid and leave behind the 5-APB-SuACD salt in solid form, which can then be used in any subsequent formulation desired.

Scheme 19

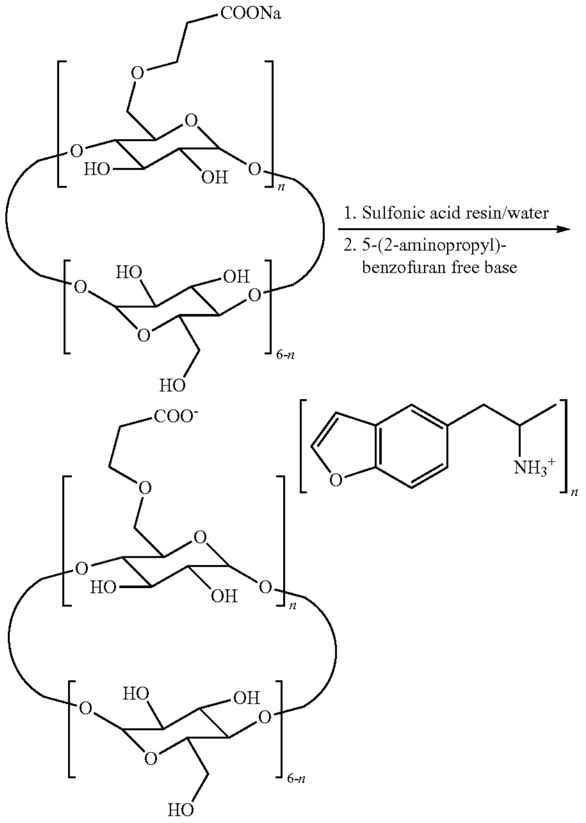

Experimental Procedure for the Preparation of 5-APB SuACD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

SuACD—Can be purchased from Arachem (M) Sdn Bhd. (Arachem) (pharmaceutical grade). The moisture content is verified by Karl Fisher analysis. SuACD is a polysuccinylated α-cyclodextrin sodium form, with an average of ~4 succinyl groups per molecule and an average MW of ~1300

SuACD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% SuACD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting white, free-flowing shiny solid is stored in a foil-wrapped scintillation vial at −20° C.

5-APB HCl: Purchased from desired manufacturer and can be used without further purification. Free base 5-APB is prepared from the HCl salt with concentrated sodium hydroxide and isolated by vacuum filtration.

5-APB Freebase: 5-APB hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 29:
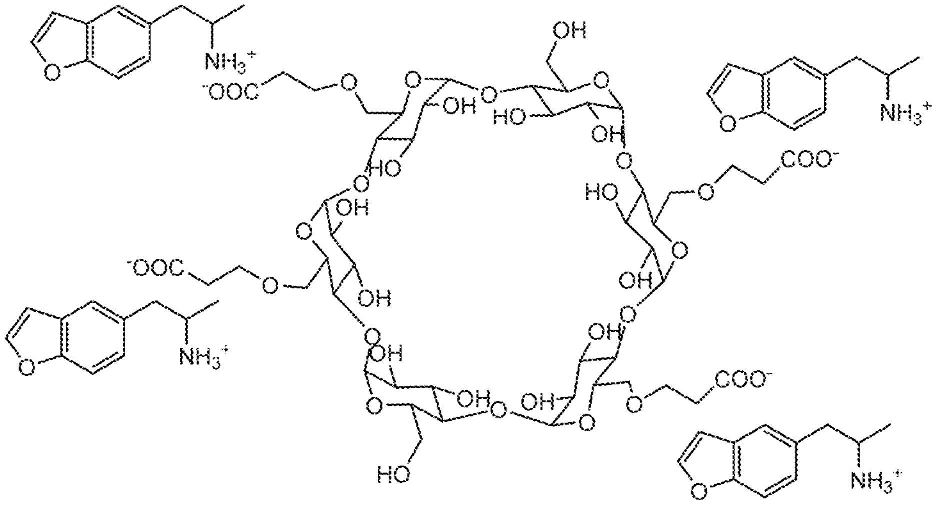
FIG. 29 shows an exemplary structure of a 5-(2-aminopropyl)-benzofuran (5-APB)-SuACD salt.

Synthesis of 5-APB-SuACD Salt: SuACD acid prepared above (moisture corrected to ascertain actual concentration) is dissolved in HPLC grade water in a test tube with a teflon stirbar. The solution is stirred vigorously and 5-APB free-base (1 equivalent per acidic functional group of SuACD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of 5-APB, at which point nearly all (~99%) of the MBDB will be protonated. The solution is syringe filtered with a 0.45 μM nylon filter and is stored in a test tube under ambient air and wrapped in aluminum foil. Part of the volume is lyophilized to produce a powder of the 5-APB-SuACD salt. This resulting powder is observed under ambient conditions to observe for any wetting, discoloration, or other observable change. The remaining volume of solution containing the 5-APB-SuACD salt is similarly monitored for visible changes. The sample is also periodically monitored by HPLC to ascertain stability over time. The structure of the resulting 5-APB-SuACD salt is shown in FIG. 29

Example 30. Preparation of a 5,6-methylenedioxy-2-aminoindane (MDAI)-CMGCD Salt A MDAI-carboxymethyl-gamma-cyclodextrin (CMGCD) salt is prepared according to the general protocol shown in Scheme 20. The protocol provided herein is used to prepare a stable, high concentration MDAI solution. This solution can be adjusted to an osmolality near physiological levels (~300 mOsm/kg) and a pH near the bottom range of the buffering capacity of the MDAI's pKa value (~2 pH units below) for use in a subcutaneous formulation. Alternatively, the aqueous solution can be lyophilized to remove the liquid and leave behind the MDAI-CMGCD salt in solid form, which can then be used in any subsequent formulation desired.

Scheme 20

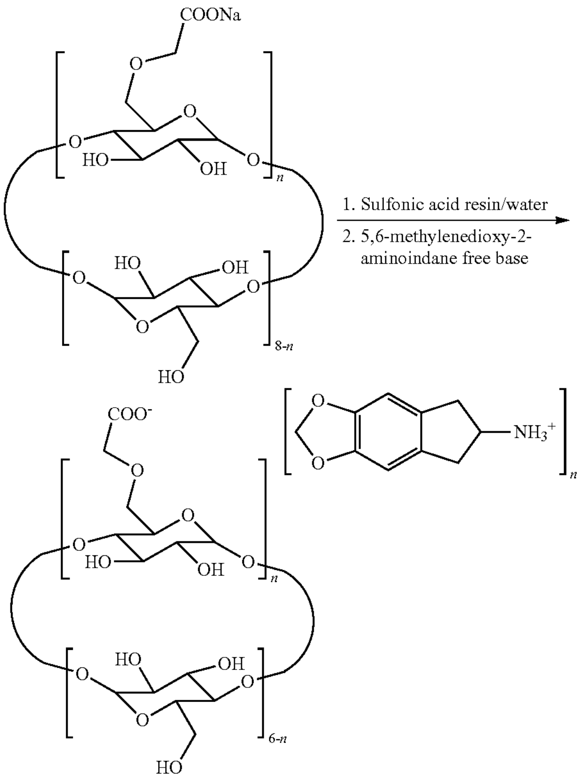

Experimental Procedure for the Preparation of MDAI-CMGCD Salt

HPLC grade solvents are used throughout all procedures unless otherwise noted. Materials are sourced from commercial suppliers and used as is unless otherwise noted. Equivalence points are determined by titration with 0.5M sodium hydroxide and the data is analyzed in Prism 8.

CMGCD—Can be purchased from Arachem (M) Sdn Bhd (Arachem). The moisture content is verified by Karl Fisher analysis. CMGCD is a carboxymethylated γ-cyclodextrin sodium form, with an average of ~4 carboxymethyl groups per molecule and an average MW of ~1600.

CMGCD Acid—Amberlite IR120 Hydrogen form resin (198 g, 4.4 meq/g, 20 equivalents) is soaked in HPLC grade water (400 mL) for 5 minutes and packed into a column (40 mm diameter). The resin is washed with 2 column volumes of HPLC grade water and is completely dried by applying compressed air for 10 minutes before the sample is applied. A solution of 15% CMGCD (90 mL) is applied to the column and allowed to flow by gravity into an Erlenmeyer flask. When the gravity flow ceased, compressed air is used to elute the remaining volume for 10 minutes. The eluent is frozen at −20° C., lyophilized and subjected to further drying via high vacuum (<0.01 mmHg) for 3 hrs. Every hour, the solid is removed from the vacuum, pulverized, and then placed back under vacuum. The final moisture content of the solid is determined by Karl-Fisher titration. The resulting solid is stored in a foil-wrapped scintillation vial at −20° C.

MDAI HCl: Purchased from desired manufacturer and can be used without further purification. Free base MDAI is prepared from the HCl salt with concentrated sodium hydroxide and isolated by vacuum filtration.

MDAI Freebase: MDAI hydrochloride is dissolved in $dH_2O$ (100 mL). 2M NaOH is added with stirring until a precipitate forms. An excess of base is added such that additional base does not lead to further precipitation. After sitting for 20 minutes the precipitate is collected by gravity filtration, washed with 300 mL of HPLC-grade water and dried under vacuum. Purity is confirmed by HPLC and water content by Karl Fisher analysis. The identity is determined by NMR and GC-MS.

Figure 30:
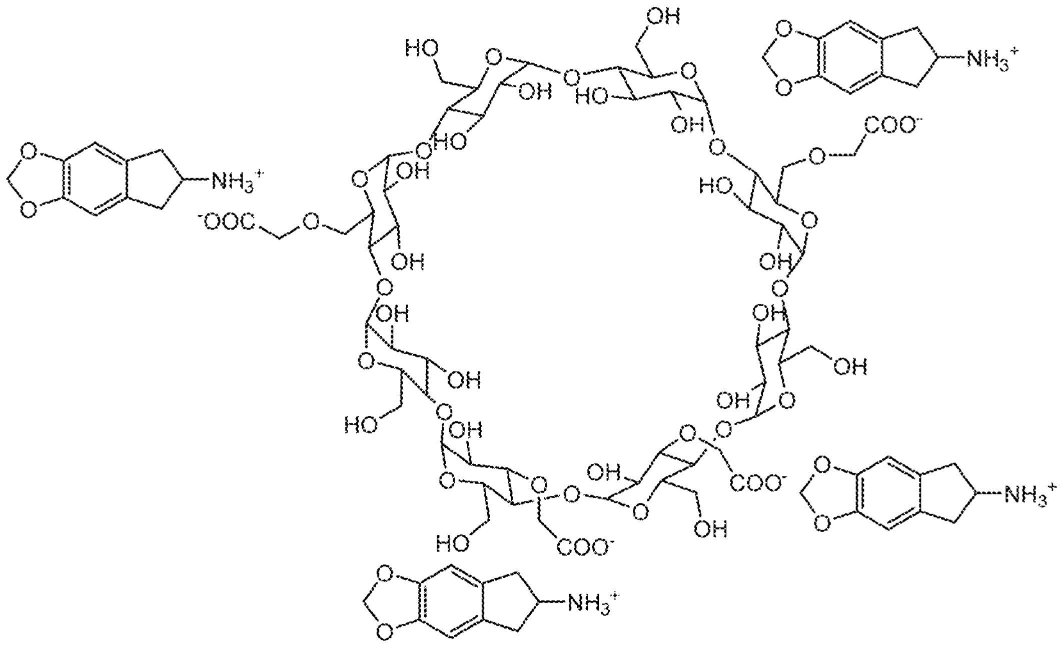
FIG. 30 shows an exemplary structure of a 5,6-methylenedioxy-2-aminoindane (MDAI)-CMGCD salt.

Synthesis of MDAI CMGCD Salt: CMGCD acid prepared above (moisture corrected to ascertain actual concentration) is dissolved in HPLC grade water in a test tube with a teflon stirbar. The solution is stirred vigorously and MDAI freebase (1 equivalent per acidic functional group of CMGCD acid) is added via spatula in ~20-40 mg portions, each portion is allowed to completely dissolve before the next was added. The solid is agitated as necessary to facilitate dissolving. When the additions are complete, 2M sodium hydroxide is added in small portions until the pH is raised to ~2 pH units below the pKa of MDAI, at which point nearly all (~99%) of the MDAI will be protonated. The solution is syringe filtered with a 0.45 μM nylon filter and is stored in a test tube under ambient air and wrapped in aluminum foil. Part of the volume is lyophilized to produce a powder of the MDAI-CMGCD salt. This resulting powder is observed under ambient conditions to observe for any wetting, discoloration, or other observable change. The remaining volume of solution containing the MDAI-CMGCD salt is similarly monitored for visible changes. The sample is also periodically monitored by HPLC to ascertain stability over time. The structure of the resulting MDAI-CMGCD salt is shown in FIG. 30.

Example 31. Sublingual Formulation of 3-Methylmethcathinone Comprising 3-Methylmethcathinone-SBEBCD Salt and Free Base 3-Methylmethcathinone The composition prepared in Example 26 comprising 3-methylmethcathinone-SBEBCD salt with an additional molar equivalent of free-base 3-methylmethcathinone is further formulated for sublingual formulation in unit dose form as a sublingual troche. An example protocol for preparation of such a formulation is as follows:

A 400 mL beaker is placed on the scales and tared. The active ingredient 3-methylmethcathinone-SBEBCD salt/free base mixture is added. A polyethylene glycol (PEG) base (e.g. PEG 1450) is prepared in a separate beaker by melting in a water bath placed over a hotplate. The melted PEG base is then added to the 400 mL beaker containing the 3-methylmethcathinone-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, buttering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the 3-methylmethcathinone is released into the saliva of the subject. The additional free base 3-methylmethcathinone acts to modulate the pH of the composition upon dissolution to closely match the pH of the saliva (~pH 7). In the saliva, soluble freebase 3-methylmethcathinone liberates for mucosal absorption from center of cyclodextrin and from 3-methylmethcathinone salts to increase bioavailability. Solubilized non-ionized 3-methylmethcathinone in equilibrium with the dynamic buffering of two mechanisms of effect from the captisol acid (e.g. protonation/salt formation of 3-methylmethcathinone and complexation of free base 3-methylmethcathinone) helps keep pH higher than 3-methylmethcathinone HCl allowing a higher proportion and more rapid mucosal absorption of drug product.

Figure 31:
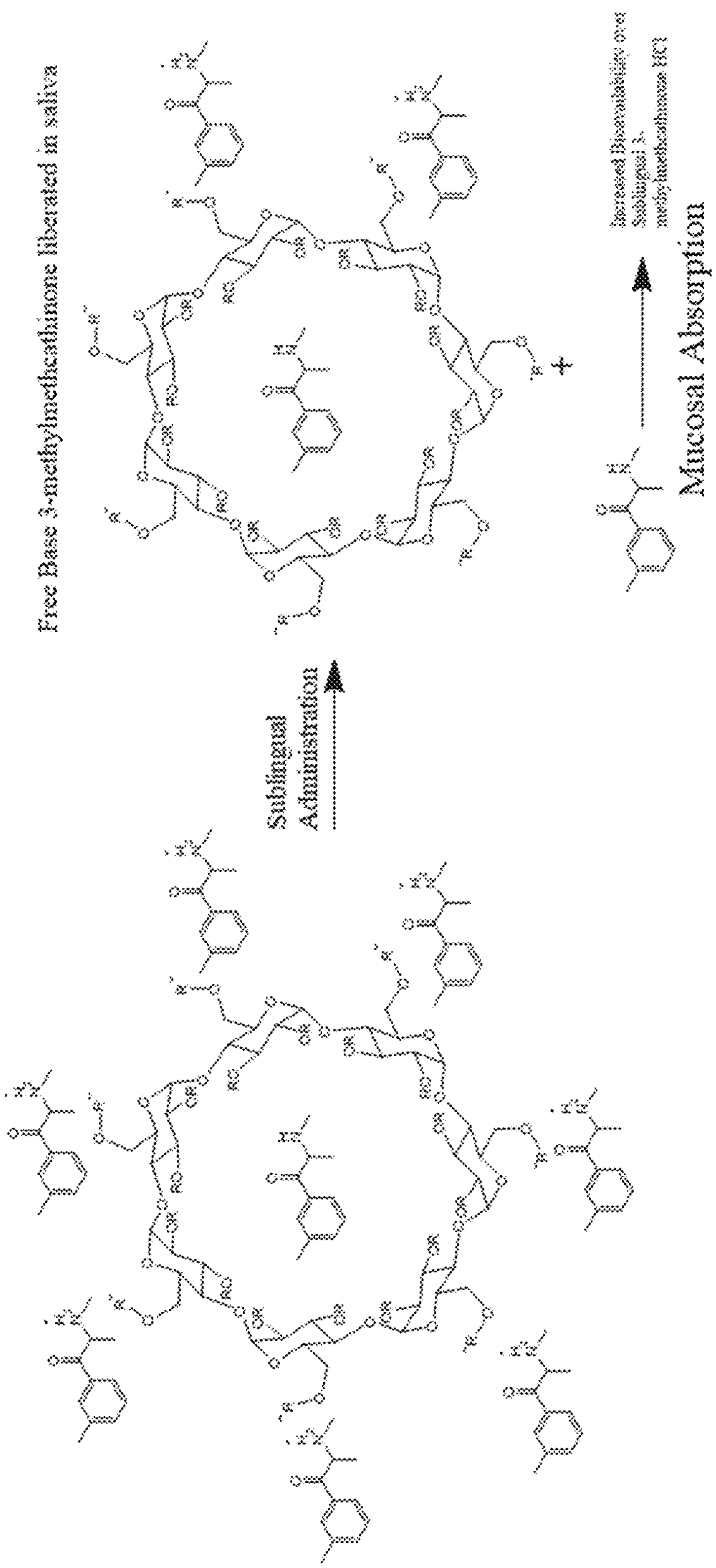
FIG. 31 shows a schematic of sublingual administration of a 3-methylmethcathinone-SBEBCD salt formulation.

This two-mechanism effect resulting in increased bioavailability is illustrated in FIG. 31, which shows non-ionized 3-methylmethcathinone within the cyclodextrin core of the SBEBCD. This is non-ionized 3-methylmethcathinone is released into the saliva which is then absorbed via mucosal absorption. Buffering effects within the saliva then convert the protonated 3-methylmethcathinone to the non-ionized state, which can be complexed with the now unoccupied cyclodextrin core to aid solubilization of the poorly soluble free base form. This process then repeats until all of the 3-methylmethcathinone is absorbed, resulting in a successful sublingual administration that is painless and prevents crashing out of the drug molecule during administration. This also produces a form of dynamic buffering that can keep the pH higher to allow the ionized 3-methylmethcathinone molecules complexed in the 3-methylmethcathinone-SBEBCD salt to become deprotonated or unionized even while in a highly solubilized state, increasing submucosal absorption capacity are rate. Compared with a similar dose in a similar troche formulation made from 3-methylmethcathinone HCl, tolerability, bioavailability, and solubility are all enhanced due to the SBECD-salt complex and free base 3-methylmethcathinone complexed within the cyclodextrin core.

Example 32. Sublingual Formulation of 3-Methylmethcathinone Comprising 3-Methylmethcathinone-SBEBCD Salt and High Molar Equivalent Free Base 3-Methylmethcathinone The 3-methylmethcathinone-SBSBCD salt prepared in Example 25 is further processed into a sublingual formulation in unit dose form as a sublingual troche. The sublingual formulation here utilizes a substantial excess of free base 3-methylmethcathinone in the formulation (10× molar equivalents compared to the 3-methylmethcathinone-SBEBCD salt in the formulation). The substantial excess of free base 3-methylmethcathinone provides numerous advantages over other formulations using compound-complexing agents salts as provided herein.

One advantage is that the presence of excess free base compound allows for pH adjustment and buffering in situ upon administration to closely match the tissue pH. The presence of excess free base molecules allows the compound to act as its own buffer, thus raising the pH compared to administration of the salt complex alone. By using the compound as its own buffer, a larger dose of the compound of interest can be applied without reaching excessive osmolality as additional base components may be omitted.

Additionally, using the compound as a buffer allows the total dosage unit (in this case a sublingual dose, but the concept is equally applicable to other dosage forms, particularly intranasal administration) to maintain the desired pH even as the material is absorbed by the relevant tissues after administration. As the compound is absorbed by the tissues, other free base molecules remain present to continue buffering the pH to a physically tolerable level. In some instances, a substantial portion of the excess of free base compound may only dissolve after administration after a certain amount of the compound has been absorbed into the mucosa, particularly when the free base compound is only sparingly soluble. In such a case, the absorption of the compound drives the equilibrium of the dissolution of the compound as it is absorbed, thus ensuring that only a desirable amount of free base compound is present at any time to act as an appropriate buffer to maintain the desired physiologically tolerable pH.

Finally, the presence of excess free base compound has the advantage of providing a consistent source of active compound, which can continuously occupy the complexing site within the cyclodextrin as the drug product compound is absorbed over time. The cyclodextrins in the formulation act as a shuttle for compound, helping to solubilize the compound, which can then be absorbed by the body. The cyclodextrin can then repeat this complexing/solubilization process with additional molecules of the compound to help solubilize the remaining excess free base.

Example Protocol The required quantities of free base 3-methylmethcathinone (560 mg, 10× molar excess compared to the amount of SBEBCD) and the lyophilized 3-methylmethcathinone-SBEBCD salt (1.0 g) prepared in Example 25 are accurately weighed (resulting molar ratio of 10:1 free base 3-methylmethcathinone:SBEBCD). A homogenous paste of lyophilized 3-methylmethcathinone-SBEBCD salt is prepared in a mortar by adding water: ethanol (1:1) to the mixture in small quantities. Free base 3-methylmethcathinone powder is then added to the paste in portions with continuous kneading for three hours. An appropriate quantity of water:ethanol mixture is added to maintain suitable consistency of the paste. This paste is then dried in a hot air oven for 24 hours. The dried complex is then powdered and sieved, then stored in an airtight container until further use.

The dried complex comprising excess free base 3-methylmethcathinone is then formulated for sublingual formulation in unit dose form as a sublingual troche. An example protocol for preparation of such a formulation is as follows:

A 400 mL beaker is placed on the scales and tared. The active ingredient 3-methylmethcathinone-SBEBCD salt/free base mixture prepared above is added. A polyethylene glycol (PEG) base (e.g. PEG 1450) is prepared in a separate beaker by melting in a water bath placed over a hotplate. The melted PEG base is then added to the 400 mL beaker containing the 3-methylmethcathinone-SBEBCD salt/free base mixture up to a total weight of 30.0 g. The beaker is placed onto a hotplate and the stirrer bar allowed to spin. Any additional ingredients, including permeation enhancers, stabilizers, lyophilization excipients, disintegrants, masking agents, flavors, binders, sweeteners, buttering agents, texturing agents, wetting agents, dispersing agents, or additional buffers are added, and the mixture allowed to spin until all active ingredients are dissolved.

The troche mixture is then poured into a mold dividing the mixture into 28 troches of ~1 g each and evened out with a spatula and allowed to dry. The top of the troche is slowly heated using a hair dryer until it begins to melt. Any excess is scraped away evenly with a clean bent spatula using the grids of the mold as a guide. The excess is used to fill any holes and even out each lozenge to an even dosage form. This may need to be repeated 2-3 times. Once even, the surface is slightly heated to finish. The mold is then cleaned outside with a damp cloth.

The troches are then administered to a subject sublingually. The troche dissolves in the mouth of the subject and the 3-methylmethcathinone is released into the saliva of the subject. The additional free base 3-methylmethcathinone acts to modulate the pH of the composition upon dissolution to closely match the pH of the saliva (~pH 7). The excess free base 3-methylmethcathinone successfully counteracts the acidic nature of the protonated 3-methylmethcathinone from the SBEBCD salt. In the saliva, soluble amounts of freebase 3-methylmethcathinone dissolve for mucosal absorption, both by eluting from the cyclodextrin and to a lesser extent by direct dissolution of the free base 3-methylmethcathinone. Solubilized non-ionized 3-methylmethcathinone is then absorbed into the nasal mucosa. This shifts the equilibrium of solubilization such that more free base 3-methylmethcathinone becomes solubilized, both in solution and through complexation with the interior of the cyclodextrin. This dynamic buffering and solubilization process is driven through two mechanisms of effect: protonation/salt formation of 3-methylmethcathinone (solubilization through forming an ion) and complexation of free base 3-methylmethcathinone. These continuous effects driven by equilibrium thus increase absorption of the compound, allowing for a high concentration of drug product to be delivered in a formulation densely populated with drug product.

Figure 32:
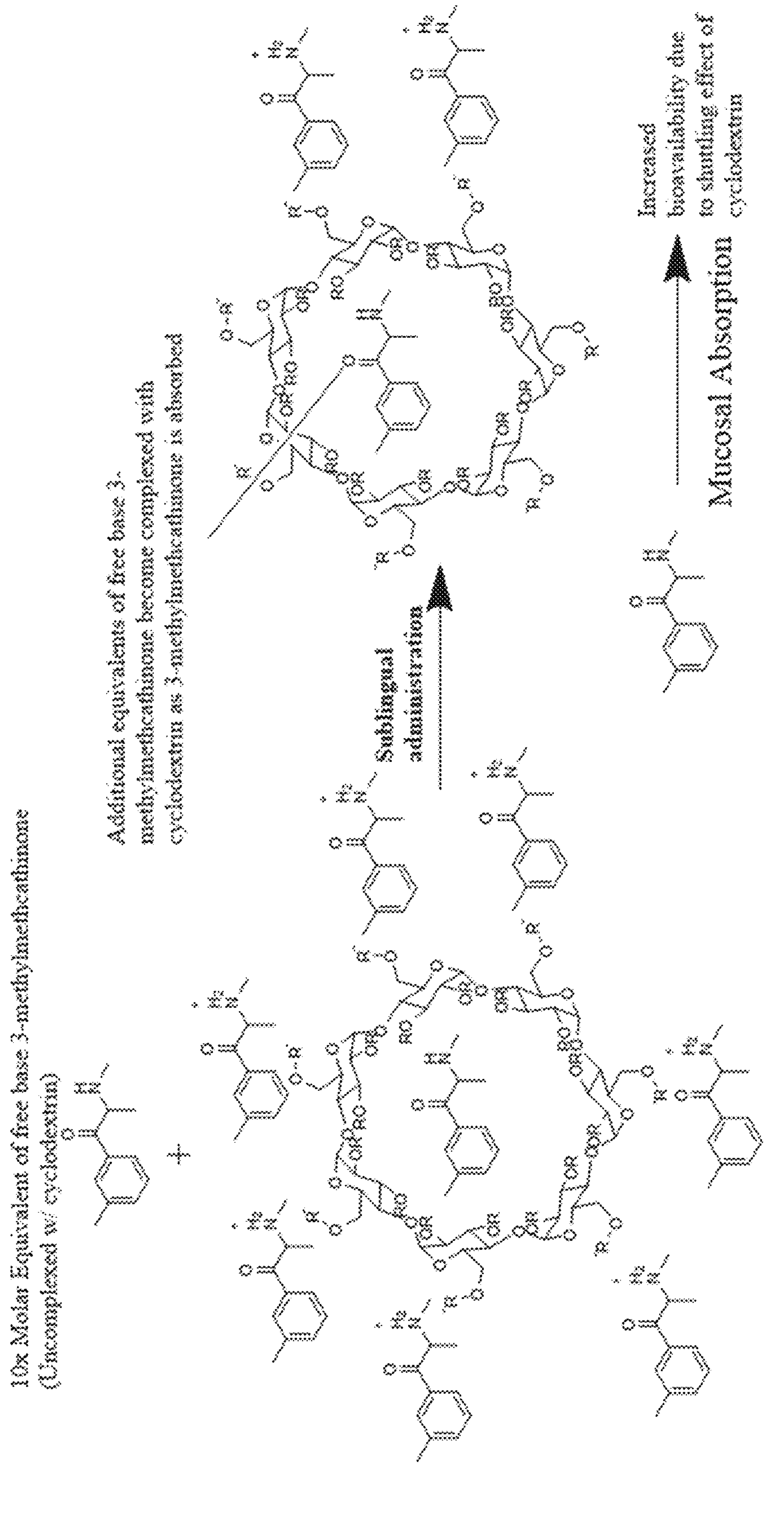
FIG. 32 shows a schematic of sublingual administration of a 3-methylmethcathinone-SBEBCD salt formulation comprising an excess of free base mescaline.

The mechanism underling these effect resulting in increased bioavailability and enhanced buffering capacity of the system is illustrated in FIG. 32, which shows non-ionized 3-methylmethcathinone within the cyclodextrin core of the SBEBCD and excess free base 3-methylmethcathinone also present. The non-ionized 3-methylmethcathinone is first released into the saliva from the cyclodextrin and then absorbed via mucosal absorption. Once absorbed, the equilibrium of the system shifts and allows more free base 3-methylmethcathinone to become dissolved in the saliva, either directly or, more substantially, through additional complexation with the now unoccupied cyclodextrin core in a shuttle-like mechanism. As the additional free base 3-methylmethcathinone solubilizes in the system, the desired physiologically tolerable pH of the formulation is maintained as the acidity of the protonated 3-methylmethcathinone molecules present in the salt form continue to be neutralized as more free base compound solubilizes. This process then repeats until all of the 3-methylmethcathinone is absorbed, resulting in a successful sublingual administration that is painless and effective. This also produces a form of dynamic buffering that can keep the pH elevated relative to a dose form without excess free base drug compound, thus allowing the ionized 3-methylmethcathinone molecules associated with the 3-methylmethcathinone-SBEBCD salt to become deprotonated or unionized even while in a highly solubilized state, increasing submucosal absorption capacity and rate. Compared with a similar dose in a similar troche formulation made from 3-methylmethcathinone HCl, tolerability, bioavailability, and solubility are all enhanced due to the SBECD-salt complex and free base 3-methylmethcathinone complexed within the cyclodextrin core.

Example 33. Characterization of a Captisol Acid (CA)-N,N-Dimethyltryptamine (DMT) Salt A CA-DMT salt was prepared according to the general protocol shown in Scheme 21 according to the following process.

Scheme 21

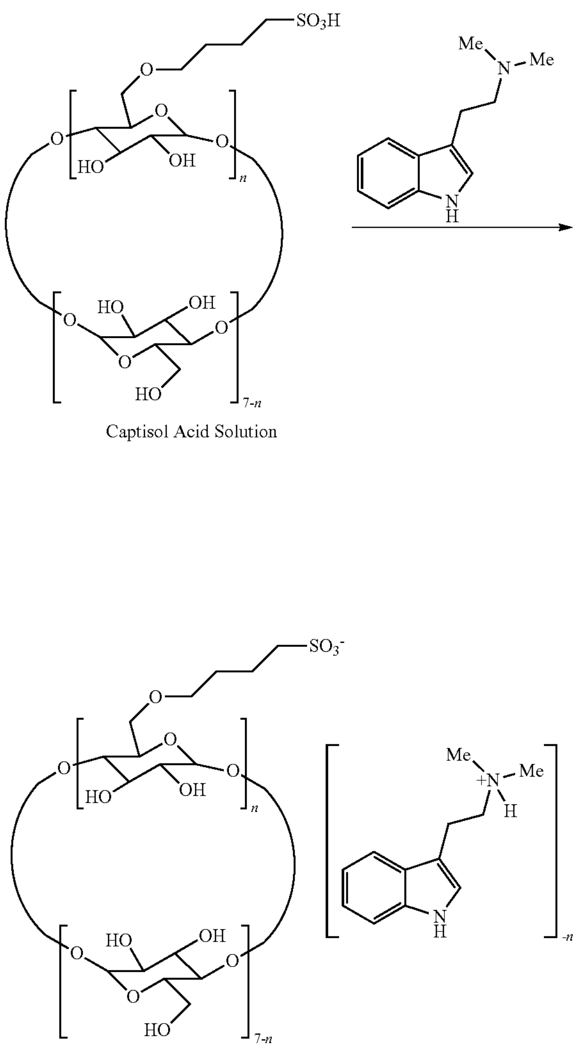

Captisol Acid Solution

1:1 Captisol acid:DMT salt
Sulfobutyl Ether β-Cyclodextrin DMT Salt

Captisol® sodium form was converted to Captisol Acid via a sulfonic acid containing H ion exchange resin, Amberlite FPC16 UPS and isolated as an aqueous solution. Using the DMT, 1:1 DMT:Captisol Acid salts were generated. Assuming 6.5 sulfobutyl acid equivalents per Captisol Acid scaffold, 6.5 equivalents of DMT free base were used in preparation of each 1:1 amine: Captisol Acid salt. Each amine:Captisol acid salt was then compounded into a bulk drug substance (BDS) and their parameters adjusted based on specifications. A solution of the CA-DMT salt was prepared using the ingredients listed in Table 1.

TABLE 1

| Reagents | MW | Eq. | g | L |
|---|---|---|---|---|
| Captisol Acid Solution | 16.38 wt. % | 1.0 | 50.44 | |
| DMT | 188.27 | 6.5 acid equiv. | 5.01 | |
| Water | | As needed | | |
| 1:1 Captisol acid:DMT salt | | | 13.27 | |

To determine the concentrations of DMT in Captisol Acid containing solutions, DMT:captisol acid salts (1:1) were generated and isolated. The testing procedure is as follows. Captisol Acid (1 equiv.) solution was added to a nitrogen flushed round bottom flask (RBF) equipped with a stir bar and nitrogen gas. Since there is 6.5 molecules of sulfobutyl acid per Captisol Acid scaffold, 6.5 equivalent of DMT free base was added to the RBF to form a solution. Water was added as needed to aid in solution formation. Once the amine was dissolved, the solution was filtered through a 0.45 micron filter and lyophilized. The resulting powder was further dried via high vacuum to obtain the Captisol Acid: amine salt (1:1). 10.49 g of an off-white sticky solid DMT: Captisol acid salt (1:1) was generated.

To determine the maximum concentration of 1:1 DMT: Captisol acid in an aqueous solution, DMT: Captisol acid salt (1:1) added portion-wise to HPLC grade water until the solid can no longer dissolve. After each addition (0.5-1.0 g of the 1:1 salt), the appearance, weight, and pH of the solution was recorded. After every other addition, the osmolality was recorded. The estimated concentration of DMT in solution was back calculated with the unit's mg/g of solution. The test progressed until the starting material was depleted. The initial solution (Row 2, Table 2) contains 0.610 g of 1:1 salt in water for a total solution weight of 8.046 g. Based on the estimated concentration of DMT solution, the estimated concentration of Captisol Acid (CA) was back calculated. The test was conducted in a 40 mL vial. An analytical balance was used for all weight measurements. The chemical and physical properties of the solution of the Captisol Acid-DMT salt were characterized as shown in Table 2 below.

TABLE 2

| DMT conc. (mg/g) | Color | Clarity | pH | Osmolality (mOsm/kg) | CA conc. (mg/g) |
|---|---|---|---|---|---|
| ~27.9 | faint yellow | slightly hazy | 3.06 | 67 | ~46 |
| ~54.7 | light yellow | slightly hazy | 2.71 | — | ~90 |
| ~72.4 | light yellow | slightly hazy | 2.57 | 136 | ~119 |
| ~89.2 | light yellow | slightly hazy | 2.5 | — | ~147 |
| ~104.5 | light yellow | slightly hazy | 2.38 | 183 | ~172 |
| ~117.8 | light yellow to yellow | slightly hazy/clear | 2.3 | — | ~194 |
| ~130.4 | yellow | slightly hazy/clear | 2.24 | 382 | ~215 |
| ~152.8 | yellow and viscous | clear | 2.14 | — | ~252 |
| ~169.9 | yellow and viscous | clear | 2.06 | 566 | ~280 |
| ~184.7 | yellow to dark yellow and viscous | clear | 2 | — | ~305 |
| ~199.2 | dark yellow and very viscous | clear | 1.94 | 899 | ~329 |
| ~212.9 | dark yellow and very viscous | clear | 1.86 | — | 351.4 |

As seen in Table 2 above, after each addition, the solution became darker in color, more viscous and the clarity increased. After adding a total of 9.79 g the DMT:Captisol acid salt (1:1), the solution was transparent, dark yellow, homogenous, and very viscous. As the amine:Captisol acid salt was depleted, 212.9 mg/g is the estimated final concentration of DMT from the test (Table 2). An osmolality reading was not achievable for the final concentration as the solution would not freeze/seed. The density of this final solution was determined to be 1.17 g/mL. Based on wt. assay (HPLC), the final DMT concentration is 248.4 mg/mL. Based on the estimated wt. % of DMT solution, the estimated wt. % of captisol acid (CA) was back calculated.

There are approximately 6.5 equiv. of sulfobutyl acid residues per Captisol scaffold, 6.5 equiv. of DMT is required to quench the acid. This test was to determine whether excess DMT (>6.5 equiv.) could dissolve in a solution that contains 1:1 DMT:Captisol acid. An additional, non-chelated, DMT could adjust the pH to physiological pH, without the need of external base such as NaOH. To a solution containing 1:1 DMT:Captisol acid, with a starting concentration of ~124 mg/g DMT (Row 1, Table 3), was added 54 mg DMT free base. At this concentration, 54 mg of DMT free base accounted for ~0.25 acid equiv. of excess amine for a total acid equiv. of –6.75 of amine in the solution. After vortex, not all of the solid went into solution and the mixture was filtered through a 0.45 micron filter and analyzed via appearance, wt. assay (HPLC), pH, and osmolality (Row 2, Table 3). Based on the estimated concentration of DMT solution, the estimated concentration of captisol acid (CA) was be back calculated.

TABLE 3

| DMT conc. (mg/g) | Color | Clarity | pH | Osmolality (mOsm/kg) | CA conc. (mg/g) |
|---|---|---|---|---|---|
| ~124 | Light yellow and slightly viscous | slightly hazy | 2.34 | 235 | ~204 |
| 131.5 | Light yellow slightly viscous | clear | 7.84 | 240 | ~203 |

The density of this final solution was determined to be 1.087 g/mL. Based on wt. assay (HPLC), the final DMT concentration is 142.9 mg/mL (131.5 mg/g based on density). Based on the above test, the pH of the solution can be adjusted to pH 7-8 with added amine (<6.75 total acid equiv. amine). Fine tuning are required to accurately obtain the acid equiv. of amine required to reach pH 6.8±0.5.

DMT BDS Fining Tuning

For clinical studies, the final BDS will have a pH of 6.8±0.5 and an osmolality of 300±30 mOsm/kg. To determine whether these specifications can be achieved for the DMT BDS solution, a ~110 mg/g DMT solution in Captisol Acid was prepared and the pH and osmolality adjusted accordingly. The appearance, pH, and osmolality of the solution were recorded before and after each adjustment and are listed in Table 4 below. The pH was first adjusted to pH 6.87 with 150 μL of 0.5 N NaOH (second row, Table 4) to form a slightly hazy and faint to light yellow solution. A slight increase in osmolality was observed following the pH adjustment. Next, the osmolality was adjusted to 296 mOsm/kg with 17 mg NaCl (third row, Table 4). The density of this final solution was determined to be 1.076 g/mL. Based on the wt. assay analysis (HPLC), the final DMT concentration was calculated to be 121.27 mg/mL (112.7 mg/g based on density). Based on the estimated concentration of DMT solution, the estimated concentration of captisol acid (CA) was be back calculated.

TABLE 4

| DMT conc. (mg/g) | Color | Clarity | pH | Osmolality (mOsm/kg) | CA conc. (mg/g) |
|---|---|---|---|---|---|
| ~110 | Light yellow to yellow and slightly viscous | slightly hazy | 2.38 | 200 | ~181 |
| ~108 | Faint to light yellow and slightly viscous | slightly hazy | 6.87 | 209 | ~179 |
| 112.7 | Faint to light yellow and slightly viscous | slightly hazy | 6.86 | 296 | 200.9 |

Based on the above test, aqueous NaOH can be used to adjust the pH of the solution to pH 6.9 without observable precipitation. Minimal amount of NaCl is required to adjust the osmolality of the solution to 296 mOsm/kg at a DMT concentration of 121.27 mg/mL, without observable precipitation. The clarity of the solution can be restored upon filtration through a 0.45 micron filter.

To accompany the 112.7 mg/g DMT study, a BDS solution with a concentration of approximately 56.4 mg/g DMT was generated and the pH and osmolality adjusted to pH 6.8±0.5 and 300±30 mOsm/kg, respectively. The appearance, pH, and osmolality of the solution were recorded before and after each adjustment (Table 5). The pH was adjusted from pH 2.41 to 6.98 using ~1.0 ml of 0.5 N NaOH (second row, Table 5) to form a light yellow solution and slightly hazy solution. Next, the osmolality was adjusted from 134 to 301 mOsm/kg with 336 mg NaCl and the solution filtered through a 0.45 micron filter (third row, Table 5). The density of the resulting faint to light yellow and clear solution was determined to be 1.041 g/mL. Based on wt. assay analysis (HPLC), the final DMT concentration is 58.5 mg/mL (56.2 mg/g based on density). Based on the estimated concentration of DMT solution, the estimated concentration of captisol acid (CA) was be back calculated.

TABLE 5

| DMT conc. (mg/g) | Color | Clarity | pH | Osmolality (mOsm/kg) | CA conc. (mg/g) |
|---|---|---|---|---|---|
| ~56.4 | Light yellow to yellow | slightly hazy | 2.41 | 134 | —93 |
| ~56 | light yellow | slightly hazy | 6.98 | 134 | —93 |
| 56.2 | Faint to light yellow | clear | 7.01 | 301 | 92.8 |

Based on the above test, aqueous NaOH can be used to adjust the pH of the solution to pH 7.0 without observable precipitation. Minimal amount of NaCl is required to adjust the osmolality of the solution to 301 mOsm/kg at DMT concentration of 58.48 mg/mL, without observable precipitation. It should be noted that the viscosity of the final solution is slightly higher than that of water.

Example 34. Characterization of a Captisol Acid (CA)-5-methoxy-N,N-dimethyltryptamine (5-MeO-DMT) Salt A CA-5-MeO-DMT salt was prepared according to the general protocol shown in Scheme 22 according to the following procedure similar to the one in Example 33.

Scheme 22

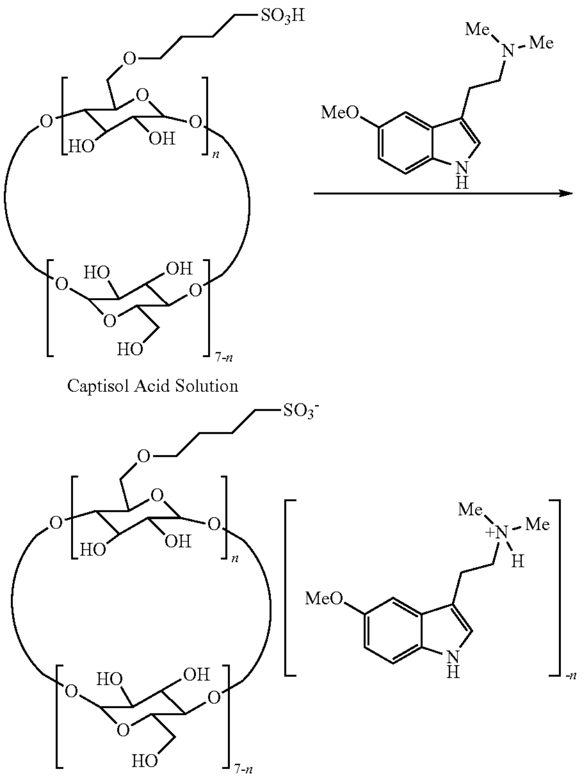

Captisol Acid Solution

1:1 Captisol acid:5-MeO-DMT salt
Sulfobutyl Ether β-Cyclodextrin DMT Salt

Captisol® sodium form is converted to Captisol Acid via a sulfonic acid containing H ion exchange resin, Amberlite FPC16 UPS and isolated as an aqueous solution. Using 5-MeO-DMT, 1:1 5-MeO-DMT:Captisol acid salts were generated. There is 6.5 sulfobutyl acid equivalents per Captisol acid scaffold, 6.5 equivalents of 5-MeO-DMT free base were used in preparation of each 1:1 amine: Captisol acid salt. Each amine: Captisol acid salt was then compounded into a bulk drug substance (BDS) and their parameters adjusted based on specifications. A solution of the CA-5-MeO-DMT salt was prepared using the ingredients listed in Table 6.

TABLE 6

| Reagents | MW | Eq. | g | L |
|---|---|---|---|---|
| Captisol Acid Solution | 16.38 wt. % | 1.0 | 43.50 | |
| 5-MeO-DMT | 218.30 | 6.5 acid equiv. | 5.01 | |
| Water | | As needed | | |
| 1:1 Captisol acid:5-MeO-DMT salt | | | 12.13 | |

To determine the concentrations of 5-MeO-DMT in captisol acid containing solutions, 5-MeO-DMT:Captisol Acid salts (1:1) were generated and isolated. The procedure is as follows. Captisol acid (1 equiv.) solution was added to a nitrogen flushed RBF equipped with a stir bar and nitrogen gas. There is 6.5 acid equivalents per captisol acid scaffold, 6.5 equiv. of 5-MeO-DMT free base was added to the RBF to form a solution. Water was added as needed to aid in solution formation. Once the amine was dissolved, the solution was filtered through a 0.45 micron filter and lyophilized. The resulting powder was further dried via high vacuum to afford the captisol acid:amine salt (1:1). 10.66 g of an off-white fluffy/crispy solid 5-MeO-DMT:Captisol acid salt (1:1) were generated.

To determine the concentration of 1:1 5-MeO-DMT: Captisol acid in an aqueous solution, 5-MeO-DMT:Captisol acid salt (1:1) was added portion-wise to HPLC grade water until the solid could no longer dissolve. After each addition (0.5-1.0 g of the 1:1 salt), the appearance, weight, and pH of the solution was recorded. After every other addition, the osmolality was recorded. The estimated concentration of 5-MeO-DMT in solution was back calculated with the unit's mg/g of solution. Based on the estimated concentration of 5-MeO-DMT in solution, the estimated concentration of captisol acid (CA) was back calculated. The test progressed until the starting material was depleted. The initial solution (Row 1, Table 7) contains 0.515 g of 1:1 salt in water for a total solution weight of 10.01 g. The test was conducted in a 40 mL vial. An analytical balance was used for all weight measurements. The chemical and physical properties of the solution of the CA-5-MeO-DMT salt were characterized as shown in Table 7 below.

TABLE 7

| 5-MeO-DMT conc. (mg/g) | Color | Clarity | pH | Osmolality (mOsm/kg) | CA conc. (mg/g) |
|---|---|---|---|---|---|
| ~20.7 | faint yellow | slightly hazy | 2.94 | 46 | ~29 |
| ~39.4 | light yellow | slightly hazy | 2.63 | — | ~56 |
| ~56.5 | light yellow | slightly hazy | 2.46 | 98 | ~80 |
| ~73.1 | light yellow to yellow | slightly hazy | 2.33 | — | ~104 |
| ~87.3 | yellow | slightly hazy | 2.23 | 133 | ~124 |
| ~101.1 | dark yellow | slightly hazy | 2.16 | — | ~144 |
| ~113.7 | dark yellow | slightly hazy | 2.10 | 179 | ~162 |
| ~125.0 | dark yellow | slightly hazy | 2.04 | — | ~178 |
| ~146.5 | dark yellow | slightly hazy/clear | 1.95 | 239 | ~209 |
| ~163.9 | dark yellow and viscous | almost clear | 1.86 | — | ~233 |
| ~179.7 | dark yellow and very viscous | clear | 1.85 | 503 | ~256 |
| ~193.4 | dark yellow and very viscous | clear | 1.75 | — | ~275 |
| ~215.4 | dark yellow and very viscous | clear | 1.70 | 949 | 306.6 |

As seen in Table 7 above, after each addition, the solution became darker in color, more viscous and the clarity increased. After adding a total of 9.98 g the amine:Captisol acid salt (1:1), the solution was transparent, dark yellow, homogenous, and very viscous. As the amine:Captisol acid salt was depleted, 215.4 mg/g is the estimated final concentration of 5-MeO-DMT from this test (Table 7). The density of this final solution was determined to be 1.15 g/mL. Based on wt. assay (H PLC), the final 5-MeO-DMT concentration is 247.7 mg/mL. Based on the estimated wt. % of 5-MeO-DMT solution, the estimated wt. % of captisol acid (CA) was back calculated.

This test was to determine whether excess 5-MeO-DMT (>6.5 equiv.) could dissolve in a solution that contains 1:1 5-MeO-DMT:Captisol acid. To a solution containing 1:1 5-MeO-DMT:Captisol acid, with a starting concentration of ~148 mg/g 5-MeO-DMT (Row 1, Table 8), was added 129 mg of 5-MeO-DMT free base. At this concentration, 129 mg of 5-MeO-DMT free base accounts for ~0.40 acid equiv. of excess amine for a total acid equiv. of ~6.90 of amine in the solution. After vortex, not all of the solid went into solution and the mixture was filtered through a 0.45 micron filter and analyzed via appearance, wt. assay (HPLC), pH, and osmolality (Row, Table 8). Based on the estimated concentration of 5-MeO-DMT solution, the estimated concentration of captisol acid (CA) was be back calculated.

TABLE 8

| 5-MeO-DMT conc. (mg/g) | Color | Clarity | pH | Osmolality (mOsm/kg) | CA conc. (mg/g) |
|---|---|---|---|---|---|
| ~141 | yellow/light brown | slightly hazy | 2.02 | 222 | ~201 |
| 148.3 | yellow/light brown and viscous | clear | 8.07 | 214 | ~197 |

The density of this final solution was determined to be 1.084 g/mL. Based on wt. assay, the final 5-MeO-DMT concentration is 160.8 mg/mL (148.3 mg/g based on density). Based on the above test, the pH of the solution can be adjusted to pH 8.07 with added amine (<6.90 total acid equiv. amine). Fine tuning will be required to accurately obtain the acid equiv. of amine required to reach pH 6.8±0.5.

5-MeO-DMT BDS Fine Tuning

5-MeO-DMT BDS solutions were generated and adjusted to meet the specifications disclosed herein. To test a concertation BDS solution, a ~135 mg/g 5-MeO-DMT BDS solution was prepared and the pH and osmolality of the solution adjusted accordingly. The appearance, pH, and osmolality of the solution were recorded before and after each adjustment (Table 9). First the pH was adjusted to pH 6.82 using 200 μL of 0.5 N NaOH (second row, Table 9) to form a light yellow/brown, clear to slightly hazy, and slightly viscous solution. A slight osmolality increase from 203 to 217 mOsm/kg was observed following the pH adjustment. Next, the osmolality was adjusted to 303 mOsm/kg with 15 mg NaCl (third row). The density of this final solution was determined to be 1.072 g/mL. After wt. assay analysis (HPLC), the final 5-MeO-DMT concentration of the adjusted BDS solution was 144.69 mg/mL (135.0 mg/g based on density). Based on the estimated wt. % of 5-MeO-DMT in solution, the estimated concentration of captisol acid (CA) was back calculated.

TABLE 9

| 5-MeO-DMT conc. (mg/g) | Color | Clarity | pH | Osmolality (mOsm/kg) | CA conc. (mg/g) |
|---|---|---|---|---|---|
| ~135 | Light yellow/brown and slightly viscous | slightly hazy | 2.03 | 203 | ~192 |
| ~133 | Light yellow/brown and slightly viscous | Clear to slightly hazy | 6.82 | 217 | ~190 |
| 135.0 | Light yellow/brown and slightly viscous | Clear to slightly hazy | 6.83 | 303 | 192.2 |

As seen with DMT BDS solutions, aqueous NaOH can be used to adjust pH of the 5-MeO-DMT BDS solution to pH 6.8 without observable precipitation (Table 9). A small amount of NaCl is required to adjust the osmolality of the solution to 303 mOsm/kg at 5-MeO-DMT concentration of 144.69 mg/mL, without observable precipitation. The clarity of the solution can be restored upon filtration through a 0.45 micron filter.

To accompany the 135.0 mg/g 5-MeO-DMT test, a BDS solution with a concentration of approximately 67.5 mg/g 5-MeO-DMT was generated and the pH and osmolality adjusted to pH 6.8±0.5 and 300±30 mOsm/kg, respectively. The appearance, pH, and osmolality of the solution were recorded before and after each adjustment (Table 10). First, the pH of the solution was adjusted from pH 2.42 to 6.94 using ~1.0 mL of 0.5 N NaOH (second row, Table 10) to form a light yellow/brown and slightly hazy solution. Next, the osmolality was adjusted from 113 to 294 mOsm/kg with 430 mg NaCl and filtered through a 0.45 micron filter (third row, Table 10). The resulting light yellow/brown and clear solution had a density of 1.044 g/mL and a concentration of 70.09 mg/mL (67.1 mg/g based on density) 5-MeO-DMT based on wt. assay analysis (HPLC). Based on the estimated concentration of DMT solution, the estimated concentration of captisol acid (CA) was back calculated.

TABLE 10

| 5-MeO-DMT conc. (mg/g) | Color | Clarity | pH | Osmolality (mOsm/kg) | CA conc. (mg/g) |
|---|---|---|---|---|---|
| ~67.5 | Yellow/brown | slightly hazy | 2.42 | 113 | ~96 |
| ~67 | Light yellow/brown | slightly hazy | 6.94 | 113 | ~96 |
| 67.1 | Light yellow/brown | clear | 6.93 | 294 | 95.5 |

Based on the above test, aqueous NaOH can be used to adjust pH of the solution to pH 6.9 without observable precipitation (Table 10). A small amount of NaCl is required to adjust the osmolality of the solution to 294 mOsm/kg at 5-MeO-DMT concentration of 70.09 mg/mL, without observable precipitation. It should be noted that the viscosity of the solution is slightly higher than that of water.

Example 35. Stability Analysis of a Captisol Acid (CA)-N,N-Dimethyltryptamine (DMT) Salt Solution and a Captisol Acid (CA)-5-Methoxy-N,N-Dimethyltryptamine (5-MeO-DMT) Salt Solution Different concentrations of solutions for each of CA-DMT and CA-5-MeO-DMT salt prepared according to the protocol in Examples 33 and 34 were stored at ambient temperature, in presence or absence of light, for up to 54 days. The appearance, amine concentration and purity, pH, and osmolality of the solutions were recorded. The results are listed in Table 11 (CA-DMT) and Table 12 (CA-S-MeO-DMT).

TABLE 11

| Batch # | 21-0853 | 21-0853 | 21-0861 | 21-0861 | 21-0861-D | 21-0861-D |
|---|---|---|---|---|---|---|
| Storage Conditions | Light/25° C. | Light/25° C. | Light/25° C. | Light/25° C. | Dark/25° C. | Dark/25° C. |
| Time | 0 days | 54 days | 0 days | 34 days | 0 days | 34 days |
| Color | Faint to light yellow | Faint to light yellow | Faint to light yellow | Faint to light yellow | Faint to light yellow | Faint to light |
| Viscosity | slightly viscous | slightly viscous | slightly viscous | slightly viscous | slightly viscous | slightly viscous |

TABLE 11-continued

| Batch # | 21-0853 | 21-0853 | 21-0861 | 21-0861 | 21-0861-D | 21-0861-D |
|---|---|---|---|---|---|---|
| Clarity | slightly hazy | slightly hazy | clear | clear | clear | clear |
| DMT Conc. (mg/mL) | 121.27 | 121.36 | 58.48 | 58.16 | 58.48 | 58.27 |
| % Purity (HPLC) | 98.82 | 98.73 | 98.94 | 98.89 | 98.94 | 98.90 |
| pH | 6.86 | NA | 7.01 | 6.96 | 7.01 | 6.96 |
| Osmolality (mOsm/kg) | 296 | NA | 301 | 304 | 301 | 304 |

TABLE 12

| Batch # | 21-0855 | 21-0855 | 21-0862 | 21-0862 | 21-0862-D | 21-0862-D |
|---|---|---|---|---|---|---|
| Storage Conditions | Light/25° C. | Light/25° C. | Light/25° C. | Light/25° C. | Dark/25° C. | Dark/25° C. |
| Time | 0 days | 54 days | 0 days | 34 days | 0 days | 34 days |
| Color | Light yellow/ brown | Light yellow/ brown | Light yellow/ brown | Light yellow/ brown | Light yellow/ brown | Light yellow/ brown |
| Viscosity | slightly viscous | slightly viscous | slightly viscous | slightly viscous | slightly viscous | slightly viscous |
| Clarity | Clear to slightly hazy | Clear to slightly hazy | clear | clear | clear | clear |
| 5-MeO-DMT Conc. (mg/mL) | 144.69 | 184.07 | 70.09 | 70.43 | 70.09 | 69.86 |
| % Purity (HPLC) | 98.23 | 97.97 | 98.36 | 98.32 | 98.36 | 98.38 |
| pH | 6.83 | NA | 6.93 | 6.90 | 6.93 | 6.88 |
| Osmolality (mOsm/kg) | 303 | NA | 294 | 299 | 294 | 298 |

Example 36. Stability Analysis of a Captisol Acid (CA)-N,N-Dimethyltryptamine (DMT) Salt

Solution at a High Temperature

A CA-DMT salt solution was tested for stability at 60° C. in the presence (Table 13) and absence (Table 14) of light. The results are shown in Table 13 and Table 14.

TABLE 13

| Batch # | 21-0861-Oh | 21-0861-6h | 21-0861-12h | 21-0861-24h |
|---|---|---|---|---|
| Storage Conditions | Light/60° C. | Light/60° C. | Light/60° C. | Light/60° C. |
| Time | 0 hours | 6 hours | 12 hours | 24 hours |
| Color | Faint to light yellow | Faint to light yellow | Faint to light yellow | Faint to light yellow |
| Viscosity | Slightly viscous | Slightly viscous | Slightly viscous | Slightly viscous |
| Clarity | Clear | Clear | Clear | Clear |
| DMT Conc. (mg/mL) | 57.89 | 57.94 | 57.83 | 57.56 |
| % Purity (HPLC) | 98.61 | 99.02 | 98.92 | 98.85 |
| pH | 6.93 | 6.92 | 6.99 | 7.03 |
| Osmolality (mOsm/kg) | 302 | 302 | 303 | 303 |

TABLE 14

| Batch # | 21-0861-D-Oh | 21-0861-D-6h | 21-0861-D-12h | 21-0861-D-24h |
|---|---|---|---|---|
| Storage Conditions | Dark/60° C. | Dark/60° C. | Dark/60° C. | Dark/60° C. |

TABLE 14-continued

| Batch # | 21-0861-D-Oh | 21-0861-D-6h | 21-0861-D-12h | 21-0861-D-24h |
|---|---|---|---|---|
| Time | 0 hours | 6 hours | 12 hours | 24 hours |
| Color | Faint to light yellow | Faint to light yellow | Faint to light yellow | Faint to light yellow |
| Viscosity | Slightly viscous | Slightly viscous | Slightly viscous | Slightly viscous |
| Clarity | Clear | Clear | Clear | Clear |
| DMT Conc. (mg/mL) | 57.78 | 58.13 | 58.32 | 58.06 |
| % Purity (HPLC) | 98.64 | 98.95 | 98.90 | 98.83 |
| pH | 6.96 | 6.92 | 7.04 | 7.06 |
| Osmolality (mOsm/kg) | 302 | 302 | 304 | 302 |

Figure 33:
FIG. 33 shows the appearance of exemplary captisol acid (CA)-N,N-dimethyltryptamine (DMT) salt solutions at different time points in the absence and presence of light.

The appearance of the CA-DMT salt solution was shown in FIG. 33 at 0 hour (Top Left), 6 hours (Top right), 12 hours (Bottom Left) and 24 hours (Bottom Right) in the absence (left bottle at each hour point) and presence (right bottle at each our point) of light.

Example 37. Preparation of Flumazenil Salt Solution with Captisol Acid

A number of methods were tested to prepare a flumazenil salt solution as shown below.

To prepare a Captisol Acid-Flumazenil salt solution, Captisol acid (6.26% moisture, 8.14 mg active, 8.70 mg M.C.) was dissolved in HPLC grade $H_2O$ in a test tube and stirred vigorously. A total of 8.0 mg of flumazenil was weighed out and added in portions to the Captisol acid solution. The first portion (~2 mg) was added and stirred vigorously. The flumazenil did not immediately dissolve, but went into solution after ~30 min. A second portion (~2 mg) was then added and stirred, but substantial solids remained insoluble. The mixture was stirred overnight and solid was still suspended in solution the next day.

To prepare a Captisol-Flumazenil Complex via organic solvent, a 20 mL glass scintillation vial was charged with a magnetic Teflon stirbar and a solution of flumazenil (10 mg) dissolved in MeOH (10 mL) was added. Captisol (5.53% moisture, 214 mg active, 227 mg M.C.) was added and the suspension was stirred at rt until all solids went into solution (~30 min). The solution was added to a beaker and allowed to evaporate overnight resulting in a white, fluffy solid (214 mg). A portion of solid (90 mg) did not dissolve into HPLC grade $H_2O$ (0.5 mL). Another portion of HPLC grade $H_2O$ (0.5 mL) was added, but the solid still did not visibly dissolve. Heating of the solution from the bottom with a heat gun caused the solid to dissolve, but a solid crystalized upon cooling back to room temperature. These crystals had the same appearance as flumazenil crystallized from $H_2O$.

To prepare Flumazenil-γ-Cyclodextrin complex, a solution of γ-cyclodextrin (200 mg) was dissolved in HPLC grade $H_2O$ to make 1 mL of a 20% solution in a volumetric flask. Flumazenil (1.1 mg) was then added and stirred. While initially the flumazenil dissolved to give a transparent solution, the solution became cloudy over time. Sonication and vigorous stirring did not cause the precipitate to dissolve. This prompted the investigation of saturating γ-cyclodextrin solution with flumazenil. An additional portion of flumazenil (49 mg, 50.1 mg total) was added to the cloudy solution and the mixture was stirred with a magnetic Teflon stirbar for 48 h at room temperature. The suspension was filtered through a 0.45 μm syringe filter and diluted in duplicate to determine the concentration of flumazenil by HPLC. [Flumazenil]: 2.41 mg/mL.

To prepare another flumazenil solution, hydroxypropyl-β-cyclodextrin (800 mg) was dissolved in HPLC grade $H_2O$ in a volumetric flask to make 2 mL of a 40% solution. Flumazenil (50 mg) and a magnetic Teflon stirbar were added and the test tube sealed with parafilm, covered in aluminum foil, and allowed to stir for 48 h at room temperature. The mixture was then filtered through a 0.45 μm syringe filter and osmolality measured. The sample was also diluted in duplicate to determine the concentration of flumazenil by HPLC. Osmolality: 652 mOsm/kg. [Flumazenil]: 3.8 mg/mL.

To prepare a Captisol-Ethylenediamine-Flumazenil complex solution without pH adjustment, Captisol-ethylenediamine (40% Captisol acid equivalent) was prepared by titrating a solution of Captisol acid in HPLC grade $H_2O$ with ethylenediamine (0.5 molar equivalent). Specifically, Captisol acid (6.41% moisture, 2.0 g active, 2.14 g M.C.) was dissolved in HPLC grade $H_2O$ (3.5 mL) and ethylene diamine (215 μL, 193 mg) was added in 5 portions via micropipette. The solution was allowed to stir for ~2 min between aliquot additions. When the addition was complete, the solution was diluted with HPLC grade $H_2O$ to a final volume of 5 mL in a volumetric flask. The solution was diluted to 30% Captisol (acid equivalents) in a test tube and flumazenil (7.5 mg) was added to make a target concentration of 1.5 mg/mL. The transparent, yellow solution was sealed with parafilm, covered in aluminum foil, and stirred for 48 h at rt. The solution was filtered through a 0.45 μm syringe filter and osmolality measured. The sample was also diluted in duplicate to determine the concentration of flumazenil by HPLC and this was repeated three times. The sample was stored in a parafilm sealed 20 mL glass scintillation vial and covered in aluminum foil to protect from light. Final pH: 6.41. Osmolality: 702 mOsm/kg. [Flumazenil]: 1.15±0.05 mg/mL.

To prepare a Captisol-Ethylenediamine-Flumazenil Complex with pH adjustment, Captisol acid (8.81% moisture, 1.50 g active, 1.64 g M.C.) was dissolved in HPLC grade $H_2O$ (3 mL) in a test tube with a magnetic Teflon stirbar and stirred vigorously via magnetic stirring. Ethylenediamine (161 μL, 144.9 mg) was added in a single portion with stirring followed by adding benzethonium chloride (50 μL of 1% solution, final concentration 0.01%). The solution was then titrated with 2M HCl (90 μL total) until a final pH of 4.99. The solution was diluted to a final volume of 5 mL in a volumetric flask and then flumazenil (7.6 mg) was added directly to the volumetric flask. The mixture was sealed with parafilm, covered in aluminum foil, and allowed to stand at room temperature for 48 h with periodic agitation. The mixture was filtered through a 0.45 μm syringe filter and osmolality was measured. The sample was also diluted in duplicate to determine the concentration of flumazenil by HPLC and repeated three times. The solution was stored in a parafilm sealed scintillation vial and covered in aluminum foil to protect from light. Osmolality: 875.3 mOsm/kg. [Flumazenil]: 1.35±0.07 mg/mL. Final pH: 4.99.

Figure 34:
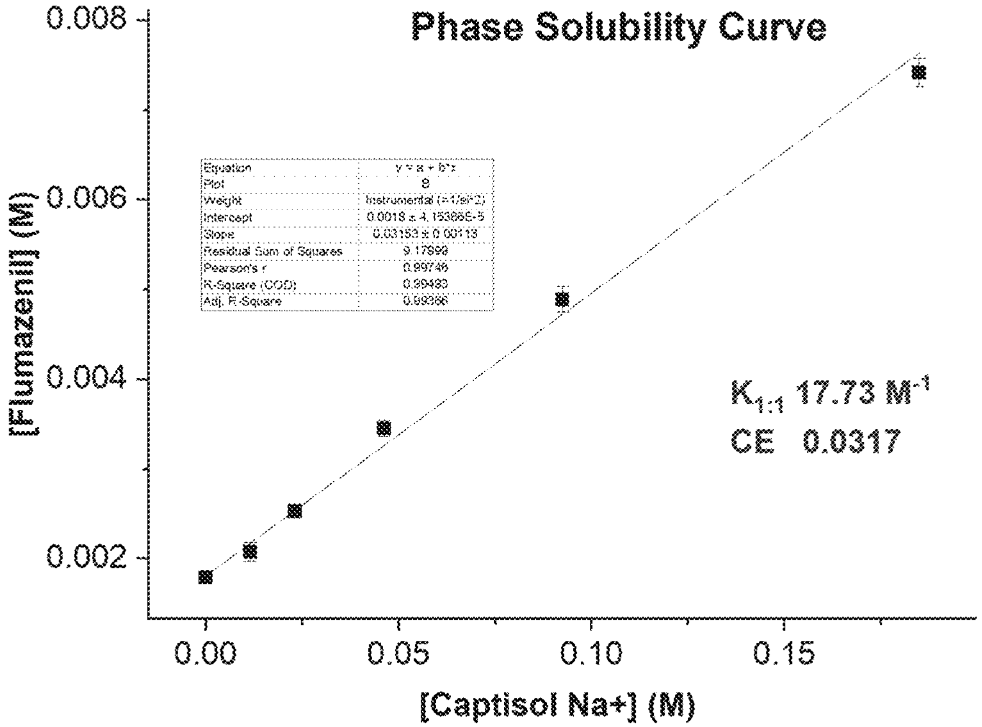
FIG. 34 shows a phase solubility curve with captisol and flumazenil.
Figure 35:
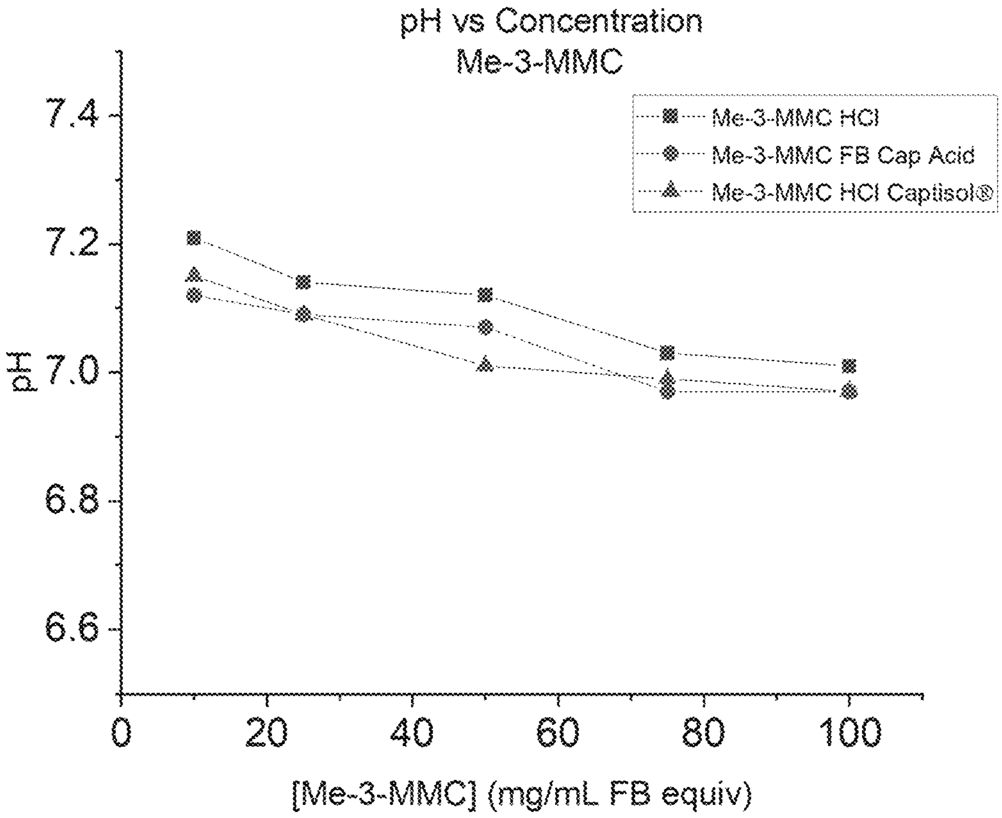
FIG. 35 shows a pH vs. concentration measurement curve of Me-3-MMC formulations (pH 7.0±0.1).
Figure 36:
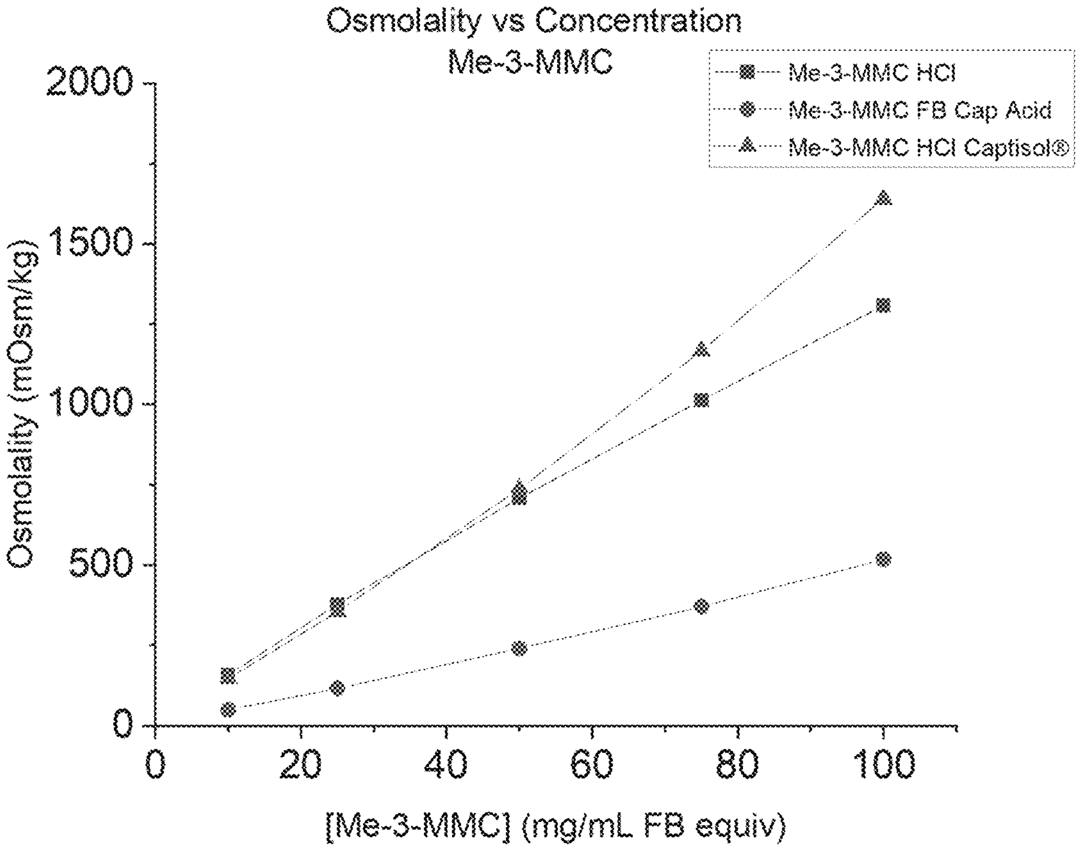
FIG. 36 shows an osmolality vs concentration measurement curve of Me-3-MMC formulations (pH 7.0±0.1).
Figure 37:
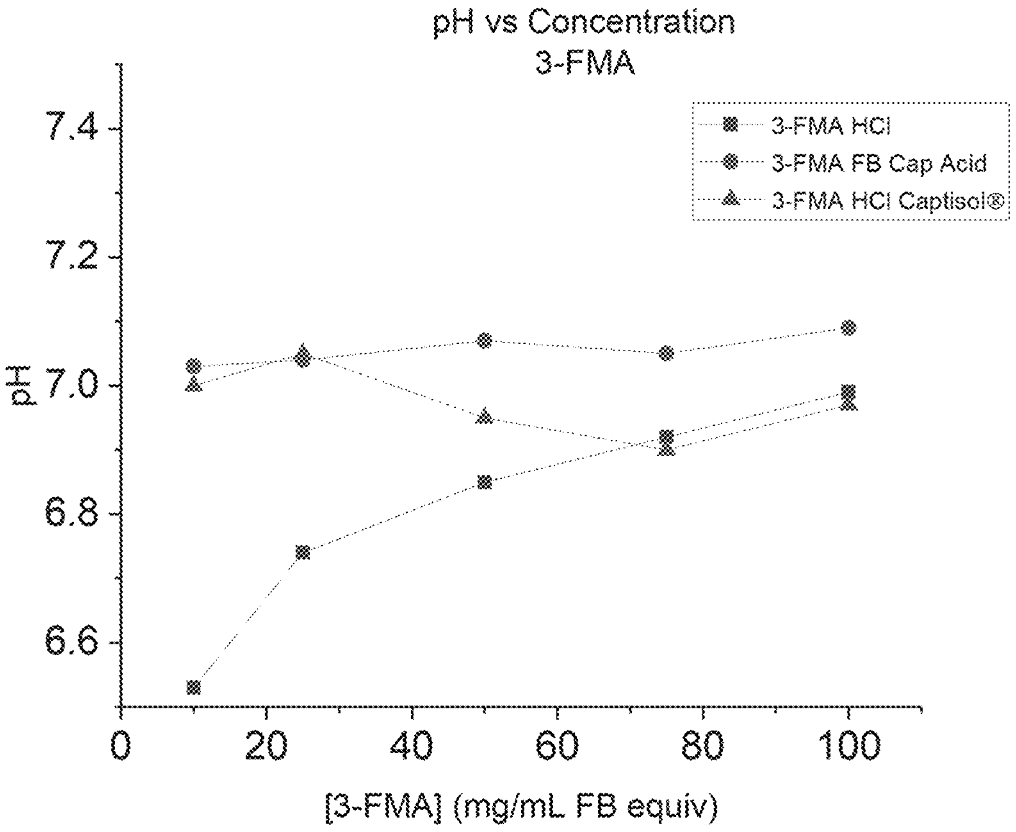
FIG. 37 shows a pH vs. concentration measurement curve of 3-FMA formulations (pH 7.0±0.1).
Figure 38:
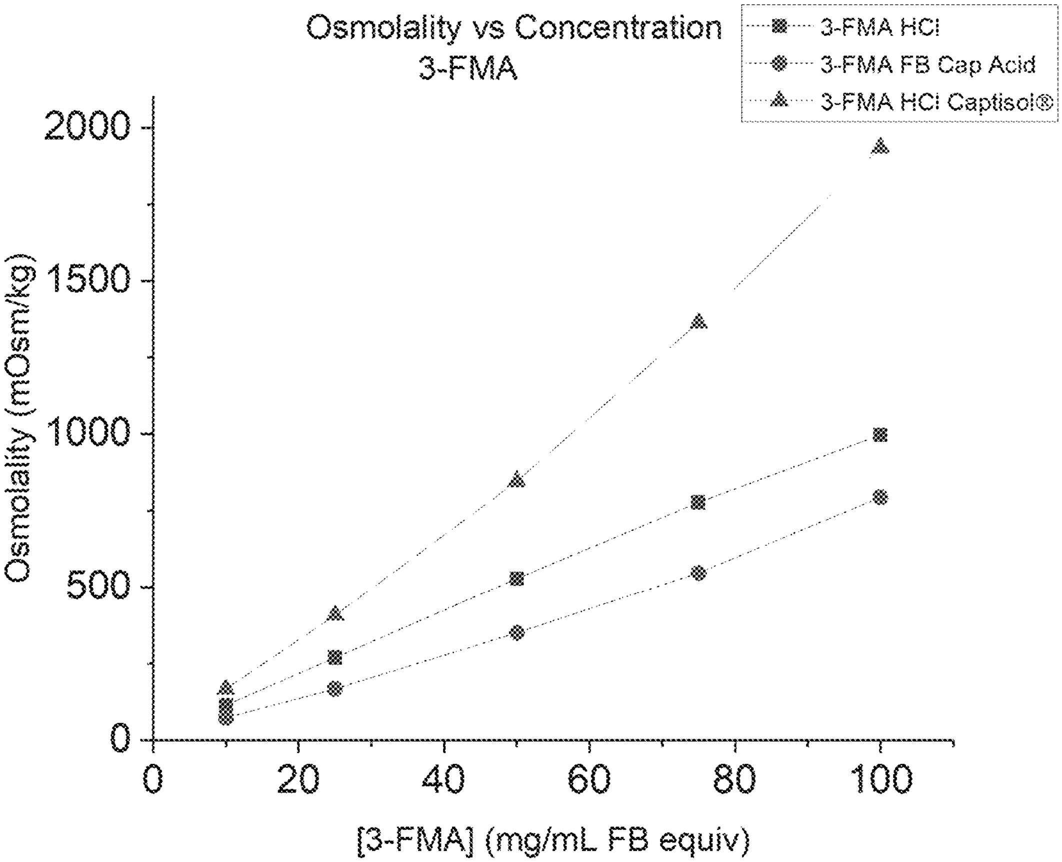
FIG. 38 shows an osmolality vs concentration measurement curve of 3-FMA formulations (pH 7.0±0.1).
Figure 39:
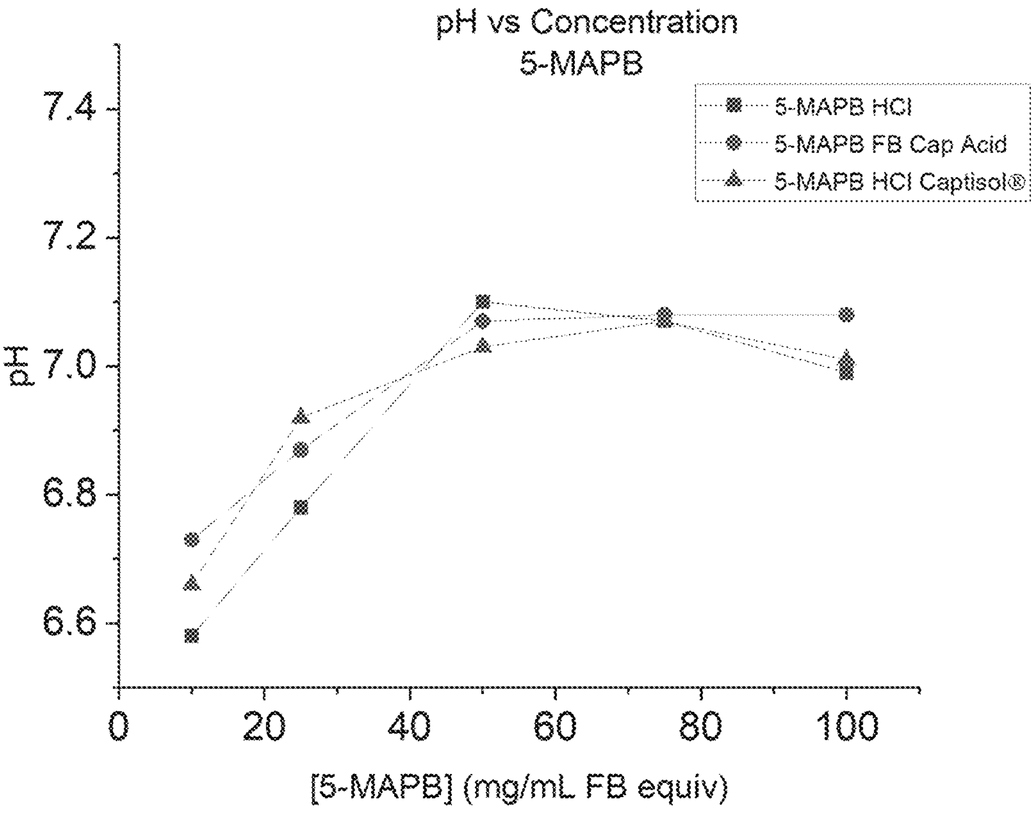
FIG. 39 shows a pH vs. concentration measurement curve of 5-MAPB formulations (pH 7.0±0.1).
Figure 40:
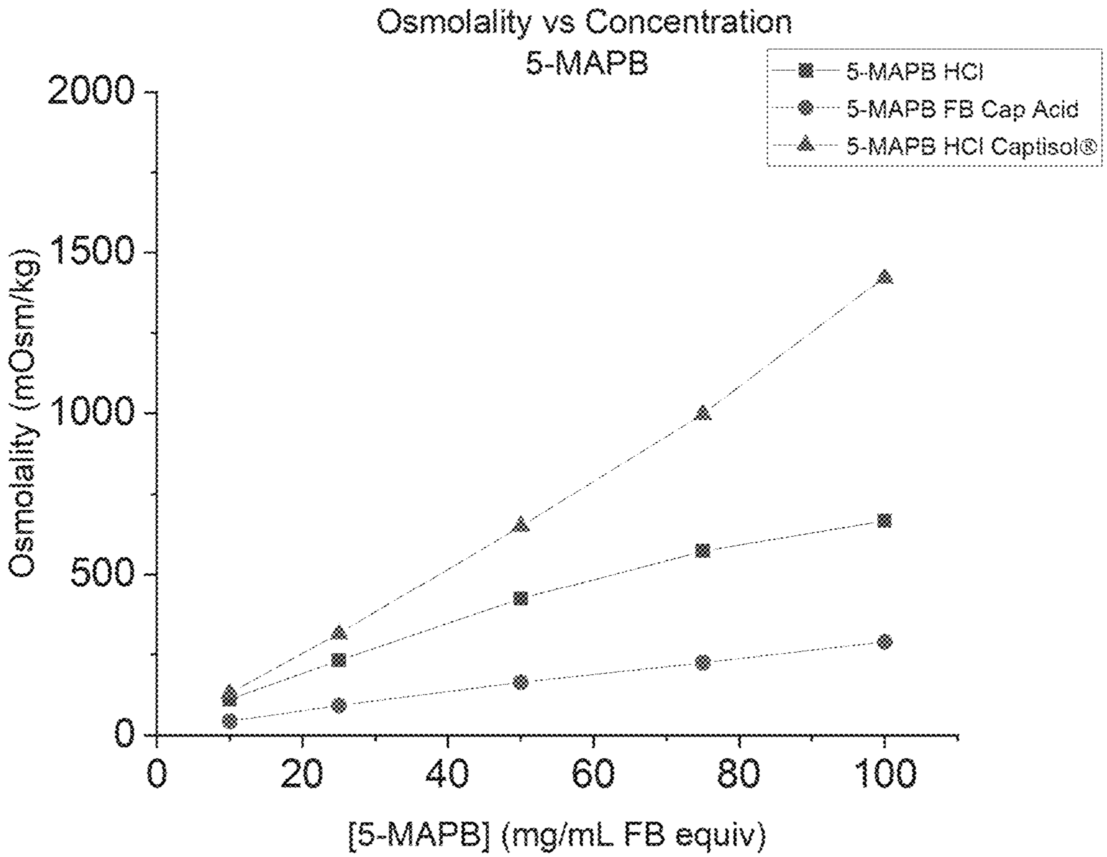
FIG. 40 shows an osmolality vs concentration measurement curve of 5-MAPB formulations. (pH 7.0±0.1).
Figure 41:
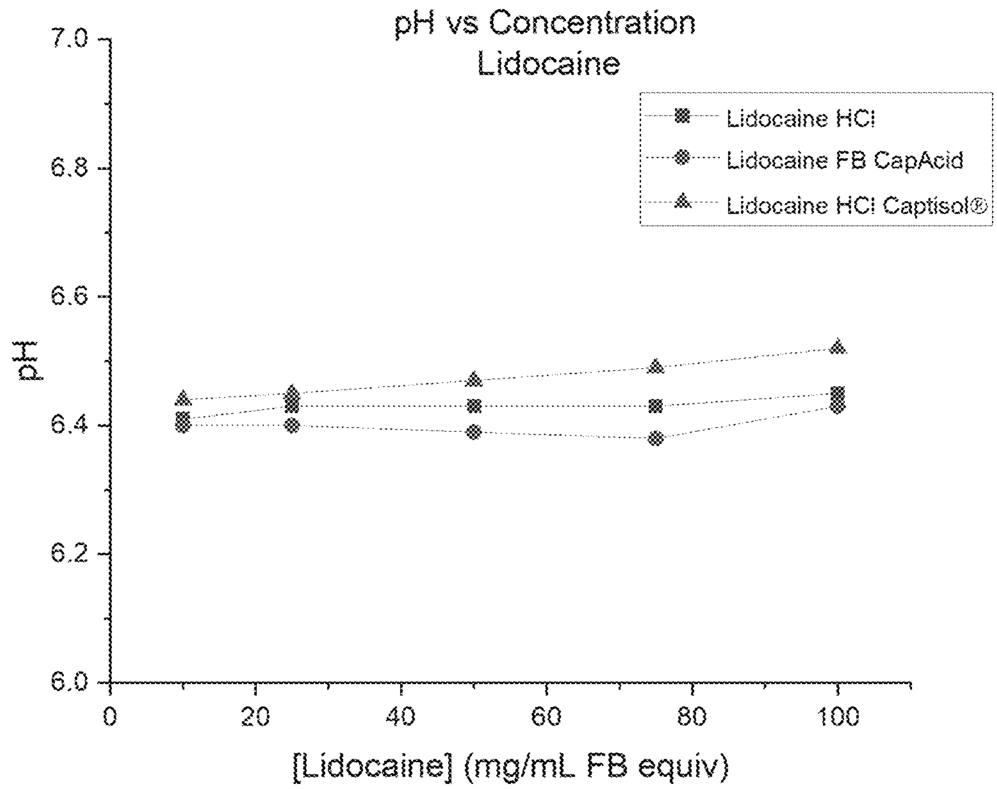
FIG. 41 shows a pH vs. concentration measurement curve of Lidocaine formulations diluted starting from 100 mg/mL Lidocaine (in FB equiv) (pH 6.5±0.1).
Figure 42:
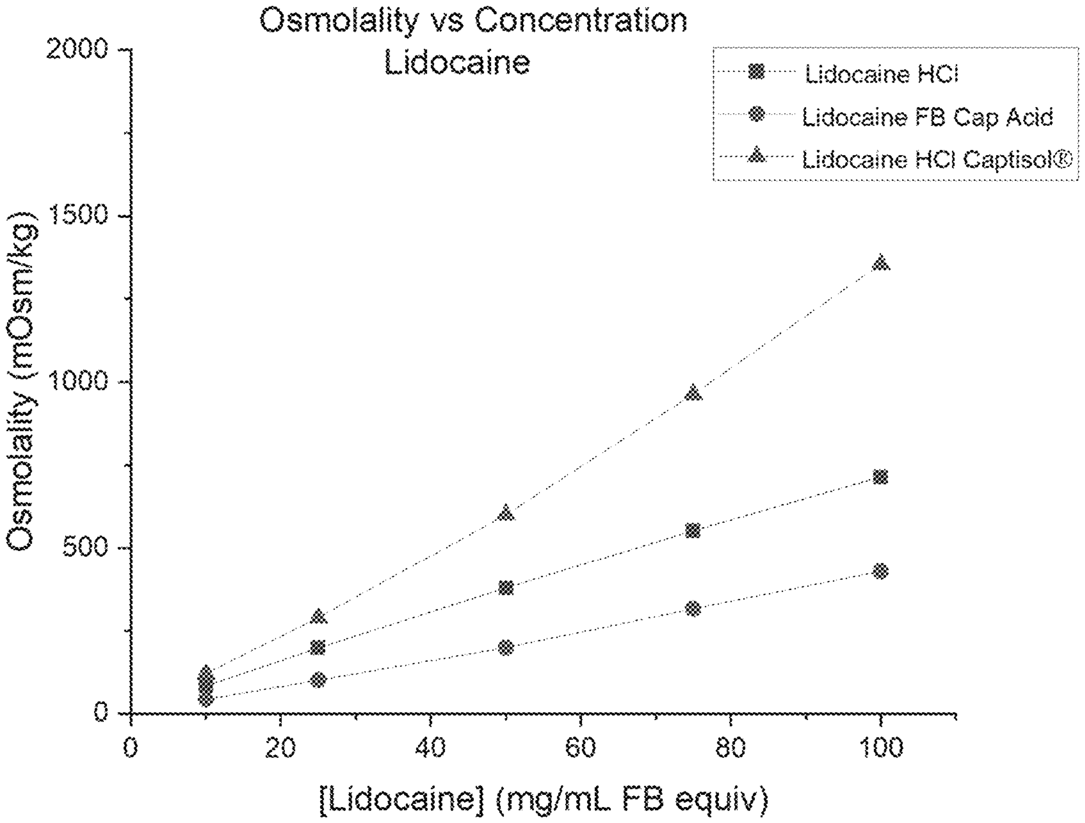
FIG. 42 shows an osmolality vs concentration measurement curve of Lidocaine formulations diluted starting from 100 mg/mL Lidocaine (in FB equiv) (pH 6.5±0.1).
Figure 43:
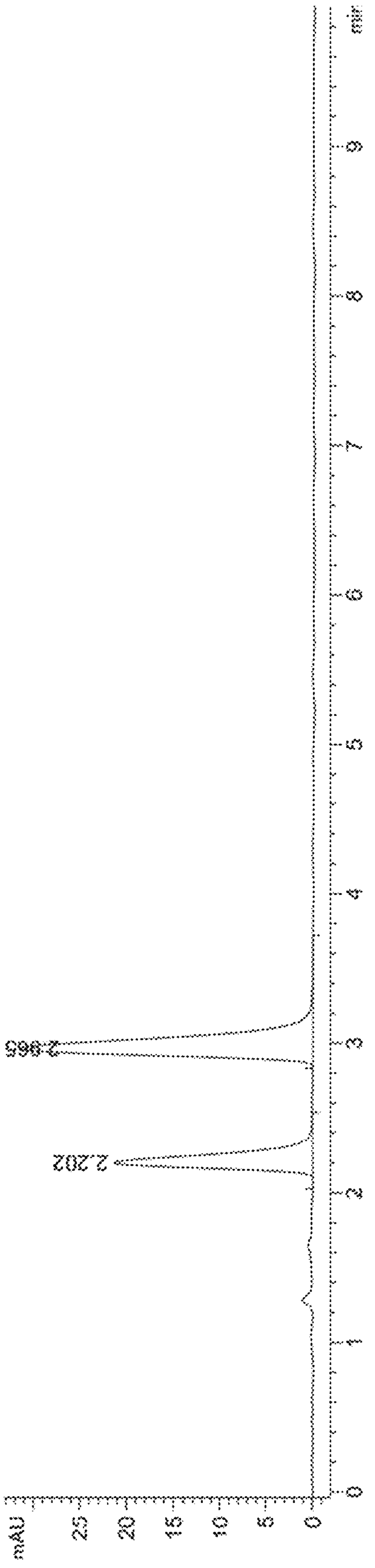
FIG. 43 shows a representative HPLC trace for concentration determination: 2-F-DCK FB-CapAcid Formulation, Procaine (2.202 min), 2-F-DCK (2.965 min), Mobile phase 80% 10 mM aqueous ammonium formate buffer: 20% acetonitrile.
Figure 44:
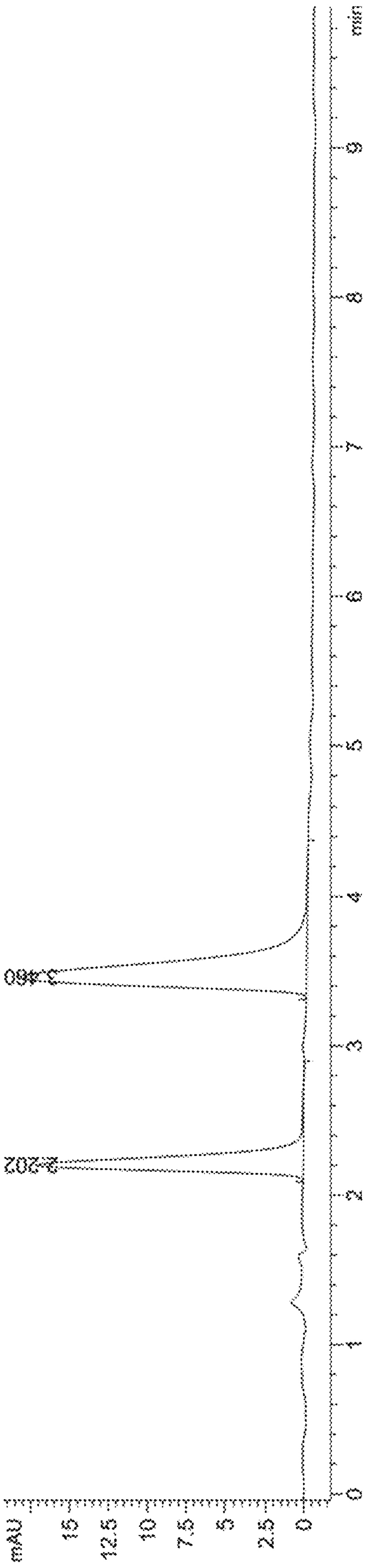
FIG. 44 shows a representative HPLC trace for concentration determination: 3-FMA FB-CapAcid Formulation, Procaine (2.202 min), 3-FMA (3.460 min), Mobile phase 80% 10 mM aqueous ammonium formate buffer:20% acetonitrile.
Figure 45:
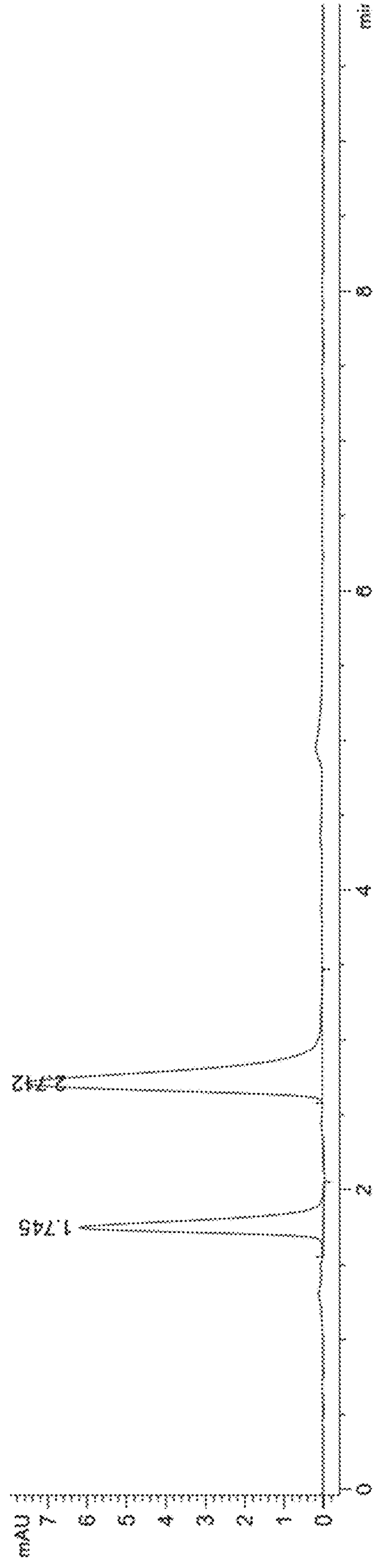
FIG. 45 shows a representative HPLC trace for concentration determination: 5-IAI FB-CapAcid Formulation. Procaine (1.745 min), 5-IAI (2.712 min), Mobile phase 70% 10 mM aqueous ammonium formate buffer:30% acetonitrile.
Figure 46:
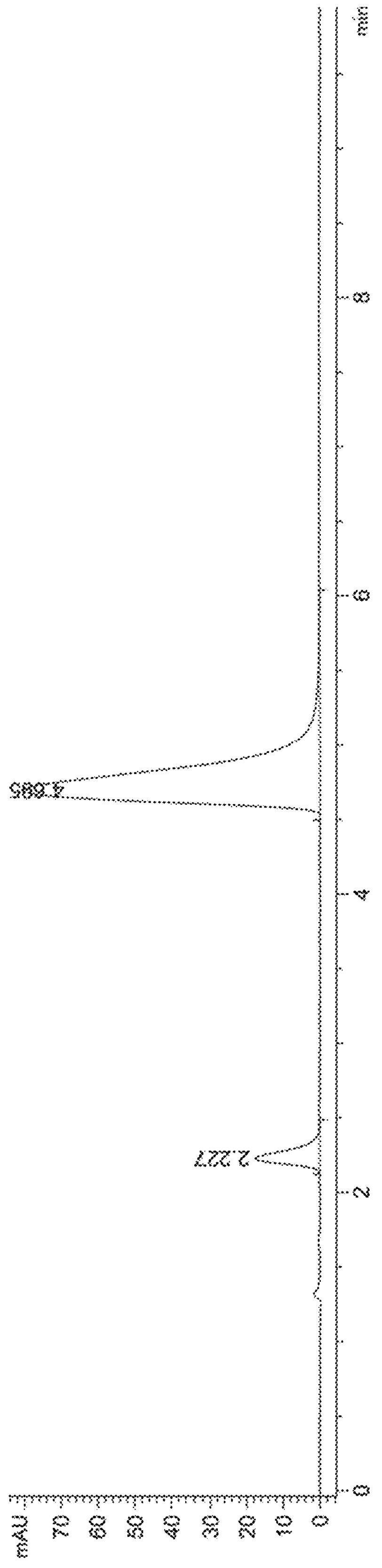
FIG. 46 shows a representative HPLC trace for concentration determination: 5-MAPB FB-CapAcid Formulation. Procaine (2.227 min), 5-MAPB (4.695 min), Mobile phase 80% 10 mM aqueous ammonium formate buffer:20% acetonitrile.
Figure 47:
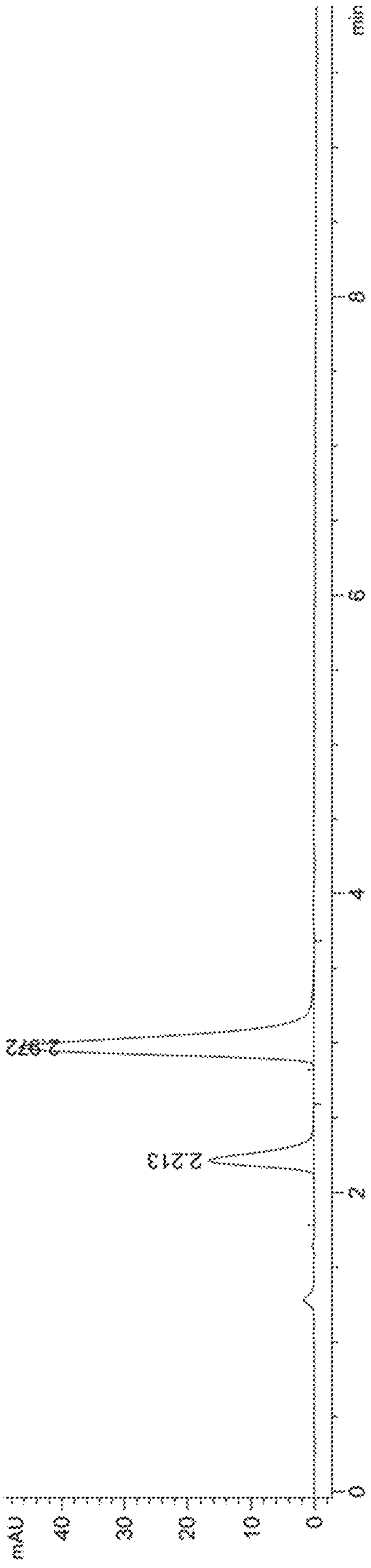
FIG. 47 shows a representative HPLC trace for concentration determination: DCK FB-CapAcid Formulation. Procaine (2.213 min), DCK (2.972 min), Mobile phase 80% 10 mM aqueous ammonium formate buffer:20% acetonitrile.
Figure 48:
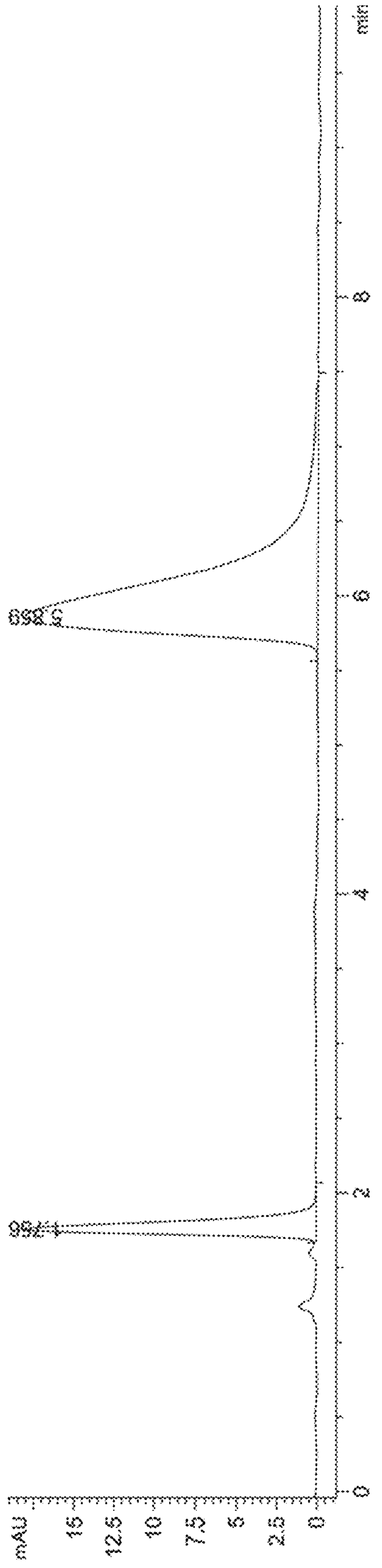
FIG. 48 shows a representative HPLC trace for concentration determination: DXM FB-CapAcid Formulation. Procaine (1.756 min), DXM (5.859 min), Mobile phase 70% 10 mM aqueous ammonium formate buffer:30% acetonitrile.
Figure 49:
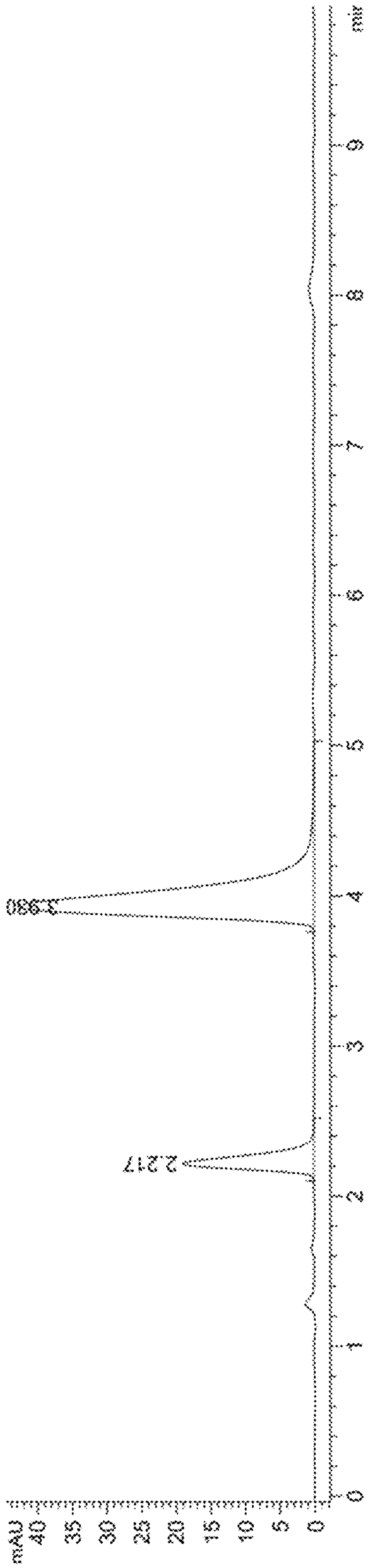
FIG. 49 shows a representative HPLC trace for concentration determination: Me-3-MMC FB-CapAcid Formulation. Procaine (2.217 min), Me-3-MMC (3.930 min), Mobile phase 80% 10 mM aqueous ammonium formate buffer:20% acetonitrile.
Figure 50:
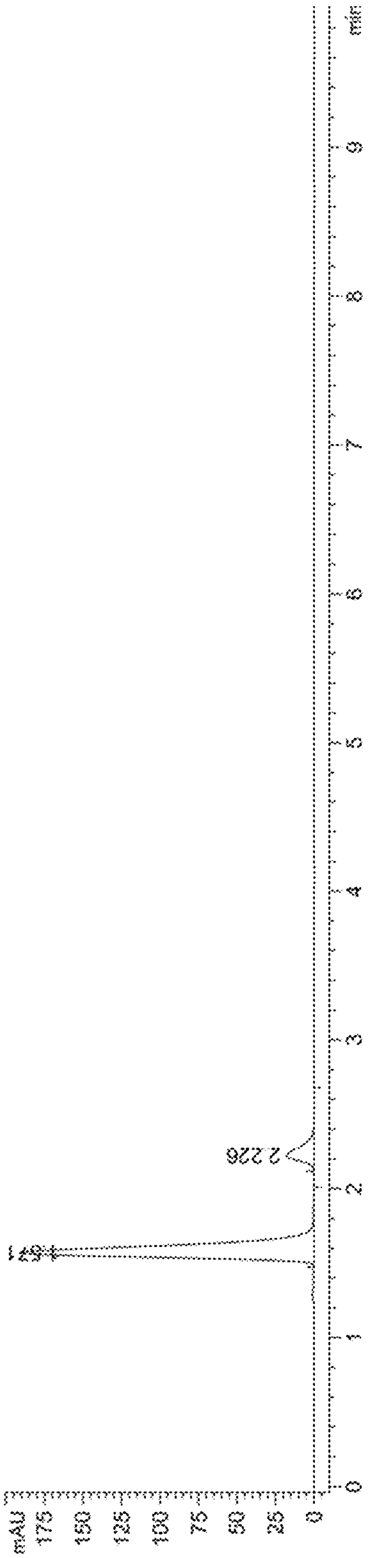
FIG. 50 shows a representative HPLC trace for concentration determination: Morphine FB CapAcid Formulation; Procaine (2.226 min); morphine (1.571 min); Mobile phase 80% 10 mM aqueous ammonium formate buffer:20% acetonitrile.
Figure 51:
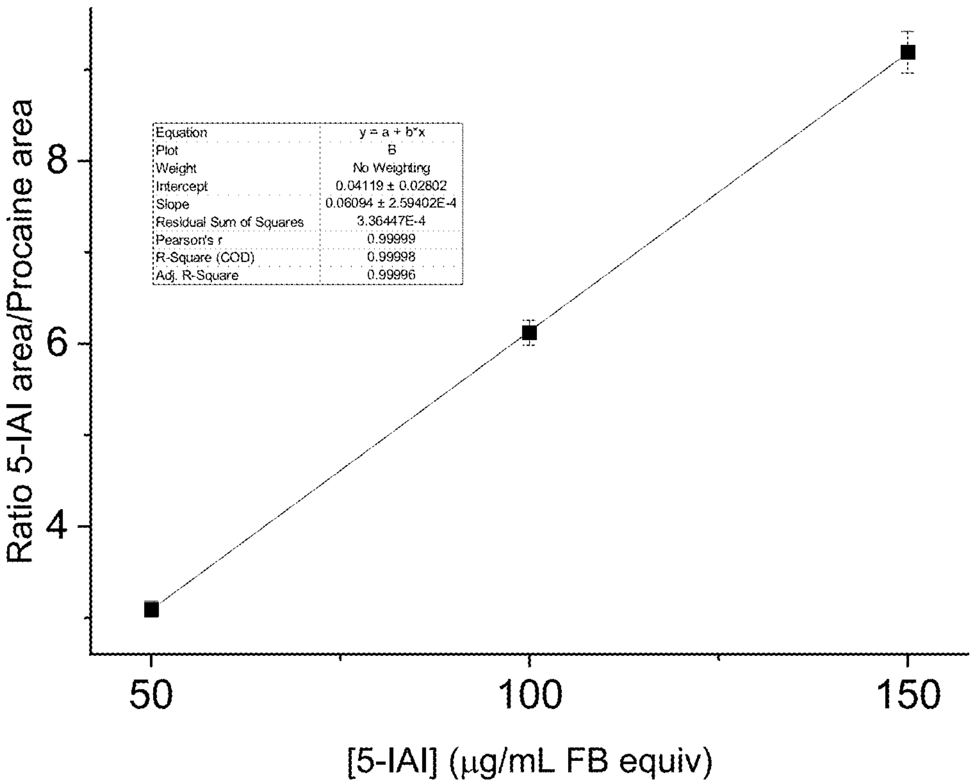
FIG. 51 shows a representative three-point calibration curve for concentration determination by HPLC: 5-IAI. N=3, error bars are SEM.
Figure 52:
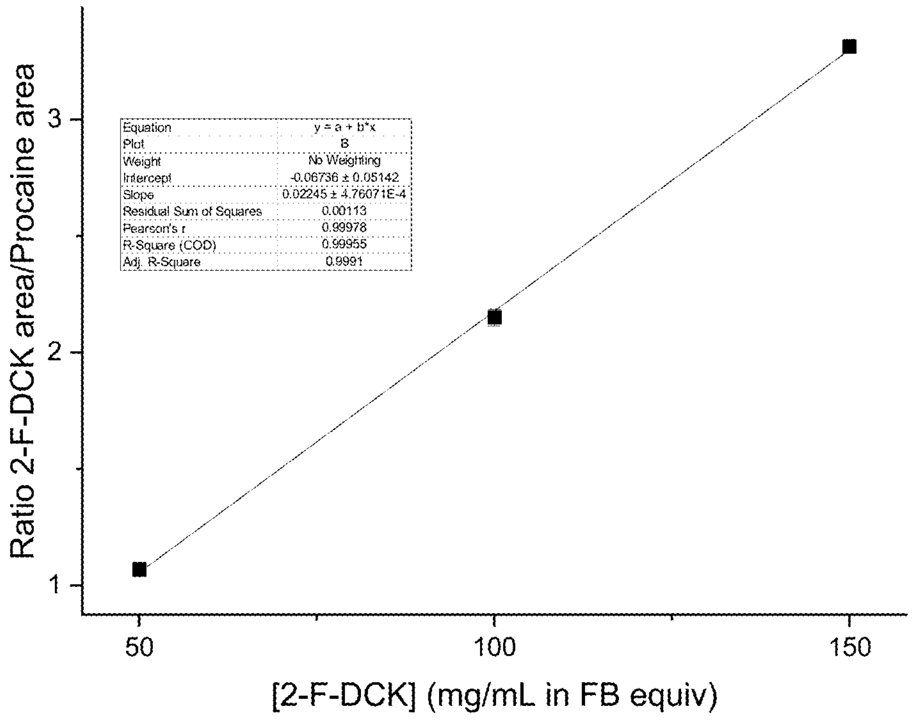
FIG. 52 shows a representative three-point calibration curve for concentration determination by HPLC: 2-F-DCK. N=3, error bars are SEM.
Figure 53:
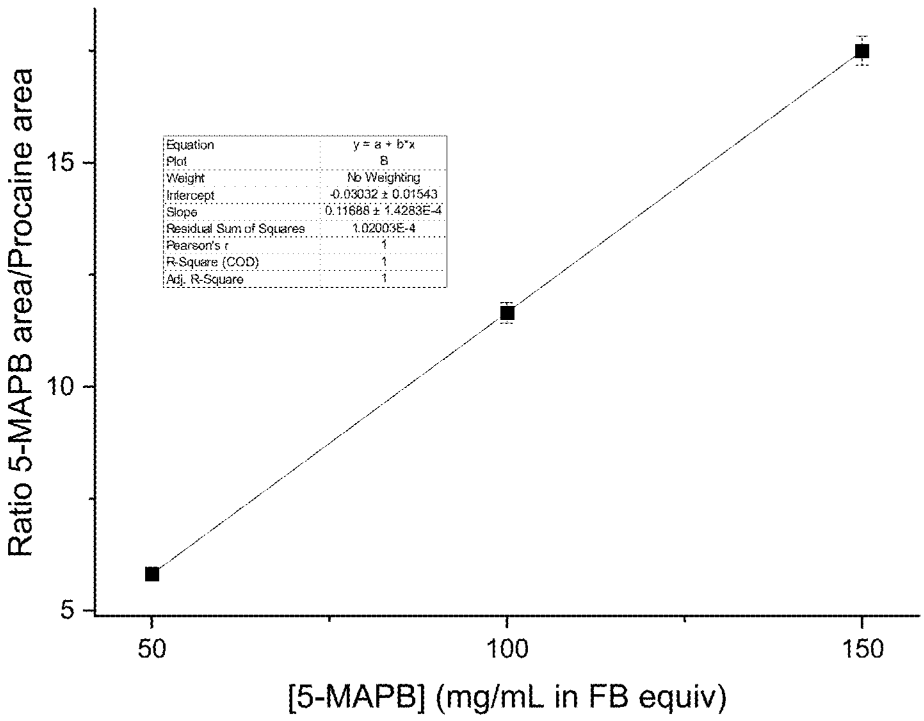
FIG. 53 shows a representative three-point calibration curve for concentration determination by HPLC: 5-MAPB. N=3, error bars are SEM.
Figure 54:
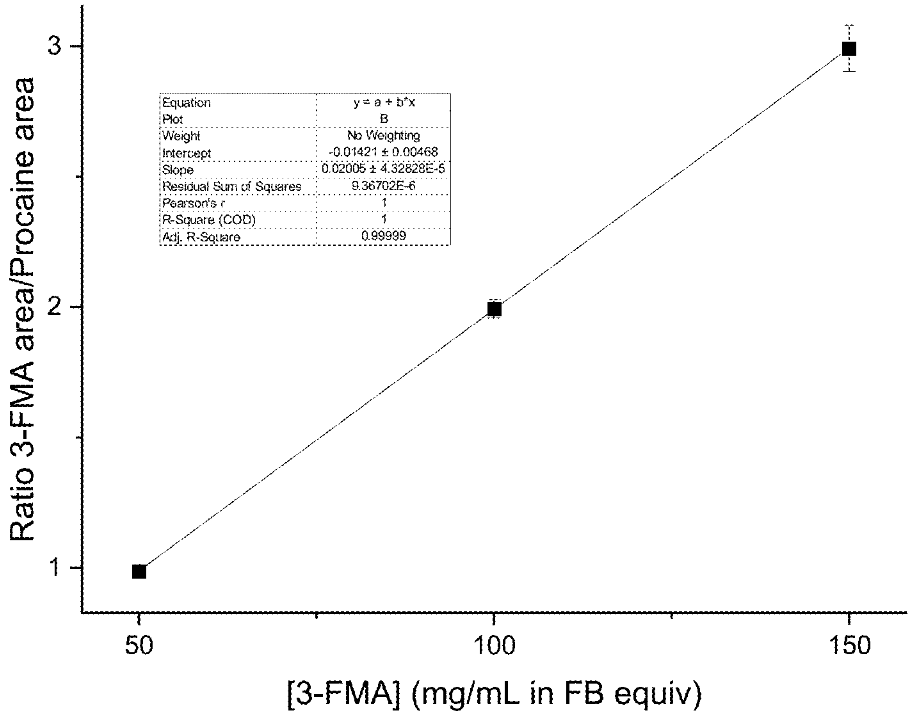
FIG. 54 shows a representative three-point calibration curve for concentration determination by HPLC: 3-FMA. N=3, error bars are SEM.
Figure 55:
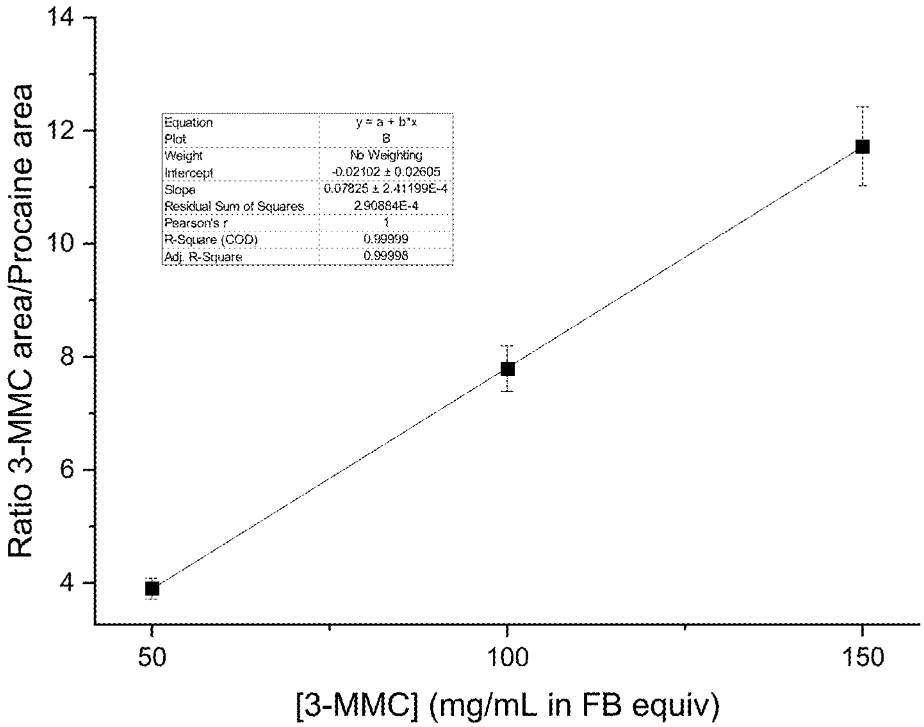
FIG. 55 shows a representative three-point calibration curve for concentration determination by HPLC: 3-MMC. N=3, error bars are SEM.
Figure 56:
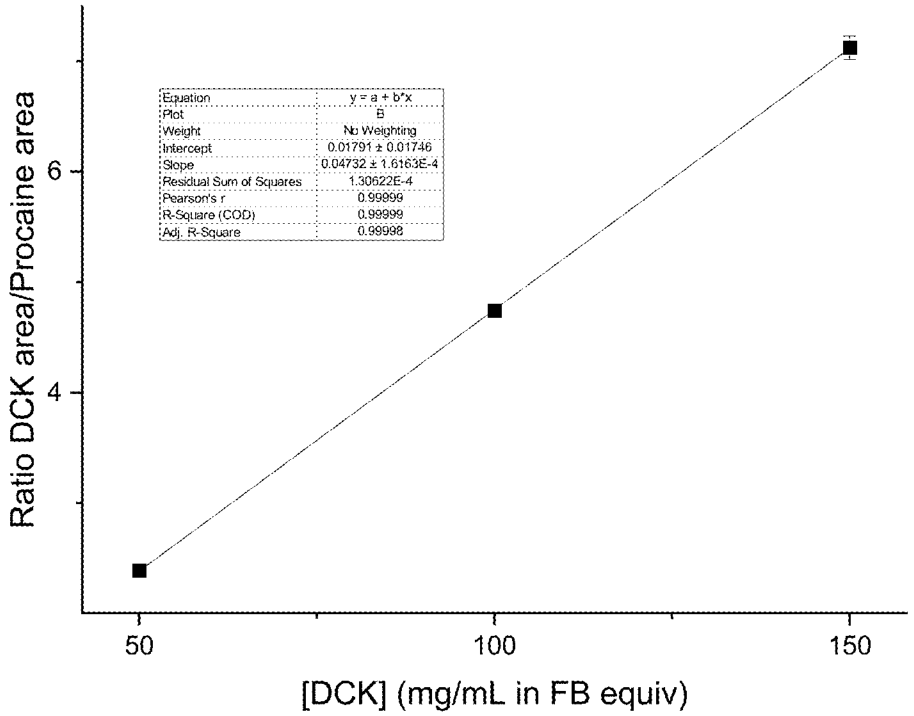
FIG. 56 shows a representative three-point calibration curve for concentration determination by HPLC: DCK. N=3, error bars are SEM.
Figure 57:
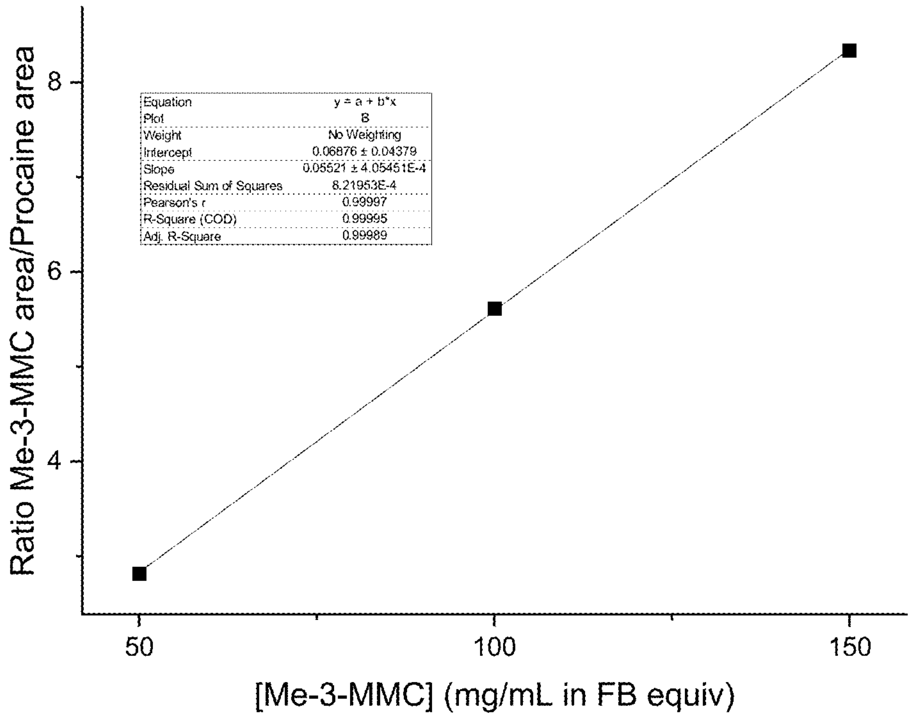
FIG. 57 shows a representative three-point calibration curve for concentration determination by HPLC: Me-3-MMC. N=1.
Figure 58:
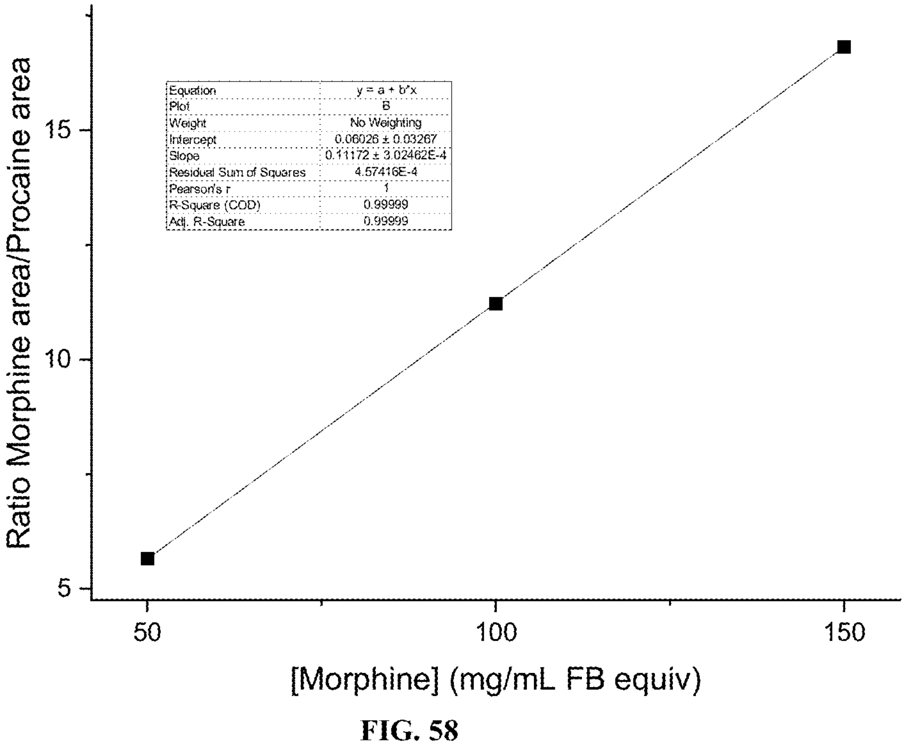
FIG. 58 shows a representative three-point calibration curve for concentration determination by HPLC: Morphine. N=1.

The phase solubility curve with Captisol and Flumazenil was shown in FIG. 34. The different formulations of flumazenil were listed in Table 15.

TABLE 15

| Formulation | [Flumazenil] (mg/mL) | Osmolality (mOsm/kg) | pH |
|---|---|---|---|
| 30% Captisol-Ethylenediame (CapAcid equiv) pH 6.41 | 1.15 | 702 | 6.41 |
| 30% Captisol-Ethylenediame (CapAcid equiv) pH 4.99 | 1.35<br>1.39 (1 Month Stability) | 873.3 | 4.99 |
| 40% Hydroxypropyl-β-cyclodextrin | 3.80 | 652 | ND |
| 20% γ-cyclodextrin | 2.41 | ND | ND |
| 40% Captisol (Phase solubility) | 2.24 | ND | ND |
| 20% Captisol (Phase solubility) | 1.48 | ND | ND |

ND: Not Determined

Example 38. Animal and Human Pharmacokinetics (PK) Study of Captisol Acid Drug Formulations

Animal PK Study

Plasma pharmacokinetics (PK) of Captisol Acid formulations of pharmacological compounds disclosed herein and original formulations of the pharmaceutical compounds are assessed in either rodent species, e.g., mouse and rat, and/or non-rodent species, e.g., dog, to evaluate bioavailability (BA) following different routes of administration, e.g. oral administration (PO) and intravenous administration (IV).

The PK data of Captisol Acid formulations of pharmacological compounds are then compared to the PK data of the existing formulations of respective pharmaceutical compounds. The original formulations of pharmaceutical compounds have poor solubility profiles that make them untenable as viable pharmaceuticals or require them to be delivered through IV.

Metabolism and PK studies are conducted in male and female young adult animals. The number of animals used in these studies are sufficient to reliably estimate population variability. Drug formulations are delivered to animals via oral gavage (PO), and either tail vein injection (e.g., mouse) or jugular vein cannula (e.g., rat and dog) to facilitate both bolus injection and withdrawal of blood samples. Cannulas are washed with normal saline to avoid the possibility of carry-over.

Both single-dose and multiple-dose studies are performed within appropriate dose range and dose intervals. Appropriate time points for each route of administration (ROA) (e.g., 5, 15, 30, 60, 120, 240 min for IV and 15, 30, 60, 120, 240 and 360 min for PO) and numbers of animals (including control groups) are chosen for each pharmaceutical compound.

Blood plasma samples are collected and the compound concentrations are measured using mass spectrometry and HPLC techniques. Pharmacokinetic parameters (e.g., $C_{max}$, $T_{max}$, AUC, clearance, half-life) of each administered pharmaceutical compound are calculated and compared.

Human PK Study

Human studies are conducted to evaluate the bioavailability of novel Captisol Acid formulations of pharmaceutical compounds compared with their existing formulations following intravenous or oral administration in normal healthy volunteers.

The human PK studies are carried out in a double-blind, crossover manner with appropriate numbers of subjects enrolled to obtain sufficient statistical power. Following a fasting period of at least 8 hours, subjects are randomized to receive either oral or intravenous administration of Captisol Acid formulations or existing formulations, Each dosage is separated by a minimum 7-day washout period.

Plasma samples are obtained at appropriate time points after infusion, depending on the substance being tested and the route of administration. PK parameters are evaluated for all pharmaceutical compounds after both IV and oral administration, including but not limited to area under the receiver operating characteristic curve (AUC) from time 0 to the last quantifiable concentration time point ($AUC_{0-t}$), $AUC_{0-\infty}$, $C_{max}$, time to reach $C_{max}$ ($T_{max}$), terminal elimination half-life ($T_{1/2}$), and bioavailability.

The animal and human PK study results indicate that Captisol Acid-formulated pharmaceutical compounds improve drug solubility and bioavailability and potentially therapeutic efficacy compared with their original formulations. As a result, the Captisol Acid-formulated pharmaceutical compounds allow successful delivery by different routes of administration, such as oral administration.

The animal and human PK study results also indicate that Captisol Acid formulations of pharmaceutical compounds delivered through IV exhibit improved bioavailability following IV administration compared with their original formulations. Therefore, the use of Captisol Acid formulations of pharmaceutical compounds leads to positive improvements in a drug's solubility, dissolution and bioavailability, as well as other properties such as stability and biological activity in vivo.

Example 39. Preparation of a Captisol Acid:Mescaline Salt

A Captisol Acid-Mescaline salt was prepared according to the general protocol shown in Scheme 23.

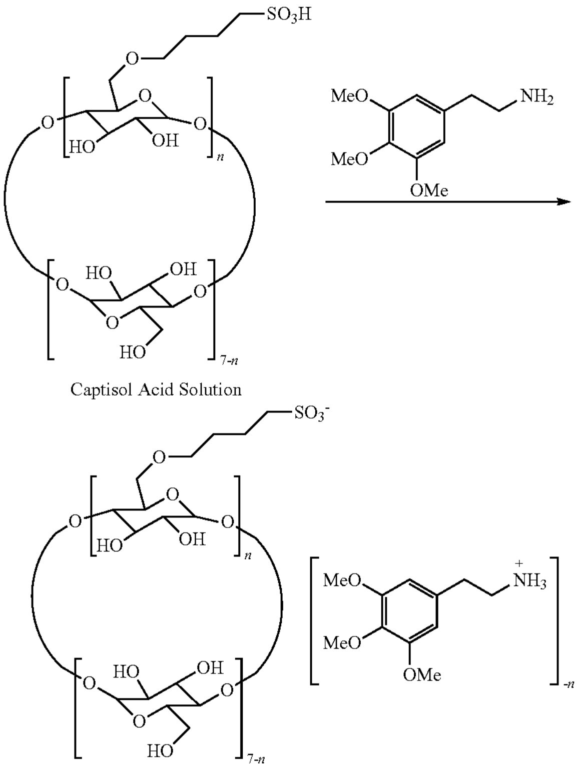

Captisol Acid Solution

1:1 Captisol acid:Mescaline salt

Sulfobutyl Ether β-Cyclodextrin Mescaline Salt

The Captisol Acid-Mescaline salt was prepared using the ingredients listed in Table 16.

TABLE 16

| Reagents | MW | Eq. | g L |
|---|---|---|---|
| Captisol Acid Solution | 16.78 wt. % | 1.0 | 71.01 |
| Mescaline | 211.26 | 6.5 acid equiv. | 58.10 |
| Water | | As needed | |
| 1:1 Captisol acid: Mescaline salt | | | 20.02 |

The preparation protocol is as follows. Add 71.01 g of Captisol Acid solution to a nitrogen-flushed 250 mL round bottom flask equipped with a stir bar and thermocouple and start stirring. Add 8.10 g of mescaline salt to the Captisol solution and stir at 50° C. for 10 minutes until a homogenous solution forms. Add an appropriate amount of water to the solution to facilitate solution formation. Once a solution is formed, filter the solution and lyophilize the solution to a solid salt of Captisol Acid:Mescaline over 48 h. The resulting salt is a white fluffy solid, 17.13 g, KF=0.75%.

To prepare a solution of the Captisol Acid:Mescaline salt, add the salt in portion-wise to HPLC grade water until no solid can dissolve. After each addition (0.5-1.0 g of 1:1 salt), the appearance, weight, osmolality, and pH of the solution was recorded. The estimated concentration of Mescaline in solution was back-calculated with the units mg/g of solution. The steps were repeated until all solid was dissolved. The initial solution (first entry below) contains 0.505 g of 1:1 salt in water for a total solution weight of 10.001 g. Based on the estimated concentration of Mescaline in solution, the estimated concentration of Captisol Acid (CA) can be back calculated. The study was conducted in a 40 mL vial. An analytical balance was used for all weight measurements. The results are shown in Table 17.

TABLE 17

| Mescaline conc. (mg/g) | Color | Clarity | Viscosity | pH | Osmolality (mOsm/kg) | Captisol (mg/g) |
|---|---|---|---|---|---|---|
| 20.3 | colorless | clear | low | 3.68 | 75 | 30.3 |
| 41.7 | colorless | clear | low | 3.30 | — | 62.3 |
| 57.1 | colorless | faintly hazy | low | 3.17 | 222 | 85.3 |
| 72.2 | colorless | faintly hazy | low | 3.03 | 300 | 107.8 |
| 85.4 | very faint | faintly hazy | slightly | 2.94 | 371 | 127.6 |
| 98.8 | faint to slight | faintly hazy | slightly | 2.85 | 464 | 147.5 |
| 110.8 | slightly yellow | faintly hazy | slightly | 2.79 | 569 | 165.6 |
| 123.1 | slightly yellow | faintly hazy | slightly | 2.73 | 684 | 183.9 |
| 144.4 | slightly yellow | faintly hazy | like simple | 2.63 | 947 | 215.7 |
| 162.1 | slightly yellow | faintly hazy | like ethylene | 2.55 | 1241 | 242.1 |
| 184.6 | slightly yellow | faintly hazy | like motor oil | 2.47 | — | 275.8 |
| 201.8 | slightly yellow | clear | thick | 2.39 | — | 301.5 |

After adding a total of 9.23 g of Captisol Acid:Mescaline salt, the solution was clear, slightly yellow to yellow, homogenous, and viscous. 201.8 mg/g was the estimated maximum concentration of Mescaline in this example. An osmolality reading was not achievable for the last two entries as the solution did not freeze/seed. After wt. assay analysis (HPLC) the final Mescaline concentration in this example was 243.7 mg/mL (201.8 mg/g). Density of the final solution is 1.16 g/mL.

The solubility of DMT, 5-MeO-DMT and Mescaline in Captisol sodium solution was demonstrated according to the following procedure. An equimolar amount of Captisol Sodium form and 5 mL HPLC grade water were added to three 20 mL vials equipped with stir bars. Once a solution was formed, 638 mg of DMT, 700 mg of 5-MeO-DMT, and 700 mg of Mescaline were added to each vial. Each solution was diluted with water to a total solution weight of 10 g. The mixtures were agitated at room temperature overnight and analyzed. The results are shown in Table 18.

TABLE 18

| Amine | Amine Conc. (mg/mi) | Appearance after filtration | pH | Osmolality (mOsm/kg) |
|---|---|---|---|---|
| DMT | 13.6 | Clear/colorless | 11.10 | 300 |
| 5-MeO-DMT | 14.6 | Clear/faint yellow | 11.03 | 316 |
| Mescaline | 77.7 | Clear/light yellow | 11.69 | 570 |

A shown in Table 18, a small amount of DMT and 5-MeO-DMT was soluble in equimolar Captisol Sodium form aqueous solution, while the dissolution of Mescaline in Captisol Sodium form aqueous solution was similar to that in Captisol acid aqueous solution.

To determine the pH range of the Mescaline BDS solution, 40 mL of a 70 mg/mL stock solution of Mescaline in Captisol acid (equimolar) aqueous solution was prepared by diluting 6.68 g of the Mescaline formulation of Table 17 with HPLC grade water to 20 mL in a volumetric flask (repeated once). 7 g of the stock solution was transferred to six 20 mL vials with stir bars. The pH of each solution was adjusted to the target pH using 1 M NaOH and/or 1 M HCl. After pH adjustment, each solution was agitated overnight at room temperature, and the appearance, pH, and osmolality analyzed and the results were shown in Table 19. In a pH range of 7.5 to 5.5, there was no precipitate/residue observed in the 70 mg/mL Mescaline solutions. No significant change in osmolality was observed. The last row of Table 19 is the control.

TABLE 19

| Mescaline Conc, (mg/mi) | Appearance | pH | Osmolality (mOsm/kg) |
|---|---|---|---|
| — | Clear/yellow orange | 7.48 | 263 |
| — | Clear/yellow orange | 6.95 | 267 |
| — | Clear/yellow | 6.48 | 266 |
| — | Clear/light yellow | 6.02 | 263 |
| — | Clear/light yellow | 5.55 | 265 |
| 70.0 | Clear/faint yellow | 3.08 | 263 |

Example 40. Preparation and Characterization of Captisol Acid Formulations of Various Pharmaceutical Compounds The example illustrates the preparation and characterization of a number of pharmaceutical compounds formulated by Captisol Acid.

General Methods

General Procedures. Masses used for solutions of Captisol® and Captisol acid (CapAcid) were corrected for moisture content as determined by Karl-Fisher titration. All aqueous solutions were prepared using HPLC grade water from Sigma-Aldrich (St. Louis, MO). Linear regression analyses were performed in OriginPro 2020 (OriginLab Corporation, Northampton, MA, USA).

Chemicals and Reagents. HPLC solvents (water and acetonitrile) were all HPLC Plus grade and purchased from Sigma Aldrich (St. Louis, MO). The following chemicals were obtained and used without further purification: ammonium formate (≥99.9%, Sigma Aldrich, St. Louis, MO), procaine HCl (≥97%, Sigma Aldrich, St. Louis, MO), formic acid (≥98%, Sigma Aldrich, St. Louis, MO), Amberlite IRC120 H hydrogen form resin (Sigma Aldrich, St. Louis, MO), ethanol (200 proof, Pharmco, Greenfield Global, Toronto, Canada), sodium hydroxide (≥97%, Sigma Aldrich, St. Louis, MO), sodium chloride (Certified ACS crystalline, Fisher Scientific, Fair Lawn, NJ), Benzethonium chloride (≥99%, Sigma Aldrich, St. Louis, MO), Captisol® (Lot #NC-04A-180185, Cydex Pharmaceuticals, Lawrence, KS). The following basic amine active pharmaceutical ingredients (APIs) were purchased: S-(−)-nicotine (Alfa Aesar, Ward Hill, MA), Lidocaine (Spectrum Chemical, Gardena, CA), sumatriptan succinate (Stoichiometric salt, Spectrum Chemical, Gardena, CA), dextromethorphan HBr hydrate (Sigma-Aldrich, St. Louis, MO), 5-iodo-2-aminoindane (5-IAI, A2B Chem, San Diego, CA), and DXM freebase (1PlusChem, San Diego, CA). The following active pharmaceutical ingredients (APIs) were purchased from Smokeys Chem Site: 3-fluoromethamphetamine (3-FMA), deschloroketamine (DCK), 2-fluoro-deschloroketamine (2-F-DCK), and 1-(benzofuran-5-yl)-N-methylpropan-2-amine (5-MAPB).

Instrumentation pH and Mass Measurements. pH values were measured with an Orion 3 star (Thermo Scientific, USA) pH meter equipped with either a Thermo pH electrode (9142BN) or an Orion 8103BNUWP Ross Ultra Semi-micro pH probe (Thermo Scientific, USA). Probes were filled with 3M KCl ROSS Orion filling solution (Thermos Scientific, USA). Masses were measured on An Ohaus ADVENTURER AX124 analytical balance (Ohaus, New Jersey, USA) on 3×3 inch low nitrogen weighing Fisherbrand paper (Fisherbrand, Pittsburgh, USA). Masses of at least 5 mg were weighed for any given sample to reduce measurement error. Both the pH meter and balance were calibrated directly prior to use. Balance calibration was confirmed with a 5 mg standard weight (Troemner, Thorofare, NJ) with 5±0.1 mg cutoff.

High Performance Liquid Chromatograpy (HPLC). HPLC analyses were performed on an Agilent 1260 Infinity system. The system includes a 1260 quaternary pump VL, a 1260 ALS autosampler, a 1260 Thermostatted Column Compartment, and a 1200 DAD Multiple Wavelength Detector (Agilent Technologies, Santa Clara, CA, USA). The detection wavelength was set at 220 nm. Separation of API from internal standard was achieved using a Zorbax Eclipse Plus-C18 analytical column (5 μm, 4.6×150 mm) from Agilent (Agilent Technologies, Santa Clara, CA, USA). Mobile phase A consisted of 10 mM aqueous ammonium formate buffer adjusted to pH 4.5 and mobile phase B consisted of acetonitrile. The injection volume was set to 40 μL, flow rate was set to 1.0 mL/min, and the column temperature was set at 40° C. Samples were injected in duplicate and a wash of the injector (20:80 A:B or 30:70 A:B) was performed between runs. Run times were 10 minutes with a mobile phase ratio (isocratic) of either 80% A and 20% B or 70% A and 30% B. The resulting chromatograms were analyzed using Agilent ChemStation Software (Agilent Technologies, Santa Clara, CA, USA).

Nuclear Magnetic Resonance Spectroscopy. $^{1}H$ and $^{13}C$ NMR spectra data were obtained on a Bruker Avance III with PA BBO 400S1 BBF-H-D-05 Z plus probe (Bruker Corporation, Billerica, MA, USA). Products were prepared at a concentration of ~20 mg/mL in DMSO-$d_6$ (Sigma-Aldrich, St. Louis, MO). Chemical shifts are reported in parts per million (ppm) relative to the DMSO-$d_6$ resonance (6=2.50 ppm) for $^{1}H$ and (6=39.52 ppm) for $^{13}C$.

Moisture Readings. Moisture ($H_2O$) percentage on samples were obtained on a Mettler Toledo C20 Coulometric Karl Fischer titrator (Mettler Toledo, Columbus, OH, USA) containing HYDRANAL™-Coulomat AG reagent from Honeywell Fluka™. HYDRANAL™ (10 mg water/g solution) water standard from Honeywell Fluka™ was run directly prior to use as a positive control. The measurements were made on masses >50 mg.

Osmolality. Osmolality readings were obtained on an Advanced Instruments Advanced™ Micro Osmometer Model 3300 (Advanced Instruments, Inc. Norwood, MA, USA). Saline solutions (0.9% and 3%) were freshly prepared with sodium chloride (Fisher Scientific, Fair Lawn, NJ) and run as positive controls. Each sample was calculated as the mean from back-to-back triplicate measurements.

Lyophilization. Lyophilization was performed on an SP Scientific Wizard 2.0 lyophilizer. Samples were subjected to a cycle of freezing at −60° C. at ~400 mmHg for 2 hrs and then drying at 30 mmHg for 48 hrs. The door of the lyophilizer was covered with aluminum foil to protect samples from light.

High Resolution Mass Spectral Analysis (HRMS). HRMS data were obtained on a Thermo Orbitrap Exactive Mass Spectrometer with an Orbitrap mass analyzer. The instrument was calibrated using electrospray ionization with Pierce™ LTQ ESI Positive Ion Calibration Solution from ThermoFisher Scientific. Samples were introduced as either amine salt or freebase into the instrument using a melting point tube and ionized via an Atmospheric Solids Analysis Probe (ASAP). The following settings were used: Spray voltage—3.50 V; Capillary temperature-275° C.; Capillary voltage—25.00 V; Tube lens voltage—65.00 V; Skimmer voltage—14.00 V; Heater temperature-100° C. Data was analyzed in the Thermo Xcalibur Qual Browser software and elemental composition confirmed if <5 ppm error.

Experimental

Synthesis of Captisol Acid (CapAcid). Amberlite IR120 Hydrogen form resin (62 g, 4.4 meq/g, 20 equivalents) was added to a borosilicate glass beaker. The resin was then soaked in HPLC grade water (250 mL) for 5 minutes. The resin was carefully loaded onto a borosilicate glass column (30 mm diameter) containing a rinsed (HPLC grade water) plug of cotton. The resin was washed with 2 column volumes of HPLC grade water and then dried for 10 minutes using air flow. An aqueous solution of 15% Captisol (30 mL) in HPLC-grade water was then added to the column and air pressure used to elute the acid into a tared, aluminum foil-wrapped borosilicate glass beaker. The resin was then washed once more with HPLC grade water (30 mL) which was collected into a separate tared, aluminum foil-wrapped borosilicate glass beaker. The eluents were frozen and then subjected to lyophilization on an SP Scientific Wizard 2.0 lyophilizer at 30 mmHg for 48 hr. The resulting solids were crushed with a glass stir rod, weighed, and moisture content determined by Karl-Fisher titration. The resulting white, shiny solids (3.30-4.04 g, 78.5-96% recovery, 4.40-7.80% moisture, n=5) was stored in an aluminum foil-wrapped and parafilm sealed 20 mL glass scintillation vial at −20° C. until use.

Synthesis of 3-MMC hydrochloride. To a dry round-bottom flask with a Teflon-coated magnetic stirbar was added 3-methylpropiophenone (10.1 g, 68.1 mmol) followed by 3 Å molecular sieves-dried DCM (40 mL). The solution was stirred with a Teflon-coated magnetic stirbar at room temperature (RT) and the flask was fitted with a dry addition funnel. A solution of $Br_2$ (3.6 mL, 11.2 g, 70.2 mmol) in 3 Å molecular sieves-dried DCM (20 mL) was added to the addition funnel and the solution was added dropwise to the reaction over 2 h at RT. The reaction was then stirred at RT overnight. The mixture was quenched with 5% $NaHCO_3$ (~50 mL), diluted with DCM (~100 mL), and transferred to a separatory funnel. The mixture was extracted with DCM (2×100 mL) and the combined organics were washed with brine (100 mL). The organics were dried over anhydrous $Na_2SO_4$ and concentrated under vacuum to afford the intermediate bromide as an orange oil (22.6 g) that was used without further purification. The intermediate bromide was dissolved in dry ACN (200 mL) and triethylamine (22 mL, 15.9 g, 157 mmol) was added with magnetic stirring. Methylamine solution (2M in THF, 60 mL, 120 mmol) was added to the reaction in one portion at rt and the mixture was monitored by TLC until completion (3 h). The reaction was worked up in two portions: each half of the reaction was diluted with EtOAc (200 mL) and the organic layer was extracted with 1M HCl (3×200 mL). The combined aqueous layers were basified with solid KOH flakes and back extracted with EtOAc (2×200 mL). The combined organics were washed with brine (100 mL), dried over anhydrous $Na_2SO_4$, and concentrated to a clear oil that was immediately converted to the hydrochloride salt using the following method. The oil was dissolved in 200 proof EtOH (80 mL) and titrated with concentrated HCl until the pH was acidic (pH <1). Solvent and excess HCl were removed with a warm stream of air and the resulting white solids were washed with $Et_2O$ (3×~20 mL). The resulting hydrochloride salt was crystallized three times by dissolving in a minimum amount of boiling 200 proof EtOH and layering with $Et_2O$ to afford 3-MMC hydrochloride (8.1 g, 47% over two steps) as a white, powdery crystalline solid. $^1$H NMR (400 MHz, DMSO-66) δ 9.49 (bs, 2H), 7.86 (s, 1H), 7.83 (d, J=7.7 Hz, 1H), 7.56 (d, J=7.6 Hz, 1H), 7.48 (t, J=7.6 Hz, 1H), 5.15 (q, J=7.2 Hz, 1H), 2.57 (s, 3H), 2.40 (s, 3H), 1.44 (d, J=7.2 Hz, 3H). $^{13}$C NMR (101 MHz, DMSO-$d_6$) δ 196.40, 138.71, 135.25, 133.00, 129.10, 129.04, 126.01, 58.16, 30.60, 20.78, 15.44.

Synthesis of Me-3-MMC hydrochloride. Prepared as described for 3-MMC HCl except with dimethylamine (2M in THF) to afford Me-3-MMC hydrochloride (13.3 g, 87% over two steps) as a white, powdery crystalline solid. $^1$H NMR (400 MHz, DMSO-$d_6$) δ 10.79 (s, 1H), 7.87 (s, 1H), 7.85 (d, J=8.0 Hz, 1H), 7.57 (d, J=7.5 Hz, 1H), 7.50 (t, J=7.6 Hz, 1H), 5.44 (q, J=7.2 Hz, 1H), 2.86 (s, 6H), 2.40 (s, 3H), 1.49 (d, J=7.2 Hz, 3H). $^{13}$C NMR (101 MHz, DMSO-$d_6$) δ 196.33, 138.70, 135.34, 133.50, 129.14, 129.04, 126.04, 63.71, 20.78, 13.83.

General procedure for preparation of API freebase from API salt. The API salt (~1.0 g) was dissolved in a small amount of deionized water and added to a solution of 10% sodium hydroxide. The suspension was then transferred to a separatory funnel and extracted with EtOAc (3×~75 mL). The combined organic layers were washed with brine (1×50 mL) and dried over anhydrous $Na_2SO_4$. The solution was concentrated under vacuum, transferred to a beaker using a small amount of EtOAc, and the solvent removed using a steam of warm to afford the API freebase. The freebase was then flushed with argon, covered with foil, and the beaker sealed with parafilm. The product was stored at −20° C. until use. NMR and HPLC were performed to confirm structural identity and estimate purity. In the case of 3-MMC a modified procedure was used due to decomposition. This procedure is described below.

5-iodo-2,3-dihydro-JH-inden-2-amine (5-IAI) FB. Light brown oil. $^1$H NMR (400 MHz, DMSO-$d_6$) δ 7.53 (s, 1H), 7.44 (dd, J=7.9, 1.5 Hz, 1H), 7.00 (d, J=7.9 Hz, 1H), 3.70-3.61 (m, 1H), 2.98 (td, 15.6, 6.8 Hz, 2H), 2.53 (td, J=16.5, 5.5 Hz, 2H), 2.52-2.49 (m, 1H). $^{13}$C NMR (101 MHz, DMSO-$d_6$) δ 145.59, 142.26, 134.61, 133.18, 126.85, 91.36, 52.82, 42.22, 41.67. HRMS (ASAP) m/z calculated for $C_9H_{10}IN$ (M+H)$^+$: 259.9931, found 259.9918, δ ppm: −5.00 ppm.

2-(2-fluorophenyl)-2-(methylamino)cyclohexan-1-one (2-F-DCK) FB. White, powdery solids. $^1$H NMR (400 MHz, DMSO-$d_6$) δ 7.46 (td, J=7.8, 1.8 Hz, 1H), 7.34-7.27 (m, 1H), 7.19 (td, J=7.5, 1.2 Hz, 1H), 7.10 (ddd, J=11.6, 8.0, 1.2 Hz, 1H), 2.74 (s, 1H), 2.59-2.48 (m, 1H), 2.28-2.16 (m, 2H), 1.97 (s, 3H), 1.95-1.81 (m, 2H), 1.79-1.65 (m, 2H), 1.60-1.50 (m, 1H). $^{13}$C NMR (101 MHz, DMSO-$d_6$) δ 206.86, 160.28 (d, J=244.9 Hz), 129.11 (d, J=12.5 Hz), 128.82 (d, J=8.7 Hz), 128.50 (d, J=5.0 Hz), 123.95 (d, J=3.0 Hz), 115.64 (d, J=23.1 Hz), 67.36 (d, J=3.2 Hz), 38.70 (d, J=1.5 Hz), 38.32, 29.27, 26.31, 20.52. HRMS (ASAP) m/z calculated for $C_{13}H_{17}FNO$ (M+H)$^+$: 222.1289, found 222.1287, δ ppm: −0.90 ppm.

1-(benzofuran-5-yl)-N-methylpropan-2-amine (5-MAPB) FB. Clear light amber tinted oil. $^1$H NMR (400 MHz, DMSO-$d_6$) δ 7.92 (d, J=2.2 Hz, 1H), 7.47 (d, J=8.4 Hz, 1H), 7.42 (d, J=1.3 Hz, 1H), 7.10 (dd, J=8.5, 1.7 Hz, 1H), 6.88 (dd, J=2.2, 0.9 Hz, 1H), 2.79 (dd, J=12.7, 5.9 Hz, 1H), 2.72-2.62 (m, 1H), 2.54-2.47 (m, 1H), 2.27 (s, 3H), 0.89 (d, J=6.2 Hz, 3H). $^{13}$C NMR (101 MHz, DMSO-$d_6$) δ 152.97, 145.92, 134.30, 127.16, 125.67, 121.39, 110.68, 106.52, 56.52, 42.41, 33.72, 19.33. HRMS (ASAP) m/z calculated for $C_{12}H_{16}NO$ (M+H)$^+$: 190.1226, found 190.1221, δ ppm: −2.62 ppm.

2-(methylamino)-1-(m-tolyl)propan-1-one (3-MMC) FB. Transparent colorless oil. $^1$H NMR (400 MHz, DMSO-$d_6$) δ 7.82-7.77 (m, 2H), 7.47-7.41 (m, 1H), 7.40 (t, J=7.7 Hz, 1H), 4.23 (q, J=6.9 Hz, 1H), 2.37 (s, 3H), 2.21 (s, 3H), 1.13 (d, J=6.9 Hz, 3H). $^{13}$C NMR (101 MHz, DMSO-$d_6$) δ 203.18, 138.19, 135.72, 133.82, 128.66, 128.47, 125.37, 58.61, 33.78, 20.86, 18.61. HRMS (ASAP) m/z calculated for $C_{11}H_{16}NO$ (M+H)$^+$: 178.1226, found 178.1224, δ ppm: −1.12 ppm.

1-(3-fluorophenyl)-N-methylpropan-2-amine (3-FMA) FB. Light yellow oil. $^1$H NMR (400 MHz, DMSO-$d_6$) δ 7.34-7.26 (m, 1H), 7.04-6.96 (m, 3H), 2.79-2.66 (m, 2H), 2.49-2.41 (m, 1H), 2.28 (s, 3H), 0.89 (d, J=6.2 Hz, 3H). NMR (101 MHz, DMSO-$d_6$) δ 162.08 (d, J=242.8 Hz), 142.70 (d, J=7.4 Hz), 129.86 (d, J=8.5 Hz), 125.37 (d, J=2.6 Hz), 115.84 (d, J=20.6 Hz), 112.58 (d, J=20.9 Hz), 55.78, 41.80, 33.34, 19.02. HRMS (ASAP) m/z calculated for $C_{10}H_{15}FN$ (M+H)$^+$: 168.1183, found 168.1181, δ ppm: −1.19 ppm.

2-(dimethylamino)-1-(m-tolyl)propan-1-one (Me-3-MMC) FB. Light yellow oil. $^1$H NMR (400 MHz, DMSO-$d_6$) δ 7.84-7.80 (m, 1H), 7.79 (s, 1H), 7.43-7.39 (m, 1H), 7.37 (t, J=7.4 Hz, 1H), 4.22 (q, J=6.7 Hz, 1H), 2.36 (s, 3H), 2.17 (s, 6H), 1.08 (d, J=6.7 Hz, 3H). NMR (101 MHz, DMSO-$d_6$) δ 200.22, 137.71, 136.35, 133.43, 128.82, 128.31, 125.85, 62.35, 40.81, 20.91, 8.73. HRMS (ASAP) m/z calculated for $C_{12}H_{18}NO$ (M+H)$^+$: 192.1383, found 192.1380, δ ppm: −1.56 ppm.

1-(3-(2-(dimethylamino)ethyl)-1H-indol-5-yl)-N-methylmethanesulfonamide (Sumatriptan) FB. White, powdery solid. $^1$H NMR (400 MHz, DMSO-$d_6$) δ 10.82 (s, 1H), 7.49 (s, 1H), 7.30 (d, J=8.3 Hz, 1H), 7.15 (d, J=1.7 Hz, 1H), 7.06 (dd, J=8.3, 1.3 Hz, 1H), 6.77 (s, 1H), 4.33 (s, 2H), 2.79 (t, J=7.8 Hz, 2H), 2.53 (s, 3H), 2.51-2.47 (m, 2H), 2.20 (s, 6H). $^{13}$C NMR (101 MHz, DMSO-$d_6$) δ 135.87, 127.26, 123.68, 123.09, 120.75, 119.65, 112.68, 111.10, 60.00, 56.55, 45.16, 28.93, 23.10. HRMS (ASAP) m/z calculated for $C_{14}H_{22}N_3O_2S$ (M+H)$^+$: 296.1427, found 296.1419, δ ppm: −3.25 ppm.

2-(methylamino)-2-phenylcyclohexan-1-one (DCK) FB. Transparent colorless oil. $^1$H NMR (400 MHz, DMSO-$d_6$) δ 7.37-7.31 (m, 2H), 7.26-7.20 (m, 3H), 2.48-2.40 (m, 2H), 2.17 (ddd, J=13.8, 8.8, 5.0 Hz, 1H), 1.89 (s, 3H), 1.88-1.78 (m, 2H), 1.78-1.67 (m, 2H), 1.61-1.49 (m, 1H). $^{13}$C NMR (101 MHz, DMSO-$d_6$) δ 210.23, 140.35, 128.14, 127.31, 126.76, 69.41, 39.11, 37.51, 28.93, 26.80, 21.27. HRMS (ASAP) m/z calculated for $C_{13}H_{18}NO$ (M+H)$^+$: 204.1383, found 204.1377, δ ppm: −2.93 ppm.

General procedures for preparation of API hydrochloride salts. The API FB (0.5-1.0 g) was dissolved in absolute EtOH (20-40 mL) and concentrated HCl (1.1 molar equivalent) was added via a micropipette. The solution was mixed until homogenous and excess HCl removed by evaporation with a steam of warm air and continued additions of absolute EtOH (3×~10 mL). The resulting solids were washed with $Et_2O$ (3×10 mL) and recrystallized by dissolving in a minimum volume of absolute EtOH and layering with $Et_2O$. Crystallization was repeated three times. The resulting solids were then dried in an oven at 60-70° C. for four hours followed by storage under high vacuum overnight. API HCl salts were stored under argon at −20° C. until use.

2-F-DCK HCl. White, powdery solid. $^1H$ NMR (400 MHz, DMSO-$d_6$) δ 10.17 (s, 1H), 9.42 (s, 1H), 7.83 (td, J=8.0, 1.5 Hz, 1H), 7.68-7.60 (m, 1H), 7.45 (td, J=7.6, 1.0 Hz, 1H), 7.39 (ddd, J=11.8, 8.3, 1.0 Hz, 1H), 3.27 (ddd, J=14.0, 6.9, 2.7 Hz, 1H), 2.45-2.39 (m, 2H), 2.20 (s, 3H), 2.04-1.93 (m, 2H), 1.84-1.75 (m, 1H), 1.69-1.53 (m, 1H), 1.46 (qt, J=13.7, 3.6 Hz, 1H). $^{13}C$ NMR (101 MHz, DMSO-$d_6$) δ 205.54, 160.60 (d, J=247 Hz), 133.19 (d, J=9.4 Hz), 130.83 (d, J=2.9 Hz), 125.66 (d, J=3.0 Hz), 118.13 (d, J=12.1 Hz), 116.85 (d, J=22.7 Hz), 68.68, 38.60 (d, 2.3 Hz), 34.39, 28.29, 27.21, 21.07. HRMS (ASAP) m/z calculated for $C_{13}H_{17}FNO$ $(M+H)^+$: 222.1289, found 222.1284, δ ppm: −2.25 ppm.

3-FMA HCl. White, powdery solid. $^1H$ NMR (400 MHz, DMSO-$d_6$) δ 9.25 (s, 2H), 7.37 (td, J=8.0, 6.3 Hz, 1H), 7.18-7.12 (m, 1H), 7.10 (d, J=7.4 Hz, 1H), 7.11-7.05 (m, 1H), 3.43-3.36 (m, 1H), 3.23 (dd, J=13.2, 4.3 Hz, 1H), 2.69 (dd, J=12.9, 9.9 Hz, 1H), 2.54 (s, 3H), 1.10 (d, J=6.5 Hz, 3H). $^{13}C$ NMR (101 MHz, DMSO-$d_6$) δ 162.25 (d, J=243 Hz), 139.65 (d, J=7.7 Hz), 130.45 (d, J=8.4 Hz), 125.47 (d, J=2.7 Hz), 115.99 (d, J=21.2 Hz), 113.61 (d, J=20.9 Hz), 54.90, 37.75 (d, J=1.4 Hz), 29.48, 14.95. HRMS (ASAP) m/z calculated for $C_{10}H_{15}FN$ $(M+H)^+$: 168.1183, found 168.1181, δ ppm: −1.19 ppm.

5-MAPB HCl. White, powdery solid. $^1H$ NMR (400 MHz, DMSO-$d_6$) δ 9.14 (s, 2H), 7.98 (d, J=2.1 Hz, 1H), 7.55 (d, J=9.4 Hz, 1H), 7.54 (s, 1H), 7.20 (dd, J=8.5, 1.7 Hz, 1H), 6.92 (d, J=2.0 Hz, 1H), 3.28 (dd, J=13.0, 3.3 Hz, 1H), 2.75 (dd, J=12.8, 9.8 Hz, 1H), 2.55 (s, 3H), 1.11 (d, J=6.5 Hz, 3H). $^{13}C$ NMR (101 MHz, DMSO-$d_6$) δ 153.36, 146.37, 131.26, 127.49, 125.59, 121.78, 111.25, 106.58, 55.61, 38.10, 29.51, 14.90. HRMS (ASAP) m/z calculated for $C_{12}H_{16}NO$ $(M+H)^+$: 190.1226, found 190.1224, δ ppm: −1.05 ppm.

3-MMC HCl. White, powdery solid. $^1H$ NMR (400 MHz, DMSO-$d_6$) δ 9.76 (bs, 1H), 9.28 (bs, 1H), 7.86 (s, 1H), 7.83 (d, J=7.8 Hz, 1H), 7.56 (d, J=7.6 Hz, 1H), 7.48 (t, J=7.6 Hz, 1H), 5.15 (q, J=7.1 Hz, 1H), 2.57 (s, 3H), 2.40 (s, 3H), 1.45 (d, J=7.2 Hz, 3H). $^{13}C$ NMR (101 MHz, DMSO-$d_6$) δ 196.41, 138.71, 135.26, 133.01, 129.10, 129.05, 126.02, 58.17, 30.60, 20.79, 15.45. HRMS (ASAP) m/z calculated for $C_{11}H_{16}NO$ $(M+H)^+$: 178.1226, found 178.1223, δ ppm: −1.68 ppm.

DCK HCl. White, crystalline solid. $^1H$ NMR (400 MHz, DMSO-$d_6$) δ 10.11 (bs, 1H), 9.39 (bs, 1H), 7.58-7.48 (m, 3H), 7.44-7.39 (m, 2H), 3.15 (ddd, J=13.8, 6.4, 2.5 Hz, 1H), 2.42-2.35 (m, 1H), 2.34-2.23 (m, 1H), 2.16 (td, 13.5, 3.8 Hz, 1H), 2.10 (s, 3H), 2.01-1.92 (m, 1H), 1.85 (dd, =11.8, 2.0 Hz, 1H), 1.69-1.49 (m, 2H). $^{13}C$ NMR (101 MHz, DMSO-$d_6$) δ 205.92, 130.25, 130.11, 129.62, 128.41, 70.89, 38.96, 31.06, 26.89, 26.63, 21.18. HRMS (ASAP) m/z calculated for $C_{13}H_{18}NO$ $(M+H)^+$: 204.1383, found 204.1385, δ ppm: 0.98 ppm.

Me-3-MMC HCl. White, powdery solid. $^1H$ NMR (400 MHz, DMSO-$d_6$) δ 10.78 (bs, 1H), 7.87 (s, 1H), 7.84 (d, J=7.7 Hz, 1H), 7.57 (d, J=7.6 Hz, 1H), 7.49 (t, J=7.6 Hz, 1H), 5.44 (q, =7.3 Hz, 1H), 2.85 (s, 6H), 2.40 (s, 3H), 1.48 (d, J=7.2 Hz, 3H). $^{13}C$ NMR (101 MHz, DMSO-$d_6$) δ 196.33, 138.70, 135.34, 133.50, 129.14, 129.04, 126.04, 63.71, 20.78, 13.83. HRMS (ASAP) m/z calculated for $C_{12}H_{18}NO$ $(M+H)^+$: 192.1383, found 192.1379, δ ppm: −2.08 ppm.

Lidocaine HCl. White, powdery solid. $^1H$ NMR (400 MHz, DMSO-$d_6$) δ 10.51 (bs, 1H), 10.06 (bs, 1H), 7.13-7.05 (m, 3H), 4.24 (s, 2H), 3.23 (q, J=7.4 Hz, 4H), 2.17 (s, 6H), 1.27 (t, J=7.3 Hz, 6H). $^{13}C$ NMR (101 MHz, DMSO-$d_6$) δ 163.31, 135.01, 133.85, 127.83, 126.94, 52.03, 48.33, 18.17, 8.97. HRMS (ASAP) m/z calculated for $C_{14}H_{23}N_2O$ $(M+H)^+$: 235.1805, found 235.1804, δ ppm: −0.42 ppm.

5-LAI HCl. Light grey, powdery solid. $^1H$ NMR (400 MHz, DMSO-$d_6$) δ 8.44 (bs, 3H), 7.65 (s, 1H), 7.53 (dd, J=8.0, 1.5 Hz, 1H), 7.09 (d, J=8.0 Hz, 1H), 3.99-3.88 (m, 1H), 3.22 (td, J=16.7, 7.7 Hz, 2H), 2.97 (ddd, J=17.1, 5.5 Hz, 2H). $^{13}C$ NMR (101 MHz, DMSO-$d_6$) δ 143.00, 139.79, 135.49, 133.38, 126.95, 92.41, 50.24, 36.94, 36.90. HRMS (ASAP) m/z calculated for $C_9H_{10}IN$ $(M+H)^+$: 259.9931, found 259.9925, δ ppm: −2.30 ppm.

Preparation of 3-MMC Captisol Formulation (70 mg/mL). 3-MMC FB was prepared directly prior to use. 3-MMC HCl (1.0 g) was basified with 10% NaOH and transferred to a separatory funnel. The aqueous phase was extracted with $Et_2O$ (2×100 mL) and the combined organics washed with brine. The organic phase was dried over anhydrous $Na_2SO_4$ and concentrated on a rotary evaporator with the water bath set to 30° C. and vacuum set between 600-700 mbar. The resulting oil was further dried on the rotary evaporator at 15 mbar for 10 minutes and a portion of the oil (141.2 mg) immediately measured out into a 5 mL borosilicate glass test tube. A solution of CapAcid (8.47% moisture, 270 mg active, 294.9 mg moisture corrected) in HPLC grade $H_2O$ (1.5 mL) was added to the test tube and the mixture was vortexed until the solution was homogenous. Benzethonium chloride (20 μL of a 1% solution, 0.01% final concentration) was added and the pH adjusted to 7.0 with 2M NaOH. The solution was diluted to 2 mL in a volumetric flask and then filtered through a 0.45 μm syringe filter. The final pH after dilution was measured and osmolality was immediately measured along with 0.9% saline and 3% saline standards.

General procedure for the preparation of API salt-Captisol $Na^+$ formulations. Formulations were prepared on a 2 mL scale. In a 5 mL borosilicate glass test tube containing a Teflon-coated magnetic stirbar, API salt (70 mg/mL FB equiv) and Captisol® (1.1 molar equiv in CapAcid equiv moisture corrected) were dissolved in HPLC grade $H_2O$ (1.5 mL). While stirring, benzethonium chloride (20 μL of a 1% solution, 0.01% final concentration) was added via micropipette and the pH was adjusted to the desired pH with either 1M or 2M aqueous sodium hydroxide. The solution was then transferred to a 2 mL volumetric flask and diluted up to 2 mL with HPLC grade $H_2O$. The final pH after dilution was measured and osmolality was immediately measured along with 0.9% saline and 3% saline standards.

General procedure for the preparation of API FB-CapAcid formulations. Formulations were prepared on a 2 mL scale. In a 5 mL borosilicate glass test tube containing a Teflon-coated magnetic stirbar, API FB (140 mg, 70 mg/mL) was added, followed by a solution of CapAcid (1.1 molar equiv moisture corrected) in HPLC grade $H_2O$ (1.5 mL). The mixture was stirred until a homogenous solution formed and benzethonium chloride (20 μL of a 1% solution, 0.01% final concentration) was added via micropipette. The pH was adjusted to ~7.0 with either 1M or 2M sodium hydroxide and then transferred to a 2 mL volumetric flask and diluted up to 2 mL with HPLC grade $H_2O$. The final pH after dilution was measured and osmolality was immediately measured along with 0.9% saline and 3% saline standards. Some samples were analyzed for concentration by HPLC. The concentrations of API formulations as determined by HPLC are shown in Table 20.

TABLE 20

| Sample | Theoretical Concentration (mg/mL in FB equiv) | HPLC Concentration (mg/mL in FB equiv) |
|---|---|---|
| Me-3-MMC HCl-Captisol ® | 70 | 69.2 ± $1.4^+$ |
| Me-3-MMC FB-CapAcid | 70 | 69.9 ± $4.8^+$ |
| 5-IAI FB-CapAcid | 70 | 69.6 ± $2.1^+$ |
| DCK FB-CapAcid | 70 | Initial concentration 65.4 ± $3.0^+$ 5-month stability 64.5 ± $2.3^+$ |
| 2-F-DCK FB-CapAcid | 70 | 74.2 ± $1.8^+$ |
| 3-FMA FB-CapAcid | 70 | 72.0 ± $2.9^+$ |
| 5-MAPB FB-CapAcid | 70 | Initial concentration 74.5* 1-month stability 69.2* |
| 5-MAPB HCl-Captisol ® | 70 | 71.3 ± $0.6^\delta$ |
| 3-MMC FB-CapAcid | 70 | 58.9 ± $0.3^+$ |
| 3-MMC HCl-Captisol ® | 70 | 55.8 ± $0.5^+$ |
| Morphine FB-CapAcid | 70 | 64.2* |
| Morphine sulfate pentahydrate-Captisol ® | 60 | 57.6* |

*N = 1,
$^\delta$N = 2,
$^+$N = 3

General procedure for the preparation of API salt formulations. Formulations were prepared on a 1 mL scale. API salt (70 mg/mL in FB equivalent) was dissolved in HPLC grade $H_2O$ (1.5 mL) and benzethonium chloride (10 μL of a 1% solution, 0.01% final concentration) was added. The solution was diluted to 1 mL in a volumetric flask, pH was recorded, and osmolality was measured along with 0.9% and 3% saline standards. DXM HBr had a max solubility of 16.4 mg/mL (freebase equivalents) as determined by HPLC and for that reason a solution of 15 mg/mL (freebase equivalents) was prepared. For similar reasons, 5-IAI HCl was prepared at 35 mg/mL.

Preparation of DXM FB-CapAcid stoichiometric salt. To a stirred solution of CapAcid (8.47% moisture, 3.21 g active, 3.51 g moisture corrected), 1.58 mmol Captisol, 10.4 mmol if') in HPLC grade $H_2O$ (25 mL) was added DXM FB (2.91 g, 10.7 mmol). The mixture was stirred until dissolved. A small amount of residual suspended particles were removed by filtration through a 0.45 μm syringe filter. The pH of the resulting solution was 4.44. The solution was transferred to a 20 mL borosilicate glass scintillation vial, frozen and subjected to lyophilization on an SP Scientific Wizard 2.0 lyophilizer at 30 mmHg for 48 hr. The resulting white solids were pulverized into a free-flowing powder (5.97 g), further dried under high vacuum (<0.05 mmHg) stored in a parafilm-sealed scintillation vial at −20° C. until use.

Determination of the saturation point of DXM HBr hydrate and DXM FB-CapAcid salt. Two-5 mL borosilicate glass test tubes with Teflon-coated magnetic stir bars were charged with HPLC grade $H_2O$ (1.0 mL). DXM HBr hydrate and DXM FB-CapAcid salt were added to their respective vials in small portions until they appeared visually saturated. Another portion of solid was then added to each vial to ensure saturation, the vials were covered with aluminum foil, and the mixtures were stirred for 48 hr at rt. The DXM HBr hydrate suspension was filtered through a 0.45 μm syringe filter into a centrifuge tube and diluted to a range of 50-150 μg/mL DXM for HPLC analysis. The DXM FB-CapAcid salt produced a viscous, homogenous solution with a substantial increase in volume. A portion of the solution was added to a 1 mL volumetric flask and that 1 mL portion was then carefully diluted into a 25 mL volumetric flask to decrease viscosity. The solution was then diluted to a range of 50-150 μg/mL DXM for HPLC analysis. The samples were analyzed by HPLC with a standard curve of DXM HBr hydrate (50-150 μg/mL DXM FB equivalent) to determine the concentration of DXM. Table 21 shows saturation point solubilities of DXM HBr hydrate and DXM FB-CapAcid salt determined by HPLC.

TABLE 21

| Sample | [DXM] (mg/mL in FB equiv) |
|---|---|
| DXM HBr hydrate | 16.4 |
| DXM FB-CapAcid salt | >310.8* |

*Solution did not reach saturation point, though further addition were deemed unfeasible due to viscosity.

Preparation of Nicotine FB-CapAcid stoichiometric salt. To a stirred solution of CapAcid (4.76% moisture, 1.908 g active, 2.00 g moisture corrected, 0.94 mmol Captisol, 6.13 mmol $H^+$) in HPLC grade $H_2O$ (10 mL) was added S-(−)-nicotine FB (990 μL, 1.0 g, 6.16 mmol). The mixture was stirred until homogenous and filtered through a 0.45 μm syringe filter. The solution was then transferred to a 20 mL borosilicate glass scintillation vial, frozen, and subjected to lyophilization for 48 hours. The resulting yellow, hygroscopic solids were further dried under high vacuum (>0.05 mmHg) and pulverized into a free-flowing powder (2.85 g).

Preparation of Nicotine Fumarate formulation. Formulation was prepared on al mL scale. Nicotine FB (69.8 mg, 0.430 mmol) was dissolved in HPLC grade $H_2O$ (0.7 mL) in a 5 mL borosilicate glass test tube and fumaric acid (50.0 mg, 0.430 mmol) was added. The mixture was vortexed until homogenous and then benzethonium chloride (10 μL of a 1% solution, 0.01% final concentration) was added. The solution was diluted to 1 mL in a volumetric flask, the final pH measured, and the osmolality was measured along with 0.9% and 3% saline standards.

Preparation of Nicotine Fumarate-Captisol® formulation. Formulation was prepared on a 1 mL scale. Nicotine FB (139.8 mg, 0.862 mmol) was dissolved in HPLC grade $H_2O$ (1.3 mL) in a 5 mL borosilicate glass test tube and fumaric acid (100.1 mg, 0.862 mmol) was added. The mixture was vortexed until homogenous and then benzethonium chloride (20 μL of a 1% solution, 0.01% final concentration) was added. Captisol® (315.8 mg active, 334.3 mg moisture corrected, 0.146 mmol) was then added and vortexed until dissolved. The pH was adjusted to 7 with 2M NaOH and diluted to 2 mL in a volumetric flask with HPLC grade $H_2O$. The final pH was measured and the osmolality was measured along with 0.9% and 3% saline standards.

Preparation of Morphine-CapAcid Stoichiometric Salt. Morphine freebase (540 mg, 1.89 mmol) was added to a stirred solution of CapAcid (8.47% moisture, 646.7 mg active, 706.5 mg moisture corrected, 0.32 mmol Captisol, 2.08 mmol $H^+$) in HPLC grade $H_2O$ (12 mL). The mixture was stirred until dissolved and residual suspended particles were removed by filtration through a 0.45 μm syringe filter. The solution was transferred to a 20 mL borosilicate glass scintillation vial and subjected to lyophilization on an SP Scientific Wizard 2.0 lyophilizer at 30 mmHg for 48 hr. The resulting white solids were pulverized using a glass stir rod into a free-flowing white powder (1.14 g) and stored in a parafilm-sealed scintillation vial at −20° C. until use.

Determination of the Solubility of Morphine-CapAcid Stoichiometric Salt. A 5 mL borosilicate glass test tube was charged with morphine-CapAcid salt (500 mg) and HPLC grade $H_2O$ was added until the solution appeared saturated (200 μL). The mixture was sealed with parafilm, covered with aluminum foil, and allowed to stand at room temperature overnight. The morphine FB-CapAcid salt produced a viscous, homogenous solution with a substantial increase in volume. A portion of the solution was taken by pipette and diluted in duplicate to a concentration range of 50-150 μg/mL morphine for HPLC analysis. Concentrations were determined by HPLC with a standard curve of morphine sulfate pentahydrate (50-150 μg/mL morphine FB equiv) to determine the concentration of morphine. Table 22 shows solubility of morphine FB-CapAcid salt determined by HPLC.

TABLE 22

| Sample | [Morphine] (mg/mL in FB equiv) |
|---|---|
| Morphine sulfate pentahydrate (Literature) | 48 mg/mL FB equiv 64 mg/mL Morphine sulfate (Sigma-Aldrich)[+] |
| Morphine-CapAcid salt | >409.0* |

*Solution did not reach saturation point

[+]https://www.sigmaaldrich.com/deepweb/assets/sigmaaldrich/product/documents/305/559/m8777dat.pdf Forced precipitation of API HCl salt and API FB-CapAcid formulation. Solutions of API HCl (70 mg/mL free base equiv) and API FB-CapAcid (70 mg/mL FB and 1.1 equiv CapAcid) were freshly prepared on a 1 mL scale by the following procedures: API HCl: API HCl (70 mg in FB equiv) was added to a 5 mL borosilicate glass test tube and dissolved in HPLC grade $H_2O$ (0.7 mL). The mixture was stirred or vortexed until homogenous. Benzethonium chloride (10 μL of 1% solution, 0.01% final concentration) was added via micropipette and the pH was adjusted to 7.0±0.1 with either 0.5M, 1M, or 2M aqueous NaOH. The solution was then diluted to 1 mL using a volumetric flask and placed back into a 5 mL borosilicate glass test tube with a Teflon-coated magnetic stir bar. The pH of the solution was then recorded. API FB-CapAcid: API FB (70 mg) was added to a 5 mL borosilicate glass test tube followed by a solution of CapAcid (1.1 molar equiv moisture corrected) in HPLC grade $H_2O$ (0.7 mL) and stirred or vortexed until homogenous. Benzethonium chloride (10 μL of 1% solution, 0.01% final concentration) was added via micropipette and the pH was adjusted to 7.0±0.1 with either 0.5M, 1M, or 2M aqueous NaOH. The solution was then diluted to 1 mL using a volumetric flask, and placed back into a 5 mL borosilicate glass test tube with a Teflon-coated magnetic stir bar. The pH of the solution was then recorded.

The respective solutions were titrated with 2M NaOH in increments of 1 μL. The solutions were allowed to stir for 30 seconds between additions of base with pH monitoring. Precipitation was defined as visible solids or if the solution remained cloudy from precipitation.

Table 23 shows forced precipitation of API-Captisol formulations versus API HCl salt (1 mL scale) by addition of 1 μL increments of 2M NaOH. Starting pH of the formulation was 7.0±0.1.

TABLE 23

| Sample (70 mg/mL API in FB equivalents) | Volume of Base need for Precipitation (μL) |
|---|---|
| Me-3-MMC HCl | 6.5* |
| Me-3-MMC Cap | 9.5* |
| 5-MAPB HCl | 47* |
| 5-MAPB Cap | 30* |
| 3-FMA HCl | 37 |
| 3-FMA Cap | 45 |
| Lidocaine HCl | 5 |
| Lidocaine Cap | 8 |

*Average of 2 experiments pH and Osmolality versus concentration of API HCl, API HCl-Captisol® Formulation, and API FB-CapAcid Formulation. Solutions of API HCl (100 mg/mL FB equivalent), API FB-CapAcid (100 mg/mL FB and 1.1 equivalent CapAcid), and API HCl-Captisol® (100 mg/mL FB equiv and 1.1 molar equivalent Captisol®) were freshly prepared on a 1 mL scale by the following procedures: API HCl: API HCl (100 mg in FB equiv) was added to a 5 mL borosilicate glass test tube and dissolved in HPLC grade $H_2O$ (0.7 mL). The mixture was stirred or vortexed until homogenous. Benzethonium chloride (10 μL of 1% solution, 0.01% final concentration) was added via micropipette and the pH was adjusted to 7.0±0.1 with either 0.5M, 1M, or 2M aqueous NaOH. The solution was then diluted to 1 mL using a volumetric flask and placed back into a 5 mL borosilicate glass test tube with a Teflon-coated magnetic stir bar. The pH of the solution was then measured. API FB-CapAcid: API FB (100 mg) was added to a 5 mL borosilicate glass test tube followed by a solution of CapAcid (1.1 molar equiv moisture corrected) in HPLC grade $H_2O$ (0.7 mL) and stirred or vortexed until homogenous. Benzethonium chloride (10 μL of 1% solution, 0.01% final concentration) was added via micropipette and the pH was adjusted to 7.0±0.1 with either 0.5M, 1M, or 2M aqueous NaOH. The solution was then diluted to 1 mL using a 1 mL volumetric flask and placed back into a 5 mL borosilicate glass test tube with a Teflon-coated magnetic stir bar. The pH of the solution was then measured. API HCl-Captisol®: API HCl (100 mg FB equiv) and Captisol® (1.1 molar equiv in CapAcid equiv moisture corrected) were added to a 5 mL borosilicate glass test tube and dissolved in HPLC grade $H_2O$ (0.7 mL). The mixture was stirred or vortexed until homogenous. Benzethonium chloride (10 μL of 1% solution) was added via micropipette and the pH was adjusted to 7.0±0.1 with either 0.5M, 1M, or 2M aqueous NaOH. The solution was then diluted to 1 mL using a volumetric flask, and then placed back into a 5 mL borosilicate glass test tube with a Teflon-coated magnetic stir bar. The pH of the solution was then measured.

The solutions were serial diluted to 75, 50, 25, and 10 mg/mL and the pH measured for each dilution. Portions of each dilution were taken for osmolality readings. The osmolality of each sample was measured in triplicate along with 0.9% and 3% saline standards. Some Captisol Acid formulations have low osmolarity, as shown in Table 24. Table 24 shows prepared API Captisol® formulations and API salt solutions with final pH and average osmolalities.

TABLE 24

| Active Pharmaceutical Ingredient | CapAcid—API Freebase Formulation (70 mg/mL API FB, 1.1 molar equiv CapAcid) Osmolality (mOsm/kg) | pH | Captisol ®—API HCl salt formulation (70 mg/mL API HCl salt in FB equiv, 1.1 molar equiv Captisol ® in CapAcid equiv) Osmolality (mOsm/kg) | pH | API HCl salt (70 mg/mL in FB equiv) ^ Osmolality (mOsm/kg) | pH |
|---|---|---|---|---|---|---|
| 3-MMC | 312 | 6.99 | 1,190* | 6.98 | 636 | 4.76 |
| 3-FMA | 337 | 6.78 | 1,388 | 7.01 | 706 | 5.17 |
| 2-F-DCK | 373 | 6.97 | 1,046 | 6.93 | 560 | 4.27 |
| DCK | 310 | 7.00 | 1,086 | 6.98 | 601 | 4.73 |
| DXM | 113 | 6.95 | (DXM HBr 15 mg/mL FB equiv) 145* | 7.05 | (DXM HBr 15 mg/mL FB equiv) 91 | 5.47 |
| 5-MAPB | 215 | 7.10 | 1,004 | 7.15 | 556 | 3.16 |
| 5-IAI | 119 | 6.97 | 621 | 6.98 | (5-IAI HCl 35 mg/mL FB equiv) 221 | 4.62 |
| Me-3-MMC | 321 | 6.95 | 1,151 | 7.00 | 578 | 4.44 |
| Lidocaine | 304 | 6.99 | 844 | 6.95 | 543 | 4.60 |
| Sumatriptan | 109 | 7.06 | (Sumatriptan stoichiometric succinate salt) 858 | (Sumatriptan stoichiometric succinate salt) 6.99 | (Sumatriptan stoichiometric succinate salt) 293 | 4.57 |
| Nicotine | 555* | 7.02* | (Stoichiometric Fumarate salt) 2,006 | (Stoichiometric Fumarate salt) 6.97 | (Stoichiometric Fumarate salt) 682 | (Stoichiometric Fumarate salt) 3.80 |
| Morphine | 166 | 6.09 | (Sulfate pentahydrate salt 60 mg/mL FB equiv) 415 | (Sulfate pentahydrate salt 60 mg/mL FB equiv) 6.00 | (Sulfate pentahydrate salt 45 mg/mL FB equiv) 157 | (Sulfate pentahydrate salt 45 mg/mL FB equiv) 4.28 |

*n = 2

^ concentrations 70 mg/mL unless otherwise specified.

The effect of Captisol Acid formulation on the APIs, e.g., pH and osmolarity, are shown in FIGS. 35 to 42. FIGS. 43 to 58 show the HPLC measurements of concentration and the calibration curves.

In the process of applying the formulation techniques disclosed herein to a wide number of molecules having an ionizable amine nitrogen, a super complexing phenomena was discovered that was both unexpected and is of value in further reducing the osmolality of solutions, or other formulations targeted to intranasal, sublingual, intramuscular, intravenous, per rectal, or oral routes of administration. Osmolality for a number of Captisol Acid:API formulations was substantially lower than the calculated osmolarity for the APIs, and these data were documented in Table 25. Super complexing of specific API-Captisol salt formulations, which exhibit osmolalities further lowered relative to other molecules, such as ketamine, lidocaine, 2-F-DCK and nicotine, which have osmolalities close to the theoretical calculated osmolarity. In other words, these experimentally measured osmolalities are notably below what would be expected from stoichiometric ratios based upon the average number of substitutions present on the Captisol ring (which equals approximately 6.5 sulfobutyl groups ending in a sulfonate per Captisol molecule) and the addition of approximately 1:1 molar equivalent of the API to these sulfonate groups.

Specifically, it was demonstrated that some process of super complexing was capable of substantial further lowering measured osmolality beyond what would be expected, based upon calculation of expected osmolarity. As can be seen in data presented in Table 25, the observed osmolality was less than 50% of the calculated osmolarity for DXM, 5-IAI, Sumatriptan and 5-MAPB, less than 65% of the calculated osmolarity for morphine and 3-FMA and less than or equal to 75% of the calculated osmolarity for 3-MMC and Me-3-MMC.

TABLE 25

Theoretical vs Measured osmolarities of API-Cap Formulations at 70 mg/mL freebase equivalents.

| API | Theoretical Osmolarity (mOsmol/L) | Measured Osmolality (mOsmol/L) | Percentage of Theoretical |
|---|---|---|---|
| DXM | 301.7 | 113 | 37.5% |
| 5-IAI | 315.7 | 119 | 37.7% |
| Sumatriptan | 271.1 | 109 | 40.2% |
| 5-MAPB | 432.6 | 215 | 49.7% |
| Morphine | 286.8 | 166 | 57.9% |
| 3-FMA | 534.2 | 337 | 63.1% |
| 3-MMC | 416.7 | 312 | 74.9% |
| Me-3-MMC | 427.9 | 321 | 75.0% |
| DCK | 402.2 | 310 | 77.1% |
| Ketamine | 343.8 | 291 | 84.6% |
| Lidocaine | 349.3 | 304 | 87.0% |
| 2-F-DCK | 369.8 | 373 | 100.9% |
| Nicotine | 503.9 | 555 | 110.1% |

Potential experimental approaches that can elucidate the mechanisms involved in this super-complexing process include, depending on the size of the complexes, Dynamic Light Scattering (DLS) and turbidity measurements performed upon the solutions, which can prove particle size and concentration, respectively. Cryo Transmission Electron Microscopy (CryoTEM) is an alternative approach to characterizing the nature of this super complexing finding by cooling the samples to cryogenic temperatures and embedding them in an environment of amorphous or vitreous water, applying a sample to a grid-mesh, plunge-freezing in liquid ethane, and determining the complex's biomolecular structures. Nuclear magnetic resonance (NMR) is another measurement tool that can be used to identify and characterize the structural nature of the supramolecular complexes by comparing the chemical shift differences of the uncomplexed to complexed species and running 2-D NMR tests including Rotating-frame nuclear Overhauser effect spectroscopy (ROESY), Diffusion-ordered spectroscopy (DOSY), and Nuclear Overhauser Effect Spectroscopy (NOESY) (NMR Literature: Jahed, V., Zarrabi, A., Bordbar, A. K. and Hafezi, M. S., 2014. NMR (1H, ROESY) spectroscopic and molecular modelling investigations of supramolecular complex of β-cyclodextrin and curcumin. *Food chemistry,* 165, pp. 241-246; Pastor, A. and Martinez-Viviente, E., 2008. NMR spectroscopy in coordination supramolecular chemistry: A unique and powerful methodology. *Coordination Chemistry Reviews,* 252(21-22), pp. 2314-2345).

Example 41. Captisol Acid: Vancomycin Formulation

This example illustrates the benefits and advantages of Captisol Acid formulation of vancomycin. Vancomycin is an essential antibiotic indicated for the treatment of serious, life-threatening infections by Gram-positive bacteria unresponsive to other antibiotics. This glycopeptide antibiotic is approved for intravenous (IV) administration for the treatment of infective endocarditis at 15 to 20 mg/kg/dose IV every 8 to 12 hours. This represents dosing that is likely impossible with an oral route of delivery when referring to the serum blood levels that are required for response. It makes treatment of endocarditis impossible outside of a hospital environment with IV capacities.

While there are oral protocols and approved indications for oral vancomycin, these indications and uses specifically rely upon the poor bioavailability of orally delivered vancomycin, to specifically ensure that the drug remains in the (gastrointestinal) GI lumen for treatment of pseudomembranous colitis due to *Clostridium difficile*. Oral dosing recommendations are 125 mg oral administration (PO) 4 times daily for 10 days as a first line therapy option for both non-severe and severe initial cases and as treatment for a first recurrence in patients previously treated with metronidazole. For a 70 kg individual receiving vancomycin for these two vastly different indications, the IV dose would be 4,200 mg/day for indications directed toward systemic as opposed to intraluminal GI infection, while the dose would be 500 mg per day for a GI specific indication.

For someone skilled in the art, it is clear that the established poor oral bioavailability of vancomycin specifically permits this intraluminal therapeutic indication via oral delivery, but that this also clarifies that oral dosing cannot be relied upon for any serious systemic infection for which vancomycin might be a critical treatment. A parenteral delivery formulation and/or delivery system that improves systemic delivery of vancomycin in the home environment would be of substantial potential value in that it would notably improve upon current at-home oral delivery approaches, substantially increasing blood levels of the active API and permitting treatment of systemic conditions responsive to vancomycin in the home environment. This potential benefit is expected to produce improvement in the current art in home delivery of this molecule currently only available through oral delivery techniques. Regarding problems associated with poor bioavailability in vancomycin delivery, it should be noted that alternative paths have been innovated by physicians who are trained in the art, leading to extemporaneous compounding of rectally administered formulations to solve issues related to poor oral bioavailability and other non-ideal aspects of vancomycin pharmacokinetics. One skilled in the art should see that, if an oral vancomycin formulation based upon the techniques disclosed herein increased oral bioavailability, there would be substantial value and new utility in such a product for many clinical applications. For example, such a product might enable extended treatment with vancomycin in the home environment during continued rehabilitation and recovery from a wide variety of conditions shown to respond to vancomycin.

Example 42. Pharmaceutical Compound Candidates for Captisol Acid Formulations

The value offered by the formulation techniques disclosed herein, is notable. There are numerous APIs and categories of medically treatment that might benefit from application of this technology. Because many antibiotics have an ionizable nitrogen within their structure it is possible to create a Captisol salt with these APIs, lyophilize the complex and press into tablets or encapsulate for oral delivery. The increase solubility that the formulation technique affords is expected to increase surface contact of the drug with the gut mucosal layer allowing increased efflux or uptake and increased bioavailability. These potential benefits also can be expected to apply to sublingual, intranasal and per rectal formulations. In addition, the ability of the formulation techniques disclosed herein to produce concentrated liquid formulations, with documented advantages in improving tonicity or osmolality and pH to ranges that are more closely matching that of subcutaneous or intramuscular tissues, is also expected to produce repurposing or refreshing value in many APIs because this can allow delivery via pumps or other devices in more convenient fashion in supervised setting or even enable delivery of these valuable treatments in a home setting or over a longer time frame than is generally possible in inpatient settings due to the realities of inpatient medical economics. For example, an important antibiotic that was previously only available by intravenous delivery in-office can be delivered by a wearable patch pump over the course on one to many days at home, increasing convenience, safety, access and reducing costs.

Table 26 lists potential APIs that bear one or more theoretically ionizable nitrogen that makes formulation techniques described herein produce valuable benefits and improvements upon the current art. This list is not meant to be complete or imply that other molecules and APIs may exist that this technique can be applied to.

TABLE 26

| Category | List of APIs |
|---|---|
| Antibiotics | acetyl sulfisoxazole, amphotericin B, cefotaxime, cefoxitin, cefiderocol, clavulanic acid, dalbavancin, finafloxacin, minocycline, nafcillin, plazomicin, tigecycline, vaborbactam |
| Anti-coagulants | Enoxaparin |
| Anti-diabetics | sitagliptin, linaglipin |
| Antifungals | caspofungin, micafungin |
| Anti-inflammatories | flunixin, nifulmic acid |
| Anti-migraine | almotriptan, alniditan, avitriptan, donitriptan, eletriptan, frovatriptan, lasmiditan, naratriptan rizatriptan, sumatriptan, zolmitriptan |
| Anti-neoplastics | 6-TG, actinomycin, adriamycin, chlorambucil, chlormethine, copanlisib, cyclophosphamide, dactinomycin, daunomycin, daunorubicin, doxyrubacin, gemcitabine, goserelin, methamnetamine, methotrexate, mitocins, nadoxolol, naphthylisopropylamine, nimodipine, nitroprusside, nintedanib, pamidronic acid, plabociclib, rotigotine, seliciclib (or roscovitine), sunitinib, tamoxifen, temozolomide, toremifene, theotepa, trimetrexate |
| Antiviral and anti-COVID | remdesivir |
| Piperazines | related piperazine structures with substitutions but containing the piperazine ring structure |
| Naphthylpropylamines | naphthylaminopropanes, naphthylisopropylamines and substitutions such as methamnetamine and other substituted versions. |
| Phenidates | methylphenidate, ethylphenidate and other substituted versions |
| Other | angiotensin II, cinacalcet, chloroprocaine, difelikefalin, fosdenopterin, ganirelix, indanylaminopropane, indanylmethylaminopropane, levoleucovorin, levothyroxine, meperidine, methylene blue and methylene blue derivatives, mifamurtide, milrinone, tofacitinib, trolamine or triethanolamine |

Example 43. Osmolarity and pH of Ketamine-Captisol Formulations

This Example illustrates the effects of Captisol Acid formulations on ketamine through methods disclosed herein.

Table 27 shows the average osmolality of Racemic Ketamine HCl and Racemic Ketamine complexes/co-solvents.

TABLE 27

| Sample | [Ketamine] mg/mL FB equiv. | Average osmolality (mOsm/kg) ± SEM |
|---|---|---|
| Ketamine HCl-10% Captisol | 70 | 938.5 ± 2.18 |
| Ketamine HCl-10% Captisol | 96 | 1419.7 ± 23.4 |
| Ketamine-Captisol (BB106) | 70 | 291.4 ± 4.00 |
| Ketamine-Captisol (BB105) | 96 | 448.0 ± 4.40 |
| Ketamine HCl | 70 | 527 ± 2.69 |
| Ketamine HCl | 96 | 704.4 ± 9.95 |
| Ketamine HCl | 100 | 736.83 ± 3.7 |
| Ketamine HCl 10% HPBCD | 70 | 622.2 ± 3.156 |
| Ketamine HCl + 10% Propylene glycol* | 70 | 1,940 ± 21.64 |

*Sample diluted 2:1 in HPLC water for osmolality reading and osmolality was back-calculated from this dilution factor.

Table 28 shows forced precipitation of Racemic Ketamine with 2M NaOH after pH 5.5, starting pH ranging from 4.49-5.59. The tests were conducted on a 2 mL volume. Base was added in 1-2 µL volumes.

TABLE 28

| Sample | Mean Volume Base to precip (µL) ± SEM |
|---|---|
| Ketamine HCl (70 mg/mL FB equiv.) | 4 ± 0 |
| Ketamine HCl-10% Captisol Na (70 mg/mL Ketamine FB eqiv.) | 9 ± 1 |
| Ketamine HCl-10% HPBCD (70 mg/mL Ketamine FB equiv.) | 8 ± 2 |
| Ketamine HCl + 10% Propylene glycol (70 mg/mL Ketamine FB equiv.) | 5 ± 1 |
| Ketamine-Captisol Acid (70 mg/mL Ketamine) | 12 ± 1.15 |

Figure 59:
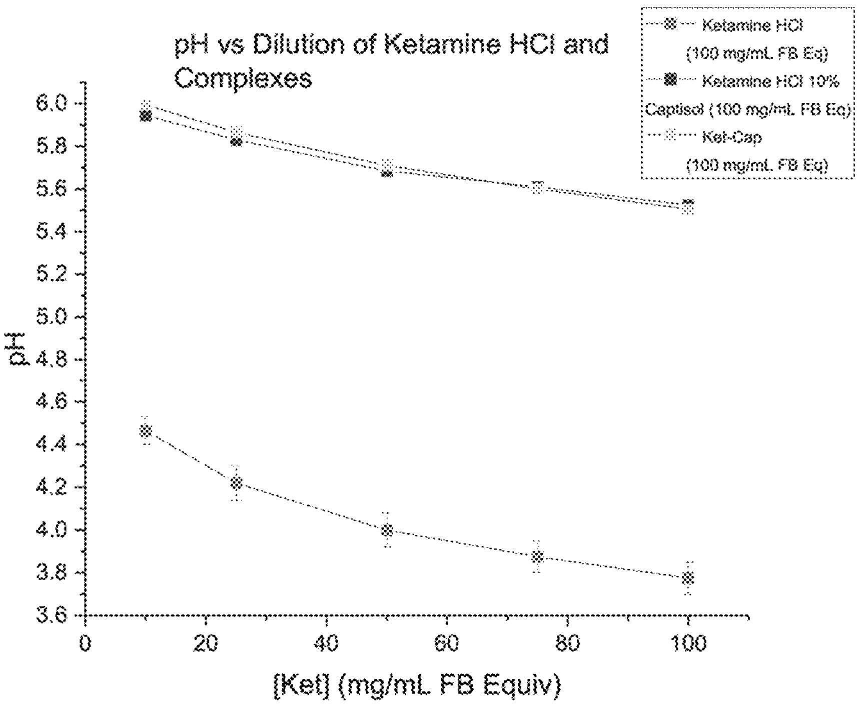
FIG. 59 shows the measurement of pH of Racemic Ketamine HCl and Racemic Ketamine Complexes upon dilution.
Figure 60:
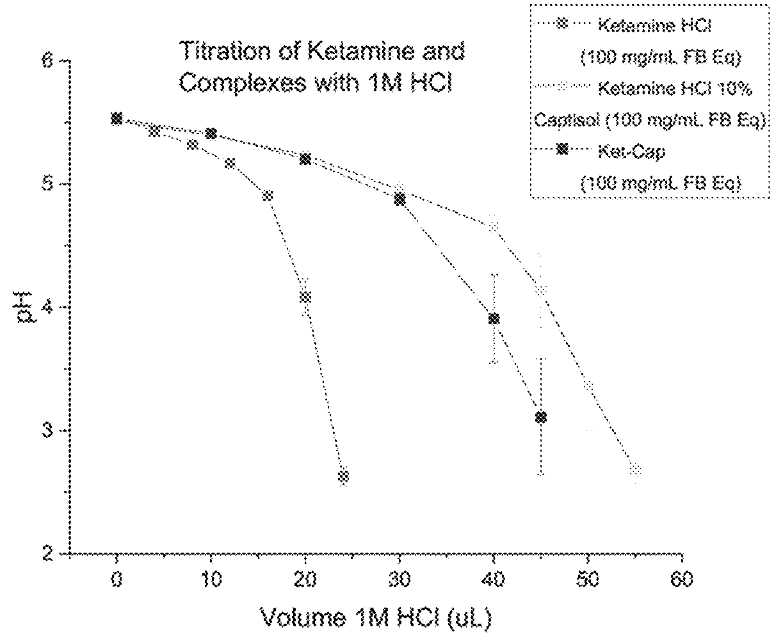
FIG. 60 shows the titration of Ketamine HCl and Ketamine complexes with 1M HCl.
Figure 61:
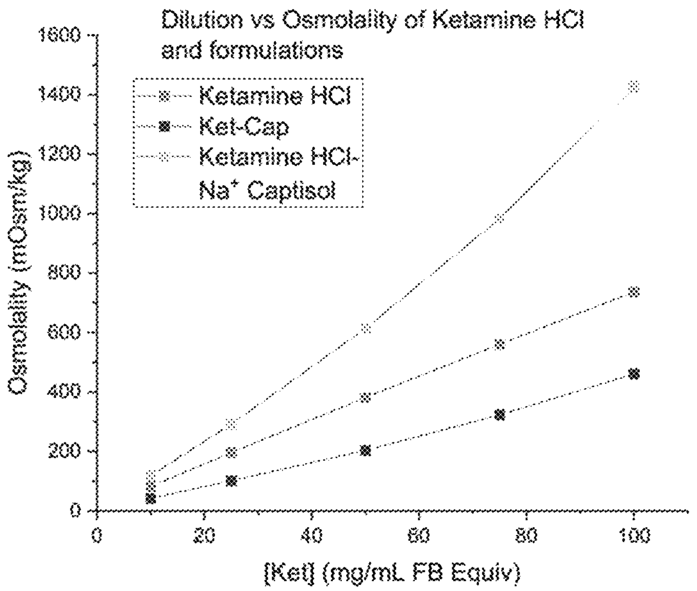
FIG. 61 shows the measurement of osmolalities of Ketamine HCl and Ketamine complexes upon dilution.

FIG. 59 shows the pH measurement curve of Racemic Ketamine HCl and Racemic Ketamine Complexes upon dilution. FIG. 60 shows the titration curve of Ketamine HCl and Ketamine complexes with 1M HCl. FIG. 61 shows the osmolalities of Ketamine HCl and Ketamine complexes upon dilution.

As a comparison, Table 29 shows the pH measurement of commercial Ketamine HCl solutions (n=3). Table 30 shows the osmolality measurement of commercial Ketamine HCl solutions (Samples were compared to 0.9% saline standard: 290.0±0.527 mOsm/kg, n=3).

TABLE 29

| Ketamine Sample | pH ± SEM |
|---|---|
| Mylan (50 mg/mL Ketamine HCl) | 4.18 ± 0.032 |
| Ketalar ® (50 mg/mL Ketamine HCl) | 4.09 ± 0.014 |
| Hospira (100 mg/mL Ketamine HCl) | 3.88 ± 0.028 |
| West-Ward (100 mg/mL Ketamine HCl) | 3.94 ± 0.017 |

TABLE 30

| Ketamine Sample | Osmolality ± SEM (mOsm/kg) |
|---|---|
| Mylan (50 mg/mL Ketamine HCl) | 378.7 ± 0.878 |
| Ketalar ® (50 mg/mL Ketamine HCl) | 382.7 ± 0.924 |
| Hospira (100 mg/mL Ketamine HCl) | 748.3 ± 1.59 |
| West-Ward (100 mg/mL Ketamine HCl) | 755.3 ± 2.11 |

Table 31 shows the osmolality measurement of Racemic Ket-Cap complexes and controls.

TABLE 31

| Sample | Mean Osmolality (mOsm)* | Standard Deviation | Standard Error of Mean | 95% Confidence interval | N (number of samples) |
|---|---|---|---|---|---|
| Ketamine-Captisol (BB-105) (96 mg/mL) | 448.0 | 9.8 | 4.4 | 439.5-456.6 | 5 |
| Ketamine-Captisol (BB-106) (70 mg/mL) | 291.4 | 10.6 | 4.0 | 283.5-299.2 | 7 |
| 0.9% Saline | 291.0 | 6.9 | 1.9 | 287.2-294.8 | 13 |
| Ketamine HCl (100 mg/mL) | 703.0 | 10.9 | 3.6 | 695.9-710.1 | 3 |
| Ketamine HCl (75 mg/mL) | 533.3 | 2.5 | — | — | 1 |
| Captisol ® | 429.3 | 14.4 | 5.9 | 417.8-440.9 | 2 |
| HPLC HPLC $H_2O$ | 0 | — | — | — | |

*Each sample was run in triplicate

Table 32 shows the measurement of average osmolality of Ketamine HCl with and without additives and Ketamine Captisol complexes.

TABLE 32

| Sample | [Ketamine] (mg/mL FB eq) | Average Osmolality (mOsm/kg) ± SEM |
|---|---|---|
| 0.9% Saline | — | 290.8 ± 1.1 |
| Ketamine HCl | 70 | 527.0 ± 2.7 |
| Ketamine HCl | 96 | 704.4 ± 9.9 |
| Ketamine HCl | 100 | 736.83 ± 3.7 |
| Racemic Ketamine-Captisol (BB105) | 96 | 448.0 ± 4.4 |
| Racemic Ketamine-Captisol (BB 106) | 70 | 291.4 ± 4.0 |
| Esketamine-Captisol (BB107) | 70 | 298.2 ± 9.5[+] |
| Arketamine-Captisol (BB108) | 70 | 289.3* |
| Ket HCl-Cap Nat | 70 | 938.5 ± 2.2 |
| Ket HCl-Cap Nat | 96 | 1419.7 ± 23.4 |
| Ket HCl-10% HPBCD | 70 | 622.2 ± 3.2 |
| Ket HCl + 10% Propylene glycol[1] | 70 | 1,940 ± 21.6 |

[1]Sample diluted 2:1 in HPLC water for osmolality reading and osmolality was back-calculated from this dilution factor.
[+]N = 2.
*N = 1.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

Although the disclosure has been described with reference to the above examples, it will be understood that modifications and variations are encompassed within the spirit and scope of the disclosure. Accordingly, the disclosure is limited only by the following claims.

What is claimed is:

1. A pharmaceutical composition, comprising:

(i) a cationic pharmaceutical compound, or an enantiomer, a mixture of enantiomers, or an isotopic variant thereof, comprising a protonated nitrogen atom, wherein the cationic pharmaceutical compound is not ketamine; and (ii) a substituted cyclodextrin comprising a plurality of anionic functional groups, wherein substantially all of the plurality of anionic functional groups of the substituted cyclodextrin are deprotonated, and at least one of the plurality of anionic functional groups acts as a counterion for the protonated nitrogen atom of the cationic pharmaceutical compound, wherein a molar ratio of the cationic pharmaceutical compound to the substituted cyclodextrin is greater than 1:1, and wherein the pharmaceutical composition comprising effective amounts of the cationic pharmaceutical compound and the substituted cyclodextrin has an osmolality, when in solution, that is at least about 10% less than a corresponding pharmaceutical composition prepared from a salt of the cationic pharmaceutical compound and a sodium salt of the substituted cyclodextrin.

2. The pharmaceutical composition of claim 1, wherein the substituted cyclodextrin is substituted with 3 to 8 anionic functional groups.

3. The pharmaceutical composition of claim 2, wherein the substituted cyclodextrin is sulfobutylether-β-cyclodextrin.

4. The pharmaceutical composition of claim 1, wherein the pharmaceutical composition has a molar ratio of the substituted cyclodextrin to the cationic pharmaceutical compound from about 1:2 to about 1:10.

5. The pharmaceutical composition of claim 4, wherein the substituted cyclodextrin acts as the counterion to between 5 to 10 molecules of the cationic pharmaceutical compound.

6. A method of therapy comprising:

administering a pharmaceutical composition to a human subject in need thereof, wherein the pharmaceutical composition comprises:

(i) a cationic pharmaceutical compound, or an enantiomer, a mixture of enantiomers, or an isotopic variant thereof, comprising a protonated nitrogen atom, wherein the cationic pharmaceutical compound is not ketamine; and (ii) a substituted cyclodextrin comprising a plurality of anionic functional groups, wherein substantially all of the plurality of anionic functional groups of the substituted cyclodextrin are deprotonated, and at least one of the plurality of anionic functional groups acts as a counterion for the protonated nitrogen atom of the cationic pharmaceutical compound, wherein a molar ratio of the cationic pharmaceutical compound to the substituted cyclodextrin is greater than 1:1, and wherein the pharmaceutical composition comprising effective amounts of the cationic pharmaceutical compound and the substituted cyclodextrin has an osmolality, when in solution, that is at least about 10% less than a corresponding pharmaceutical composition prepared from a salt of the cationic pharmaceutical compound and a sodium salt of the substituted cyclodextrin.

7. The method of claim 6, wherein the substituted cyclodextrin is substituted with 3 to 8 anionic functional groups.

8. The method of claim 7, wherein the substituted cyclodextrin is sulfobutylether-β-cyclodextrin.

9. The method of claim 6, wherein the pharmaceutical composition has a molar ratio of the substituted cyclodextrin to the cationic pharmaceutical compound from about 1:2 to 1:10.

10. The method of claim 9, wherein the substituted cyclodextrin acts as the counterion to between 5 to 10 molecules of the cationic pharmaceutical compound.

11. The pharmaceutical composition of claim 1, wherein the pharmaceutical composition is formulated as an inhalable powder.

12. The pharmaceutical composition of claim 1, wherein the cationic pharmaceutical compound and the substituted cyclodextrin has an osmolality, when in solution, that is at least about 20% less than a corresponding pharmaceutical composition prepared from a salt of the cationic pharmaceutical compound and a sodium salt of the substituted cyclodextrin.

13. The pharmaceutical composition of claim 1, wherein the pharmaceutical composition is formulated as a solid.

14. The pharmaceutical composition of claim 1, wherein the pharmaceutical composition is formulated as a liquid.

15. The pharmaceutical composition of claim 14, wherein the pharmaceutical composition has a pH that is within about 0.2 pH units to about 2 pH units of the pKa of the cationic pharmaceutical compound.

16. The pharmaceutical composition of claim 14, wherein the pharmaceutical composition has a pH of about 4 to about 7.

17. The pharmaceutical composition of claim 1, wherein the cationic pharmaceutical compound comprises a basic nitrogen atom having a pKa of about 4 to about 12.

18. The pharmaceutical composition of claim 1, wherein the osmolality of the solution is determined on an osmometer.

19. The pharmaceutical composition of claim 18, wherein the osmolality is determined using saline solutions freshly prepared with sodium chloride and run as positive controls.

20. The pharmaceutical composition of claim 18, wherein the osmolality is determined by calculating the mean from back-to-back triplicate measurements.

21. The pharmaceutical composition of claim 6, wherein the osmolality of the solution is determined on an osmometer.

22. The pharmaceutical composition of claim 6, wherein the cationic pharmaceutical compound and the substituted cyclodextrin has an osmolality, when in solution, that is at least about 20% less than a corresponding pharmaceutical composition prepared from a salt of the cationic pharmaceutical compound and a sodium salt of the substituted cyclodextrin.

23. A pharmaceutical composition, comprising:

(i) a cationic pharmaceutical compound, or an enantiomer, a mixture of enantiomers, or an isotopic variant thereof, comprising a protonated nitrogen atom, wherein the cationic pharmaceutical compound is not ketamine; and (ii) a substituted cyclodextrin comprising a plurality of anionic functional groups, wherein substantially all of the plurality of anionic functional groups of the substituted cyclodextrin are deprotonated, and at least one of the plurality of anionic functional groups acts as a counterion for the protonated nitrogen atom of the cationic pharmaceutical compound, wherein a molar ratio of the cationic pharmaceutical compound to the substituted cyclodextrin is greater than 1:1, and wherein the pharmaceutical composition comprising effective amounts of the cationic pharmaceutical compound and the substituted cyclodextrin, when in solution, has an osmolality that is at least about 50 mOsm/kg less than a corresponding pharmaceutical composition prepared from a salt of the cationic pharmaceutical compound and a sodium salt of the substituted cyclodextrin.

* * * * *